United States Patent
Nayudu et al.

(10) Patent No.: US 10,081,832 B2
(45) Date of Patent: Sep. 25, 2018

(54) HYPERPRIMERS

(75) Inventors: Murali Nayudu, Waramanga (AU); Andrew Franklin, Sydney (AU); Yafei Zhang, Watson (AU); Mark John Gibbs, Curtin (AU); Terry John Murphy, Aranda (AU); Adrian John Gibbs, Yarralumla (AU); Sheba Khan, Gordon (AU); Christian Samundsett, Monash (AU)

(73) Assignee: Ezygene PTY Ltd., Waramanga (AU)

( * ) Notice: Subject to any disclaimer, the term of this patent is extended or adjusted under 35 U.S.C. 154(b) by 0 days.

(21) Appl. No.: 13/514,524

(22) PCT Filed: Dec. 9, 2010

(86) PCT No.: PCT/AU2010/001659
§ 371 (c)(1),
(2), (4) Date: Aug. 6, 2012

(87) PCT Pub. No.: WO2011/069200
PCT Pub. Date: Jun. 16, 2011

(65) Prior Publication Data
US 2012/0295251 A1    Nov. 22, 2012

Related U.S. Application Data

(60) Provisional application No. 61/267,988, filed on Dec. 9, 2009.

(51) Int. Cl.
*C12Q 1/6876* (2018.01)
*C12Q 1/6844* (2018.01)
*C12Q 1/686* (2018.01)

(52) U.S. Cl.
CPC ........... *C12Q 1/6846* (2013.01); *C12Q 1/686* (2013.01); *C12Q 2525/179* (2013.01)

(58) Field of Classification Search
CPC ........ C12Q 1/68; C12Q 1/686; C12Q 1/6846; C07H 21/04
See application file for complete search history.

(56) References Cited

U.S. PATENT DOCUMENTS

| | | | | |
|---|---|---|---|---|
| 5,472,672 A | * | 12/1995 | Brennan | B01J 19/0046 422/110 |
| 5,700,637 A | * | 12/1997 | Southern | B01J 19/0046 422/50 |
| 5,861,479 A | | 1/1999 | Jin et al. | 530/324 |
| 6,884,351 B1 | * | 4/2005 | Lytal | C02F 3/341 210/601 |
| 2003/0134272 A1 | * | 7/2003 | Messiaen et al. | 435/5 |
| 2004/0137466 A1 | * | 7/2004 | Jofuku | C12Q 1/6895 435/6.12 |
| 2010/0173287 A1 | * | 7/2010 | Nakashima et al. | 435/6 |

FOREIGN PATENT DOCUMENTS

| | | |
|---|---|---|
| CN | 1 482 259 | 3/2004 |
| WO | WO 2007/046158 | * 4/2007 |

OTHER PUBLICATIONS

Data sheet—Maloy [Down loded from the internet www.sci.sdsu. edu/~smaloy], p. 1, printed on Jun. 28, 2013.*
*University of Utah* vs *Ambry Genetics Corp*, CAFC decision, printed on Dec. 17, 2014, pp. 1-19.*
Blast Aanlysis Data Sheet 1 [Down loaded from the internet http://blast.ncbi.nlm.nih. gov], printed on Dec. 24, 2014, pp. 1-5.*
SEQ ID No. 6 position in NF1 mRNA Data Sheet [Down loaded from the internet http://www.ncbi.nlm.nih. gov], printed on Dec. 24, 2014, p. 1.*
Fletcher et al., "Isolation and Identification of Six Pneumocystis Carinii Genes Utilizing Codon Bias", Gene, 129:167-174, 1993.
Rose et al., "Consensus-Degenerate Hybrid Oligonucleotide Primers for Amplification of Distantly Related Sequences", Nucleic Acids Research, vol. 26, No. 7, pp. 1628-1635, 1998.
International Preliminary Report on Patentability, International Application No. PCT/AU2010/001659, 7 pages, Jun. 12, 2012.
Armbrust, E. Virginia, "Structural Features of Nuclear Genes in the Centric Diatom Thalassiosira Weissflogii (Bacillariophyceae)," Journal of Phycology, 36(5):942-946 (2000).
Hakki et al., "RT-PCR amplification of a Rhizopus oryzae lactate dehydrogenase gene fragment," Enzyme and Microbial Technology, 28(2-3):259-264 (2001).
Harlow, L., "Phycologia Online—S-adenosylmethionine synthetase genes from eleven marine dinoflagellates," Retrieved from the Internet: URL:http://www.phycologia.org/doi/abs/10.2216/06-28.1 [retrieved on Jan. 22, 2014] (2007) (Abstract).
Supplementary European Search Report issued in EP10835300 dated Jan. 22, 2014 (8 pages).
Tao et al., "PCR-based cloning of the full-length Neurospora eukaryotic initiation factor 5A cDNA: polyhistidine-tagging and overexpression for protein affinity binding," The Biochemical Journal, 517-525 (1994).
Ventura et al., "Bifidobacterium lactis DSM 10140: Identification of the atp (atpBEFHAGDC) Operon and Analysis of Its Genetic Structure, Characteristics, and Phylogeny," Applied and Environmental Microbiology, 70(5):3110-3121 (2004).
Zurovcova et al., "Lack of Nucleotide Plymorphism in the Y-Linked Sperm Flagellar Dynein Gene Dhc-Yh3 of *Drosophila melanogaster* and *D. simulans*," Genetics, 1709-1715 (1999).

* cited by examiner

*Primary Examiner* — Narayan Bhat
(74) *Attorney, Agent, or Firm* — Fish & Richardson P.C.

(57) ABSTRACT

The present invention relates to methods for the design and/or production of a probe or primer that is capable of hybridizing to a plurality of sites in a sample comprising nucleic acid. Furthermore, the present invention provides methods for detecting and amplifying nucleic acid using such a probe or primer, for example, for identification of a strain, species or genera. Probe or primer sequences are determined by reference to codon usage bias of a target nucleic acid. In addition, the present invention provides methods for determining codon distribution and/or base pair distance between codons in a nucleic acid.

27 Claims, 51 Drawing Sheets
Specification includes a Sequence Listing.

5' CCTGAAAGGCATGATCAAGT 3' - 11 mismatches
5' CAGAACAGGCCCCGCGAAGT 3' - 7 mismatches
5' GATTTTGCGATGAGGCGTAGG 3' - 5 mismatches
5' GACGTCGAGCTCGGCGAAGT 3' - 4 mismatches

Figure 15

```
>gb|AE004091.2|  Pseudomonas aeruginosa PAO1, complete genome
Length=6264404

Features in this part of subject sequence:
   conserved hypothetical protein
   conserved hypothetical protein Score = 1574 bits (852),  Expect = 0.0
 Identities = 856/858 (99%), Gaps = 0/858 (0%)
 Strand=Plus/Plus Query  2        ACAGCTACTACCGCCCGGCGGTGAAAGCCAAGTGCCGCGACGGCTTCTGCCCGCTCGGTC  61
                ||||||||||||||||||||||||||||||||||||||||||||||||||||||||||||
Sbjct  4609892  ACAGCTACTACCGCCCGGCGGTGAAAGCCAAGTGCCGCGACGGCTTCTGCCCGCTCGGTC  4609951

Query  62       CACAACTGGTGCCGGTGCAAGAGATCGTCGATCCCCATGCGCTGGAGCTGAAGCTGTACG  121
                ||||||||||||||||||||||||||||||||||||||||||||||||||||||||||||
Sbjct  4609952  CACAACTGGTGCCGGTGCAAGAGATCGTCGATCCCCATGCGCTGGAGCTGAAGCTGTACG  4610011

Query  122      TCAACGGCGAACTGCGCCAGCGCAACAACACCGCCAACCTGGTGCGCGACATCCCGCGGC  181
                ||||||||||||||||||||||||||||||||||||||||||||||||||||||||||||
Sbjct  4610012  TCAACGGCGAACTGCGCCAGCGCAACAACACCGCCAACCTGGTGCGCGACATCCCGCGGC  4610071

Query  182      TGATCGCCGAGATCAGCGAGTTCATGACCCTGCACGCCGGCGACGTGCTGATCACCGGCA  241
                ||||||||||||||||||||||||||||||||||||||||||||||||||||||||||||
Sbjct  4610072  TGATCGCCGAGATCAGCGAGTTCATGACCCTGCACGCCGGCGACGTGCTGATCACCGGCA  4610131

Query  242      CCCCCGAAGGGCGCGTCGATGTGCATCCCGGCGACCGCGTCGAGGTCGAGATCGACGGCC  301
                ||||||||||||||||||||||||||||||||||||||||||||||||||||||||||||
Sbjct  4610132  CCCCCGAAGGGCGCGTCGATGTGCATCCCGGCGACCGCGTCGAGGTCGAGATCGACGGCC  4610191

Query  302      TCGGCCGCCTCGCCAACAGCATCGTCGCGGAATGAGGAACCGACCATGAAACACGCACGC  361
                ||||||||||||||||||||||||||||||||||||||||||||||||||||||||||||
Sbjct  4610192  TCGGCCGCCTCGCCAACAGCATCGTCGCGGAATGAGGAACCGACCATGAAACACGCACGC  4610251

Query  362      ATCCGCTACCAGGGCCGGGTTCACCAGGTCACCGTGGAAGACGCCAACGCCGTCCGCCTG  421
                ||||||||||||||||||||||||||||||||||||||||||||||||||||||||||||
Sbjct  4610252  ATCCGCTACCAGGGCCGGGTTCACCAGGTCACCGTGGAAGACGCCAACGCCGTCCGCCTG  4610311

Query  422      GCCGACGGCACCCTGCTCGCCGAGGACCGGGTGGAGTGGCTGCCGCCGGCCACCGGGAGC  481
                ||||||||||||||||||||||||||||||||||||||||||||||||||||||||||||
Sbjct  4610312  GCCGACGGCACCCTGCTCGCCGAGGACCGGGTGGAGTGGCTGCCGCCGGCCACCGGGAGC  4610371

Query  482      ATGTCCGCCCTCGGCCTGAACTACGCCGACCATGCCGCCGAACTGTTGTTCAAGGCGCCC  541
                ||||  ||||||||||||||||||||||||||||||||||||||||||  ||||||||||
Sbjct  4610372  ATGTTCGCCCTCGGCCTGAACTACGCCGACCATGCCGCCGAACTGTCGTTCAAGGCGCCC  4610431

Query  542      AGCGAACCGCTGGCGTTCCTCAAGTCGCCGGGCACCTACACCGGCCACCGCCAGGTCAGC  601
                ||||||||||||||||||||||||||||||||||||||||||||||||||||||||||||
Sbjct  4610432  AGCGAACCGCTGGCGTTCCTCAAGTCGCCGGGCACCTACACCGGCCACCGCCAGGTCAGC  4610491

Query  602      TGGCGTCCGGACAACGTCGACTACATGCACTACGAGTGCGAACTGGTGGCGGTGATCGGC  661
                ||||||||||||||||||||||||||||||||||||||||||||||||||||||||||||
Sbjct  4610492  TGGCGTCCGGACAACGTCGACTACATGCACTACGAGTGCGAACTGGTGGCGGTGATCGGC  4610551

Query  662      AAGCCGGCGCGCAACGTCCGCCGCGAGGACGCCCTCGGCTACCTGGCCGGCTACACGGTG  721
                ||||||||||||||||||||||||||||||||||||||||||||||||||||||||||||
Sbjct  4610552  AAGCCGGCGCGCAACGTCCGCCGCGAGGACGCCCTCGGCTACCTGGCCGGCTACACGGTG  4610611

Query  722      TGCAACGACTACGCGATCCGCGACTACCTGGAGAACTACTACCGGCCCAACCTGCGGGTG  781
                ||||||||||||||||||||||||||||||||||||||||||||||||||||||||||||
Sbjct  4610612  TGCAACGACTACGCGATCCGCGACTACCTGGAGAACTACTACCGGCCCAACCTGCGGGTG  4610671

Query  782      AAGAACCGCGACGCCACCACCCCGGTGGGGCCGTGGATCGTCGACGCGGCCGAGGTTCCC  841
                ||||||||||||||||||||||||||||||||||||||||||||||||||||||||||||
Sbjct  4610672  AAGAACCGCGACGCCACCACCCCGGTGGGGCCGTGGATCGTCGACGCGGCCGAGGTTCCC  4610731

Query  842      GAGCCGAACCGGCTGACC  859
                ||||||||||||||||||
Sbjct  4610732  GAGCCGAACCGGCTGACC  4610749
```

Figure 32

```
>gb|AE004091.2|  Pseudomonas aeruginosa PA01, complete genome
Length=6264404

Features in this part of subject sequence:
   probable outer membrane receptor for iron transport Score = 1110 bits (601),  Expect = 0.0
 Identities = 601/601 (100%), Gaps = 0/601 (0%)
 Strand=Plus/Plus Query  1        GTCGGTGAAGTTGTCCTGCTTGGCGGTCTTGCTGATCAGGTTCAGGCTGCCACCGGTGGA  60
                ||||||||||||||||||||||||||||||||||||||||||||||||||||||||||||
Sbjct  5055296  GTCGGTGAAGTTGTCCTGCTTGGCGGTCTTGCTGATCAGGTTCAGGCTGCCACCGGTGGA  5055355

Query  61       GCCGGCGCCGGTGTAGGCCGAGCCCGGGCCCTTGCTGACCTCGATCTGCTCGACGTTGAA  120
                ||||||||||||||||||||||||||||||||||||||||||||||||||||||||||||
Sbjct  5055356  GCCGGCGCCGGTGTAGGCCGAGCCCGGGCCCTTGCTGACCTCGATCTGCTCGACGTTGAA  5055415

Query  121      CACCTCGCGGGTTTGCGAGGCGACGTCGCGCATACCGTCGAGGAACGTATCGCTCTCGGC  180
                ||||||||||||||||||||||||||||||||||||||||||||||||||||||||||||
Sbjct  5055416  CACCTCGCGGGTTTGCGAGGCGACGTCGCGCATACCGTCGAGGAACGTATCGCTCTCGGC  5055475

Query  181      GTTGAAGCCACGGATGAATGGCCGGTCGCCTGCGGGGTTGCCGCCCTCGCCCGCGCCGAA  240
                ||||||||||||||||||||||||||||||||||||||||||||||||||||||||||||
Sbjct  5055476  GTTGAAGCCACGGATGAATGGCCGGTCGCCTGCGGGGTTGCCGCCCTCGCCCGCGCCGAA  5055535

Query  241      GGTGATACCCGGGGTGGTGCGCAGTGCGTCGGCCAGGGTCAGGGCGCCAGTGTCCTTGAT  300
                ||||||||||||||||||||||||||||||||||||||||||||||||||||||||||||
Sbjct  5055536  GGTGATACCCGGGGTGGTGCGCAGTGCGTCGGCCAGGGTCAGGGCGCCAGTGTCCTTGAT  5055595

Query  301      CACCTGCTGCGGGATCACGGTCACGGTCTTCGGCGTATCCAGCAGCGGCGCGGTGTACTT  360
                ||||||||||||||||||||||||||||||||||||||||||||||||||||||||||||
Sbjct  5055596  CACCTGCTGCGGGATCACGGTCACGGTCTTCGGCGTATCCAGCAGCGGCGCGGTGTACTT  5055655

Query  361      CTTCGACGCCGAGCGGTCGACGTTATAGGTGGTTTCGTCCTGCTGCTCGCCGACGATGGT  420
                ||||||||||||||||||||||||||||||||||||||||||||||||||||||||||||
Sbjct  5055656  CTTCGACGCCGAGCGGTCGACGTTATAGGTGGTTTCGTCCTGCTGCTCGCCGACGATGGT  5055715

Query  421      AGCCGCATCCAGCGACAGTACGCGGTCCTTGTCGGTCTTTTTCTGCCCGGCCTCGTCGGC  480
                ||||||||||||||||||||||||||||||||||||||||||||||||||||||||||||
Sbjct  5055716  AGCCGCATCCAGCGACAGTACGCGGTCCTTGTCGGTCTTTTTCTGCCCGGCCTCGTCGGC  5055775

Query  481      CTGGGCTGCCTGCGGTGCGGCGATGGCGGTGATGGCGACACCGATGGCAGAAGCCAGCAG  540
                ||||||||||||||||||||||||||||||||||||||||||||||||||||||||||||
Sbjct  5055776  CTGGGCTGCCTGCGGTGCGGCGATGGCGGTGATGGCGACACCGATGGCAGAAGCCAGCAG  5055835

Query  541      ACGTTGCGAAGAAACGGCGGTATCCGTGGACTGACGCGACATTCGAAACCCCTCCCCGGG  600
                ||||||||||||||||||||||||||||||||||||||||||||||||||||||||||||
Sbjct  5055836  ACGTTGCGAAGAAACGGCGGTATCCGTGGACTGACGCGACATTCGAAACCCCTCCCCGGG  5055895

Query  601      A  601
                |
Sbjct  5055896  A  5055896
```

Figure 33

```
>gb|CP001637.1| Escherichia coli DH1, complete genome
Length=4630707

Features in this part of subject sequence:
   glycoside hydrolase family 3 domain protein Score = 1736 bits (940),  Expect = 0.0
 Identities = 946/949 (99%), Gaps = 0/949 (0%)
 Strand=Plus/Minus Query  2        CGGTCAGTACGGTCACGGATTGATCGGCAACACCGGCTGCGGACCAGCTGCCCATCACGT  61
                ||||||||||||||||||||||||||||||||||||||||||||||||||||||||||||
Sbjct  1656202  CGGTCAGTACGGTCACGGATTGATCGGCAACACCGGCTGCGGACCAGCTGCCCATCACGT  1656143

Query  62       CACGTTTACTGTCCGCCAGTGGCCCAACCACCGCAATGGTGGCCGATTTTTTCAGCGGTA  121
                ||||||||||||||||||||||||||||||||||||||||||||||||||||||||||||
Sbjct  1656142  CACGTTTACTGTCCGCCAGTGGCCCAACCACCGCAATGGTGGCCGATTTTTTCAGCGGTA  1656083

Query  122      ACGTTTCGAGACGGTTTTTCAGCAACACCAAGCTTTCGCGCGCCACTTCACGCGCTTCTT  181
                ||||||||||||||||||||||||||||||||||||||||||||||||||||||||||||
Sbjct  1656082  ACGTTTCGAGACGGTTTTTCAGCAACACCAAGCTTTCGCGCGCCACTTCACGCGCTTCTT  1656023

Query  182      TACGGTGCAGGCGGCTTTCGGCATTGGTATCCACCGGGTCAGACTCTTTCGGCCCCAAAT  241
                ||||||||||||||||||||||||||||||||||||||||||||||||||||||||||||
Sbjct  1656022  TACGGTGCAGGCGGCTTTCGGCATTGGTATCCACCGGGTCAGACTCTTTCGGCCCCAAAT  1655963

Query  242      GGCTGTATGGGTCGTTAAACAACCCCATATCATATTTAACGTTCAGTACATGGCGGGCAG  301
                ||||||||||||||||||||||||||||||||||||||||||||||||||||||||||||
Sbjct  1655962  GGCTGTATGGGTCGTTAAACAACCCCATATCATATTTAACGTTCAGTACATGGCGGGCAG  1655903

Query  302      CATCGTCCAGCTCTGCCATCGTCACTTTGCCGGATTTAATCAACCCAGGCAGATACTTCG  361
                ||||||||||||||||||||||||||||||||||||||||||||||||||||||||||||
Sbjct  1655902  CATCGTCCAGCTCTGCCATCGTCACTTTGCCGGATTTAATCAACCCAGGCAGATACTTCG  1655843

Query  362      AGTAGTACTCGTCGCTCATGCTCATGTTGATTCCGGATTTCAGCGCCACGCGCACCGCAT  421
                ||||||||||||||||||||||||||||||||||||||||||||||||||||||||||||
Sbjct  1655842  AGTAGTACTCGTCGCTCATGCTCATGTTGATTCCGGATTTCAGCGCCACGCGCACCGCAT  1655783

Query  422      CTTCCGGGTCTGCCGCCGTGCCATGTTTAATCAGCTCCTTGATTGCACCGTGATCGGAAA  481
                |||||||||||||||||||||||||||||||||||| |||||||||||||||||||||||
Sbjct  1655782  CTTCCGGGTCTGCCGCCGTGCCATGTTTAATCAGCTCTTTGATTGCACCGTGATCGGAAA  1655723

Query  482      CGGTGATGCCTTTAAAGCCCCACTGGTCGCGCAGAACATCTTTCAGCAGCCAGGAATCGG  541
                ||||||||||||||||||||||||||||||||||||||||||||||||||||||||||||
Sbjct  1655722  CGGTGATGCCTTTAAAGCCCCACTGGTCGCGCAGAACATCTTTCAGCAGCCAGGAATCGG  1655663

Query  542      AGGTGGCTGGCGTGCCGTTCAGCGAGTTCAGCGCCACCATCACCGCGCCGCTGCCTGCGT  601
                ||||||||||||||||||||||||||||||||||||||||||||||||||||||||||||
Sbjct  1655662  AGGTGGCTGGCGTGCCGTTCAGCGAGTTCAGCGCCACCATCACCGCGCCGCTGCCTGCGT  1655603

Query  602      CCAGCCCCGCTTTGTACGGCGGCATACAATCATTAAACAGGCGCTGCGGACTCATATCGA  661
                |||||||||||||||||||||||||| ||||||||||||||||||||||||||||||||
Sbjct  1655602  CCAGCCCCGCTTTGTACGGCGGCATATAATCATTAAACAGGCGCTGCGGACTCATATCGA  1655543

Query  662      CGGTGTTGTACTCTTTACCGCCTTCTACCGCGCCGTATGCGGCAAAGTGTTTGACGCTGG  721
                ||||||||||||||||||||||||||||||||||||||||||||||||||||||||||||
Sbjct  1655542  CGGTGTTGTACTCTTTACCGCCTTCTACCGCGCCGTATGCGGCAAAGTGTTTGACGCTGG  1655483

Query  722      TCATCACCGAGTAGCGATCTGCCGGGCTTTTACCCTGCATCGCTTCCACCATGGTTTTAC  781
                ||||||||||||||||||||||||||||||||||||||||||||||||||||||||||||
Sbjct  1655482  TCATCACCGAGTAGCGATCTGCCGGGCTTTTACCCTGCATCGCTTCCACCATGGTTTTAC  1655423

Query  782      CCATTGTTGAGGTGAGATACGTATCTTCGCCAAAACCTTCGGAAGCACGTCCCCAGCGCG  841
                ||||||||||||||||||||||||||||||||||||||||||||||||||||||||||||
Sbjct  1655422  CCATTGTTGAGGTGAGATACGTATCTTCGCCAAAACCTTCGGAAGCACGTCCCCAGCGCG  1655363

Query  842      GATCGCGCGAGACATCGACCATCGGTGCCCAGGTCATATTCAGGCCATCATCTGCCGCTT  901
                ||||||||||||||||||||||||||||||||||||||||||||||||||||||||||||
Sbjct  1655362  GATCGCGCGAGACATCGACCATCGGTGCCCAGGTCATATTCAGGCCATCATCTGCCGCTT  1655303

Query  902      CATAAGCAGAGACACGTCCGACCGTTTTCACTGCATCGAGGCTAAAAGA  950
                |||||||||||||||||||||||| |||||||||||||||| |||||||
Sbjct  1655302  CATAAGCAGAGACACGTCCGACCGTTTTCACTGCATCGAGGTTAAAAGA  1655254
```

Figure 34

```
>gb|CP001637.1| Escherichia coli DH1, complete genome
Length=4630707

Features in this part of subject sequence:
   Protein of unknown function CsiD

Score = 1572 bits (851),  Expect = 0.0
 Identities = 858/861 (99%), Gaps = 1/861 (0%)
 Strand=Plus/Plus Query  5        TCGGTGAAGGTGAGTTCCAGCAGACGCGGGGATTGCGCCGACGGGGTGAGGGTGAATCCG  64
                ||||||||||||||||||||||||||||||||||||||||||||||||||||||||||||
Sbjct  1094662  TCGGTGAAGGTGAGTTCCAGCAGACGCGGGGATTGCGCCGACGGGGTGAGGGTGAATCCG  1094721

Query  65       CTATAGTCCTGGCCTGAATCGACAGCGTTATTTTGTACGGCGGTCAGTGCATTCATCAGA  124
                ||||||||||||||||||||||||||||||||||||||||||||||||||||||||||||
Sbjct  1094722  CTATAGTCCTGGCCTGAATCGACAGCGTTATTTTGTACGGCGGTCAGTGCATTCATCAGA  1094781

Query  125      AGCGATCCTCTTATGAGATGTAGGGTGACATGGCGATGCTCATTTCGTAGCCATAATCTA  184
                ||||||||||||||||||||||||||||||||||||||||||||||||||||||||||||
Sbjct  1094782  AGCGATCCTCTTATGAGATGTAGGGTGACATGGCGATGCTCATTTCGTAGCCATAATCTA  1094841

Query  185      AAAATATCTACATTTCTGAAAAATGCGCACAAAAGCGACATATTGTTTTCTTATTGTGAT  244
                ||||||||||||||||||||||||||||||||||||||||||||||||||||||||||||
Sbjct  1094842  AAAATATCTACATTTCTGAAAAATGCGCACAAAAGCGACATATTGTTTTCTTATTGTGAT  1094901

Query  245      CAAAAGCAACAAATTAGTAACATTTAACGTAGGGTATTAAAGCAAAGTGAGACAGGAAAT  304
                |||||||||||||||||||||||||||||||||||||| |||||||||||||||||||||
Sbjct  1094902  CAAAAGCAACAAATTAGTAACATTTAACGTAGGGTATTAAGGCAAAGTGAGACAGGAAAT  1094961

Query  305      GAATAACTAAAGCAACAGGTTAGGGGGAGTTAACATTAGAGAACAGATTATCTGGTCGAT  364
                ||||||||||||||||||||||||||||||||||||||||||||||||||||||||||||
Sbjct  1094962  GAATAACTAAAGCAACAGGTTAGGGGGAGTTAACATTAGAGAACAGATTATCTGGTCGAT  1095021

Query  365      AAAAAACAGTAAATGGCTTCACTGCAAAATGACCGTTAGTAAACTAAACATATTATCTGC  424
                ||||||||||||||||||||||||||||||||||||||||||||||||||||||||||||
Sbjct  1095022  AAAAAACAGTAAATGGCTTCACTGCAAAATGACCGTTAGTAAACTAAACATATTATCTGC  1095081

Query  425      CCCGTTTTATCGGGGCAGATATAACATTAAATTATAAATAGAGATAGTTCGGCGGTTCTC  484
                ||||||||||||||||||||||||||||||||||||||||||||||||||||||||||||
Sbjct  1095082  CCCGTTTTATCGGGGCAGATATAACATTAAATTATAAATAGAGATAGTTCGGCGGTTCTC  1095141

Query  485      CTGTTTTCCCTAAAAGAAGAGCGCTACGCCCAGGAATATTGATATTTAGAGTTCCGCCTC  544
                ||||||||||||||||||||||||||||||||||||||||||||||||||||||||||||
Sbjct  1095142  CTGTTTTCCCTAAAAGAAGAGCGCTACGCCCAGGAATATTGATATTTAGAGTTCCGCCTC  1095201

Query  545      TAAGCGTAAATACTTTACCAGGGGGGATAATTTTTCGGGTATTATTAATAATAATGTTAA  604
                ||||||||||||||||||||||||||||||||||||||||||||||||||||||||||||
Sbjct  1095202  TAAGCGTAAATACTTTACCAGGGGGGATAATTTTTCGGGTATTATTAATAATAATGTTAA  1095261

Query  605      CGCTATTACTCCCCATGTTTT-GTATATTCCAGGTTGCAATTTGTTAGGCCAGGTACCTT  663
                ||||||||||||||||||||| ||||||||||||||||||||||||||||||||||||||
Sbjct  1095262  CGCTATTACTCCCCATGTTTTTGTATATTCCAGGTTGCAATTTGTTAGGCCAGGTACCTT  1095321

Query  664      CAACTTCTTCGTTTCCTTTATTTATTATAACTAGTCCATCATGAGGAGAGTGATTAATGT  723
                ||||||||||||||||||||||||||||||||||||||||||||||||||||||||||||
Sbjct  1095322  CAACTTCTTCGTTTCCTTTATTTATTATAACTAGTCCATCATGAGGAGAGTGATTAATGT  1095381

Query  724      TCACAGAATCCCCACGACTAAAGGCCAGAACGTTTTAGTTGCAGATACACCCTCAAATG   783
                ||||||||||||||||||||||||||||||||||||||||||||||||||||||||||||
Sbjct  1095382  TCACAGAATCCCCACGACTAAAGGCCAGAACGTTTTAGTTGCAGATACACCCTCAAATG   1095441

Query  784      CGCTCCATATTCCTGCTTTATCTATATATAATGCGTGGAATTCATTGTAGAGCTGCCGAT  843
                |||||||||||||||||||||||||||||||||||||||||||||||||||||||| |||
Sbjct  1095442  CGCTCCATATTCCTGCTTTATCTATATATAATGCGTGGAATTCATTGTAGAGCTGCTGAT  1095501

Query  844      AGGTAGAGCAACCTTTATTAA  864
                |||||||||||||||||||||
Sbjct  1095502  AGGTAGAGCAACCTTTATTAA  1095522
```

Figure 35

```
>emb|AL009126.3|  Bacillus subtilis subsp. subtilis str. 168 complete genome
Length=4215606

Features in this part of subject sequence:
   ribonuclease J2
   protein export-enhancing factor Score = 3766 bits (2039),  Expect = 0.0
 Identities = 2284/2404 (95%), Gaps = 9/2404 (0%)
 Strand=Plus/Minus Query  2        AGCCGAACGGGATGAATCGTCATCGTTGCTGTTTCAGCAATATAGCTGTAATCACAGGAT  61
                |||| ||| |||||||||||||||||||||||||||| || |||||||||||||||||||
Sbjct  1751652  AGCCTAACTGGATGAATCGTCATCGTTGCTGTTTCGGCGATATAGCTGTAATCACAGGAT  1751593

Query  62       ACCGCAATCGGAACGCCGATGGAATGACCTCCGCCAAGCACGATGGAAACGGTCGATTTT  121
                || ||||||||||||||||| ||||| || ||||||||||||||||| |||||||| |||
Sbjct  1751592  ACAGCAATCGGAACGCCGATTGAATGCCCCCCGCCAAGCACGATAGAAACGGTCGGTTTC  1751533

Query  122      GATAATGATGCCAGCATTTCCGCTATTGCAAGACCCGCCTCAACATCTCCTCCGACAGTA  181
                ||||| ||||| ||||||||||||| |||||||||| ||||||||||||||||||||||
Sbjct  1751532  GATAAAGATGCAAGCATTTCCGCTATGGCAAGACCAGCTTCAACATCTCCTCCGACAGTA  1751473

Query  182      TTTAATATAATCAGCAGGCCTTCAATTTTGGGATTCTGTTCAATCGCCACGATCTGCGGG  241
                |||||||| |||||||||||| ||||||||||||| ||||||||||| |||| |||||||
Sbjct  1751472  TTTAATATGATCAGCAAGCCTTCAATTTTGGGATTTTGTTCAATTGCCACAATCTGCGGG  1751413

Query  242      ATGACATGCTCATATTTTGTTGTTTTGTTTTGCGGAGGAAGCTGAACATGGCCTTCTATT  301
                |||||||| ||||||||||||||||||||| ||||||||||||||||||||||||| |||
Sbjct  1751412  ATGACATGTTCATATTTTGTTGTTTTGTTTTGCGGAGGAAGCTGAACATGGCCTTCAATT  1751353

Query  302      TGTCCGATAATGGTCAGACAATGAATATTTGTATCTTGGGGCAGCTGCGGAAGCGTCGTT  361
                ||||||||||||||||||||||||||||||||||||||||||||||||||||||||||||
Sbjct  1751352  TGTCCGATAATGGTCAGACAATGAATATTTGTATCTTGGGGCAGCTGCGGAAGCGTCGTT  1751293

Query  362      TCACCAAGCTGCTGTATTTTATTCATAATGCTGTCTTTCGCGTCAtttttttCAGGACGC  421
                |||||||||||||||||||||||||||||||||| ||||||||||||| ||||||||||
Sbjct  1751292  TCACCAAGCTGCTGTATTTTATTCATAATGCTGTCCTTCGCATCATTTTTTTCAGGACGC  1751233

Query  422      TCTTCTTCTGCGTTTTCCATACGATGATCCATTTCGCTTTCACCCTTTCCGAATTTCTCT  481
                |||||||||| ||||||||||||||||||||||| |||||||| |||||||| |||||||
Sbjct  1751232  TCTTCTTCTGTGTTTTCCATACGATGATCCATCTCGCTTTCATCCTTTCCGAGTTTCTCT  1751173

Query  482      TTGTATTATGAACAAAGATAC-TCAATTCAATCCCGGCTTGAAAGGCa-aaaaaaTAAAG  539
                ||||||||||||||||||||| ||||||||||||||||||||| |||| |||||||||||
Sbjct  1751172  TTGTATTATGAACAAAGATACTTC-ATTCAATCCCGGCTTG-AAGG-ACAAAAAATAAAG  1751116

Query  540      ACCGGAGCAGCTCCGGTCTTTAGTCAGACATTATACTTCCATAATAATTGGGATGATCAT  599
                ||||||||||||||||||||||||||| ||||||||||||||||||||||||||||||||
Sbjct  1751115  ACCGGAGCAGCTCCGGTCTTTAGTCAGTCATTATACTTCCATAATAATTGGGATGATCAT  1751056

Query  600      CGGTTTACGTTTCGTTTTTTCATATAGGAATTGGTTCAGAGCATCTCGCATTGCCTGCTT  659
                ||||||||||||||||||||||||| |||||||||||| |||||||| ||||||||||||
Sbjct  1751055  CGGTTTACGTTTCGTTTTTTCATAAAGGAATTGGTTCAAAGCATCCCGCATTGCCTGCTT  1750996

Query  660      CAGCGTTGACCATTCAACATTTGATGTTCCAGTCGCTTCTGTCACGATGGAACGGACAAG  719
                |||||||||||||| ||||||||||| |||||||||||||||||||||||||| ||||||
Sbjct  1750995  CAGCGTTGACCATTCGACATTTGATGTTTCAGTCGCTTCTGTCACGATGGACCGTACAAG  1750936

Query  720      CTCAGTAGCCTGTACGATAAGGCCTTCAGACTCTCTTACATAAACAAAACCGCGAGTGAT  779
                |||||||||||||||||||||| |||||||||||||||||||||||| ||||||||||||
Sbjct  1750935  CTCAGTAGCCTGTACGATAAGACCTTCAGACTCTCTTACATAAACAAAGCCGCGAGTGAT  1750876

Query  780      AATTTCTGGTCCTGATACAAGATGTTTCTTTTGTTTATCAAGTGTAATGACAACAATTAA  839
                |||||||||||||||||||||||||||||||||||||||||||||||||||||||| |||
Sbjct  1750875  AATTTCTGGTCCTGATACAAGATGTTTCTTTTGTTTATCAAGTGTAATGACAACGATTAA  1750816

Query  840      AATCCCGTCCTGTGAAAGCAAGCGGCGGTCTCTCAATACGATATTGCCGATATCACCGAC  899
                ||| ||||||||||||||||||||||||||||||||||||||||||||||||||||||||
Sbjct  1750815  AATTCCGTCCTGTGAAAGCAAGCGGCGGTCTCTCAATACGATATTGCCGATATCACCGAC  1750756

Query  900      ACCCAAACCATCAATTAAAATATTGCCGTACGGAACTTTATCCCCAATTTTTACGTTTTG  959
                || ||||||||||||||||||||||||| ||||||||||||||||||||||||||||||
Sbjct  1750755  ACCTAAACCATCAATTAAAATATTGCCGTAAGGAACTTTATCCCCAATTTTTACGTTTTG  1750696

Query  960      GCCGCGGAATTCAACGACGTCTCCTTTTTCAATTAAGGAGATATCACTGCGCTTCATGCC  1019
                |||||||||||||||||||| |||||||||||||||| ||||| ||||||||||||||||
Sbjct  1750695  GCCGCGGAATTCAACGACGTCGCCTTTTTCAATTAAGAAGATGTCACTGCGCTTCATGCC  1750636
```

Figure 36

```
Query    1020      GATTTCTTCAGCGATTCTCGAATGAGCTTTTTGCATTCTGTATTCGCCGCTTACAGGAAT      1079
                   ||||||||||||| | |||||||||||||||||||||||||||| ||||||||||
Sbjct    1750635   GGTTTCTTCAGCGATTTTTGAATGAGCTTTTTGCATTCTGTATTCGCCGTTTACAGGAAT      1750576

Query    1080      TAAATATTTTGGTTTAAGCAGATTGATCATCAGCTTTAACTCTTCTTGTGAACCATGGCC      1139
                   |||||||||||||||||||| |||||||||||||||||||||||||||||| || |||||
Sbjct    1750575   CAAATATTTTGGTTTAAGCAGGTTGATCATCAGCTTTAACTCTTCTTGTGAGCCGTGGCC      1750516

Query    1140      AGATACATGGACACGCTTTTGTGCAAAGATGACTTGTGCACCGGCTCTCGCAAGAAGATC      1199
                   ||||||||| ||||||||||| |||||||||||||||||||||||||||||||||||||
Sbjct    1750515   TGATACATGAACACGCTTTTGGGCAAAGATGACTTGTGCACCGGCTCTCGCAAGAAGATC      1750456

Query    1200      TACTGTTTTAGAATAAATGAGTTCCTGCCCAGGG-ATTGGAGTTGACGCAATGACAACCG      1258
                   ||||||||||| ||||||||||||||||||||   ||| || |||||||||||||| |||
Sbjct    1750455   TACTGTTTTAGAGTAAATGAGTTCCTGCCC-GGGAATCGGAGTTGACGCAATGACCACCG      1750397

Query    1259      TATCCCCTTCTTCAATGTTCAGCTGTTTGTGCGCTTTGTTTGCCATTCTTGTCAGTGCAG      1318
                   |||||||||||||||| ||||||||||||| ||||||||||||||||||||||| ||||
Sbjct    1750396   TATCCCCTTCTTCAATGTTCAGCTGTTTGTGAGCTTTGTTTGCCATTCTTGTCAAAGCAG      1750337

Query    1319      CTAACGGTTCACCTTGGCTGCCTGCTGTAATAATGGCCACTTCGCGCTTCGGATATTTCT      1378
                   |||| ||||||||||||||  ||||||||||||||||||||||||||||||||| ||| |
Sbjct    1750336   CTAATGGTTCACCTTGGCTTCCGGCTGTAATAATGGCCACTTCGCGCTTCGGATATTTTT      1750277

Query    1379      TGACATCCTGTACAGAAATAAACAATTCATCATCTGCTTCAATATATCCGAGCTTTCTTG      1438
                   ||||||||||||||||||||||||||||||||||||||||||||||||||| ||||| |
Sbjct    1750276   TGACATCCTGTACAGAAATAAACAATTCATCATCTGCTTCAATATATCCTAACTTTCTCG      1750217

Query    1439      CCAGCTGCAGGACAGACTGAAGATTTTTTCCGGCAACGGCAATCTTTCTGCCATTTTGAG      1498
                   |||||||||||||||| |||||||||||||||||| ||||||||||||||||||||||||
Sbjct    1750216   CCAGCTGCAGGACAGATTGAAGATTTTTTCCGGCTACGGCAATCTTTCTGCCATTTTGAG      1750157

Query    1499      CCGCTGCATGAATGACTTGCTGGATCCGGTTAATATTGGATGCGAAAACAGCAATAATCA      1558
                   |||||||||||||||||||||| |||||||||||||||||||||||||||||||||||||
Sbjct    1750156   CCGCTGCATGAATGACTTGCTGAATCCGGTTAATATTGGATGCGAAAACAGCAATAATCA      1750097

Query    1559      CTCGGTTCACTGAATTATACAGCGCGTCCGAAATTTCTCCGCTGACAGCAGCTTCTGAAG      1618
                   | |||||   |||||||||||||||| |||||||||||||||||||||| ||||| ||||
Sbjct    1750096   CCCGGTTCTGTGAATTATACAGCGCATCCGAAATTTCTCCGCTGACAGCCGCTTCCGAAG      1750037

Query    1619      GTGTATAGCCCGGGCGCTCCGCATTTGCACTGTCGGAAAGCAGGGCAAGTACGCCGCTAT      1678
                   | || ||  ||||| ||| ||||||||||||||| |||||||| || |||||||||||||
Sbjct    1750036   GGGTGTAACCCGGCCGTTCCGCATTTGCACTGTCAGAAAGCAGAGCGAGCACGCCGCTAT      1749977

Query    1679      TGCCGATCTTGGCGATCTCCCCAATGTCGCACGTTTGGTTAAGTGCAGGCGTTTGGTCAA      1738
                   |||||||||||||||||||  ||||||||||||| ||||| ||||||||||| |||||||
Sbjct    1749976   TGCCGATCTTGGCGATCTCGCCAATGTCGCACGTCTGATTAAGTGCAGGTGTTTGGTCAA      1749917

Query    1739      ATTTGAAGTCTCCCGTGCATACAATAGATCCAAGTGATGTTTT-AAGACTCACACCTACA      1797
                   ||||||||||||||||||||||||||||||||||||||||||   |||| ||||||||||
Sbjct    1749916   ATTTGAAGTCTCCCGTGCATACAATAGATCCAAGTGATGTTTTAAAG-CTCACACCTACA      1749858

Query    1798      GAATCAGGGATGCTGTGAATCGTTCTAAAGAACGATACTTTTGTCGATTCAAATGTAATG      1857
                   ||||||||  ||||||||||||||||||||||||||| |||||| ||||||||||||||
Sbjct    1749857   GAATCAGGAATGCTGTGAATCGTTCTAAAGAACGATACCTTTGTTGATTCAAATGTAATG      1749798

Query    1858      ACAGATTTGGAGTGAATTTCTCTTAAATCAGTTTTTCGGTTATGTCCGTATTGTTTTAAT      1917
                   ||||||||||||||||||||||||||||||||||||||||||||||||||||||||||||
Sbjct    1749797   ACAGATTTGGAGTGAATTTCTCTTAAATCAGTTTTTCGGTTATGTCCGTATTGTTTTAAT      1749738

Query    1918      TTTTCTCTTAATAGCGCAAGCGTCAGCTTTGTTCCGTACACTGGAACGGACAGCTTGTTC      1977
                   || |||||||| ||| ||||||||||| ||||||||||||||||||||||||||||||||
Sbjct    1749737   TTCTCTCTTAACAGTGCAAGCGTCAGTTTTGTTCCGTACACTGGAACGGACAGCTTGTTT      1749678

Query    1978      AATAAGTAAAAAACGCCGCCGATATTTTCATCGTGCCCGTGCGTTAAAAAGATTGCCTTG      2037
                   ||||||||||||||||||||||||||||||||||||||||||||||||||||||||||||
Sbjct    1749677   AATAAGTAAAAAACGCCGCCGATATTTTCATCGTGCCCGTGCGTTAAAAAGATTGCCTTG      1749618

Query    2038      ACGCGGTCAGCCCGTTCAATCAAATATGATATGTCAGGAATCACCACATCAATACCGAGC      2097
                   |||||||||||||||||||||||||||||||||||||||||||| |||||||||||||||
Sbjct    1749617   ACGCGGTCAGCCCGTTCAATCAAATATGATATGTCAGGAATCACTACATCAATACCGAGC      1749558

Query    2098      ATTTCGTTTTCTGGATGCATAAGGCCGGCATCTACAACAAATATGTCTGAGTCAATTTCG      2157
                   ||||||||||||||||||||||||||||||||  |||||||||||||||||||||||||
Sbjct    1749557   ATTTCGTTTTCTGGATGCATAAGGCCGGCATCAACGACAAATATGTCTGAGTCAATTTCA      1749498

Query    2158      ATGACATAAAGGTTCTTCCCAATTTCTCCGACACCGCCAAGGGCGATAATTCTAACGTTT      2217
                   ||||||||||||||||||||| |||||||||||||||||||||||||||||| |||||||
Sbjct    1749497   ATGACATAAAGGTTCTTCCCAATCTCTCCGACACCGCCAAGGGCGATAATTCTAACGTTT      1749438
```

Figure 36 (Continued)

```
Query  2218     TCTGTATTTTTCTTCTTCAAAATCTATATCCTCCTAGTCTCATACCCGTCCATCATCACT  2277
                ||||||||||||| |||||||||||||||||||||||||||||||||||||||||||||
Sbjct  1749437  TCTGTATTTTTCTTTTTCAAAATCTATATCCTCCTAGTCTCATACCCGTCCATCATCACT  1749378

Query  2278     TGTTCCTATTATAACTGAAAGTAAATTTAGAAAATAAGATAAAGCAGAAGGTTTAGGGAA  2337
                |||||||||||||||||||||||||||||||||| |||||||||||||||||||||||||
Sbjct  1749377  TGTTCCTATTATAACTGAAAGTAAATTTAGAAAACAAGATAAAGCAGAAGGTTTAGGGAA  1749318

Query  2338     AGCCAATATGTATAAGAAACGGTCATACTCAGCTGAATATGAGAATGACCGCGTTTGTTT  2397
                | |||||||||| ||||||||||| | |||||||||||| |||||||||||||||||||
Sbjct  1749317  AACCAATATGTAAAAGAAACGGTCAAACTCAGCTGAATGTGAGAATGACCGCGTTTGTTT  1749258

Query  2398     CACT  2401
                ||||
Sbjct  1749257  CACT  1749254
```

Figure 36 (Continued)

```
>emb|AL009126.3|  Bacillus subtilis subsp. subtilis str. 168 complete genome
Length=4215606

Features in this part of subject sequence:
   putative aldo/keto reductase
   dephosphocoenzyme A kinase Score = 1081 bits (585),  Expect = 0.0
 Identities = 724/789 (91%), Gaps = 17/789 (2%)
 Strand=Plus/Minus Query  1        TCATCCTGCAGTCAGGCACGAAATGCTCAATCGCCGTGATAAAGCCATAGCAAATCGCGA  60
                ||||||  ||||||||| ||||||||||||||||||||| |||||| |||||||||| ||
Sbjct  2971252  TCATCCCGCAGTCAGGCAGGAAATGCTCAATCGCCGTGATGAAGCCGTTGCAAATCGGGA  2971193

Query  61       GGCCTTTGTTGTATTAGATATCCCGCTATTATTTGAAAGCAAATTGGAATCTTTAGTTGA  120
                ||| ||||||||||| ||||||||||||| ||| ||||||||||||||||| || || ||
Sbjct  2971192  GGCATTTGTTGTATTGGATATCCCGCTATTGTTCGAAAGCAAATTGGAATCATTGGTTGA  2971133

Query  121      TAAAATTATTGTGGTCAGTGTGACCGAAGAGCTTCAGCTGGAACGTCTGATGAAGCGCAA  180
                |||||||||||||||||||||||| |||||||||||| ||||||||||||||||||||||
Sbjct  2971132  TAAAATTATTGTGGTCAGTGTGACAAAAGAGCTTCAACTGGAACGTCTGATGAAGCGCAA  2971073

Query  181      TCAGCTGACGGAAGAAGAAGCGGTCAGCCGTATCCG-TGCTCAAATGCCCTTAGAGGAAA  239
                |||||||| |||||||||||||||| ||||| ||||  |||||||||||||| |||||||
Sbjct  2971072  TCAGCTGACAGAAGAAGAAGCAGTCAGCCGTATCCGCT-CTCAAATGCCCTTAGAGGAAA  2971014

Query  240      AAACAGCAAGAGCAGATCGAGTCATCGATAACAGCGGCACGCTTGCAGAGACCAAACA-G  298
                |||||||||||||||||| |||||| ||||||||||||||||||| |||||||||||  |
Sbjct  2971013  AAACAGCAAGAGCAGATCAAGTCATTGATAACAGCGGCACGCTTGAAGAGACCAAA-AGG  2970955

Query  299      CAGCTTGATGACATCAT-CACTAGCTGGGCATAATAC--AAAACACCGTTCGTTA-TGAA  354
                |||||||||| |||||| || ||||||||||||||||  ||||||||||||| || ||||
Sbjct  2970954  CAGCTTGATGAAATCATGAAC-AGCTGGGCATAATACAAAAAAACACCGTTC-ATATTGAA  2970897

Query  355      CGGTGTTTTTT---CATTAAAAATCAAAGTTGTCCGGATCAGGACCGACGCGCAGGTTTT  411
                |||||||||||   |||||||||||||||||||||||||||||||||||||||||| |||
Sbjct  2970896  CGGTGTTTTTTGGCCATTAAAAATCAAAGTTGTCCGGATCAGGACCGACGCGCAAGTTTT  2970837

Query  412      CATTCAGCGCATCGATTCGGTTCATGTCATCCTGTGTTAATTCAAAGTCAAACACACTGG  471
                |||||| ||||||||||||||||||||||||||| || |||||||||||||||| || |
Sbjct  2970836  CATTCAGTGCATCGATTCGGTTCATGTCATCCTGCGTTAATTCAAAGTCAAATACGCTTG  2970777

Query  472      CATTTTCTTTAATGCGGTGTTCCTTCGTTGATTTAGGAATCGTAATGATGCCATGCTGCA  531
                ||||||||||||||||||||||||||||||||||||||||||| || |||||||||||||
Sbjct  2970776  CATTTTCTTTAATGCGGTGTTCCTTCGTTGATTTAGGAATCGTTATAATGCCATGCTGCA  2970717

Query  532      GATCCCAGCGCAAAATGATTTGGGCGACAGATTTGTTATATGTTTGAGCGATGTCTGCCA  591
                ||||||||||||||||| ||||| ||||||||||  |||||||||||||||||| |||||
Sbjct  2970716  GATCCCAGCGCAAAATAATTTGTGCGACAGATTTATTATATGTTTGAGCGATGTCAGCCA  2970657

Query  592      GTACAGGGTGATCCAACAGCTGTCCCTGCATTAAAGGTGACCAAGCTTCCATCTGGATGC  651
                 ||||||||||||| ||||||||||||||||||||||||||||||| |||||||||||||
Sbjct  2970656  ATACAGGGTGATCCAGCAGCTGTCCCTGCATTAAAGGTGACCAAGCCTCCATCTGGATGC  2970597

Query  652      CTTGTTTTGGCAGTATGCC-ATCAACTCTTTTTGTGTAAGGCGCGGGTGTAATTCCACT   710
                |  | ||||||||||||| ||| |||||||||| ||||| |||||||| |||||||||||
Sbjct  2970596  CCTGATTTTGGCAGTAT-CTTATCAACTCTTTTTGTGTGAGGCGCGGGTGAAATTCCACT  2970538

Query  711      TGGTTGATCATAGGCTTCAATT-CAGCAGCCGTCATCAGGTCTTCAAGATGATGGGTTTG  769
                ||||| ||||||||||| |||  |||||||||||||||| ||||||||||| ||  ||||
Sbjct  2970537  TGGTTAATCATAGGCTT-AATTTCAGCTGCCGTCATCAGATCTTCAAGATGGTGAATTTG  2970479

Query  770      GAAGTTGCT  778
                |||||||||
Sbjct  2970478  GAAGTTGCT  2970470
```

Figure 37

```
>gb|EF624064.1| Triticum monococcum subsp. aegilopoides clone TbBAC30, complete
sequence
Length=84332

Score = 1262 bits (683),  Expect = 0.0
 Identities = 788/838 (94%), Gaps = 10/838 (1%)
 Strand=Plus/Plus Query  1      GCACGGTCAGCCTGACCACGAAGGTCTATTCCTGCAAGCAATCGAAGAACGAGCAAGAAT  60
              ||||||||||||||||||||||||||||||||||||||||||||||||||| ||||||||
Sbjct  52459  GCACGGTCAGCCTGACCACGAAGGTCTATTCCTGCAAGCAATCGAAGAACAAGCAAGAAT  52518

Query  61     ATGATAAAGCAATCTGAATATTGCAAATA-ATATGAAGTATTGATAATGGTGAGGATCCG  119
              ||||||||||||||||||||||||||||| |||||||||||||||||||||| |||||||
Sbjct  52519  ATGATAAAGCAATCTGAATATTGCAAATATATATGAAGTATTGATAATGGTGGGGATCCG  52578

Query  120    GAAGCGGTCTTGGTCTGGTCGTTGGACACAAACGAAGTACACGAAGTTGCAATGGCTAAC  179
              ||||||||||||||||||||||||||||||||||||||||||||||||||||||||||||
Sbjct  52579  GAAGCGGTCTTGGTCTGGTCGTTGGACACAAACGAAGTACACGAAGTTGCAATGGCTAAC  52638

Query  180    TTTTAACTAAACAAATCCCAAGGAAAT-GCTATTAGATGGATCTACTTATATAGGAGCAA  238
              |||||||||||||||||||||||||||  |||| | |||||||||||||||||||||| |
Sbjct  52639  TTTTAACTAAACAAATCCCAAGGAAAAAGCTACTGGATGGATCTACTTATATAGGAGCAA  52698

Query  239    GGGGTGGCGTCCAAGGAGGTGGTAGGACGTCCCAAGGCAGCCTAAAACTAAATCTAGGTC  298
              ||||||||| ||||||||||||  |||||||||||||||||||||||| |||  ||||||
Sbjct  52699  GGGGTGGCGGCCAAGGAGGTGGGAGGACGTCCCAAGGCAGCCTAAAACTAACCCTAGGTC  52758

Query  299    GTGCAAGGC-AATGGGCCCAAGTGGAGGTGATGTAACACCTTTGGACTTGTAGTTTGAC  357
              ||  ||||| | ||||||||||||||||||||| ||||||||||| |||||||||||||
Sbjct  52759  GTACAAGGCTCA-TGGGCCCAAGTGGAGGTGATGCAACACCTTTGGGCTTGTAGTTTGAC  52817

Query  358    TCGGATTCTGCTGCAGCATCAGATTGTTTCGTGCACAACTCAACGCTCCGGAAGAATTTG  417
              |||||||||||||| |  ||||||||||||| ||| ||||||||||||||| |||||| |
Sbjct  52818  TCGGATTCTGCTGCAACGTCAGATTGTTTCGTCCATAACTCAACGCTCCGGACGAATTCG  52877

Query  418    AAGGTGATTCCAATTGGGTTGGAAAGTGCACGAAATCTAGTTTCCAACaaaaaaaGAATC  477
              ||||||| ||||||||| |||||||| |||||||||||||||||||||||||||| ||||
Sbjct  52878  AAGGTGAATCCAATTGGGTTGGAAAGAGCACGAAATCTAGTTTCCAACAAAAAAAGAATC  52937

Query  478    ACCCAATTCGGAGTCCGTATGAATAACTTGTGTG-CGTTTTGAGTCAGGTGTGTCTGTGC  536
              |||||||||||||||||||||| |   |||||||  |||||||||||||| ||||| |||
Sbjct  52938  ACCCAATTCGGAGTCCGTATGAAAAAGTTGTGT-TGGCGTTTTGAGTCAGGTATGTCTGTGC  52996

Query  537    AGTCCGAATCTGAATCCAGAACGTGAGAGACTTGGACTCTATCTTCTCTTGGGCCGAAAG  596
              |||||||||||||||||||||||||||||||||||||||||||||||||| ||||  ||||
Sbjct  52997  AGTCCGAATCTGAATCCAGAACGTGAGAGACTTGGACTCTATCTTCTCTTGGCCCAAAAG  53056

Query  597    TGACGTGAGAGAACTTTTTGGACAGCAAAT-AAACATCTCTTTCTTCC-TTATCTTCATA  654
              ||||||||||| ||||||||| ||  |||| ||| |||||| |||||  ||||||||||
Sbjct  53057  TGACGTGAGAGGACTTTTTGAACA-CAACCGAAACTTCTCCTT-TTCCCTTATCTTCATA  53114

Query  655    TGTGGATTGTACAAATGTCCCATACGCCTGCAATTAGACAAAACACAAAAGTGTGTGAAG  714
              ||||||||||||||||||||| |||  || ||||||||||||| |||||||| |||||||
Sbjct  53115  TGTGGATTGTACAAATGTCCAATACACCTACAATTAGACAAAACACAAAAGTATGTGAAG  53174

Query  715    TATTTTTGTTCTGGATAACATAAATAGATTATTGAATAGTTTGCACTAGAAATCACCTTA  774
              ||||||||||| ||||||||||||||||||| ||||||||||||| |||||||||||| |
Sbjct  53175  TATTTTTGTTCTGAATAACATAAATAGATTATTGAATAGTTTGCATTAGAAATCACCTGA  53234

Query  775    CAAATATGCATATATGCAATATTTTTGGTCATATCCAAGGTAGTCATGTCCTTATCAA  832
              |||||||||||||||||||||||||||||| |||||||||||||||||||| |||||||
Sbjct  53235  CAAATATGCATATATGCAATATTTTTGGTCGTATCCAAGGTAGTCATGTCCTCATCAA  53292
```

Figure 38

```
>gb|AY663392.1|  Triticum aestivum cultivar Renan clone BAC 930H14, complete sequence
Length=153766

Score =  675 bits (365),  Expect = 0.0
 Identities = 396/411 (96%), Gaps = 1/411 (0%)
 Strand=Plus/Plus Query  1      GAAAGAACATGCGGTGCCCCCATGTTTGGTTTTGGTAATTGATGACAATCTCTATGGACT  60
              ||||||||||||||||||||||||||||||||||||||||||||||||||||||||||||
Sbjct  36900  GAAAGAACATGCGGTGCCCCCATGTTTGGTTTTGGTAATTGATGACAATCTCTATGGACT  36959

Query  61     AATGGTTGCCTTGAGTTATATTTGAAGGTTTT-GTCCATAGGCTTTTCTTGAAGTACATG  119
              ||||||||||||||||||||||||| ||||| ||| |||||||||||||||| |||||||
Sbjct  36960  AATGGTTGCCTTGAGTTATATTTGAATGTTTTTGTCTATAGGCTTTTCTTGGAGTACATG  37019

Query  120    TGTTGGTTTCAAGGAGAGTTTGTGTCGACCAAGGTGCTATTCAAGGAATTACCTAAAGAT  179
              ||||||||||||||||| |||||||||||||||| | ||||||||||||||||||||| |
Sbjct  37020  TGTTGGTTTCAAGGAGAGTTTGTGTCGACCAAGGTTCTATTCAAGGAATTACCTAAAGAG  37079

Query  180    TGGTCTTGTGAGAGGTTGATCAAGACTAAGTTAAAGAGTGAATCAAGATGATCAACCCAC  239
              ||||||| ||||||||||||||||||||||| |||||||||||||||| || ||||||||
Sbjct  37080  TGGTCTTATGAGAGGTTGATCAAGACTAAGTCAAAGAGTGAATCAAGTTGACCAACCCAC  37139

Query  240    AAAGCGTAGAAGATGTACCGAGAGGGATCAAGTGATCCCATGGTATGGTAAGCATTGTCA  299
              ||||||||||||||||||||||||||||||||||||||||||||||||||||||||||||
Sbjct  37140  AAAGCGTAGAAGATGTACCGAGAGGGATCAAGTGATCCCATGGTATGGTAAGCATTGTCA  37199

Query  300    ATTACGCTTTGTGTACTAACCCATGGTCTTCGTGGGGGTTCTTTGTGGGGTTAGGTTGCG  359
              |||| |||||||||||||||||||||||||||||| |||||||||||||||||||||||
Sbjct  37200  ATTATGCTTTGTGTACTAACCCATGGTCTTCGTGAGGGTTCTTTGTGGGGTTAGGTTGCG  37259

Query  360    GTGTGTAAGTTCAAGTGGAGCACCACGAAGAGATCAAATGCTTGAAGCTTG       410
              ||||| |||||||||||||||||| || ||||||||||||||||||||||
Sbjct  37260  GTGTGCAAGTTCAAGTGGAGCATCACAAAGAGATCAAATGCTTGAAGCTTG      37310
```

Figure 39

```
>emb|AL161583.2|  Arabidopsis thaliana DNA chromosome 4, contig fragment No. 79
Length=199536

Score =  876 bits (474),  Expect = 0.0
 Identities = 478/480 (99%), Gaps = 0/480 (0%)
 Strand=Plus/Plus Query  1      GTCGGTGAAGCAAGAAAAACACCAAATCCCCATGCAACCCCTAAGCCCACCTCCCCAAAA  60
              |||||||||||||||||||||||||||||| |||||||||||||||||||||||||||||
Sbjct  48753  GTCGGTGAAGCAAGAAAAACACCAAATCCTCATGCAACCCCTAAGCCCACCTCCCCAAAA  48812

Query  61     ACGAAATCTTGTCTCTCGATCTACCACATTTATAGAAAACTTGCTCACAAAAACCAGAAT  120
              ||||||||||||||||||||||||||||||||||||||||||||||||||||||||||||
Sbjct  48813  ACGAAATCTTGTCTCTCGATCTACCACATTTATAGAAAACTTGCTCACAAAAACCAGAAT  48872

Query  121    TTGGGGAAAAGTAACGGAATTCGGAAAGCCCAGATAGAATTGAGAGGAAACAGAATTGAA  180
              ||||||||||||||||||||||||||||||||||||||||||||||||||||||||||||
Sbjct  48873  TTGGGGAAAAGTAACGGAATTCGGAAAGCCCAGATAGAATTGAGAGGAAACAGAATTGAA  48932

Query  181    TCTCTAATTCTGGATTTAAAGTGACGGGAAGGAGAAGATCAAACGCTAATCTGATTCAGG  240
              ||||||||||||||||||||||||||||||||||||||||||||||||||||||||||||
Sbjct  48933  TCTCTAATTCTGGATTTAAAGTGACGGGAAGGAGAAGATCAAACGCTAATCTGATTCAGG  48992

Query  241    ATTAGGGTTTGAGAGAAATGAAAAGGTAGAATCGGATCAGATCTTGCGAGGGGCGAGTAG  300
              ||||||||||||||||||||||||||||||||||||||||||||||||||||||||||||
Sbjct  48993  ATTAGGGTTTGAGAGAAATGAAAAGGTAGAATCGGATCAGATCTTGCGAGGGGCGAGTAG  49052

Query  301    AGGCATATTGTGAGGTTTCTTTGGAAGAAAAGGTGGTCGATGATATAATCTGGATGCCGA  360
              ||||||||||||||||||||||||||||||||||||||||||||||||||||||||||||
Sbjct  49053  AGGCATATTGTGAGGTTTCTTTGGAAGAAAAGGTGGTCGATGATATAATCTGGATGCCGA  49112

Query  361    TTCGgaagaagaagcaaaataaaaatcggcgaaaatgggaagggaatgataaaaattaaa  420
              ||||||||||||||||||||||||||||||||||||||||||||||||||||||||||||
Sbjct  49113  TTCGGAAGAAGAAGCAAAATAAAAATCGGCGAAAATGGAAAGGGAATGATAAAAATTAAA  49172

Query  421    aagacaaactaatcgcgaaaCACAAGGGACTTTGGAAGTCTTTGGTTCTTGCTTCACCG  480
              ||||||||||||||||||||||||||||||||||||||||||||||||||||||||||||
Sbjct  49173  AAGACAAACTAATCGCGAAACACAAGGGACTTTGGAAGTCTTTGGTTCTTGCTTCACCG  49232
```

Figure 40

```
>gb|AC126672.3|  Mus musculus BAC clone RP24-473A18 from chromosome 9, complete
sequence
Length=191730

Score = 1402 bits (759),  Expect = 0.0
 Identities = 766/769 (99%), Gaps = 1/769 (0%)
 Strand=Plus/Plus Query  1       ACATGACGCACGGTCAGCAGTTGCCGAATGCCTGGAACACCATGCTTTCAACAAACAGTT  60
               ||| ||||| |||||||||||||||||||||||||||||||||||||||||||||||||
Sbjct  116871  ACA-GACGCCCGGTCAGCAGTTGCCGAATGCCTGGAACACCATGCTTTCAACAAACAGTT  116929

Query  61      TCCTTTCCTTAAATAGAGAAGTCGAAAGAATAGAATCTGGAAACTGTCTCAGACCCTGAA  120
               ||||||||||||||||||||||||||||||||||||||||||||||||||||||||||||
Sbjct  116930  TCCTTTCCTTAAATAGAGAAGTCGAAAGAATAGAATCTGGAAACTGTCTCAGACCCTGAA  116989

Query  121     GCCAAACCTCTCCCCGTACCCAGTCATGCATTCATTCAACAACACAGGAAAAACGGACCT  180
               |||| ||||||||||||||||||||||||||||||||||||||||||||||||||||||
Sbjct  116990  GCCAAACCTCTCCCCGTACCCAGTCATGCATTCATTCAACAACACAGGAAAAACGGACCT  117049

Query  181     GTGCTGGAGGCTAGGGGCACAGGAGCAGGACCACACCCTCCTAAAATGCCCCTGCTGATA  240
               ||  ||||||||||||||||||||||||||||||||||||||||||||||||||||||
Sbjct  117050  GTGCTGGAGGCTAGGGGCACAGGAGCAGGACCACACCCTCCTAAAATGCCCCTGCTGATA  117109

Query  241     GGGAAAGTGAACCCCACCAATTACAAAGCATTGCTATGAGCATGCAGTGGGCTTGAACAG  300
               ||||||||||||||||||||||||||||||||||||||||||||||||||||||||||
Sbjct  117110  GGGAAAGTGAACCCCACCAATTACAAAGCATTGCTATGAGCATGCAGTGGGCTTGAACAG  117169

Query  301     AGTGCTGTGGAGCTCCTCAGCAAGGGCAGTGGGTAGCTCTTAGAAGGCAAGGAAGGGGAC  360
               |||||||||||||||||||||||||||||||||||||||||||||| ||||||||||||
Sbjct  117170  AGTGCTGTGGAGCTCCTCAGCAAGGGCAGTGGGTAGCTCTTAGAAGGCAAAGAAGGGGAC  117229

Query  361     GTATCCGTGAAAGCCTTCTAGAGGACATGATTTTTGAACTGGATGGATGAGGGAAGACCT  420
               |||||||||||||||||||||||||||||||||||||||||||||||||||||||||||
Sbjct  117230  GTATCCGTGAAAGCCTTCTAGAGGACATGATTTTTGAACTGGATGGATGAGGGAAGACCT  117289

Query  421     AATTTAGAAACACTGGTCTCTGAGCTGATTGACTCACCATAAGCTGACTGGTTTATTCCT  480
               ||||||||||||||||||||||||||||||||||||||||||||||||||||||||||
Sbjct  117290  AATTTAGAAACACTGGTCTCTGAGCTGATTGACTCACCATAAGCTGACTGGTTTATTCCT  117349

Query  481     GAGATGGAGCCCCTGGGGAGCTACTCTTTAGAGAACTCATAGTGTCCTCTAAAATGGGCA  540
               ||||||||||||||||||||||||||||||||||||||||||||||||||||||||||
Sbjct  117350  GAGATGGAGCCCCTGGGGAGCTACTCTTTAGAGAACTCATAGTGTCCTCTAAAATGGGCA  117409

Query  541     GAGCCCCCTAGACCCAAACATTCAAGAGTCACAGCCATCAGTCAATAGTCCCTTAGTGAT  600
               ||||||||||||||||||||||||||||||||||||||||||||||||||||||||||
Sbjct  117410  GAGCCCCCTAGACCCAAACATTCAAGAGTCACAGCCATCAGTCAATAGTCCCTTAGTGAT  117469

Query  601     ACTTTCTCTTTCTAGTCCAGTACCCACCAGCCGACAAATGGCTGGCTTATCTTTAAATGG  660
               |||||||||||||||||||||||||||||||||||||||||||||||||||||||||
Sbjct  117470  ACTTTCTCTTTCTAGTCCAGTACCCACCAGCCGACAAATGGCTGGCTTATCTTTAAATGG  117529

Query  661     CTTTTGAAAGCAAATGTTTATCTAAAGAGTAACTTGGTATGGTAACCCTAAATGAAAACT  720
               ||||||||||||||||||||||||||||||||||||||||||||||||||||||||||
Sbjct  117530  CTTTTGAAAGCAAATGTTTATCTAAAGAGTAACTTGGTATGGTAACCCTAAATGAAAACT  117589

Query  721     CAGCCTCACAGGAGCTAGTCATGAACAATGTGCCAGAGCTAGCTAGCCC  769
               |||||||||||||||||||||||||||||||||||||||||||||||
Sbjct  117590  CAGCCTCACAGGAGCTAGTCATGAACAATGTGCCAGAGCTAGCTAGCCC  117638
```

Figure 41

```
>emb|AL607083.17|  Mouse DNA sequence from clone RP23-206E3 on chromosome 11 Contains
a novel gene, complete sequence
Length=189495

Score =  407 bits (220),  Expect = 1e-110
 Identities = 224/226 (99%), Gaps = 0/226 (0%)
 Strand=Plus/Plus Query  14      GTCGGTGAAGGACCCATGGCACAGCTGCATCTGCCTTGTCAGAAACCTGCCACCATCCCC  73
               ||||||||||||||||||||||||||||||||||||||||||||||||||||||||||||
Sbjct  137105  GTCGGTGAAGGACCCATGGCACAGCTGCATCTGCCTTGTCAGAAACCTGCCACCATCCCC  137164

Query  74      TAGGATGTCATCGTATCCCATCATCTTCTACTGTGGGTGGAGCCTTAGCTAGGGAAGCAC  133
               ||||||||||||||||||||||||||||||||||||||||||||||||||||||||||||
Sbjct  137165  TAGGATGTCATCGTATCCCATCATCTTCTACTGTGGGTGGAGCCTTAGCTAGGGAAGCAC  137224

Query  134     TTTCCAGGACAGCTGTATTCAGAGCCTTTAGAGCCCAGCAGGACCAGTGGCTCCAGGATT  193
               ||||||||||||||||||||||||||||||||||||||||||||||||||||||||||||
Sbjct  137225  TTTCCAGGACAGCTGTATTCAGAGCCTTTAGAGCCCAGCAGGACCAGTGGCTCCAGGATT  137284

Query  194     GGCATTAACTGTTTGACTAACATACTTAGCTCTGCTTCACCGACTC  239
               ||||||||||||| |||||||||||||||||||||||||| ||||
Sbjct  137285  GGCATTAACTGTCTGACTAACATACTTAGCTCTGCTTCACCCACTC  137330
```

Figure 42

```
>ref|NG_007988.1| Homo sapiens CTD (carboxy-terminal domain, RNA polymerase II,
polypeptide A) phosphatase, subunit 1 (CTDP1) on chromosome
18
Length=81707

Score = 1127 bits (610),  Expect = 0.0
 Identities = 617/620 (99%), Gaps = 2/620 (0%)
 Strand=Plus/Minus Query  1      CACGGTCAGAACAGGCGGAACACCCAGGGCCACGCTGGTCCTGAATGCTGCATGCGGTCC  60
              ||||||||||||||||| |||||||||||||||||||||||||||||||||||||||||
Sbjct  81158  CACGGTCAGAACAGGC-GAACACCCAGGGCCACGCTGGTCCTGAATGCTGCATGCGGTCC  81100

Query  61     GGCCCCTCCCGTCACCAGGCCCCGCGCAGCCAGCTACCACGCCACCCTCCTCCCGTCCTC  120
              ||||||||||||||||||||||||||||||||||||||||||||||||||||||||||||
Sbjct  81099  GGCCCCTCCCGTCACCAGGCCCCGCGCAGCCAGCTACCACGCCACCCTCCTCCCGTCCTC  81040

Query  121    TTCACCCCTAGGCCAGACCCAGCAGCAGAGGTCCCCGTTCTCGCTGCCCCTGCAGCACCA  180
              ||||||||||||||||||||||||||||||||||||||||||||||||||||||||||||
Sbjct  81039  TTCACCCCTAGGCCAGACCCAGCAGCAGAGGTCCCCGTTCTCGCTGCCCCTGCAGCACCA  80980

Query  181    CCTGTATTTCCACGCTGTGTTTAAGGAGGCCTTGCAGAGCCTCATTAACACCCCCATGAA  240
              |||||||||||||||||||||||||||||||||||||||||||||||||||||||||||
Sbjct  80979  CCTGTATTTCCACACTGTGTTTAAGGAGGCCTTGCAGAGCCTCATTAACACCCCCATGAA  80920

Query  241    GCCAGAGGGGACTCGGCCAAGAGCAGAACAAGGGGCCACCTTGGTCCCAGCAGGACCAAC  300
              ||||||||||||||||||||||||||||||||||||||||||||||||||||||||||||
Sbjct  80919  GCCAGAGGGGACTCGGCCAAGAGCAGAACAAGGGGCCACCTTGGTCCCAGCAGGACCAAC  80860

Query  301    CACACGCAGAATCGCCTTCAGGGAGAAACCACTGTGGAAGGAGGGAAGGTCTCCCAGCCT  360
              ||||||||||||||||||||||||||||||||||||||||||||||||||||||||||||
Sbjct  80859  CACACGCAGAATCGCCTTCAGGGAGAAACCACTGTGGAAGGAGGGAAGGTCTCCCAGCCT  80800

Query  361    TTCCCAGAGGTCTCCACACAGCATCAAGGCCTCGTTCATCGGccccctgccccccaccccc  420
              ||||||||||||||||||||||||||||||||||||||||||||||||||||||||||||
Sbjct  80799  TTCCCAGAGGTCTCCACACAGCATCAAGGCCTCGTTCATCGGCCCCTGCCCCCCACCCCC  80740

Query  421    GGCACATTACTCCCTGCACGTTTTGTGCCCCTCCCTATAAACTGTAGAATCTTCTGCTTT  480
              |||||||||||||||||||||||||||||||||||||||||||||||||||||||||||
Sbjct  80739  GGCACATTACTCCCTGCACGTTTTGTGCCCCTCCCTATAAACTGTAGAATCTTCTGCTTT  80680

Query  481    CTTTGGGTATCAACTTGTACATCTATTTTTGTTTTCTGTCCAATTCATCTTACATTCTTG  540
              ||||||||||||||||||||||||||||||||||||||||||||||||||||||||||||
Sbjct  80679  CTTTGGGTATCAACTTGTACATCTATTTTTGTTTTCTGTCCAATTCATCTTACATTCTTG  80620

Query  541    CTCGTGGCGAAATCGGACCTGAGGTGGGCCCAGTTCACCTCCTGCTTCTCTGGACAGGAG  600
              ||||||||||||||||||||||||||||||||||||||||||||||||||||||||||||
Sbjct  80619  CTCGTGGCGAAATCGGACCTGAGGTGGGCCCAGTTCACCTCCTGCTTCTCTGGACAGGAG  80560

Query  601    GAACTCCCTGACCGTGCGTC   620
              ||||||||||||||| |||||
Sbjct  80559  GAACTCCCTGACCG-GCGTC   80541
```

Figure 43

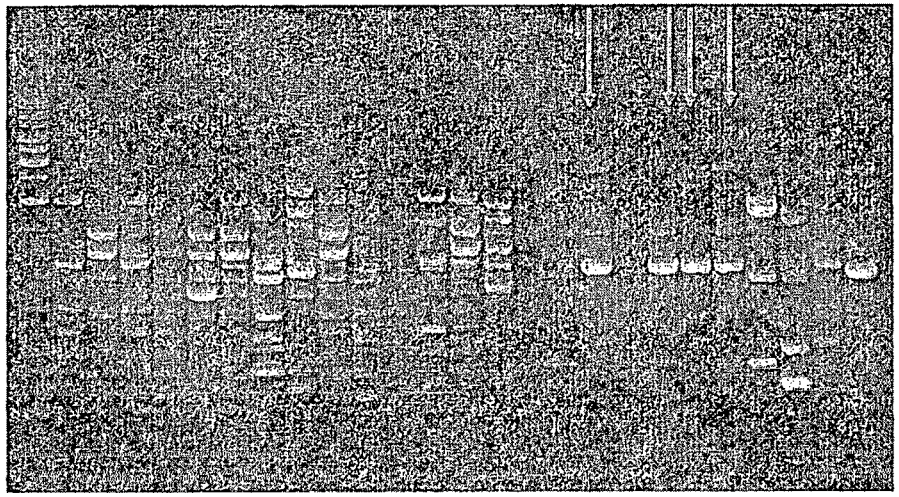
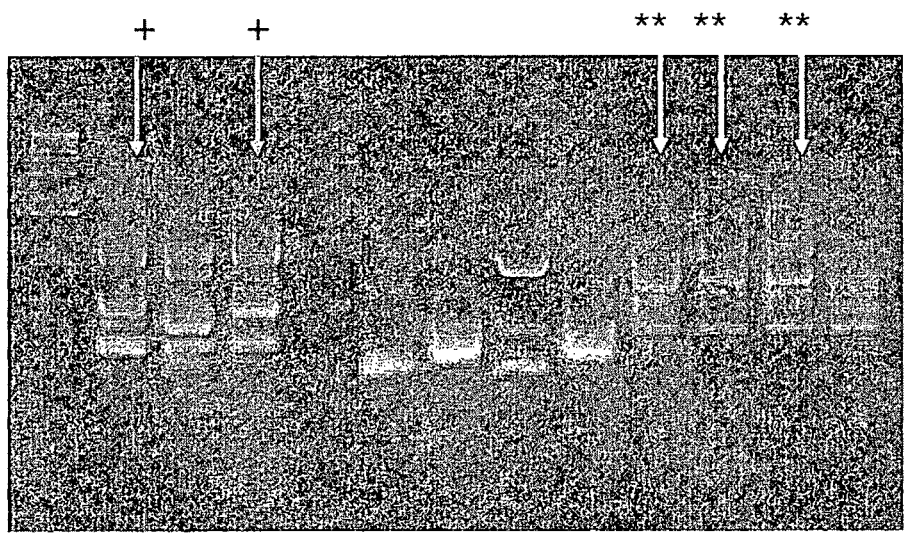
Figure 44

```
>gb|EU624442.1| Bacillus pumilus strain SS-02 16S ribosomal RNA gene, partial
sequence
Length=1511

Score =  793 bits (429),  Expect = 0.0
 Identities = 429/429 (100%), Gaps = 0/429 (0%)
 Strand=Plus/Minus Query  1    CGTCAAGGTGCGAGCAGTTACTCTCGCACTTGTTCTTCCCTAACAACAGAGCTTTACGAT  60
            ||||||||||||||||||||||||||||||||||||||||||||||||||||||||||||
Sbjct  482  CGTCAAGGTGCGAGCAGTTACTCTCGCACTTGTTCTTCCCTAACAACAGAGCTTTACGAT  423

Query  61   CCGAAAACCTTCATCACTCACGCGGCGTTGCTCCGTCAGACTTTCGTCCATTGCGGAAGA  120
            ||||||||||||||||||||||||||||||||||||||||||||||||||||||||||||
Sbjct  422  CCGAAAACCTTCATCACTCACGCGGCGTTGCTCCGTCAGACTTTCGTCCATTGCGGAAGA  363

Query  121  TTCCCTACTGCTGCCTCCCGTAGGAGTCTGGGCCGTGTCTCAGTCCCAGTGTGGCCGATC  180
            ||||||||||||||||||||||||||||||||||||||||||||||||||||||||||||
Sbjct  362  TTCCCTACTGCTGCCTCCCGTAGGAGTCTGGGCCGTGTCTCAGTCCCAGTGTGGCCGATC  303

Query  181  ACCCTCTCAGGTCGGCTACGCATCGTCGCCTTGGTGAGCCATTACCCCACCAACTAGCTA  240
            ||||||||||||||||||||||||||||||||||||||||||||||||||||||||||||
Sbjct  302  ACCCTCTCAGGTCGGCTACGCATCGTCGCCTTGGTGAGCCATTACCCCACCAACTAGCTA  243

Query  241  ATGCGCCGCGGGTCCATCTGTAAGTGACAGCCGAAACCGTCTTTCATCCTTGAACCATGC  300
            ||||||||||||||||||||||||||||||||||||||||||||||||||||||||||||
Sbjct  242  ATGCGCCGCGGGTCCATCTGTAAGTGACAGCCGAAACCGTCTTTCATCCTTGAACCATGC  183

Query  301  GGTTCAAGGAACTATCCGGTATTAGCTCCGGTTTCCCGGAGTTATCCCAGTCTTACAGGC  360
            ||||||||||||||||||||||||||||||||||||||||||||||||||||||||||||
Sbjct  182  GGTTCAAGGAACTATCCGGTATTAGCTCCGGTTTCCCGGAGTTATCCCAGTCTTACAGGC  123

Query  361  AGGTTACCCACGTGTTACTCACCCGTCCGCCGCTAACATCCGGGAGCAAGCTCCCTTCTG  420
            ||||||||||||||||||||||||||||||||||||||||||||||||||||||||||||
Sbjct  122  AGGTTACCCACGTGTTACTCACCCGTCCGCCGCTAACATCCGGGAGCAAGCTCCCTTCTG  63

Query  421  TCCGCTCGA  429
            |||||||||
Sbjct  62   TCCGCTCGA  54
```

Figure 46

```
>dbj|AB271742.1| Bacillus sphaericus gene for 16S rRNA, partial sequence
Length=1477

Score =  809 bits (438),  Expect = 0.0
 Identities = 438/438 (100%), Gaps = 0/438 (0%)
 Strand=Plus/Plus Query  1    ATGCAAGTCGAGCGAACAGAGAAGGAGCTTGCTCCTTTGACGTTAGCGGCGGACGGGTGA  60
            ||||||||||||||||||||||||||||||||||||||||||||||||||||||||||||
Sbjct  28   ATGCAAGTCGAGCGAACAGAGAAGGAGCTTGCTCCTTTGACGTTAGCGGCGGACGGGTGA  87

Query  61   GTAACACGTGGGCAACCTACCCTATAGTTTGGGATAACTCCGGGAAACCGGGGCTAATAC  120
            ||||||||||||||||||||||||||||||||||||||||||||||||||||||||||||
Sbjct  88   GTAACACGTGGGCAACCTACCCTATAGTTTGGGATAACTCCGGGAAACCGGGGCTAATAC  147

Query  121  CGAATAATCTTTTGTCCCTCATGGGACAATACTGAAAGACGGTTTCGGCTGTCGCTATAG  180
            ||||||||||||||||||||||||||||||||||||||||||||||||||||||||||||
Sbjct  148  CGAATAATCTTTTGTCCCTCATGGGACAATACTGAAAGACGGTTTCGGCTGTCGCTATAG  207

Query  181  GATGGGCCCGCGGCGCATTAGCTAGTTGGTGAGGTAACGGCTCACCAAGGCAACGATGCG  240
            ||||||||||||||||||||||||||||||||||||||||||||||||||||||||||||
Sbjct  208  GATGGGCCCGCGGCGCATTAGCTAGTTGGTGAGGTAACGGCTCACCAAGGCAACGATGCG  267

Query  241  TAGCCGACCTGAGAGGGTGATCGGCCACACTGGGACTGAGACACGGCCCAGACTCCTACG  300
            ||||||||||||||||||||||||||||||||||||||||||||||||||||||||||||
Sbjct  268  TAGCCGACCTGAGAGGGTGATCGGCCACACTGGGACTGAGACACGGCCCAGACTCCTACG  327

Query  301  GGAGGCAGCAGTAGGGAATCTTCCACAATGGGCGAAAGCCTGATGGAGCAACGCCGCGTG  360
            ||||||||||||||||||||||||||||||||||||||||||||||||||||||||||||
Sbjct  328  GGAGGCAGCAGTAGGGAATCTTCCACAATGGGCGAAAGCCTGATGGAGCAACGCCGCGTG  387

Query  361  AGTGAAGAAGGATTTCGGTTCGTAAAACTCTGTTGTAAGGGAAGAACAAGTACAGTAGTA  420
            ||||||||||||||||||||||||||||||||||||||||||||||||||||||||||||
Sbjct  388  AGTGAAGAAGGATTTCGGTTCGTAAAACTCTGTTGTAAGGGAAGAACAAGTACAGTAGTA  447

Query  421  ACTGGCTGTACCTTGACG  438
            ||||||||||||||||||
Sbjct  448  ACTGGCTGTACCTTGACG  465
```

HYPERPRIMERS

CROSS REFERENCE TO RELATED APPLICATIONS

This application is the U.S. national stage under 35 USC § 371 of International Application Number PCT/AU2010/001659, filed on 9 Dec. 2010, which claims priority to U.S. Application No. 61/267,988, filed on 9 Dec. 2009, the entire contents of which is hereby incorporated by reference.

SEQUENCE LISTING

The instant application contains a Sequence Listing which has been filed electronically in ASCII format and is hereby incorporated by reference in its entirety. Said ASCII copy, created on Sep. 10, 2014, is named 23287203.txt and is 36 kilobytes in size.

FIELD OF THE INVENTION

The present invention relates to methods for the design and/or production of a probe or primer that is capable of hybridizing to a plurality of sites in a sample comprising nucleic acid. Furthermore, the present invention provides methods for detecting and amplifying nucleic acid using such a probe or primer, for example, for identification of a strain, species or genera. In addition, the present invention provides methods for determining codon distribution and/or base pair distance between codons in a nucleic acid.

BACKGROUND OF THE INVENTION

General

This specification contains nucleotide and amino acid sequence information prepared using PatentIn Version 3.1, presented herein. Each nucleotide sequence is identified in the sequence listing by the numeric indicator <210> followed by the sequence identifier (e.g. <210>1, <210>2, <210>3, etc). The length and type of sequence (DNA, protein (PRT), etc), and source organism for each nucleotide sequence, are indicated by information provided in the numeric indicator fields <211>, <212> and <213>, respectively. Nucleotide sequences referred to in the specification are defined by the term "SEQ ID NO:", followed by the sequence identifier (e.g., SEQ ID NO: 1 refers to the sequence in the sequence listing designated as <400>1).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each example described herein is to be applied mutatis mutandis to each and every other example unless specifically stated otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific examples described herein, which are intended for the purpose of exemplification only. Functionally-equivalent products, compositions and methods are within the scope of the invention, as described herein.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in the following texts that are incorporated by reference:

1. Sambrook, Fritsch & Maniatis, Molecular Cloning: A Laboratory Manual, Cold Spring Harbor Laboratories, New York, Second Edition (1989), whole of Vols I, II, and III;
2. DNA Cloning: A Practical Approach, Vols. I and II (D. N. Glover, ed., 1985), IRL Press, Oxford, whole of text;
3. Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151;
4. Nucleic Acid Hybridization: A Practical Approach (B. D. Hames & S. J. Higgins, eds., 1985) IRL Press, Oxford, whole of text;
5. Perbal, B., A Practical Guide to Molecular Cloning (1984);
6. Methods In Enzymology (S. Colowick and N. Kaplan, eds., Academic Press, Inc.), whole of series;

DESCRIPTION OF THE RELATED ART

Since the development of the polymerase chain reaction (PCR) by Saiki et al. in the 1980s (described in U.S. Pat. Nos. 4,683,202; 4,800,159; and 4,965,188) this process has become routinely used for a variety of applications, such as, for example, cloning of nucleic acid sequences and diagnosis of diseases, disorders or conditions. Furthermore, several alternative methods that do not use PCR based technology, e.g., ligase chain reaction and nucleic acid sequence based amplification (NASBA), have also been developed for the rapid amplification of nucleic acids, for example, for nucleic acid detection and/or cloning.

PCR is an in vitro enzyme-based process for the replication of sequences of nucleic acid. Generally, PCR uses two oligonucleotide primers designed to hybridize to opposite strands and flank the region of interest on the target nucleic acid. Strands of nucleic acid in a sample are separated, typically by thermal denaturation, and the primers then allowed to hybridize (by annealing if thermal cycling is used) to the single strand templates. An enzyme, such as, for example, a DNA polymerase or reverse transcriptase extends the primers on the templates. Both the original sequences of nucleic acid and the newly synthesized sequences of nucleic acid may then be used as templates for further amplification cycles. Several cycles of PCR results in an exponential amplification in the number of copies of the nucleic acid flanked by the primer oligonucleotide.

Many variations of the basic PCR process have been developed since its conception, with the majority of these methods requiring oligonucleotide primers designed to specific known sequences that flank or are adjacent to a target nucleic acid.

Furthermore, other amplification methods such as, for example, self-sustained replication (3SR) or NASBA also rely on the use of two or more nucleic acid probes or primers that are capable of hybridizing to nucleic acid that flank the target nucleic acid.

As the majority of nucleic acid amplification methods require the use of at least two oligonucleotide primers that are each homologous or identical to a region of nucleic acid that flanks a nucleic acid of interest, the sequence of at least these flanking regions is required to design suitable probes and/or primers. Previously, it has been necessary to sequence regions of nucleic acid of interest, for example using di-deoxy sequencing, to determine sequences suitable for the design of primers.

Primer sequences are generally designed by reference to nucleotide sequence databases such as, for example, Genbank at NCBI (The National Center for Biotechnology Information) or EMBL-Bank (European Molecular Biology Laboratory Nucleotide Sequence Database). Software that is designed to determine those regions of a nucleotide sequence that are specific to a target sequence may assist in primer design to enhance specificity. Using such software, it is generally expected that the derived primer sequences are merely suitable for amplifying a target nucleic acid (i.e., the primers will specifically amplify the target of interest).

The suitability of the majority of nucleic acid amplification methods in use today is limited to those templates having a known sequence. However, the sequence of the majority of organisms is unknown and even those genomes that have been completely sequenced comprise unsequenced regions. Accordingly, there is a need for amplification methods that do not demand detailed knowledge of a specific target sequence as a prerequisite for amplification.

One method of amplifying a target DNA having an unknown sequence is described in U.S. Pat. Nos. 5,759,822 and 5,565,340. This technology requires several DNA templates to be processed by restriction endonuclease digestion, purified and ligated to an adaptor, prior to being used in the PCR reaction. However, the requirement for restriction endonuclease digestion and subsequent ligation of adaptors makes this method complicated, expensive and time-consuming.

In an alternative method described by William et al. (*Nucleic Acids Res.* 18: 6531-6535, 1990), short arbitrary oligonucleotides are used to amplify polymorphic regions of DNA. This form of analysis, known as RAPD (random amplified polymorphic DNA) can be used to map the position of nucleotide polymorphisms in organisms. RAPD PCR uses oligonucleotides of a random, predetermined sequence. Usually these primers are 6 to 10 nucleotides in length with a Guanine and Thymidine content in excess of 40%. A RAPD PCR reaction generally requires low stringency hybridization conditions to be used (e.g., a hybridization temperature of about 35° C. to 40° C.) due to the relatively short oligonucleotides and the requirement that the primers hybridize to many sites throughout the genome to facilitate PCR amplification. Of interest, Williams et al., 1990, supra observed that even single base changes in the sequence of a RAPD primer cause completely different patterns of amplification (i.e., different targets are amplified). The authors extrapolated from this result to conclude that single base mismatches between a target nucleic acid and a primer (e.g. in the presence of a mutation) would prevent an amplification product being produced. Accordingly, the amplification products detected in a RAPD PCR protocol are heavily dependent upon the actual sequence of the target nucleic acid and/or the primer/probe.

An additional disadvantage of the RAPD PCR method is that results are often irreproducible (Herzberg et al., *Int. J. Syst. Evol. Microbiol.* 52: 1423-1433, 2002; and Jeffreys and Dubrova, *Proc. R. Soc. Lond B. Biol. Sci.,* 268: 2493-2494, 2001).

A further disadvantage of traditional methods of amplification is that they are routinely designed to amplify a specific known sequence (i.e., the isolation of useful genes or gene products). Accordingly, these methods are of little use in, for example, bioprospecting or isolating related genes from uncharacterized organisms or environments. This is because sequences amplified in methods such as bioprospecting are often not highly homologous or identical to the sequence used to design a primer.

One method used by researchers to overcome this problem is to design a set of degenerate PCR primers to regions of the genome of an organism that are highly conserved. For example, a family of genes of interest may have highly conserved regions of nucleic acid sequence, or may encode conserved regions in a polypeptide. By aligning each of these regions a researcher may determine those nucleotides that are conserved between all genes, and those nucleotides that are not. A set of oligonucleotide primers is then designed and/or produced that encompasses all of the known combinations of nucleotide sequences. These primers are then used in a PCR reaction (usually under relatively low hybridization conditions) to amplify regions of the genome or transcriptome of an organism. The disadvantage of this method is that it produces a large number of false positives and high background. Furthermore, the method requires the production of a large number of variations in a primer (or a large number of oligonucleotides wherein each oligonucleotide is a variant of another).

Accordingly, there is a clear need in the art for a method that facilitates rapid and accurate amplification of a nucleic acid of interest from an uncharacterized region of a genome. Such a method has a clear application in, for example, bioprospecting.

SUMMARY OF INVENTION

In work leading up to the present invention the inventors sought to develop a method for the rapid identification and/or isolation of uncharacterized nucleic acid sequences that were adjacent to a characterized region of an organism, using a transposon insertion site in the genome of *Pseudomonas* strain AN5 as a model test system. While the known sequence of the transposon facilitated design of one primer for the PCR reaction, the adjacent region of the genome was unknown, and thus could not be used to design a primer using traditional methods. Furthermore, methods using RAPD primers were not found to be useful in the isolation of the sequence adjacent to the transposon because they produced non-specific and non-reproducible results. As exemplified herein, the inventors found that PCR primers of at least 18 nucleotides in length designed to hybridize to specific regions of the *Pseudomonas* strain AN5 genome were capable of producing multiple PCR products under moderate to high stringency conditions. By screening a number of such primers in individual PCR reactions with one such primer in combination with a primer complementary to a region of the transposon, the inventors were able to isolate and characterize nucleic acid adjacent to the site of insertion of the transposon.

The inventors also found that such individual primers were capable of producing multiple amplification products when used alone or in combination with other primer(s). Several of the multiple PCR products generated were strain-specific. In particular, the present inventors have found that by using a primer designed using sequence from *Pseudomonas* strain AN5 they are able to differentiate between nucleic acid from *Pseudomonas* strain AN5 and nucleic acid from *Escherichia coli*, *Pseudomonas fluorescens*, *Pseudomonas putida* and *Bacillus subtilis*.

Furthermore, the present inventors have shown that using such primer(s) they were able to differentiate between *Pseudomonas* strain AN5 and other closely related *Pseudomonas* species.

The inventors have also shown that such a primer is useful for differentiating between different varieties of the same species of fungus and even different isolates of the same variety of fungus. The inventors have also demonstrated that screening such primers has lead to the identification of ones that can differentiate between different cultivars of wheat. The inventors have also reasoned that such primers are useful for differentiating between twins.

The inventors have established general principles which permit probes and/or primers to be produced capable of routinely and reproducibly amplifying unknown regions of genomes in any eukaryotic or prokaryotic organism. In particular, the inventors demonstrated that primers produced according to defined criteria are capable of producing amplicons specific to mice, humans, wheat, and bacteria. In fact, the present inventors have used a single primer to differentiate between different species and cultivars of wheat. For example, specific genes of interest may be amplified using a primer based on a region of the gene that is conserved in a related species. The inventors have also been able to use primers designed according to the method of the invention to differentiate between closely related organisms based on low levels of genetic variation present, i.e., between bacterial strains and/or isolates. For example, primers designed according to the method of the invention were useful in typing bee gut bacterial isolates and effective in determining phylogenetic relatedness of the bacterial isolates. The inventors have also found that this has further application for quickly discriminating between different bacterial species that inhibit Chalkbrood for further analysis. Based on sequencing data, amplicons generated using primers designed according to the method of the invention were also validated by the inventors as PCR generated DNA fragments specific to the DNA template added to the PCR reaction of the invention.

Accordingly, the present invention provides a method for identifying or determining a probe or primer capable of hybridizing to a plurality of sites in a nucleic acid template derived from an organism, said method comprising:
(i) determining one or more codons and the complements thereof used by the organism or a related organism in accordance with the codon usage bias of said organism or related organism; and
(ii) providing, producing, selecting or determining a probe or primer comprising or consisting of the one or more codons and/or the complements thereof, wherein the sequence of each codon is determined at (i) and wherein said probe or primer is capable of hybridizing to a plurality of sites in a nucleic acid derived from an organism.

In the present context, the term "related organism" shall be taken to mean an organism having a substantially identical codon usage preference to the organism at paragraph (i) supra (i.e., the organism-of-interest). Codon-choice patterns are believed to have been well conserved during the course of evolution. Differences in the actual populations of isoaccepting tRNAs between organisms, tRNA, G+C content including G+C content in the third position of a codon, and context-dependent nucleotide bias are parameters affecting codon usage bias between organisms. For example, codon usage bias correlates with GC composition of genomes. For example, Wan et al., *BMC Evolutionary Biology* 4, 19 (2004) showed by regression analyses that there is a strong correlation between GC composition and codon usage bias in bacteria ($r=0.91$; $n=70$) and archaea ($r=0.89$; $n=16$). Analysis of genome-wide codon bias shows that genome GC content and context-dependent nucleotide bias, calculated for example, from non-translated intergenic sequences, can be used to differentiate codon usage bias within eubacteria (e.g., non-mammalian eukaryotes) and archaea (Chen et al., *Proc. Nat. Acad. Sci. USA* 101(10), 3480-3485, 2004). For mammals, in which GC content varies widely among isochors, context-dependent nucleotide bias, determined for example by mutational processes, is the preferred means for determining relatedness.

Thus, related organisms can include organisms from two or more strains of the same species. As exemplified herein, the codon usage bias data for *Pseudomonas* strain AN5 are useful for producing a probe or primer that hybridizes to a number of sites in the genomes of related organisms, for example *Pseudomonas syringae* tomato and *Pseudomonas fluorescens*. Similarly, codon usage bias data for *Pseudomonas syringae* tomato or *Pseudomonas fluorescens* are suitable for hybridizing to nucleic acid from *Pseudomonas* strain AN5. Related organisms can also include organisms from two or more subspecies of the same species of organism or organisms from two or more species of the same genera of organisms. Related organisms can also include phylogenetically-distant organisms. For example, the codon usage bias data for *Pseudomonas* strain AN5 are useful for producing a probe or primer that hybridizes to a number of sites in the genome of a mouse, a mouse cell line, a human cell line and a number of strains of wheat.

By "plurality of sites" means that the probe or primer hybridizes to more than one site in the "template" nucleic acid thereby, for example, producing multiple hybridizing bands in a Southern hybridization or multiple amplified fragments in an amplification reaction as detected by gel electrophoresis, capillary electrophoresis, reverse phase chromatography or other art-recognized means for detecting nucleic acids of different size and/or sequence.

In one example, the present invention provides a method for producing or providing a probe or primer comprising:

(i) determining or identifying a probe or primer using a method described supra; and (ii) producing, synthesizing or providing a probe or primer designed at (i).

In another example, the present invention provides a method for identifying or determining a probe or primer comprising:

(i) providing or producing a probe or primer comprising nucleotides corresponding or complementary to a codon or sequence of codons used by an organism or a related organism thereto in accordance with the codon usage bias of said organism or related organism; and (ii) selecting a probe or primer from (i) that hybridizes to a plurality of sites in nucleic acid derived from the organism at (i) under medium, and preferably high stringency conditions.

As will be apparent to the skilled artisan from the foregoing, the inventive method involves at least two stages: (i) the provision or production of one or more probes/primers that satisfy specific sequence requirements with respect to a target nucleic acid in an organism; and (ii) the screening of those probes/primers to select those probes/primers that hybridize (e.g., in a standard Southern hybridization or PCR reaction) to multiple sites in the target nucleic acid.

As exemplified herein, a probe or primer that hybridizes to a plurality of sites in a nucleic acid from an organism is useful for, for example, identifying an organism. This is because, such a probe or primer is capable of hybridizing to polymorphic nucleic acid between organisms.

In one example, at least one of the plurality of sites has been uncharacterized previously for the organism.

As used herein, the term "uncharacterized" shall be taken to mean that the fine structure of a nucleic acid at the nucleotide sequence level (e.g., a hybridizing site in nucleic acid of the organism-of-interest) has not been determined previously. In general, this means that the sequence of a nucleic acid has not been determined and/or that a specific polymorphism has not been determined for the nucleic acid and/or that the localization of the nucleic acid in the genome of the organism-of-interest has not been determined by mapping. This does not impose a strict requirement for the genome of an organism to be substantially unknown, merely that a specific portion of sequence in a nucleic acid-of-interest has not been determined precisely, or that the order of known sequences in nucleic acid-of-interest has not been determined precisely.

For example, the method of the invention is useful for determining a probe or primer that hybridizes to a plurality of sites in a genome that is relatively uncharacterized, e.g., the genome has not been sequenced.

Each of the plurality of sites to which the probe or primer hybridizes can comprise a nucleotide sequence having at least about 40% identity to the complement of the probe or primer.

Standard means are used to determine hybridization of the probe or primer to a plurality of sites in the nucleic acid, including classical Southern hybridization, Northern hybridization, and amplification. An amplification method useful for the method of the present invention includes polymerase chain reaction (PCR), reverse transcriptase (RT) mediated amplification (e.g., RT-PCR), nested PCR, strand displacement amplification (SDA), nucleic acid sequence based amplification (NASBA), transcription mediated amplification (TMA), cycling probe technology (CPT) and Q-beta replicase (QBR) amplification.

The nucleic acid "template" used in the hybridization reaction can be any nucleic acid derived directly or indirectly from the organism or related organism, such as single-stranded or double-stranded genomic DNA, mRNA or cDNA. The present invention is not limited by the nature or source of the nucleic acid. The nucleic acid can be in a tissue or cellular sample obtained previously from the organism, or present in an aqueous or non-aqueous extract of a tissue or cellular sample.

By providing or producing a probe or primer comprising nucleotides corresponding or complementary to a codon or sequence of codons means that the probe or primer will hybridize to nucleic acid that encodes a protein or part thereof, or complementary nucleic acid thereto. It is to be understood in this context that the probe or primer need not encode an entire polypeptide or protein because, notwithstanding that the invention may rely in part upon codon usage preferences to design primers/probes capable of hybridizing to imperfect complementary sequences in a target nucleic acid, only short probes and primers (i.e., less than a full open reading frame) are required for such amplification to occur.

The sequence of the probe or primer can be based further on known sequence information for a protein or part thereof in an entirely unrelated organism to the organism from which the "template" nucleic acid for the hybridization is derived. This is true even in cases where the protein or portion thereof in the unrelated organism has a very low sequence identity to that protein in the organism from which the "template" nucleic acid for the hybridization is derived. By combining known sequence data for the protein or portion thereof in one or more organisms other than the organism-of-interest with codon preference data for the organism-of-interest, informative nucleotide sequence for the design of useful probes and primers is derived.

As a prerequisite to providing or producing a suitable probe or primer corresponding or complementary to a codon or sequence of codons in the organism or related organism, the nucleic acid that comprises the codon or sequence of codons can be characterized. By "sequence of codons" is meant a series of contiguous amino acid-encoding nucleotides wherein each of said amino acid-encoding nucleotides consists of three contiguous nucleotides encoding an amino acid residue (i.e., a series of contiguous codons).

As used herein, the term "characterized" means that the fine structure of nucleic acid has been determined at the nucleotide level e.g., by determination of a nucleotide sequence for a region of the nucleic acid, or by other art-recognized means sufficient to facilitate design of a probe or primer for use in a standard hybridization or amplification reaction. It is to be understood that this does not necessarily impart a strict requirement for the entire nucleotide sequence of a characterized nucleic acid to be determined. As will be understood by the skilled artisan, single nucleic acid substitutions, deletions or insertions may occur in a characterized nucleic acid that do not necessarily adversely affect the ability of a probe or primer to hybridize under medium stringency or high stringency conditions.

A plurality of such "characterized" regions of a nucleic acid can be relied upon to facilitate design of a probe/primer or a panel of probes or primers, for subsequent selection. For example, sequences of codon preference data can be obtained for codons or sequences of codons from multiple genes, cDNAs or genomes.

As used herein the term "codon or sequence of codons used" or similar term includes a notional use, predicted use or actual codon usage. Codon usage may be established by standard means, e.g., by reference to a published codon preference for the organism(s) in question, by calculation of Relative Synonymous Codon Usage (RSCU) values for the dataset, or by calculation of the Codon Adaptation Index (CM) for a particular dataset. The skilled artisan will be aware that "RSCU" is a measure of the number of times a particular codon is observed in a particular gene or representative dataset of genes, relative to the number of times that the codon would be observed in the absence of any codon usage bias. In the absence of any codon usage bias, the RSCU value would be 1.00. A codon that is used less frequently than expected will have a value of less than 1.00 and a codon that is used more frequently than expected will have a value in excess of 1.00. "CM" is the geometric average of the RSCU values corresponding to each codon in a gene divided by the geometric average of the maximum possible CAI values for a gene of the same amino acid composition.

A characterized region of a target nucleic acid that comprises a codon or sequence of codons or a complement thereof can be analysed to determine, for example, a region comprising at least about six contiguous nucleotides that recurs within it (e.g., a perfect or imperfect hexanucleotide or heptanucleotide or octanucleotide or nonanucleotide repeat e.g., based on frequent codon or anti-codon usage). Such a region of at least about six contiguous nucleotides is then further analysed to determine a recurring region that comprises at least about six contiguous nucleotides at the 5' end or the 3' end. In this way a region of a target nucleic acid that comprises a codon or sequence of codons or a complement thereof sufficient for the design of a probe or primer of the invention is determined.

Alternatively, a sequence of codons or complement thereof comprising at least about 18 contiguous nucleotides that recurs within it. A sequence of codons or complement thereof comprising 18 or more contiguous nucleotides that occurs more often than expected by chance or more often than another sequence of codons or complement of similar length, is a preferred target for the design of a suitable probe or primer. It is to be understood that the recurring sequence need not be a perfect repeat and nucleotide substitutions, deletions or insertions are permitted when comparing such repeated sequences. For example, nucleotides at an end of each repeated or recurring sequence in the target nucleic acid can be at least about 60% identical or 70% identical or 80% identical or 90% identical or 95% identical.

It will be apparent from the foregoing description that the probe and/or primer may comprise at least about 18 nucleotides in length and/or have a sequence that is at least about 60% identical to a contiguous sequence of nucleotides that has been characterized previously in nucleic acid derived from the organism or related organism. Preferably, at least about 60% or at least about 70% or at least about 80% or at least about 90% or at least about 95 or 99% identity occurs between the 5'-end and/or the 3'-end of a primer and its complementary target nucleic acid. For example, the probe or primer may include a region of non-complementarity and a region of complementarity with the target nucleic acid, a region of non-complementarity interspersed with a region of complementarity, or a region of complementarity interspersed with a region of non-complementarity. For example, a nucleotide or sequence of nucleotides in the probe or primer that will not hybridize to the codon or sequence of codons or complement thereof (i.e., it is not complementary in this region) can be flanked on at least one side, and preferably two sides by nucleotides, with a nucleotide or sequence of nucleotides that will hybridize to the codon or sequence of codons or complement thereof (i.e., it is complementary in this region).

The present inventors have shown that a primer comprising 18-24 nucleotides hybridizes to a sufficient number of genomic sites in nucleic acid from an organism to amplify a plurality of amplification products when the probe or primer is used in an amplification reaction. Longer probes/primers are contemplated such as, for example, probes/primers comprising at least about 30 or 35 nucleotides.

At least about 50% of the length of a probe or primer can comprise a sequence of codons or complementary sequence thereto. This encompasses probes and primers that comprise sequences of codons comprising at least about 60% or at least about 70% or at least about 80% or at least about 90% or at least about 99% of the full length of the probe or primer.

The present invention encompasses the use of bioinformatics means, such as, for example, the use of a mathematical algorithm or computer program, or a computer-assisted means, to identify a suitable probe or primer based on the foregoing criteria.

It is also to be understood that the present invention does not necessarily require more than a single probe or primer to be employed. For example, the present inventors have demonstrated, using a single probe or primer of the invention, amplification of a plurality of amplification products from the genome of an organism.

In one example of the invention, there is provided a method for identifying or determining a probe or primer comprising:
(i) providing or producing a probe or primer comprising a sequence of nucleotides having at least about 60% identity to a sequence of at least about 6 codons used by an organism or a related organism thereto or a complementary sequence thereto, wherein at least three contiguous nucleotides at the 3'-end and/or at the 5'-end of the probe or primer correspond or are complementary to a terminal codon in the sequence of at least 6 codons; and
(ii) selecting a probe or primer from (i) that hybridizes to a plurality of sites in nucleic acid derived from the organism under medium, and preferably high stringency conditions, wherein at least one of the plurality of sites has been uncharacterized previously for the organism.

For amplification reactions, at least three contiguous nucleotides at the 3'-end of the primer will preferably correspond to, or be complementary to, a terminal codon in the sequence of at least 6 codons.

In the various examples described herein, the present invention encompasses determining the codon or sequence of codons used by the organism or related organism thereto, such as, for example, by reference to codon preferences for the organism or related organism. Alternatively or in addition, the codon or sequence of codons is determined by an analysis of one or more open reading frames for the organism or related organism, or by reference to the actual codons in the nucleic acid of the organism or related organism being amplified or hybridized.

The present invention additionally encompasses selecting the codon or sequence of codons used by an organism or a related organism thereto. As will be apparent from the preceding description, such a selection may consist of a process comprising determining a codon preference for an organism or related organism thereto and/or determining a perfect or imperfect repetitive sequence of codons for an organism or related organism thereto.

In another example, the present invention additionally comprises providing, producing or synthesizing a probe or primer.

It will be apparent from the present disclosure that the inventors have produced a probe or primer produced to amplify nucleic acid that is specific to, but not limited in use to, an individual, an isolate of an organism, a cultivar, a strain, a variety, a species or a genus.

Accordingly, the present invention additionally provides a probe or primer comprising or consisting of a plurality of codons wherein each codon and its complement are used by an organism in accordance with the codon usage bias of the organism or a related organism. Preferably, the probe or primer comprises at least about six codons. Even more preferably, the probe or primer comprises a sequence of at least about six codons.

In one example, each codon comprises a nucleotide sequence set forth in Table 1 and/or Table 2. Where more than one different codon is used, each is preferably selected in accordance with the codon usage of the same organism.

Exemplary probes/primers are described by reference to any one of SEQ ID NOs: 1-63, 69, 70, 73, 75 and 77 to 87.

Complementary sequences, and variant sequences comprising nucleotide substitutions, deletions or insertions are encompassed by the invention, the only requirement being that they are capable of hybridizing to multiple sites in the nucleic acid of the same organism(s) as the base sequences from which they are derived. It will be apparent from the preceding description that substantial flexibility is permitted in designing such variant sequences without adversely affecting function. It is preferred that any such variant sequences satisfy the same structural criteria as the base probes/primers in comprising codons and complements thereof that are used by an organism in accordance with the codon usage bias of the organism or a related organism or in retaining at least about 60-70% identity to the target nucleic acid. It is also preferred that any nucleotide substitutions, deletions or additions relative to the base sequence occur in the internal region of the probe/primer instead of at the 5'-end or 3'-end or the 5'- or 3'-terminal codons.

The present invention also encompasses kits including a probe or primer of the invention.

The inventive method is applicable for determining relationships between individuals, isolates, cultivars, strains, varieties, species and genera, based upon the ability of the probe or primer to cross-hybridize between these entities. In accordance with this application of the inventive method there is provided a method comprising:
(i) performing a method supra to thereby identify, determine, produce or provide a probe or primer
(ii) hybridizing a probe or primer from (i) to nucleic acid from one or more individuals, isolates, cultivars, strains, varieties, species or genera; and
(iii) identifying from (ii) hybridization to polymorphic nucleic acid between two or more of said individuals, isolates, cultivars, strains, varieties, species or genera wherein said polymorphic nucleic acid indicates that the probe or primer is capable of distinguishing between individuals, isolates, cultivars, strains, varieties, species or genera or within an isolate, cultivar, strain, variety, species or genus.

The polymorphic nucleic acid may be determined previously for a predetermined probe or primer, in which case the method may comprise, for example:
(i) hybridizing a probe or primer comprising a sequence set forth in any one of SEQ ID NOs: 1-1-63, 69, 70, 73, 75 and 77 to 87 or a variant thereof or complementary sequence thereto to nucleic acid from one or more individuals, isolates, cultivars, strains, varieties, species or genera; and
(i) identifying from (i) hybridization to polymorphic nucleic acid between two or more said individuals, isolates, cultivars, strains, varieties, species or genera wherein said polymorphic nucleic acid indicates that the probe or primer is capable of distinguishing between individuals, isolates, cultivars, strains, varieties, species or genera or within an isolate, cultivar, strain, variety, species or genus.

For example, one or more hybridizations can be carried out using a single probe or primer, each hybridization comprising nucleic acid from a different individual, isolate, cultivar, strain, variety, species or genus. By comparing the hybridizing bands obtained for each sample, informative polymorphisms are detected. As will be apparent from the preceding description, this example is equally amenable to the use of any standard amplification process for determining polymorphic hybridization between the samples.

The present invention encompasses the further step of selecting a probe or primer that is capable of providing hybridization to polymorphic nucleic acid between two or more individuals, isolates, cultivars, strains, varieties, species or genera, or within an isolate, cultivar, strain, variety, species or genus.

It will be apparent from the foregoing that the present invention may be useful for any typing of an organism within or between groups, or for differentiating between individuals e.g., in forensic applications, paternity/maternity testing or for determining other genetic relationships. The skilled worker will also recognize the potential applicability of the invention for determining whether or not a sample (e.g., a food sample) comprises a foreign agent e.g., a bacterial or viral or fungal agent such as a pathogen. Furthermore, the present invention may have application in the identification of agents associated with bioterrorism or that require quarantine.

Accordingly, the present invention additionally provides a method comprising:
(i) performing a method supra to thereby identify, determine, produce or provide a probe or primer
(ii) hybridizing a probe or primer from (i) to nucleic acid from one or more individuals, isolates, cultivars, strains, varieties, species or genera;
(iii) identifying from (ii) hybridization to polymorphic nucleic acid between two or more of said individuals, isolates, cultivars, strains, varieties, species or genera wherein said polymorphic nucleic acid indicates that the probe or primer is capable of distinguishing between individuals, isolates, cultivars, strains, varieties, species or genera;
(iv) selecting a probe or primer from (iii) that hybridizes to polymorphic nucleic acid between two or more of said individuals, isolates, cultivars, strains, varieties, species or genera; and
(v) hybridizing a probe or primer from (iv) to nucleic acid derived from one or more individuals, isolates, cultivars, strains, varieties, species or genera wherein the hybridization obtained characterizes the individual(s), isolate(s), cultivar(s), strain(s), variety or varieties, species, genus or genera.

The polymorphic nucleic acid may be designed previously for a predetermined probe or primer, in which case the method may comprise, for example, hybridizing a probe or primer comprising a sequence set forth in any one of SEQ ID NOs: 1-1-63, 69, 70, 73, 75 and 77 to 87 or a variant thereof or complementary sequence thereto to nucleic acid derived from one or more individuals, isolates, cultivars, strains, varieties, species or genera wherein the hybridization obtained characterizes the individual(s), isolate(s), cultivar(s), strain(s), variety or varieties, species, genus or genera.

The present invention further encompasses comparing the hybridization obtained at (v) to the hybridization of a reference sample such as, for example, a hybridization obtained at (iii). Naturally, the same read-out for the hybridization should be employed at (v) and (iii) e.g., Southern hybridization or Northern hybridization or a specific amplification format to permit comparisons to be made. For example, should the probe or primer hybridize to nucleic acid in a test sample that is the same form as that for a reference sample, the test sample and reference sample are identified as being the same. Similarly, differences between the test sample and one or more reference samples indicate divergence or non-identity.

In yet another example, the inventive method is performed a plurality of times using different probes/primers, to thereby establish a hybridization profile. In the case of hybridizations which comprise performing an amplification reaction, such a hybridization profile may take the form of a library of amplification products obtained using the different probes or primers in one or more amplification reactions. Such a library is particularly useful for comparing to individual test samples. In this regard each of the amplification reactions may be analyzed substantially simultaneously (e.g., electrophoresed together) or separately.

The present invention further provides a method of diagnosing an infection or a disease or disorder in a subject caused by an infectious agent comprising:
(i) performing a method supra to thereby identify, determine, produce or provide a probe or primer
(ii) hybridizing a probe or primer from (i) to nucleic acid (a) from an individual related to the subject that is known to not carry the infectious agent, and (b) from the infectious agent or an organism related thereto;
(iii) identifying from (ii) hybridization to polymorphic nucleic acid between nucleic acid (a) and (b) wherein said polymorphic nucleic acid indicates that the probe or primer is capable of distinguishing between (a) and (b);
(iv) selecting a probe or primer from (iii) that hybridizes to polymorphic nucleic acid between (a) and (b); and
(v) hybridizing a probe or primer from (iv) to nucleic acid derived from a subject carrying the infectious agent or suspected of carrying the infectious agent or having the disease or disorder caused by the infectious agent or suspected of having a disease or disorder caused by the infectious agent; and
(vi) detecting the hybridization wherein hybridization to the polymorphic nucleic acid of the infectious agent indicates that the subject carries the infectious agent or has the disease or disorder caused by the infectious agent.

The polymorphic nucleic acid may be determined previously for a predetermined probe or primer, in which case the method may comprise, for example:
(i) hybridizing a probe or primer comprising a sequence set forth in any one of SEQ ID NOs: 1-63, 69, 70, 73, 75 and 77 to 87 or a variant thereof or complementary sequence thereto to nucleic acid derived from a subject carrying the infectious agent or suspected of carrying the infectious agent or having the disease or disorder caused by the infectious agent or suspected of having a disease or disorder caused by the infectious agent; and
(ii) detecting the hybridization wherein hybridization to polymorphic nucleic acid of the infectious agent indicates that the subject carries the infectious agent or has the disease or disorder caused by the infectious agent.

In one example, the method for diagnosing a disease or disorder is performed using a sample isolated previously from the subject being tested. Accordingly, the method is performed ex vivo. Accordingly, in one example, the method of diagnosis additionally comprises providing the sample.

It will be readily apparent that the methods described herein are equally applicable to distinguishing between a plurality of infectious agents.

The examples described herein are to be taken to apply mutatis mutandis to the diagnosis of any disease or disorder, e.g., cancer, wherein a diseased cell or tissue has a distinguishable expression profile or genome sequence (e.g., by virtue of a nucleotide substitution, insertion or deletion) compared to a healthy cell or tissue or a cell or tissue from a healthy organism. For example, a genetic rearrangement in a tumorigenic state can be detectable by virtue of a suitable probe or primer hybridizing differently to polymorphic nucleic acid between the rearranged and normal states. Similarly, amplifications of chromosomal regions in cancer can cause particular polymorphic hybridizations to be differentially represented between normal and diseased states.

The present invention is also useful for detecting low levels of genetic diversity or a small genetic change, such as, for example, the insertion of a transposon, into a chromosome of an organism.

BRIEF DESCRIPTION OF THE DRAWINGS

FIG. 15 is a tabular representation showing the sequence of primers of the invention that are known to hybridize to a region of the pqq gene of *Pseudomonas* strain AN5. (CCT-GAAGGCATGATCAAGT (SEQ ID NO: 160); CAGAACAGGCCCCGC GAAGT (SEQ ID NO: 161); GATTTTGCGATGAGGCGTAGG (SEQ ID NO: 162); GACGTCGAGCTCGGCGAAGT (SEQ ID NO: 163) Those residues that are complementary to a region of the gene are shown in bold, while non-complementary regions are underlined.

FIG. 32 is a schematic representation of the sequence alignment of 0.85 Kb/GOD1 (SEQ ID NO: 57)/*Pseudomonas aeruginosa* PAO1 hyperpriming fragment with *Pseudomonas aeruginosa* PAO1, complete genome (conserved hypothetical protein). See also Table 6.

FIG. 33 is a schematic representation of the sequence alignment of 0.85 Kb/GOD18 (SEQ ID NO: 78)/*Pseudomonas aeruginosa* PAO1 hyperpriming fragment with *Pseudomonas aeruginosa* PAO1, complete genome (probable outer membrane receptor for iron transport). See also Table 6.

FIG. 34 is a schematic representation of the sequence alignment of part of 1.1 Kb/GOD1 (SEQ ID NO: 57) *Escherichia coli* K12 hyperpriming fragment with *Escherichia coli* K12, complete genome (glycoside hydrolase family 3 domain protein). see also Table 6.

FIG. 35 is a schematic representation of the sequence alignment of 0.85 Kb/GOD18 (SEQ ID NO: 78)/*Escherichia coli* K12 hyperpriming fragment with *Escherichia coli* KU, complete genome (protein of unknown function CsiD) see also Table 6.

FIG. 36 is a schematic representation of the sequence alignment of part of 2.5 Kb/GOD1 (SEQ ID NO: 57)/*Bacillus subtilis* hyperpriming fragment with *Bacillus subtilis*, complete genome (ribonuclease J2, protein enhancing factor). See also Table 6.

FIG. 37 is a schematic representation of the sequence alignment of part of 1.2 Kb/GOD18 (SEQ ID NO: 78)/*Bacillus subtilis* hyperpriming fragment with *Bacillus subtilis*, complete genome (putative aldo/keto reductase dephosphocoenzyme A kinase). See also Table 6.

FIG. 38 is a schematic representation of the sequence alignment of the part of 1.1 Kb/GOD1 (SEQ ID NO: 57)/*Triticum aestivum* hyperpriming fragment with *Triticum monococcum*, subclone of genome. See also Table 7.

FIG. 39 is a schematic representation of the sequence alignment of part of 1.1 Kb/GOD18 (SEQ ID NO: 78)/ *Triticum aestivum* hyperpriming fragment with *Triticum aestivum* cultivar Renan clone BAC 930H14, complete sequence. See also Table 7.

FIG. 40 is a schematic representation of the sequence alignment of part of 1.2 Kb/GOD18 (SEQ ID NO: 78)/ *Arabidopsis thaliana* hyperpriming fragment with *Arabidopsis thaliana*, DNA chromosome 4. See also Table 7.

FIG. 41 is a schematic representation of the sequence alignment of part of 0.95 Kb/GOD1 (SEQ ID NO: 57)/*Mus musculus* hyperpriming fragment with *Mus musculus* BAC clone RP24-473A18 from chromosome 9, complete sequence. See also Table 7.

FIG. 42 is a schematic representation of the sequence alignment of part of 0.5 Kb/GOD18 (SEQ ID NO: 78)/*Mus musculus* hyperpriming fragment with mouse DNA sequence from clone RP23-206E3 on chromosome 11 which contains a novel gene, complete sequence. See also Table 7.

FIG. 43 is a schematic representation of the sequence alignment of part of 0.65 Kb/GOD1 (SEQ ID NO: 57)/*Homo sapien* hyperpriming fragment with *Homo sapiens* CTD (carboxy-terminal domain, RNA polymerase II, polypeptide A) phosphatase, subunit 1 (CTDP1) on chromosome 18. See also Table 7.

FIG. 44 is a photographic representation of a 1% agarose electrophoresis gel comprising banding patterns obtained with Hyperpriming PCR used to differentiate bacterial isolates from the gastro-intestinal tract of the honey bee. Hyperpriming DNA profiles for gram negative and gram positive bacterial isolates are shown. Top panel shows Hyperpriming DNA profile of gram negative bacterial strains taken from NSW bee colonies using primer P-Fw11. The arrows with (*) indicate that the banding patterns of these isolates are highly similar. Bottom panel shows Hyperpriming DNA profile of gram positive bacterial strains of samples from Victorian bee colonies using primers GI and M-Fw3. The banding patterns indicated by the (+) and (**) arrows also indicate that these isolates are similar respectively.

FIG. 46 is a schematic representation of a 16S rRNA partial sequence alignment of test bacterial isolate A of FIG. 45 with *Bacillus pumilus* strain SS-02. Test bacterial isolate A shows 100% sequence homology to *Bacillus pumilus* strain SS-02. (Query and Sbjct: SEQ ID NO: 164)

FIG. 47 is a schematic representation of a 16S rRNA partial sequence alignment of test bacterial isolate B of FIG. 45 with *Bacillus sphaericus* gene. Test bacterial isolate B shows 100% sequence homology to *Bacillus sphaericus*. (Query and Sbjct: SEQ ID NO: 165)

DETAILED DESCRIPTION OF THE PREFERRED EXAMPLES

Figure 1:
FIG. 1 a photographic representation showing a 1% agarose gel in which amplification products produced using primers designed to hybridize to specific regions of *Pseudomonas* strain AN5 have been electrophoresed. Each lane shows the PCR product produced using a single primer. The names of primers used are indicated above the lane. The size standard is shown on the outer left hand and right hand lanes. PCR was performed at 50° C./48° C.

By using codon usage information, the present inventors have designed a probe or primer capable of hybridizing to a plurality of sites in the genome of an organism.

Accordingly, the present invention provides a method for identifying or determining a probe or primer capable of hybridizing to a plurality of sites in a nucleic acid derived from an organism, said method comprising:
(i) determining one or more codons and the complements thereof used by the organism or a related organism in accordance with the codon usage bias of said organism or related organism; and
(ii) providing, producing, selecting or determining a probe or primer comprising or consisting of the one or more codons and/or the complements thereof, wherein the sequence of each codon is determined at (i) and wherein said probe or primer is capable of hybridizing to a plurality of sites in a nucleic acid derived from an organism.

In one example, the determined codons and complements at (i) are frequent codon(s) used by an organism or a related organism thereto. For example, two or more highly frequent codons in a target sequence may be utilized in accordance with the codon usage bias.

In another example, the determined complements at (i) are frequent anti-codon(s) used by an organism or a related organism thereto. For example, two or more highly frequent anti-codons in a target sequence may be utilized in accordance with the codon usage bias. As used herein, the term "anti-codon" is to be taken to mean a sequence complementary to the sequence of a codon in the context of a target nucleic acid.

Preferably, the probe or primer comprises the sequences of five, six, seven, eight, nine or ten codons and/or anti-codons. For example, the probe or primer comprises a sequence of at least about six codons and/or anti-codons, for example, at least about seven, eight, nine or ten codons and/or anti-codons.

In another example, providing, producing, selecting or determining a probe or primer at (ii) comprises repeating the sequences of frequent codons and/or anti-codons. Where the probe or primer comprises two or more copies of the same codon, it is preferred that the copies of the codons are not contiguous (i.e., consecutive).

For example, the method of the invention comprises providing, producing, identifying or selecting a probe or primer that comprises a plurality of codons and/or anti-codons set forth in Table 1 in relation to a single organism, e.g., for *Pseudomonas* a plurality of codons and/or anti-codons used by *Pseudomonas* and set forth in Table 1 are used to design a primer. The codons need not necessarily be different, i.e., the same codon and/or anti-codon may be used a plurality of times in the design of the probe or primer. However, should the probe or primer comprise multiple copies of the same codon and/or anti-codon it is preferred that each copy is not contiguous.

In another example, the method of the invention comprises providing, producing, identifying or selecting a probe or primer that comprises a plurality of complements of codons set forth in Table 1 in relation to a single organism. Alternatively, the method comprises providing, producing, identifying or selecting a probe or primer that comprises a sequence codons the codons comprising the sequence of a codon or complement thereof set forth in Table 1 in relation to a single organism.

In another example, the method of the invention comprises providing, producing, identifying or selecting a probe or primer that comprises a plurality of codons and/or anti-codons set forth in Table 2 in relation to a single organism.

In another example, the method of the invention comprises providing, producing, identifying or selecting a probe or primer that comprises a plurality of complements of codons and/or anti-codons set forth in Table 2 in relation to a single organism. Alternatively, the method comprises providing, producing, identifying or selecting a probe or primer that comprises a plurality of codons and/or anti-codons comprising the sequence of a codon or complement thereof set forth in Table 2 in relation to a single organism.

The present invention also encompasses a method for providing, producing, identifying or selecting a probe or primer using mixtures/combinations of codons and/or complements of codons from Table 1 and/or Table 2.

In one example, a plurality of the codons within the probe or primer encode the same amino acid. As will be apparent to the skilled artisan, the codons need not necessarily be the same due to the redundancy of the genetic code. For example, the present inventors have produced a probe or primer capable of hybridizing to a plurality of sites in the genome of a human that comprises repeats of codons that encode leucine (i.e., CTG or CTC). This hyperprimer hybridized to an increased number of sites in the genome of an organism compared to other hyperprimers produced according to the present invention.

In one example of the invention, at least about 50% of the probe or primer comprises a sequence of codons and/or anti-codons used by an organism in accordance with the codon usage bias of said organism. For example, at least about 60% or at least about 70% or at least about 80% or at least about 90% or at least about 99% of the probe or primer comprises a sequence of codons used by an organism in accordance with the codon usage bias of said organism.

The sequence of codons and/or anti-codons on which the primer design is based need not be consecutive in the probe or primer per se. For example, a probe or primer comprises a sequence of codons and/or anti-codons used by an organism that are interrupted by one or more intervening nucleotides.

Should the codon and/or anti-codon or sequence of codons and/or anti-codons used by an organism in accordance with the codon usage bias of said organism be interrupted (i.e. non-contiguous), the codons and/or anti-codons or sequence of codons and/or anti-codons need not necessarily be in the same reading frame. Accordingly, a single nucleotide may occur between two codons and/or anti-codons. For example, 2 nucleotides or 4 nucleotides or 5 nucleotides or 7 nucleotides or 8 nucleotides, and so on.

Determining Codon Usage Bias

A variety of measurements are known to the skilled artisan for quantifying codon preferences within sequence data. These measurements include codon preference bias (McLachlan et al., *Nucleic Acids Res.* 12(24), 9567-9575, 1984), frequency of optimal codons (Ikemura *J. Mol. Biol.* 146(1), 1-21, 1981; Ikemura *J. Mol. Biol.* 158(4), 573-97, 1982) codon bias index (Bennetzen & Hall, *J. Biol. Chem.* 257(6), 3026-3031, 1982), codon preference statistic (Gribskov et al., *Nucleic Acids Res.* 12(1), 539-549, 1984), and the CAI described by Sharp and Li *Nucleic Acids Res.* 15(3), 1281-1295, 1987) which includes a normalization for each amino acid to thereby exclude the confounding effects of variation in amino acid composition between different genes. Wright et al., *Gene* 87: 23-39, 1990 describe a method for estimating the effective number of codons. Shields et al., *Mol. Biol. Evol.* 5: 704-716 describe a scaled $\chi^2$ test for determining codon usage bias. Stenico et al., *Nucleic Acids Res.* 22: 2737-2446, 1993 describe a method for determining the frequency of optimal codons for determining codon usage bias. Fuglsan *APMIS* 111: 843-842, 2003 also describe two suitable methods for determining codon usage bias in an organism. The present invention encompasses the use of any such method to determine codon preference.

For example, to calculate CAI, a codon usage frequency table is prepared showing the RSCU value for each codon, based on a reference set of genes for a particular organism. The RSCU is determined using the algorithm;

$$RSCU_{ij} = \frac{X_{ij}}{\frac{1}{n_i}\sum_{j=1}^{x_i} X_{ij}}$$

wherein Xij is the frequency of occurrence of the jth codon for the ith amino acid and $n_i$ is the number of codons for the ith amino acid (ith codon family). However, any value of Xij that is zero would be arbitrarily assigned a value of 0.5. For each codon family, i.e., encoding the same amino acid, there is a maximum RSCU value, $RSCU_{imax}$, that is used to normalize the RSCU value for each codon, thereby yielding $w_{ij}$, a measure of the relative adaptiveness of a codon:

$$w_{ij}=RSCU_{ij}/RSCU_{imax}=X_{ij}/X_{imax},$$

This calculation is simplified by dividing the number of each codon by the number of the most common codon in the same codon family ($X_{imax}$), since the denominators in RSCU cancel out.

The CAI for a gene is defined as the geometric mean of the RSCU values corresponding to each codon in that gene divided by the geometric mean of the maximum possible CAI values for a gene of the same amino acid composition. A codon usage frequency table of $w_{ij}$ values compiled from the reference set of genes is used during the CAI calculation according to the algorithm:

$$CAI = \exp\left(\frac{1}{L}\sum_{i=1}^{18}\sum_{j=1}^{x_i} X_{ij}\ln w_{ij}\right)$$

wherein L is the number of codons in the gene excluding the number of AUG and UGG codons (because methionine and tryptophan are assigned only one codon each, they cannot exhibit codon bias and therefore only 18 codon families are meaningful) and wherein $X_{ij}$ refers to the actual number of each codon in the gene of interest but not in the reference set.

Bulmer *J. Evol. Biol.* 1, 15-26, 1988 proposed that any value for w smaller than 0.01 should be adjusted to 0.01 prior to further calculations.

Eyre-Walker *Mol. Biol. Evol.* 13(6), 864-872, 1996 used the CAI in another format:

$$CAI = \exp\left(\frac{\sum_i\sum_j n_{ij}X_{ij}}{\sum_i\sum_j n_{ij}}\right)$$

wherein $X_{ij}$ is a value for the relative usage of the jth codon in the ith codon family in the reference set of genes and $n_{ij}$ is the number of times the ijth codon appears in a gene of interest. This calculation of CAI retains a dependency on the amino acid composition of the gene for which it is calculated. Such a bias can be overcome by calculating the CAI as an un-weighted average across amino acids using the following algorithm:

$$CAI = \exp\left(\sum_i \frac{\sum_j n_{ij} X_{ij}}{\sum_j n_{ij}} / m\right)$$

wherein m is the number of codon families appearing in the gene.

Alternatively, codon usage bias of an organism is determined using a codon usage table. Such a codon usage table is available for a variety of organisms from the "Codon Usage Database" available from Kazusa DNA Research Institute. Furthermore, this database is useful for determining the codon usage bias of a subset of nucleic acids (e.g. a class of genes) within an organism. This database is based on Nakamura et al., *Nucleic Acids Res.* 28, 292, 2000.

Codon usage bias in an organism or a nucleotide sequence is also or alternatively determined, for example, using the graphical codon usage analyzer available from Universität Regensburg Naturwissenschaftliche Fakultät III.

Codon usage bias is indicated, for example, by a codon representing more than about 1% or 1.1% or 1.2% or 1.3% or 1.4% or 1.5% of all of the codons present in the genome of an organism or one or more expression products thereof.

In one example, the codon usage bias of an organism is determined with reference to the number of occurrences of a codon and its complement in a nucleic acid, for example, the genome of the organism or one or more expression products thereof. Accordingly, a codon, the sequence of which occurs frequently in a nucleic acid and the sequence of its complement also occurs frequently in the nucleic acid, is preferred.

Methods for determining the codon usage bias of an organism are known in the art and/or described herein. By determining the frequency at which a codon and its complement occur in a nucleic acid, a codon useful for design of a probe or primer of the invention is determined.

In one example, there are at least about 18 occurrences of the codon (and/or the complement thereof) in every 1000 codons analysed. Preferably, there are at least about 20 occurrences of the codon in every 1000 codons analysed, more preferably, at least about 22 occurrences of the codon, more preferably, at least about 25 occurrences of the codon and even more preferably, at least about 30 occurrences of the codon.

In another example, the frequency at which a codon occurs and its complement occur within a genome is approximately equivalent. For example, a codon and its complement occur in a nucleic acid at a ratio of approximately 10:3 wherein there are 10 occurrences of the codon for 3 occurrences of the complement of the codon or vice versa. Preferably, the ratio of occurrence is at least about 4:3, more preferably, 2:1 and even more preferably 1:1.

Accordingly, it is preferred that there are 4 occurrences of the codon for 3 occurrences of the complement of the codon (or vice versa), more preferably, 2 occurrences of the codon for 1 occurrences of the complement of the codon (or vice versa) and more preferably, the codon and the complement thereof occur at approximately equal frequencies.

Methods for determining the ratio of occurrence of a codon and its complement will be apparent to the skilled artisan. For example, the ratio of occurrence is ascertained by comparing the number of times a codon occurs in a given nucleotide sequence and the number of times the complement of the codon occurs in the given nucleotide sequence.

In a preferred example, a codon useful in the design of a probe or primer of the invention occurs frequently in the genome of an organism as does its complement and the frequency at which a codon occurs and its complement occur within a genome is approximately equivalent.

For example, a codon and its complement each occurring greater than about 30 times in 1000 codons and having a ratio of occurrence of at least about 10:3 is useful for designing, providing or producing a probe or primer of the invention. A codon and its complement each occurring at least about 25 times (and less than 30 times) in 1000 codons and having a ratio of occurrence of at least about 2:1 is useful for designing, determining, identifying, providing or producing a probe or primer of the invention. A codon and its complement each occurring at least about 18 times (and less than 25 times) in 1000 codons and having a ratio of occurrence of at least about 4:3 or 1:1 is useful for designing, determining, identifying, providing or producing a probe or primer of the invention.

By determining the frequency of occurrence of a codon and its complement in an organism and the ratio of occurrence of the codon and its complement, the inventors have determined a number of codons useful for designing, determining, identifying, providing or producing a probe or primer of the invention. Exemplary codons are set forth in Tables 1 and 2.

TABLE 1

PRIMARY PREFERED CODONS IN FOR PRODUCTION
OF A PROBE OR PRIMER OF THE INVENTION
(Frequency of codons per 1000)

| Organism | Codon/complement | | Codon/complement | | Codon/complement | | Codon/complement | | Codon/complement | | Codon/complement | | Codon/complement | |
|---|---|---|---|---|---|---|---|---|---|---|---|---|---|---|
| *Pseudomonas* | GCC | GGC | CGC | GCG | CTG | CAG | GTC | GAC | CTC | GAG | | | | |
| | 46.7 | 65.2 | 30.9 | 73.7 | 40.2 | 41.5 | 22.4 | 40.2 | 36.9 | 18.4 | | | | |
| *Pseudomonas Syringae* pv. Tomato str DC30000 | CTG | CAG | GCC | GGC | CGC | GCG | GTC | GAC | TTC | GAA | ATC | GAT | ACC | GGT |
| | 67.4 | 33.0 | 43.4 | 44.5 | 30.4 | 32.5 | 24.1 | 33.5 | 23.2 | 30.5 | 32.2 | 20.9 | 27.3 | 17.6 |
| *Escherichia coli* K-12 | CUG | CAG | AUC | GAU | UUC | GAA | UUU | AAA | CGC | GCG | GCC | GGC | ACC | GGU |
| | 52.8 | 28.8 | 25.0 | 32.2 | 16.6 | 39.6 | 22.4 | 33.6 | 22.0 | 33.6 | 25.5 | 29.4 | 23.4 | 24.9 |
| *Gluconobacter oxydans* | GCC | GGC | CTG | CAG | ATC | GAT | GTC | GAC | TTC | GAA | CGC | GCG | | |
| | 42.9 | 45.2 | 46.3 | 29.5 | 36.4 | 28.9 | 30.4 | 33.4 | 27.3 | 28.4 | 25.3 | 26.3 | | |
| *Klebsiella aerogenes* | CTG | CAG | GCC | GGC | CGC | GCG | ATC | GAT | GUT | GAC | | | | |
| | 68.4 | 37.5 | 45.3 | 48.8 | 37.5 | 42.8 | 34.1 | 28.0 | 22.8 | 27.6 | | | | |
| *Legionella pneumophila* | TTT | AAA | ATT | AAT | TTG | CAA | ATC | GAT | | | | | | |
| | 33.4 | 47.6 | 39.6 | 36.9 | 23.7 | 36.8 | 14.3 | 37.9 | | | | | | |
| *Vibrio* | TTT | AAA | ATT | AAU | ATC | GAT | | | | | | | | |

TABLE 1-continued

PRIMARY PREFERED CODONS IN FOR PRODUCTION
OF A PROBE OR PRIMER OF THE INVENTION
(Frequency of codons per 1000)

| Organism | Codon/ complement | Codon/ complement | Codon/ complement | Codon/ complement | Codon/ complement | Codon/ complement | Codon/ complement |
|---|---|---|---|---|---|---|---|
| fisheri | 32.5 | 50.6 | 42.4 | 40.0 | 15.7 | 46.8 | |
| Vibrio | ATC | GAT | CAA | TTG | TTT | AAA | TTC GAA CGC GCG ATT AAT |
| cholera 569B | 16.4 | 47.7 | 36.7 | 21.1 | 27.3 | 22.7 | 14.1 35.9 21.1 27.3 25.0 22.7 |
| Staphylococcus | TTT | AAA | ATT | AAT | TAT | ATA | |
| aureus | 32.2 | 68.2 | 49.3 | 46.9 | 32.1 | 20.9 | |
| Streptococcus | TTT | AAA | CTT | AAG | ACT | AGT | |
|  | 16.2 | 97.2 | 28.3 | 36.4 | 40.5 | 16.2 | |
| Bacillus | TTT | AAA | ATT | AAT | TAT | ATA | |
| anthracis | 32.4 | 64.3 | 44.5 | 44.0 | 31.9 | 22.7 | |
| Bacillus | TTT | AAA | ATT | AAT | TTC | GTT | |
| cereus | 29.4 | 57.5 | 43.0 | 42.1 | 13.1 | 45.4 | |
| Lactobacillus | ATT | AAT | TTT | AAA | ATC | GAT | TTC GAA AAC GTT TTG CAA |
| acidophilus | 46.1 | 34.9 | 29.9 | 41.8 | 16.3 | 43.3 | 15.3 43.7 22.2 35.9 18.3 35.0 |
| Plasmid RP4 | GCC | GGC | CUG | CAG | CGC | GCG | GUC GAC AUC GAU GAG CUC |
|  | 55.8 | 55.2 | 51.2 | 36.7 | 35.7 | 42.7 | 26.4 36.1 30.7 18.6 28.5 19.7 |
| Treponema | CUU | AAG | CUC | GAG | UUU | AAA | AUC GAU |
| pallidum | 18.2 | 36.6 | 16.7 | 36.7 | 28.9 | 17.2 | 15.6 30.4 |
| Bacteriophage | CAG | CUG | UUU | AAA | AUC | GAU | GAA UUC GCC GGC |
| lambda | 31.5 | 35.5 | 19.4 | 35.6 | 20.9 | 31.7 | 36.8 15.1 29.0 21.8 |
| Haemophilus | UUU | AAA | AUU | AAU | UUG | CAA | ACC GGU |
| influenzae | 32.9 | 64.8 | 38.4 | 50.4 | 15.2 | 34.2 | 14.2 30.7 |
| Hepatitis C virus | GCC | GGC | CUC | GAG | GUC | GAC | CCC GGG CUG CAG |
|  | 32.9 | 28.9 | 28.6 | 29.7 | 26.7 | 30.7 | 25.8 26.3 25.5 18.6 |
| Human immuno- | TGG | CCA | ATT | AAT | TAT | ATA | TTT AAA |
| deficiency | 30.2 | 24.3 | 18.0 | 33.0 | 17.2 | 33.3 | 16.8 32.6 |
| Virus 1 | | | | | | | |
| Saccharomyces | UUU | AAA | AAU | AUU | UUC | GAA | AUC GAU CAA UUG |
| cerevisiae | 26.1 | 42.0 | 35.8 | 30.1 | 18.3 | 45.7 | 17.1 37.7 27.3 27.1 |
| Gaeumannomyces | GCC | GGC | GTC | GAC | CTC | GAG | CTG CAG ACC GGT |
| graminis | 49.1 | 47.8 | 49.1 | 44.5 | 33.4 | 58.3 | 33.4 32.1 30.8 19.6 |
| Trichoderma | GCC | GGC | GUC | GAC | AUC | GAU | AGC GCU UCC GGA |
| pseudokoningii | 56.5 | 42.4 | 21.2 | 49.4 | 40.0 | 25.9 | 30.6 30.6 37.6 23.5 |
| Neurospora | CUC | GAG | GCC | GGC | GUC | GAC | AUC GAU UUC GAA |
| crassa | 26.9 | 42.7 | 36.2 | 29.2 | 24.9 | 32.5 | 26.6 23.9 22.2 22.3 |
| Aspergillus | GCC | GGC | GUC | GAC | ACC | GGU | CUC GAG AUC GAU CUG CAG AAC GUU |
| niger | 36.8 | 33.1 | 30.0 | 35.0 | 35.4 | 28.3 | 23.3 37.6 32.8 25.1 26.0 26.5 34.0 15.1 |
| Arabidopsis | CTT | AAG | ATC | GAT | TTC | GAA | AAA TTT CTC GAG AAC GTT |
| thaliana | 24.2 | 32.8 | 18.6 | 36.7 | 20.7 | 34.3 | 30.8 21.8 16.1 32.3 20.9 27.3 |
| Oryza sativa | CTC | GAG | GCC | GGC | GTC | GAC | CTT AAG |
|  | 24.8 | 38.7 | 30.8 | 29.5 | 19.9 | 28.0 | 14.8 31.7 |
| Triticum aestivum | GCC | GGC | CTC | GAG | CTG | CAG | GTC GAC |
|  | 32.2 | 32.3 | 25.8 | 38.2 | 21.6 | 26.0 | 21.4 29.1 |
| Mus musculus | CTG | CAG | CTC | GAG | TTC | GAA | GCC GGC |
|  | 40.1 | 34.3 | 20.2 | 39.9 | 22.1 | 26.8 | 26.5 21.8 |
| Homo sapiens | CTG | CAG | CTC | GAG | GCC | GGC | TTC GAA |
|  | 40.1 | 34.4 | 19.7 | 40.0 | 28.3 | 22.6 | 20.4 28.9 |

TABLE 2

SECONDARY PREFERED CODONS IN FOR PRODUCTION
OF A PROBE OR PRIMER OF THE INVENTION
(Frequency of codons per 1000)

| Organism | Codon/ complement | Codon/ complement | Codon/ complement | Codon/ complement | Codon/ complement | Codon/ complement | Codon/ complement |
|---|---|---|---|---|---|---|---|
| Pseudomonas | CAC | GTG | ATC | GAT | CCG | CGG | TTC GAA |
|  | 11.8 | 40.8 | 32.3 | 19.1 | 36.9 | 11.8 | 24.4 18.4 |
| Pseudomonas | CAC | GTG | CTC | GAG | AGC | GCT | |
| Syringae pv. Tomato str DC30000 | 13.6 | 30.5 | 14.8 | 25.8 | 22.6 | 13.7 | |
| Escherchia coli | AUU | AAU | CAU | AUG | AAC | CUU | |
| K-12 | 30.4 | 17.6 | 12.9 | 27.8 | 21.7 | 18.4 | |
| Gluconobacter | CCG | CGG | CTT | AAG | CGT | ACG | ACC GGT CTC GAG |
| oxydans | 35.3 | 11.1 | 15.0 | 30.9 | 16.7 | 28.1 | 19.3 24.8 18.0 22.3 |
| Klebsiella | TTC | GAA | CAC | GTG | GAG | CTC | |
| aerogenes | 19.0 | 29.6 | 14.5 | 33.8 | 30.1 | 14.7 | |
| Legionella | TTC | GAA | TAT | ATA | | | |
| pneumophila | 10.6 | 41.1 | 25.1 | 16.3 | | | |

TABLE 2-continued

SECONDARY PREFERED CODONS IN FOR PRODUCTION
OF A PROBE OR PRIMER OF THE INVENTION
(Frequency of codons per 1000)

| Organism | Codon/ complement | | Codon/ complement | | Codon/ complement | | Codon/ complement | | Codon/ complement | | Codon/ complement | | Codon/ complement | |
|---|---|---|---|---|---|---|---|---|---|---|---|---|---|---|
| Vibrio fisheri | TTC 10.8 | GAA 48.4 | AAC 19.8 | GTT 26.0 | TTG 10.9 | CAA 34.6 | CAT 15.4 | ATG 24.9 | | | | | | |
| Vibrio cholera 569B | CTT 19.5 | AAG 21.1 | CTC 10.9 | GAG 29.7 | GCC 21.9 | GGC 17.2 | CAT 18.0 | ATG 19.5 | | | | | | |
| Staphylococcus aureus | TTC 12.2 | GAA 54.9 | ATC 13.6 | GAT 45.3 | TTG 12.5 | CAA 34.2 | CAT 17.3 | ATG 23.8 | AAC 15.8 | GTT 25.1 | ACT 17.8 | AGT 18.0 | | |
| Streptococcus | ATT 8.1 | AAT 68.8 | GTC 8.1 | GAT 44.5 | | | | | | | | | | |
| Bacillus anthracis | TTC 10.4 | GAA 53.9 | ATC 11.9 | GAT 39.3 | CAA 32.3 | TTG 11.4 | CAT 15.5 | ATG 23.3 | ACT 21.0 | AGT 17.4 | | | | |
| Bacillus cereus | ATC 11.2 | GAT 39.5 | TAT 29.2 | ATA 16.0 | AAC 16.9 | GTT 24.7 | CTT 17.6 | AAG 17.4 | ACT 18.1 | AGT 16.5 | | | | |
| Lactobacillus acidophilus | ACT 37.1 | AGT 14.7 | CTT 16.8 | AAG 34.8 | | | | | | | | | | |
| Plasmid RP4 | UUC 21.5 | GAA 25.2 | CUU 11.3 | AAG 32.4 | | | | | | | | | | |
| Treponema pallidum | CAC 10.5 | GUG 38.8 | GCG 34.6 | CGC 13.5 | CUG 21.1 | CAG 25.8 | AUU 24.8 | AAU 16.8 | ACG 19.1 | CGU 18.5 | | | | |
| Bacteriophage lambda | CGC 17.4 | GCG 24.6 | AUU 23.3 | AAU 18.2 | AAC 20.1 | GUU 19.3 | ACC 20.2 | GGU 19.2 | | | | | | |
| Haemophilus influenzae | UUC 12.0 | GAA 44.0 | AUC 11.6 | GAU 42.4 | AAC 17.7 | GUU 22.1 | ACU 21.6 | AGU 17.3 | | | | | | |
| Hepatitis C virus | CAC 13.2 | GUG 30.0 | ACC 28.0 | GGU 13.5 | | | | | | | | | | |
| Human immuno-deficiency Virus 1 | TTC 10.5 | GAA 42.8 | TGT 14.4 | ACA 28.9 | CAT 17.2 | ATG 22.3 | CTG 16.4 | CAG 22.9 | | | | | | |
| Saccharomyces cerevisiae | AAC 24.9 | GUU 22.0 | UCU 23.4 | AGA 21.3 | UAU 18.8 | AUA 17.8 | | | | | | | | |
| Gaeumannomyces graminis | CTT 7.9 | AAG 49.1 | ATC 41.3 | GAT 8.5 | CGC 22.9 | GCG 19.0 | CAC 19.6 | GTG 19.6 | | | | | | |
| Trichoderma pseudokoningii | AAC 51.8 | GUU 16.5 | CUU 14.1 | AAG 54.1 | CUC 32.9 | GAG 16.5 | CUG 28.2 | CAG 18.8 | | | | | | |
| Neurospora crassa | CUU 14.2 | AAG 40.4 | CUG 18.2 | CAG 26.1 | ACC 24.9 | GGU 18.4 | AAC 27.1 | GUU 13.9 | AGC 17.4 | GCU 21.2 | CGC 17.7 | GCG 17.3 | | |
| Aspergillus niger | CUU 11.8 | AAG 34.5 | UUC 30.0 | GAA 15.6 | AGC 17.6 | GCU 25.1 | UCC 25.3 | GGA 15.2 | | | | | | |
| Arabidopsis thaliana | TCT 25.1 | AGA 18.9 | ATT 21.6 | AAT 22.3 | TTG 20.9 | CAA 19.3 | AGC 11.3 | GCT 28.5 | | | | | | |
| Oryza sativa | ATC 19.2 | GAT 25.1 | TTC 21.8 | GAA 22.0 | CTG 20.3 | CAG 20.6 | CGC 16.7 | GCG 26.9 | CAC 14.0 | GTG 23.9 | | | | |
| Triticum aestivum | CTT 13.2 | AAG 39.7 | TTG 11.9 | CAA 40.2 | ATC 25.1 | GAT 17.7 | TTC 25.5 | GAA 15.9 | | | | | | |
| Mus musculus | CTT 13.1 | AAG 33.9 | CAC 15.2 | GTG 29.0 | ATC 23.0 | GAT 21.2 | GTC 15.6 | GAC 26.6 | AGC 19.6 | GCT 20.2 | | | | |
| Homo sapiens | CTT 13.0 | AAG 32.2 | CAC 15.0 | GTG 28.6 | ATC 21.1 | GAT 22.0 | TTT 17.1 | AAA 24.0 | GTC 14.6 | GAC 25.5 | AGC 19.5 | GCT 18.6 | | |

Those codons identified as primary preferred codons for production of a probe or primer of the invention (Table 1) occur at least about 25 times in every 1000 codons in the genomes analyzed to date. Furthermore, the identified codons occur at a level approximately equivalent to that of the complement of the codon.

Those codons identified as secondary preferred codons for production of a probe or primer of the invention (Table 2) occur at least about 18 to at least about 24.9 or about times in every 1000 codons in the genomes analyzed to date. Furthermore, the identified codons occur at a level approximately equivalent to that of the complement of the codon.

Using the information provided in Table 1 and/or Table 2, the present inventors have produced a probe or primer capable of hybridizing to a plurality of sites in the genome of an organism. In particular, the present inventors designed a PCR primer based entirely on the preferred codons for *Homo sapiens* set forth in Table 1. This PCR primer produced a number of amplification products when used alone in an amplification reaction. In contrast, a primer produced using codons known to occur infrequently in the human genome did not produce any detectable amplification products when used alone in an amplification reaction.

Producing a Probe or Primer

In an example of the invention, the probe or primer comprises at least about 18 nucleotides. For example, the probe or primer comprises at least about 20 or 21 nucleotides. The present inventors have demonstrated that a probe or primer that comprises 20 nucleotides is capable of hybridizing to a sufficient number of sites in the genome of an organism, for example, to facilitate amplification of an amplification product when the probe or primer is used in a PCR reaction in the absence of another probe or primer.

Furthermore, the present inventors have shown that primers comprising at least about nucleotides hybridize to a sufficient number of sites in a gDNA sample from an organism to amplify a plurality of amplification products when the probe or primer is used in an amplification reaction. Accordingly, in an example of the invention, the probe or primer comprises at least about 25 nucleotides. For example, the probe or primer comprises at least about 30 or 35 nucleotides.

Results attained by the inventors indicate that primers comprising more nucleotides are capable of amplifying more products and longer products than a probe with fewer nucleotides. As such a probe or primer amplifies a larger number of products it is more likely that the probe or primer will amplify a specific product that is useful for, for example, diagnosing a disease or disorder or identifying an individual or a species or a genera, for example, using a method described herein.

Methods for producing/synthesizing a probe or primer of the present invention are known in the art. For example, oligonucleotide synthesis is described, in Gait (Ed) (In: Oligonucleotide Synthesis: A Practical Approach, IRL Press, Oxford, 1984). For example, a probe or primer may be obtained by biological synthesis (e.g., by digestion of a nucleic acid with a restriction endonuclease) or by chemical synthesis. For short sequences (up to about 100 nucleotides) chemical synthesis is preferable.

For longer sequences standard replication methods employed in molecular biology are useful, such as, for example, the use of M13 for single stranded DNA as described by J. Messing (1983) *Methods Enz.*, 101, 20-78.

Other methods for oligonucleotide synthesis include, for example, phosphotriester and phosphodiester methods (Narang, et al. *Meth. Enzymol* 68: 90, 1979) and synthesis on a support (Beaucage, et al. *Tetrahedron Letters* 22: 1859-1862, 1981) as well as phosphoramidate technique, Caruthers, M. H., et al., "Methods in Enzymology," Vol. 154, pp. 287-314 (1988), and others described in "Synthesis and Applications of DNA and RNA," S. A. Narang, editor, Academic Press, New York, 1987, and the references contained therein.

In an example, a probe or primer of the invention comprises one or more "locked nucleic acid" (LNA) residues. Probes or primers comprising one or more LNA residues have been previously shown to anneal to target nucleic acid at a higher temperature than a probe or primer that comprises substantially the same sequence but does not comprise LNA residues. Furthermore, incorporation of LNA into a probe or primer has been shown to result in increased signal produced in reactions in which the level of the probe or primer is limiting (Latorra et al., *Mol. Cell Probes* 17: 253-259, 2003). Production of a probe or primer comprising one or more LNA residues is described, for example, in Nielsen et al., *J. Chem. Soc. Perkin Trans.*, 1: 3423, 1997; Singh and Wengel, *Chem. Commun.* 1247, 1998.

In another example, a probe or primer of the invention comprises one or more so called "wobble" nucleotides or a universal nucleotide. A wobble nucleotide or a universal nucleotide is a nucleotide or nucleotide analogue that is capable of hybridizing to or base-pairing with more than one naturally occurring nucleotide or nucleotide analogue (i.e., the base-pairing is not Watson-Crick base pairing). For example, the nucleotide uracil is capable of hybridizing to, or pairing with, adenosine or guanine. The nucleoside inosine is capable of hybridizing to, or pairing with, adenosine, thymidine, uracil, guanine or cytosine. Accordingly, a probe or primer that comprises one or more of such wobble nucleotides (or analogues) is capable of hybridizing to an increased number of sites in a nucleic acid.

Alternative universal nucleotides are known in the art and described, for example, in Loakes *Nucleic Acids Res.* 29: 2437-2447 and references contained therein. For example, 3-nitropyrrole or 5-nitroindole have been described as capable of hybridizing to any naturally occurring nucleotide when incorporated into a probe or primer (Nichols et al., *Nature* 369: 492-493, 1994 and Loakes and Brown *Nucleic Acids Res.*, 22: 4039-4043, 1994. Furthermore, benzimidazole, 5-fluoroindole, indole and the pyrrolopyrimidine reported by Seela and Debelak, *Nucleic Acids Res.*, 28, 3224-3232, 2000 have been reported as suitable universal nucleotides.

Using the wobble or universal base uracil, the present inventors have produced a number or probes or primers of the invention. Surprisingly, these probes or primers produced different amplification products to probes or primers containing thymidine in place of uracil when used alone in a PCR reaction. Accordingly, the use of a universal nucleotide is useful for producing probes or primers capable of hybridizing to different sites in a nucleic acid compared to a probe or primer that does not comprise such a base.

In a preferred example, a universal or wobble nucleotide is not located at the 5' or 3' end of the probe or primer of the invention.

In one example, the probe or primer comprises one or more detectable markers. For example, the probe or primer comprises a fluorescent label. Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7, fluorescein (5-carboxyfluorescein-N-hydroxysuccinimide ester), and rhodamine (5,6-tetramethyl rhodamine). The absorption and emission maxima for some of these fluors are as follows: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm).

Alternatively, the probe or primer is labeled with, for example, a fluorescent semiconductor nanocrystal (as described, for example, in U.S. Pat. No. 6,306,610), a radiolabel or an enzyme (e.g. horseradish peroxidase (HRP), alkaline phosphatase (AP) or β-galactosidase).

Such detectable labels facilitate the detection of a probe or primer, for example, the hybridization of the probe or primer or an amplification product produced using the probe or primer. Methods for producing such a labeled probe or primer are known in the art. Furthermore, commercial sources for the production of a labeled probe or primer will be known to the skilled artisan, e.g., Sigma-Genosys, Sydney, Australia.

Hybridization of the Probe or Primer to a Plurality of Sites in a Nucleic Acid

The method of the present invention comprises selecting a probe or primer that hybridizes to a plurality of sites in nucleic acid derived from an organism. For example, the probe or primer is capable of hybridizing to at least about 2 sites in nucleic acid derived from an organism, (e.g., at least about 10 sites, or at least about 20 sites, or at least about 50 sites, or at least about 100 sites).

The method of the invention does not require determining the exact number of sites to which a probe or primer hybridizes in nucleic acid derived from an organism. For example, a Southern hybridization (using, for example, gDNA derived from an organism) may be performed and a probe or primer that hybridizes to multiple electrophoretically-separated fragments may be selected, wherein a probe or primer may hybridize a plurality of times to nucleic acid in the separated fragments of those "hybridizing bands" or, alternatively, only once.

Similarly, a probe or primer is considered to be capable of hybridizing to a plurality of sites in nucleic acid derived from an organism if, when it is used in an amplification reaction in the absence of another probe or primer, a plurality of amplification products is detected, i.e., the probe or primer is used alone in an amplification reaction or hybridization reaction. As will be apparent to the skilled artisan, multiple copies of the probe or primer are used in the amplification reaction. In this regard, the other probe or primer referred to supra is a probe or primer comprising a different nucleotide sequence.

The proximity of sites in template DNA to which one or more primers of the invention will anneal or hybridize is a consideration in primer design. Generally, it is preferred that the primers comprise a sequence or sequences that hybridize or anneal to sites in template nucleic acid that are within a range of about 50 base pairs (bp) to about 5 kilobase pairs (kb) apart such that amplification products are capable of being resolved using art recognized procedures, e.g., GCMS, reversed-phase chromatography, PAGE, capillary electrophoresis. Preferably, the primers comprise a sequence or sequences that hybridize or anneal to sites in template nucleic acid that are within a range of about 100 bp to about 4 kb apart, more preferably, about 250 bp to about 3.5 kb apart, more preferably, 500 bp to about 2.5 kb apart and even more preferably, about 500 bp to about 2 kb apart. For example, the present inventors have identified a primer capable of amplifying products from human genomic DNA between about 250 bp and about 2 kb in size and a primer capable of amplifying a PCR product up to about 4 kb in length. Should the amplification product be, for example, 2 kb in length, the primers have hybridized to the template nucleic acid approximately 2 kb apart. In the case of amplifications using a single primer the primer is preferably capable of hybridizing to alternate strands having such a proximity, to facilitate amplification and/or resolution.

As will be apparent to the skilled artisan, in, for example, a PCR reaction, a probe or primer is preferably capable of hybridizing to at least two sites (one on each strand of the template nucleic acid, or amplification product produced there from) that are sufficiently close to produce an amplification product. Accordingly, a probe or primer capable of producing a single amplification product when used alone in an amplification reaction is capable of hybridizing to a plurality of sites in a nucleic acid.

In one example, a probe or primer capable of hybridizing to a plurality of sites in a nucleic acid in a sample from an organism or subject is determined using Southern blotting or Northern blotting (described in, for example, Ausubel et al. (In: Current Protocols in Molecular Biology. Wiley Interscience, ISBN 047 150338, 1987) and Sambrook et al. (In: Molecular Cloning: Molecular Cloning: A Laboratory Manual, Cold Spring Harbor Laboratories, New York, Third Edition 2001)). Essentially these methods comprise immobilizing nucleic acid (fragmented or digested DNA in the case of a Southern blot; RNA in the case of a Northern blot) on a solid support, such as, for example, a membrane. A probe or primer that is labeled with a detectable marker (such as, for example, a fluorescent label (e.g., Texas Red or FITC), an enzymatic label (e.g., horseradish peroxidase or alkaline phosphatase or a radioactive label (e.g., $^{32}$P or $^{125}$I) is then brought into direct contact with the membrane for a time and under conditions sufficient for hybridization to occur (preferably, under moderate and more preferably high stringency conditions). Following washing to remove any non-specifically bound probe, the detectable marker is detected. Methods for detection will vary with the detectable marker used, but include, for example, densitometry, a radioactive or fluorescent label, or a colorimetric assay for an enzymatic label. A suitable method of detection will be apparent to the skilled artisan. A probe or primer that binds to multiple sites in a genome or transcriptome thereby producing a plurality of hybridizing bands under moderate and preferably high stringency conditions is considered to be capable of hybridizing to a plurality of sites in a nucleic acid. Such a probe or primer is useful for use in methods of the present invention, such as; for example, isolating nucleic acids of interest from an organism using an amplification reaction or detection of the level of genetic variation between individuals, species or genera.

Southern blotting is useful for, for example, determining a probe or primer capable of hybridizing to a plurality of sites in the genome of an organism. However, Southern blotting is also useful for determining a probe or primer capable of hybridizing to a plurality of sites in any nucleic acid that may be digested or fragmented (e.g., a plasmid or cDNA). A Northern blot is useful for determining a probe or primer useful for hybridizing to a plurality of sites in a sample comprising RNA (e.g., a pre-mRNA molecule, a 5'-capped mRNA, a polyadenylated mRNA, a ribosomal RNA and/or a mature or processed mRNA).

In another example, the hybridization of a probe or primer to a nucleic acid is determined using in situ hybridization, as described, for example, in Clark (In: In Situ Hybridization: Laboratory Companion, Vch Verlagsgesellschaft Mbh, ISBN: 3527308857). A probe or primer that labels a plurality of sites in an in situ hybridization is considered to be capable of hybridizing to a plurality of sites in a nucleic acid. Detection of hybridization of a probe or primer using in situ hybridization is usually performed using microscopy. Accordingly, labeling of the probe or primer with a visually detectable label (e.g., a fluorescent label) facilitates detection of hybridization. Alternatively, or in addition, labeling of a probe or primer with an enzyme useful in a colorimetric assay is useful for detecting the hybridization of the probe or primer to a plurality of sites in a nucleic acid derived from an organism.

As will be apparent to the skilled artisan, an amplification reaction is useful for determining hybridization of a probe or primer to a plurality of sites in a nucleic acid. Generally, an amplification reaction requires hybridization of a probe or primer to a target nucleic acid prior to amplification of the target nucleic acid. Accordingly, an amplification reaction or method is considered to be a hybridization reaction or method.

As discussed supra, a probe or primer that is capable of producing one or more amplification products when used in an amplification reaction with no other probe or primer is considered to be capable of hybridizing to a plurality of sites in the genome of an organism. For example, the present inventors have demonstrated using a single probe or primer of the invention to amplify a plurality of amplification products from the genome of an organism.

An amplification method useful for the method of the present invention will be apparent to the skilled artisan and includes, for example, an amplification method selected from the group consisting of PCR, RT-PCR, SDA, NASBA, TMA, CPT and QBR.

In one example, hybridization of a probe or primer to a nucleic acid is determined using PCR. Methods of PCR are known in the art and described, for example, in Dieffenbach (ed) and Dveksler (ed) (In: PCR Primer: A Laboratory Manual, Cold Spring Harbour Laboratories, N Y, 1995). Generally, for PCR, two non-complementary nucleic acid primer molecules comprising at least about 18 to 20 nucleotides are hybridized to different strands of a nucleic acid template molecule, and specific nucleic acid molecule copies of the template are amplified enzymatically. In the method of the present invention, a single nucleic acid probe or primer is useful in a PCR method due to the ability of the probe or primer to hybridize to a plurality of sites in nucleic acid derived from an organism. PCR products are detected, for example, using electrophoresis and detection with a detectable marker that binds nucleic acids. Other forms of detection, such as, for example, mass spectrometry are also contemplated. As a probe/primer of the present invention is capable of hybridizing to a plurality of sites in the genome of an organism, a single probe is capable of producing one or more PCR products.

In a preferred example, "touchdown" PCR is used to determine a probe or primer capable of hybridizing to a plurality of sites in a nucleic acid. As used herein, "touchdown PCR" shall be taken to mean a PCR reaction in which the annealing temperature used in the reaction is reduced as thermocycling proceeds. Accordingly, a PCR reaction may commence at one temperature and following an arbitrary number of cycles the annealing temperature is reduced. The reduction in temperature may occur in a single step (crude), or alternatively, in a stepwise manner.

Alternatively, one or more of the probes/primers are labeled with a detectable marker (e.g., a fluorophore) and the amplification product detected using, for example, a lightcycler (Perkin Elmer, Wellesley, Mass., USA). The present invention also encompasses quantitative forms of PCR, such as, for example, a Taqman assay. As will be apparent to the skilled artisan, a labeled probe or primer also facilitates detection of an amplification product using a method, such as, for example, electrophoresis or mass spectrometry.

In another example, hybridization of a probe or primer of the present invention is detected using RT-PCR. Methods for RT-PCR are known in the art and described, for example, in Dieffenbach (ed) and Dveksler (ed) (In: PCR Primer: A Laboratory Manual, Cold Spring Harbour Laboratories, N Y, 1995). A probe or primer is useful in such a reaction as it hybridizes to target nucleic acid under moderate and preferably, high stringency conditions, e.g., at high temperatures (for example, relative to a random hexamer). Such high, stringency conditions facilitate performing a RT reaction at increased temperature which is useful for overcoming difficulties associated with RNA secondary structure formation.

Alternatively, or in addition, the RT reaction is performed using a, for example, random hexamer or an oligo-dT probe or primer and the probe or primer of the invention is used to amplify a product from the cDNA template, using, for example, PCR.

In a further example, hybridization of a probe or primer to a nucleic acid is detected using NASBA or TMA. These two processes comprise similar steps, with the main difference being that NASBA relies upon the addition of RNase H for RNA degradation and TMA relies on the inherent RNase H activity of the reverse transcriptase used in the reaction. NASBA is described, for example, in U.S. Pat. No. 5,409,818, while TMA is described, for example, in U.S. Pat. No. 5,339,491 or 5,888,779.

Essentially, the NASBA and/or TMA method comprises hybridizing a probe or primer to a single stranded nucleic acid, such as, for example RNA, e.g., mRNA. Preferably, the probe or primer comprises the sequence of a RNA polymerase promoter or the complement thereof (e.g., a T7 promoter) at its 5' end. A cDNA copy of the RNA to which the probe or primer binds is then produced using a reverse transcriptase (such as, for example, AMV-RT or Moloney murine leukemia virus (MMLV)-RT). The RNA template is then degraded as described supra. A second probe or primer (which may comprise the same sequence as the first probe or primer with or without the RNA polymerase promoter) then binds to the cDNA and a DNA polymerase produces a copy of the cDNA. Following production of a copy of the cDNA, a functional RNA polymerase promoter is produced, thereby facilitating production of a RNA copy of the cDNA by a RNA polymerase (such as, for example a RNA polymerase of phage T3, phage φII, *Salmonella* phage sp6 or *Pseudomonas* phage gh-1). Methods such as TMA or NASBA are isothermal, thereby facilitating more simple amplification of nucleic acid.

QBR-mediated amplification is a RNA amplification method, similar to TMA or NASBA, however, this method utilizes a RNA-dependent RNA polymerase derived from bacteriophage Q-beta that can synthesize up to one billion strands of RNA product from a single template. Accordingly, this method rapidly amplifies the number of product generated from a single template.

In another example, hybridization of a probe or primer to nucleic acid is detected using SDA, described in, for example, Walker et al., *Proc. Natl Acad. Sci. USA* 89: 392-396, 1992. Essentially, SDA comprises hybridizing a probe or primer (e.g., a probe or primer of the present invention) that comprises a restriction enzyme cleavage site. The probe or primer is hybridized to a nucleic acid and a copy produced using a DNA polymerase. A restriction endonuclease that recognizes the cleavage site is then used to nick or cleave the nucleic acid. This nicking or cleavage facilitates a series of priming, extension and displacement reactions from a single template at a single temperature.

A variation of the standard SDA method is described, for example, in U.S. Pat. No. 5,270,184, in which there is no requirement for a restriction endonuclease cleavage site, rather a second primer (or set of primers) adjacent to the first primer is used.

In another example, ligase chain reaction (essentially as described in, for example, EU 320,308 and U.S. Pat. No. 4,883,750) is used to detect hybridization of a probe or primer of the present invention to a nucleic acid. In this regard, a nucleic acid associates with one or more probes or primers under conditions sufficient for hybridization to occur. Those probes/primers that hybridize to adjacent regions of the nucleic acid are linked using, for example, a ligase. Following dissociation of the probe(s)/primer(s), those that were linked (ligated) form a template for further rounds of annealing and ligation. The ligated fragments are then detected, for example, using electrophoresis, or MALDI-TOF. Alternatively, or in addition, one or more of the probes is labeled with a detectable marker, thereby facilitating rapid detection.

Alternatively, a ligase chain reaction utilizes a chemical ligation essentially as described in U.S. Pat. No. 5,616,464 or 5,767,259.

As will be apparent to the skilled artisan, a single probe or primer that produces an amplification product is capable of hybridizing to a plurality of sites in a nucleic acid (≥2 sites).

Methods for visualizing, identifying or characterizing one or more amplification products produced by a method of the present invention are known in the art and include, for example, electrophoresis or mass spectrometry. For example, an amplification product is isolated or characterized using native gel electrophoresis. As used herein the term "native gel electrophoresis" shall be taken to mean any form of electrophoresis that is performed under conditions that do not denature the secondary structure of a nucleic acid. That is, a nucleic acid that is electrophoresed retains its native size, conformation and/or charge. Accordingly, mobility of a nucleic acid using native gel electrophoresis depends upon both the charge of the nucleic acid and the hydrodynamic size of the nucleic acid.

For instance, a sample comprising an amplification product is electrophoresed using one dimensional native gel electrophoresis using a technique known in the art. In such cases, nucleic acids are separated by their molecular weight and charge. Accordingly, such a method is of use in separating a nucleic acid from a smaller nucleic acid.

Alternatively, a sample comprising an amplification product is electrophoresed using native two-dimensional gel electrophoresis. Two dimensional agarose gel electrophoresis is adapted from the procedure by Bell and Byers *Anal. Biochem.* 130:527, 1983. The first dimension gel is run at low voltage in low percentage agarose to separate DNA molecules in proportion to their mass. The second dimension is run at high voltage in a gel of higher agarose concentration in the presence of ethidium bromide so that the mobility of a non-linear molecule is drastically influenced by its shape.

Methods using denaturing conditions, e.g., in the presence of formamide, are also encompassed by the invention.

Alternatively, or in addition, an amplification product is characterized or isolated using capillary electrophoresis. Capillary electrophoresis is reviewed in, for example, Heller, Electrophoresis 22:629-43, 2001; Dovichi et al., *Methods Mol. Biol.* 167:225-39, 2001; Mitchelson, *Methods Mol. Biol.* 162:3-26, 2001; or Dolnik, *J Biochem. Biophys. Methods* 41:103-19, 1999. Capillary electrophoresis (CE) uses high voltage to separate molecules according to their size and charge. The column consists simply of a long capillary tube. A voltage gradient between the ends drives molecules of different sizes and charges through the tube at different rates.

Alternatively, an amplification product is identified and/or isolated using chromatography. For example, ion pair-reversed phase HPLC has been shown to be useful for isolating a PCR product (Shaw-Bruha and Lamb, *Biotechniques* 28:794-7, 2000).

a) Hybridization Stringency

As exemplified herein, a probe or primer of the present invention is capable of hybridizing to nucleic acid under moderate, and preferably, high stringency conditions.

For the purposes of defining the level of stringency referred to in the context of the present invention, for example, for a hybridization reaction/method, a low stringency is defined herein as being a hybridization and/or a wash carried out in 6×SSC buffer, 0.1% (w/v) SDS at 28° C., or equivalent conditions. A moderate stringency is defined herein as being a hybridization and/or washing carried out in 2×SSC buffer, 0.1% (w/v) SDS at a temperature in the range 45° C. to 65° C., or equivalent conditions. A high stringency is defined herein as being a hybridization and/or wash carried out in 0.1×SSC buffer, 0.1% (w/v) SDS, or lower salt concentration, and at a temperature of at least 65° C., or equivalent conditions. Reference herein to a particular level of stringency encompasses equivalent conditions using wash/hybridization solutions other than SSC known to those skilled in the art.

Alternatively, a low stringency is defined as being at about 40° C. to 45° C. during a hybridization, for example, in an amplification reaction, for example, approximately 45° C. A moderate to high stringency is defined as being at about 46° C. to about 65° C. during hybridization, for example, in an amplification reaction, for example, at about 55° C. or at about 57° C. or at about 58° C. or at about 59° C. or at about 60° C.

Generally, the stringency is increased by reducing the concentration of salt (e.g., SSC buffer), and/or increasing the concentration of a detergent (e.g., SDS) and/or increasing the temperature of the hybridization and/or wash and/or denaturation. Those skilled in the art will be aware that the conditions for hybridization and/or wash may vary depending upon the nature of the hybridization matrix used to support the sample DNA, and/or the type of hybridization probe used.

In determining the degree of stringency, the temperature at which a probe or primer denatures from a target nucleic acid (i.e., the melt temperature or Tm of a probe or primer) may be determined. Several methods for the determination of the Tm of a nucleic acid are known in the art. For example the Wallace Rule determines the G+C and the T+A concentrations in the oligonucleotide and uses this information to calculate a theoretical Tm (Wallace et al., *Nucleic Acids Res.* 6, 3543, 1979). Alternative methods, such as, for example, the nearest neighbor method are known in the art, and described, for example, in Howley, et al., *J. Biol. Chem.* 254, 4876, Santa Lucia, *Proc. Natl Acad. Sci.* USA, 95: 1460-1465, 1995 or Bresslauer et al., *Proc. Natl Acad. Sci. USA,* 83: 3746-3750, 1986. A temperature that is similar to (e.g., within 5° C. or within 10° C.) or equal to the proposed denaturing temperature of a probe or primer is considered to be high stringency. Medium stringency is to be considered to be within 10° C. to 20° C. or 10° C. to 15° C. of the calculated Tm of the probe or primer.

b) Nucleic Acid Derived from an Organism

A suitable nucleic acid used in a hybridization reaction can be any nucleic acid derived directly from or indirectly from the organism or related organism. For example, the nucleic acid is single-stranded or double-stranded DNA, genomic DNA, a phagemid, a plasmid, a cosmid, a chromosome, an artificial chromosome, cDNA, mRNA, a pre-mRNA molecule, a 5'-capped mRNA, a polyadenylated mRNA, a ribosomal RNA and mixtures thereof. Preferably, the nucleic acid is single-stranded or double-stranded genomic DNA, RNA, cDNA, mixtures thereof or hybrids thereof.

As will be apparent to the skilled artisan, any sample that comprises nucleic acid is suitable for determining whether or not a probe or primer produced using the method of the present invention is capable of hybridizing to a plurality of sites in the genome of an organism. For example, a suitable sample is selected from the group consisting of a cell, a tissue, a fragment of a tissue, a component of a tissue, an organ, a fragment of an organ and a component of an organ.

The nucleic acid can be in a tissue or cellular sample obtained previously from a subject.

The present invention provides biological samples that have been, for example, processed. For example, a cell that has been lyzed to facilitate detection of a nucleic acid within the cell.

Alternatively, the sample has been treated to isolate a nucleic acid or mixture thereof (e.g., gDNA) or to produce a nucleic acid (e.g., mRNA). Methods for isolating nucleic acid from a sample are known in the art and are described, for example, in Ausubel et al. (In: Current Protocols in Molecular Biology. Wiley Interscience, ISBN 047 150338, 1987) and Sambrook et al. (In: Molecular Cloning: Molecular Cloning: A Laboratory Manual, Cold Spring Harbor Laboratories, New York, Third Edition 2001). Generally, such a method comprises lyzing one or more cells in a sample (should they be present) using for example a solution with an alkaline pH or an enzyme, e.g., proteinase K. Cell components other than nucleic acid are then removed, for example, by precipitation or extraction. Then nucleic acid is precipitated and isolated.

The present inventors have demonstrated the applicability of the present invention to determining and/or producing a probe or primer capable of hybridizing to a plurality of sites in the genomic DNA of a variety of organisms, including, for example, a bacterium, a yeast, a plant (e.g., wheat) and a mammal (e.g., a mouse and a human). Accordingly, in a preferred example, the nucleic acid is gDNA.

The present invention also encompasses the use of a derivative of a naturally occurring nucleic acid e.g., cDNA. For example, RNA isolated from a sample may be reverse transcribed to produce cDNA. Methods for producing cDNA are known in the art and described, for example, in Ausubel et al. (In: Current Protocols in Molecular Biology. Wiley Interscience, ISBN 047 150338, 1987); Sambrook et al. (In: Molecular Cloning: Molecular Cloning: A Laboratory Manual, Cold Spring Harbor Laboratories, New York, Third Edition 2001); and Dieffenbach and Dveksler (eds) (In: PCR Primer: A Laboratory Manual, Cold Spring Harbour Laboratories, N Y, 1995). Generally such a method comprises using a RT enzyme to produce cDNA.

Preferably, the nucleic acid or sample comprising nucleic acid has been derived previously from a subject. Accordingly, the method of the present invention is performed in vitro or ex vivo.

Producing a Probe or Primer Using an Amino Acid Sequence

In one example, a probe or primer produced in accordance with the present invention hybridizes to nucleic acid that encodes a protein or part thereof in the organism or related organism. By providing, producing, identifying or selecting a probe or primer that hybridizes to a region of a genome that encodes a protein or part thereof, the present inventors have identified a number of probes or primers that hybridize to a plurality of regions in nucleic acid in a sample from an organism.

As will be apparent to the skilled artisan, the probe or primer need not be capable of hybridizing to a nucleic acid that encodes an entire protein.

In one example, the probe or primer is produced based on the amino acid sequence information for a protein or a part thereof in the organism, or a related organism.

In another example, the probe or primer is produced based on the amino acid sequence information for a protein or a part thereof in an unrelated organism to that from which the template nucleic acid is derived.

In yet another example, the probe or primer is produced based on the amino acid sequence for one or more proteins or parts of proteins from one or more organisms. In this regard, the amino acid sequence of a family or proteins or conserved proteins or conserved regions or parts of a number of proteins is useful for determining the sequence of a probe or primer of the invention.

In one example, the method of the invention comprises selecting the amino acid sequence. For example, such a method comprises determining a sequence of contiguous amino acids repeated in the amino acid sequence.

Alternatively, or in addition, the method comprises selecting an amino acid sequence that is conserved between proteins. Methods for determining conserved regions in a polypeptide generally compare the amino acid sequence of two or more amino acid sequences and determine regions of homology or identity.

To determine a region of identity between two or more amino acid sequences, those skilled in the art will be aware that it is possible to conduct a side-by-side comparison of the amino acid sequences. In such comparisons or alignments, differences will arise in the positioning of non-identical residues depending upon the algorithm used to perform the alignment. In particular, amino acid identities and similarities or regions of such identity or similarity are calculated using software of the Computer Genetics Group, Inc., University Research Park, Maddison, Wis., United States of America, e.g., using the GAP program of Devereaux et al., *Nucleic Acids Res*. 12, 387-395, 1984, which utilizes the algorithm of Needleman and Wunsch, *J. Mol. Biol*. 48, 443-453, 1970. Alternatively, the CLUSTAL W algorithm of Thompson et al., *Nucleic Acids Res*. 22, 4673-4680, 1994, is used to obtain an alignment of multiple sequences, wherein it is necessary or desirable to maximize the number of identical/similar residues and to minimize the number and/or length of sequence gaps in the alignment.

Alternatively, a suite of commonly used and freely available sequence comparison algorithms is provided by the National Center for Biotechnology Information (NCBI) Basic Local Alignment Search Tool (BLAST) (Altschul et al. *J. Mol. Biol*. 215: 403-410, 1990), which is available from several sources, including the NCBI, Bethesda, Md., USA. The BLAST software suite includes various sequence analysis programs including "blastp" that is used to align a known amino acid sequence with one or more sequences from one or more databases. Also available is a tool called "BLAST 2 Sequences" that is used for direct pairwise comparison of two nucleotide sequences.

In one example, the amino acid sequence selected comprises at least about 6 amino acids. For example, the amino acid sequence selected comprises at least about 7 amino acids or at least about 8 amino acids, or at least about 9 amino acids, or at least about amino acids, or at least about 11 amino acids, or at least about 12 amino acids.

Following selection of a region of amino acids of interest, a sequence of nucleotides capable of encoding the amino acid sequence is determined. Methods for determining a sequence of nucleotides capable of encoding a known amino acid sequence are known in the art. Generally, such methods comprise determining a codon capable of encoding each of the amino acids in the known amino acid sequence. The codon/s that encode each of the naturally occurring amino acids are known, and are as follows:

| Amino acid | Codons | IUB Depiction |
|---|---|---|
| Alanine | GCT GCC GCA GCG | GCN |
| Cysteine | TGT TGC | TGY |
| Aspartic | GAT GAC | GAY |
| Glutamic | GAA GAG | GAR |
| Phenylalanine | TTT TTC | TTY |
| Glycine | GGT GGC GGA GGG | GGN |
| Histidine | CAT CAC | CAY |
| Isoleucine | ATT ATC ATA | ATH |

| | | |
|---|---|---|
| Lysine | AAA AAG | AAR |
| Leucine | TTG TTA CTT CTC CTA CTG | TTR CTN YTR |
| Methionine | ATG | ATG |
| Asparagine | AAT AAC | AAY |
| Proline | CCT CCC CCA CCG | CCN |
| Glutamine | CAA CAG | CAR |
| Arginine | CGT CGC CGA CGG AGA AGG | CGN AGR MGR |
| Serine | TCT TCC TCA TCG AGT AGC | TCN AGY |
| Threonine | ACT ACC ACA ACG | ACN |
| Valine | GTT GTC GTA GTG | GTN |
| Tryptophan | TGG | TGG |
| Tyrosine | TAT TAC | TAY |

Software is also available from determining a sequence of nucleotides that encode an amino acid sequence of interest (or "reverse translate" an amino acid sequence). For example, "Reverse translate a protein" from Colorado State University, USA. This program provides each possible sequence of codons that are capable of encoding a particular amino acid sequence.

By combining the amino acid sequence information with the codon usage bias for the organism from which the template DNA is derived or a related organism, a nucleotide sequence that encodes the amino acid sequence is determined. For example, the amino acid sequence of interest is determined or selected and the codons most likely to encode those amino acids in the organism-of-interest or related organism are determined using codon usage bias information for that organism. By using the resulting nucleotide sequence or complement thereof, a primer is designed.

Methods for designing a probe or primer are known in the art and described, for example, in Dieffenbach and Dveksler (Eds) (In: PCR Primer: A Laboratory Manual, Cold Spring Harbour Laboratories, N Y, 1995). Furthermore, several software packages are publicly available that design optimal probes and/or primers capable of hybridizing to a known, i.e., characterized nucleotide sequence, e.g., Primer 3 available from the Center for Genome Research, Cambridge, Mass., USA. Such software determines a probe or primer that is, for example, unlikely to form a hairpin, or to self-prime.

Furthermore, a probe or primer (or the sequence thereof) is assessed to determine the temperature at which it denatures from a target nucleic acid (i.e., the Tm of the probe or primer). Methods of determining Tm are known in the art and described, for example, in Santa Lucia, Proc. Natl Acad. Sci. USA, 95: 1460-1465, 1995 or Bresslauer et al., Proc. Natl Acad. Sci. USA, 83: 3746-3750, 1986. Such information facilitates determining stringency conditions for hybridization and/or washing, as described supra.

Producing a Probe or Primer Using a Nucleotide Sequence

The present inventors have produced a probe or primer that is capable of hybridizing to a region of the genome of Pseudomonas strain AN5 that encodes a region of a protein and the probe or primer is also capable of hybridizing to the genome of a number of related and unrelated organisms. In particular, the probe or primer is capable of hybridizing to the genome of a number of related and unrelated organisms in sufficient locations to produce ≥1 amplification product from each of those genomes.

Accordingly, the present invention additionally provides a method for identifying or determining a probe or primer capable of hybridizing to a plurality of sites in a nucleic acid in a sample from an organism, said method comprising:
(i) providing or producing a probe or primer, the complement of which comprises a nucleotide sequence that is at least about 60% identical to 18 contiguous nucleotides of a characterized region of a nucleic acid that encodes a polypeptide or a fragment thereof or the complement thereof, subject to the proviso that at least three contiguous nucleotides at the 3' end and/or the 5' end of the probe or primer are complementary to the sequence of the characterized region; and
(ii) selecting a probe or primer that hybridizes to a plurality of sites in the nucleic acid under medium, or preferably, high stringency conditions.

In a preferred example of the invention, there is also provided a method for identifying or determining a probe or primer comprising:
(i) providing or producing a probe or primer comprising a sequence of nucleotides having at least about 60% identity to a sequence of at least about 6 codons used by an organism or a related organism thereto or a complementary sequence thereto, wherein at least three contiguous nucleotides at the 3'-end and/or at the 5'-end of the probe or primer correspond or are complementary to a terminal codon in the sequence of at least 6 codons; and
(ii) selecting a probe or primer from (i) that hybridizes to a plurality of sites in nucleic acid derived from the organism under medium, and preferably high stringency conditions.

In determining whether or not two nucleotide sequences fall within a particular percentage identity limitation recited herein, those skilled in the art will be aware that it is necessary to conduct a side-by-side comparison or multiple alignment of sequences.

In such comparisons or alignments, differences may arise in the positioning of non-identical residues, depending upon the algorithm used to perform the alignment. In the present context, reference to a percentage identity between two or more nucleotide sequences shall be taken to refer to the number of identical residues between said sequences as determined using any standard algorithm known to those skilled in the art. For example, nucleotide sequences may be aligned and their identity calculated using the BESTFIT program or other appropriate program of the Computer Genetics Group, Inc., University Research Park, Madison, Wis., USA (Devereaux et al, Nucleic Acids Res. 12, 387-395, 1984).

Alternatively, or in addition, a suite of commonly used and freely available sequence comparison algorithms is provided by the National Center for Biotechnology Information (NCBI) Basic Local Alignment Search Tool (BLAST) (Altschul et al. J. Mol. Biol. 215: 403-410, 1990), which is available from several sources, including the NCBI, Bethesda, Md. USA. The BLAST software suite includes various sequence analysis programs including "blastn," that is used to align a known nucleotide sequence with other polynucleotide sequences from a variety of databases and "blastp" used to align a known amino acid sequence with one or more sequences from one or more databases. Also available is a tool called "BLAST 2 Sequences" that is used for direct pairwise comparison of two nucleotide sequences.

In an example of the invention, the complement of the probe or primer comprises a nucleotide sequence that is at least about 70% identical to a characterized region, for example, at least about 75% identical to a characterized region, for example, at least about 80% to 85% identical to a characterized region, e.g., at least about 90 to 95% identical to a characterized region. For example, the present inventors have produced a probe or primer, the complement of which is identical to a characterized region of a nucleic acid of interest.

In an example, the method additionally comprises selecting the characterized region of a nucleic acid that encodes a polypeptide or the complement thereof.

Methods for determining a probe or primer capable of hybridizing to a characterized sequence are known in the art and/or described herein.

In one example, the method comprises selecting 18 or more nucleotides from the characterized region useful for the design and/or production of a probe or primer. For example, the probe or primer comprises at least about 20 or 21 nucleotides. Using such length for a probe or primer, the present inventors have identified and produced a number of probes or primers that are capable of hybridizing to a plurality of sites in a nucleic acid, e.g., the genome of an organism.

The present inventors have shown that primers comprising at least about 25 nucleotides hybridize to a sufficient number of sites in a nucleic acid sample from an organism to amplify a plurality of amplification products when the probe or primer is used in an amplification reaction. Accordingly, in an example of the invention, the probe or primer comprises at least about 25 nucleotides. For example, the probe or primer comprises at least about 30 or 35 nucleotides.

In one example, the method of the present invention additionally comprises selecting the characterized region.

In one example, a characterized region of a nucleic acid that encodes a polypeptide or fragment thereof is analysed to determine a region of 18 or more contiguous nucleotides that recur within the characterized region. For example, the characterized region of the genome is analysed to determine a region of 20 or more contiguous nucleotides, or 25 or more contiguous nucleotides, or 30 or more contiguous nucleotides, 35 or more contiguous nucleotides that recur within the characterized region. For example, the 18 or more contiguous nucleotides occur more often than expected by chance or more often than another region comprising a similar number of nucleotides from the characterized region. Alternatively, the 18 or more contiguous nucleotides selected occur more often than the average occurrence of sequences of the same length in the characterized nucleotide sequence.

The present inventors have demonstrated that a probe or primer of the invention is capable of hybridizing to a plurality of sites in the genome of an organism, notwithstanding the presence of a number of nucleotides that are incapable of hybridizing to the target sequence. Furthermore, the present inventors have demonstrated that a probe or primer is capable of producing one or more amplification products when used alone in an amplification reaction notwithstanding the presence of a number of nucleotides that are incapable of hybridizing to the target sequence/s.

Accordingly, the region that recurs need not be a perfect repeat. That is, insertions, deletions, substitutions and/or combinations thereof are permitted when determining the repeated region providing that the repeated region permits design of a probe or primer that satisfies the criteria discussed supra without compromising stringency.

Software, such as, for example, MACAW (Multiple Alignment Construction and Analysis Workbench; available from NCBI) is useful for determining the location of repeated elements within a nucleotide sequence.

Furthermore, the "Repeat" function of GCG (from Accelerys, San Diego, Calif., USA) is useful for determining a sequence that is repeated in a nucleotide sequence, including those repeats that only share a degree of sequence identity.

Other software packages useful for the identification of repetitive sequences include, for example "repEater" available from the Weizmann Institute, Rehovot 76100, Israel or "RepeatMasker" available from Institute for Systems Biology Seattle, Wash. 98103-8904, USA.

Furthermore, the Poly package (Bizzaro and Marx, *BMC Bioinformatics* 4: 22, 2003) is also useful for identifying regions of repeating nucleotides and determining the frequency of the repeats.

Manual analysis to determine a region of a characterized region of a nucleic acid that recurs is also encompassed by the present invention.

A region of a characterized nucleotide sequence that is repeated within said characterized sequence is useful for designing and/or producing a probe or primer of the invention. For example, the probe or primer is designed to hybridize to such a region or the complement thereof. Depending on the size of the repeating region the probe or primer may comprise the entire repeating region or only a portion of the repeating region.

In a related example, the characterized region is analyzed to determine a region of 18 or more contiguous nucleotides that is at least about 60% identical to the complement of a plurality of regions of 18 or more nucleotides that recur within the characterized region. For example, the 18 or more contiguous nucleotides is at least about 60% identical to the complement of a plurality of regions that occur more often than expected by chance or more often than another region comprising a similar number of nucleotides from the characterized region.

In a related example, the characterized region is analyzed to determine a region of 18 or more contiguous nucleotides that is at least about 60% identical to a plurality of regions of 18 or more nucleotides that recur within the characterized region. For example, the sequence of 18 or more contiguous nucleotides is at least about 60% identical to a plurality of regions that occur in the characterized region more often than expected by chance. Accordingly, the sequence of 18 or more contiguous nucleotides is at least about 60% identical to a plurality of regions that occur statistically more significantly than another region of the same characterized region.

However, statistical significance is not a requirement to select a repeating region. For example, the sequence of 18 or more contiguous nucleotides is at least about 60% identical to a plurality of regions that occur in the characterized region more often than another region comprising a similar number of nucleotides from the characterized region.

Methods for determining such a repeated region are known in the art and/or described herein.

Methods for determining the degree of identity of a nucleotide sequence to another nucleotide sequence are known in the art and described supra. Such methods are useful for determining "a region of 18 or more contiguous nucleotides that is at least about 60% identical to a plurality of regions of 18 or more nucleotides that recur within the characterized region". Furthermore, several software packages are useful for determining the degree of identity between two or more sequences. Such software packages include, for example, the following:

BLAST (basic local alignment search tool) available from NCBI. The various forms of BLAST are based on the teachings of Altschul et al., *J. Mol. Biol.* 215: 403-410, 1990 and Altschul et al., *Nucleic Acids Res.* 25: 3389-3402, 1997; FASTA, available from EMBL The FASTA nucleotide and amino acid comparison software is based on the teachings of Pearson and Lipman, *Proc. Natl Acad. Sci. USA.* 85: 2444-2448; and CLUSTAL. CLUSTAL is useful for the alignment of multiple nucleotide sequences. CLUSTAL is based on the teachings of, for example, Thompson et al., *Nucleic Acids Res.,* 22: 4673-4680, 1994.

Furthermore, software, such as, for example, MACAW (available from NCBI) is useful for not only determining the degree of identity between two or more sequences, but also the location of repeated elements within a nucleotide sequence.

In another example, a characterized region of a nucleic acid that encodes a polypeptide or the complement thereof is analysed to determine a region of 6 or more contiguous nucleotides, e.g., 8 or more contiguous nucleotides, e.g., 10 or more contiguous nucleotides, e.g., 12 or more contiguous nucleotides, e.g., 15 or more contiguous nucleotides that recur within the characterized region. The characterized region is then analyzed to determine a plurality of regions that each comprise the contiguous nucleotides at the 3' end or at the 5' end and that share at least about 60% identity.

Methods for determining a region of a characterized region of a nucleotide sequence that is repeated are known in the art and/or described herein. Furthermore, methods for determining the identity of two or more nucleotides sequences are known in the art and/or described herein.

In an example, a characterized region is analyzed to determine a region that is repeated that comprises fewer nucleotides than is used to produce a probe or primer of the invention. Following identification of such a region, the characterized sequence is again analysed to determine a plurality of regions that comprise the repeated region at either (or both) the 3' end and/or the 5' end and that share at least about 60% sequence identity. Such a shared sequence is then useful for the production of a probe or primer that is capable of hybridizing to a plurality of sites in a nucleic acid. For example, the region that is repeated provides sufficient hybridization for, for example, amplification in an amplification reaction, while the remaining regions of identity enable sufficient binding to the target nucleic acid (e.g., hydrogen bonding) to facilitate hybridization under medium, and preferable high stringency conditions.

In one example, should the initial repeating sequence occur at the 5' end of the region/s used to produce the probe or primer, the complement of the repeating region is used to produce the probe or primer of the invention.

In another example, the characterized region is analyzed using a simulated or arbitrary nucleotide sequence is used to determine a repeated sequence. For example, nucleotides are selected on the basis of the codon usage of the organism from which the template nucleic acid is derived to produce a sequence of nucleotides that are used as the basis of an analysis to determine a region of the characterized region that is repetitive. Alternatively, the guanine/cytosine content of the characterized region is used to determine the simulated or arbitrary nucleotide sequence.

In one example, a plurality of characterized regions of a nucleic acid are used to provide or produce the probe or primer. For example, the characterized regions are from one or more genes and/or one or more cDNAs and/or one or more genomes (i.e., that region of the one or more genomes that encodes a peptide, polypeptide or protein).

The present invention provides a computer program for identifying a region of a characterized nucleotide sequence useful for the production of a probe or primer of the present invention In an example, while a probe or primer of the invention need not be completely identical to the characterized region to which it is designed to hybridize or the complement thereof, at least 3 nucleotides at either the 3' end or the 5' end or both the 3' end and the 5' end of the probe or primer is identical to the characterized region or the complement thereof. Such a region of identity enables hybridization of at least one end of the primer, facilitating production of an amplification product in an amplification reaction. A probe or primer used in a hybridization assay, e.g., a Southern or Northern blot, need not necessarily comprise such a region of complementarity or identity at the terminal region.

The present invention provides a probe or primer in which at least 4 nucleotides or at least 5 nucleotides or at least 7 nucleotides or at least 9 nucleotides or at least 11 nucleotides from the 5' and/or 3' end of the probe or primer are identical to the characterized region or the complement thereof.

As used herein the term "5'-end" of a probe or primer shall be taken to mean the nucleotides at the 5' terminus of the probe or primer (i.e. the nucleotide with a free or unbound 5' position of its pentose ring) following contiguous nucleotides. A similar definition applies to the 3' end of the probe or primer, however the nucleotide in question has an free 3' position of its pentose ring.

In an example, the present inventors have produced a probe or primer of the invention that comprises at least 3 nucleotides at the 3' end of the primer that are identical to the complement of the characterized region used to produce the probe or primer.

As discussed supra, a probe or primer of the invention need not be identical to the nucleotide sequence of the characterized region of the nucleic acid to which it is designed to hybridize or the complement thereof. In one example of the invention, no more than 40% of the nucleotides of the probe or primer are non-complementary to the sequence of the characterized region (or identical to the characterized region). For example, no more than 30% or 20% or 10% or 5% of the nucleotides of the probe or primer are non-complementary to the sequence of the characterized region.

In one example, no more than 40% of the nucleotides of the probe or primer form a contiguous region that is non-complementary to the characterized region of the nucleic acid to which the probe or primer is designed to hybridize. For example, no more than 30% or 20% or 10% or 5% of the nucleotides of the probe or primer form a contiguous region that is non-complementary to the characterized region of the nucleic acid to which the probe or primer is designed to hybridize.

Alternatively, no more than 40% of the nucleotides of the probe or primer form a contiguous region that is non-identical to the characterized region of the nucleic acid used to design the probe or primer. For example, no more than 30% or 20% or 10% or 5% of the nucleotides of the probe or primer form a contiguous region that is non-identical to the characterized region of the nucleic acid used to design the probe or primer.

For example, a region of a probe or primer that comprises a number of nucleotides that are not the complement of the sequence of the characterized region also includes nucleotides that are complementary to the characterized region or identical to the characterized region, i.e., a region of non-complementarity is interspersed with a region of complementarity or identity.

For example, a nucleotide or region of nucleotides that will not hybridize to the characterized region (i.e., is not complementary) is flanked on at least one side, and preferably two sides, by nucleotides that will hybridize to the characterized sequence or the complement thereof. Should a nucleotide that is non-complementary or non-identical occur at a terminal residue of a probe or primer, it cannot be flanked on both sides by a complementary or identical residue.

In an example of the invention, a probe or primer is designed/identified/determined/produced that comprises a region identical (or complementary) to the characterized region used to design/identify/determine/produce the probe or primer or the complement thereof and that optionally comprises a region comprising both non-identical (or non-complementary) nucleotides and one or more nucleotides that are identical or complementary. For example, about 30% (or 50%, or 60%, or 70%, or 80%) of the probe or primer comprises contiguous nucleotides that are identical to the characterized region or the complement thereof.

In an example of the invention, each of the plurality of sites in the nucleic acid in a sample from an organism to which the probe or primer hybridizes comprise a nucleotide sequence having at least about 40% identity to the complement of the probe or primer.

In another example, the method additionally comprises designing a probe or primer the complement of which comprises a nucleotide sequence that is at least about 60% identical to 18 contiguous nucleotides of the characterized region of a nucleic acid that encodes a polypeptide or the complement thereof.

In an example of the invention, a probe or primer that is capable of producing one or more amplification products when used in an amplification reaction with no other probe or primer is considered to be capable of hybridizing to a plurality of sites in a nucleic acid derived from an organism. For example, the present inventors have demonstrated, using a single probe or primer of the invention, amplification of a plurality of products from the genome of an organism.

Methods for determining a probe or primer capable of hybridizing to a plurality of sites in nucleic acid derived from an organism are described supra and are to be taken to apply mutatis mutandis to the present example of the invention.

Source of the Characterized Nucleotide Sequence or Amino Acid Sequence

The present inventors have used the nucleotide sequence of a nucleic acid that encodes a protein in *Pseudomonas* strain AN5 to produce a probe or primer capable of hybridizing to a number of sites in the genome of the same organism. Accordingly, in an example, the characterized region of a nucleic acid that encodes a polypeptide or part thereof (or the complement thereof) is derived from genomic DNA or an expression product thereof from the organism from which the sample comprising the nucleic acid is derived.

As a probe or primer of the invention is designed to hybridize to a coding region of a nucleic acid, the present invention additionally provides designing a probe or primer to hybridize to a cDNA from an organism.

In addition, the present inventors have used the nucleotide sequence of a nucleic acid that encodes a part of a protein in *Pseudomonas* strain AN5 to produce a probe or primer capable of hybridizing to a number of sites in the genome of a related organism. For example, the inventors produced a probe or primer that hybridizes to a region of nucleic acid relatively conserved in *Pseudomonas syringae* tomato and *Pseudomonas fluorescens* that was also capable of amplifying nucleic acid from *Pseudomonas* strain AN5. In particular, the present inventors have found that a probe or primer designed to hybridize to a region conserved in *Pseudomonas syringae* tomato and *Pseudomonas fluorescens* was capable of hybridizing to nucleic acid from *Pseudomonas* strain AN5 and produce a PCR product despite 11 non-identical nucleotides.

Furthermore, the present inventors have designed a probe or primer using the nucleotide sequence from *Pseudomonas* strain AN5 that is capable of hybridizing to multiple locations in the genome of *P. fluorescens* and *P. putida*.

Accordingly, in another example, the characterized region of a nucleic acid that encodes a polypeptide (or the complement thereof) is derived from gDNA or an expression product thereof from an organism related to the organism from which the sample comprising the nucleic acid is derived. Related organisms include, for example organisms from two or more strains of the same species of organism, organisms from two or more subspecies of the same species of organism or organisms from two or more species of the same genera of organisms.

In another example, the characterized region of a nucleic acid that encodes a polypeptide (or the complement thereof) is derived from genomic DNA or an expression product thereof from an organism with a similar codon usage bias as the organism from which the sample comprising the nucleic acid is derived. Methods for determining codon usage bias are described herein as are sources for such information.

Accordingly, in an example, the invention provides a method for identifying or determining a probe or primer capable of hybridizing to a plurality of sites in a nucleic acid in a sample from an organism, said method comprising:
(i) providing or producing a probe or primer the complement of which comprises a nucleotide sequence that is at least about 60% identical to 18 contiguous nucleotides of a characterized region of a nucleic acid from the organism or a related organism that encodes a polypeptide or a part thereof, subject to the proviso that at least three contiguous nucleotides at the 3' end and/or the 5' end of the probe or primer are complementary to the sequence of the characterized region; and
(ii) selecting a probe or primer that hybridizes to a plurality of sites in a genome under medium, or preferably, high stringency conditions.

The present inventors have also exemplified the production of a probe or primer using the nucleotide sequence of a region of the genome of *Pseudomonas* strain AN5 to produce a probe or primer that is capable of hybridizing to a plurality of sites in the genome of a fungus, a mouse, a mouse cell line, a human cell line and a number of strains of wheat. Accordingly, the organism from which the sequence used to produce the probe or primer is derived need not necessarily be closely related to the organism from which the nucleic acid is derived.

As a consequence, another example of the invention provides for determining a probe or primer using any characterized region of nucleic acid that encodes a peptide, polypeptide or protein or fragment thereof, and selecting a probe or primer capable of hybridizing to a plurality of sites in a nucleic acid.

For example, the method comprises selecting a region of a characterized region from one or more organisms useful for the production of a probe or primer using a method described herein. This sequence is then analyzed to determine the codons in said sequence based on the codon usage bias of the organism/s from which it is derived. Using the codon usage bias of the organism from which the template nucleic acid is derived or a related organism a probe or primer is designed.

Nucleic acid from any source is considered useful for the production of a probe or primer of the present invention, provided that it encodes a polypeptide or part thereof and is characterized. Accordingly, nucleic acid or the sequence thereof from an organism selected from the group consisting of a virus, a bacterium, a eubacterium, a cyanobacterium, a yeast, a mould, a fungus, a protist, a dinoflagellate, an alga, a plant, an invertebrate and a vertebrate.

In an example of the invention, a probe or primer comprises a nucleotide sequence the complement of which comprises a nucleotide sequence that is at least about 60% identical to 18 contiguous nucleotides of a characterized region of the genome of a microorganism, for example, a region of the genome that encodes a polypeptide.

For example, the probe or primer comprises a nucleotide sequence the complement of which comprises a nucleotide sequence that is at least about 60% identical to 18 contiguous nucleotides of a characterized region of the genome of a prokaryote.

For example, the characterized region of the genome is from a bacterium, for example, a *Pseudomonas* sp. As exemplified herein, the present inventors have used a characterized region of the genome of *Pseudomonas* strain AN5 for the production of a probe or primer of the invention.

Nucleic acid from other bacteria are encompassed by the present invention.

In an example, the method for identifying a probe or primer of the present invention is performed using a computer program or a computer system or a computer memory adapted to perform the method of the invention. The present invention also encompasses a computer program or a computer adapted to perform the method for identifying a probe or primer of the present invention.

In another example, the method for determining a probe or primer of the present aspect of the invention additionally comprises providing, producing or synthesizing the identified or determined probe or primer. Methods for producing or synthesizing the probe or primer are known in the art and/or described herein.

The method of the invention is also useful for determining, producing or providing a probe or primer that is capable of hybridizing to an uncharacterized region of a nucleic acid (e.g., a genome) from an organism. Accordingly, the method of the invention provides the means to amplify, isolate and/or characterize an uncharacterized nucleic acid from an organism. For example, the method of the invention is useful for determining a probe or primer capable of hybridizing to a plurality of sites in nucleic acid from an organism with an uncharacterized genome, or alternatively, an uncharacterized/unidentified organism.

Accordingly, the present invention additionally provides a method for identifying or determining a probe or primer comprising:
(i) providing or producing a probe or primer comprising nucleotides corresponding or complementary to a codon or sequence of codons used by an organism or a related organism thereto in accordance with the codon usage bias of said organism or related organism; and
(ii) selecting a probe or primer from (i) that hybridizes to a plurality of sites in nucleic acid derived from the organism at (i) under medium, and preferably high stringency conditions, wherein at least one of the plurality of sites has been uncharacterized previously in the organism.

As will be apparent to the skilled artisan, the method of the invention is useful for producing a probe or primer capable of hybridizing to a plurality of sites in an uncharacterized nucleic acid based upon a characterized nucleic acid from a related organism.

In a preferred example of the invention, there is also provided a method for identifying or determining a probe or primer comprising:
(i) providing or producing a probe or primer comprising a sequence of nucleotides having at least about 60% identity to a sequence of at least about 6 codons used by an organism or a related organism thereto or a complementary sequence thereto, wherein at least three contiguous nucleotides at the 3'-end and/or at the 5'-end of the probe or primer correspond or are complementary to a terminal codon in the sequence of at least 6 codons; and
(ii) selecting a probe or primer from (i) that hybridizes to a plurality of sites in nucleic acid derived from the organism under medium, and preferably high stringency conditions, wherein at least one of the plurality of sites has been uncharacterized previously in the organism.

Probes or Primers that Hybridize to a Plurality of Sites in a Nucleic Acid

The present invention also provides a probe or primer comprising or consisting of a plurality of codons wherein each codon and its complement is used by an organism in accordance with the codon usage bias of the organism or a related organism.

In one example, the probe or primer comprises five, six, seven, eight, nine, or ten codons.

Preferably, the probe or primer comprises a sequence of at least about 6 codons. For example, at least about seven, eight, nine or ten codons.

In one example, each codon and its complement occurs at a frequency of at least about 18 occurrences in 1000 codons in a nucleic acid in the organism or a related organism. Preferable, the codon and its complement occur at a frequency of at least about 20 occurrences in 1000 codons, more preferably, 22 occurrences in 1000 codons, more preferably 25 occurrences in 1000 codons, more preferably 27 occurrences in 1000 codons, even more preferably 30 occurrences in 1000 codons and even more preferably 35 occurrences in 1000 codons.

In one example, a probe or primer that hybridizes to a plurality of sites in a nucleic acid is designed that comprises or consists of one or more codons (or the complement thereof) set forth in Table 1 and/or Table 2. Preferably, the probe or primer comprises a plurality of codons (and/or the complement/s thereof) set forth in Table 1 and/or Table 2 wherein all codons or complements thereof are from a single organism. More preferably, the probe or primer comprises a plurality of codons (and/or the complements thereof) set forth in Table 1 and/or Table 2 wherein all codons or complements thereof are from a single organism, wherein the same codon does not occur consecutively in the probe or primer.

Furthermore, the present invention provides a probe or primer comprising or consisting of a sequence of codons, wherein each codon (or the complement thereof) is set forth in Table 1 and/or Table 2. Preferably, the probe or primer comprises a sequence of at least about six codons.

Preferably, the probe or primer comprises a plurality of codons (and/or the complement/s thereof) set forth in Table 1 and/or Table 2 wherein all codons or complements thereof are from a single organism. More preferably, the probe or primer comprises a plurality of codons (and/or the complement/s thereof) set forth in Table 1 and/or Table 2 wherein all codons or complements thereof are from a single organism, wherein the same codon does not occur consecutively in the probe or primer.

In one example, the probe or primer comprises or consists of a plurality of codons (and/or the complement thereof) set forth in Table 1. Preferably, the codons or complements thereof are from a single organism. In a preferred example, a single codon does not occur consecutively within a single probe or primer (i.e., a codon is not contiguous with another copy of the codon).

In another example, the probe or primer comprises or consists of a plurality of codons (and/or the complement thereof) set forth in Table 2. Preferably, the codons or complements thereof are from a single organism. In a preferred example, a single codon does not occur consecutively within a single probe or primer (i.e., a codon is not contiguous with another copy of the codon).

In yet another example, the probe or primer comprises or consists of a plurality of codons (and/or the complement thereof) the nucleotide sequence of each codon set forth in Table 1 or Table 2. Preferably, the codons or complements thereof are from a single organism.

In a preferred example, a single codon does not occur consecutively within a single probe or primer (i.e., a codon is not contiguous with another copy of the codon).

In a particularly preferred example, the codons are arranged such that a plurality of codons encoding the same amino acid are contiguous.

In one example, the probe or primer is at least about 20 nucleotides in length. Preferably, the probe or primer is at least about 21 nucleotides in length, 24 nucleotides in length, 27 nucleotides in length, 30 nucleotides in length, 33 nucleotides in length, 36 nucleotides in length or 39 nucleotides in length.

In another preferred example, the probe or primer hybridizes to a plurality of sites in a nucleic acid, for example, in the genome of an organism, under moderate, and preferably, high stringency conditions.

Furthermore, the present invention provides a probe or primer identified and/or produced using a method of the invention. For example, the probe or primer comprises a nucleotide sequence set forth in any one of SEQ ID NOs: 1-63, 69, 70, 73, 75 and 77 to 87.

In another example, the present invention provides a kit comprising a probe or primer identified, determined, produced or provided by the method of the invention. Preferably, the kit comprises a probe or primer comprising a nucleotide sequence set forth in any one of SEQ ID NOs: 1-63, 69, 70, 73, 75 and 77 to 87.

In a preferred example, the kit comprises a plurality of probes or primers of the invention.

In another example, the kit comprises one or more primers of the invention and a probe or primer that specifically hybridizes to a known sequence. Such a kit is useful for, for example, identifying, isolating or amplifying a nucleic acid adjacent to the hybridization site of the probe or primer that specifically hybridizes to a known sequence. For example, the kit is useful for identifying a nucleic acid into which a transgene has inserted.

In yet another example, the kit is packaged with an enzyme to facilitate amplification of a nucleic acid using the probe or primer. For example, the kit comprises a DNA polymerase, a RNA polymerase and/or a ligase.

The kit may also be packaged with reagents and/or buffers required for hybridization, washing or performing an amplification reaction using a probe or primer of the invention.

Optionally, the kit is packaged with instructions for use.

Providing the Probe or Primer

In one example, the method of the invention additionally provides a method comprising:

(i) performing a method supra to thereby design identify or determine a probe or primer; and (ii) providing the probe or primer or the structure of the probe or primer such as, for example, in a paper form, machine-readable form, or computer-readable form.

Naturally, for a probe or primer that is known albeit not previously tested for its function using a screen provided by the present invention, determination of the structure of the probe or primer is implicit in step (i) supra. This is because the skilled artisan will be aware of the structure of the probe or primer at the time of performing the screen.

As used herein, the term "providing the probe or primer" shall be taken to include any chemical and/or recombinant and/or synthetic means for producing said probe or primer or alternatively, the provision of a probe or primer that has been previously synthesized by any person or means.

In a preferred example, the probe or primer or the structure of the probe or primer is provided with an indication as to its use, e.g., as determined by a method described herein.

A further example of the present invention provides a process for producing a probe or primer supra, said method comprising:

a process for identifying or determining a probe or primer supra, said method comprising:

(i) performing a method as described herein to thereby identify or determine a probe or primer;

(ii) optionally, determining the structure of the probe or primer;

(iii) optionally, providing the structure of the probe or primer such as, for example, in a paper form, machine-readable form, or computer-readable form; and (iv) providing the probe or primer.

In a preferred example, the synthesized probe or primer or the structure of the probe or primer is provided with an indication as to its use, e.g., as determined by a method described herein.

Determining Relationships Using a Probe or Primer of the Invention

The present inventors have used a probe or primer produced using the method of the present invention to generate an amplification product that is specific to an individual, an isolate of an organism, a cultivar, a strain, a variety a species and a genus.

The present invention also encompasses the identification of an organism, a cultivar, a strain, a variety a species or a genus based on the hybridization bands produced using, for example, Southern or Northern hybridization or using an amplification method.

To perform such a method, a probe or primer capable of distinguishing between individuals, isolates, cultivars, strains, varieties, species or genera or within an isolate, cultivar, strain, variety, species or genus is identified.

Accordingly, the present invention additionally provides a method comprising:

(i) performing a method supra to thereby identify, determine, provide or produce a probe or primer;

(ii) hybridizing a probe or primer from (i) to nucleic acid from one or more individuals, isolates, cultivars, strains, varieties, species or genera; and (iii) identifying from (ii) hybridization to polymorphic nucleic acid between two or more of said individuals, isolates, cultivars, strains, varieties, species or genera wherein said polymorphic nucleic acid indicates that the probe or primer is capable of distinguishing between individuals, isolates, cultivars, strains, varieties, species or genera or within an isolate, cultivar, strain, variety, species or genus.

The polymorphic nucleic acid may be determined previously for a predetermined probe or primer, in which case the method may comprise, for example:
(i) hybridizing a probe or primer comprising a sequence set forth in any one of SEQ ID NOs: 1-63, 69, 70, 73, 75 and 77 to 87 or a variant thereof or complementary sequence thereto to nucleic acid from one or more individuals, isolates, cultivars, strains, varieties, species or genera; and
(ii) identifying from (i) hybridization to polymorphic nucleic acid between two or more of said individuals, isolates, cultivars, strains, varieties, species or genera wherein said polymorphic nucleic acid indicates that the probe or primer is capable of distinguishing between individuals, isolates, cultivars, strains, varieties, species or genera or within an isolate, cultivar, strain, variety, species or genus.

Methods for determining the hybridization to polymorphic nucleic acid will be apparent to the skilled artisan. For example, a Southern blot is used, e.g., a nucleic acid (e.g., gDNA) is digested with one or more restriction endonucleases. This process is performed with nucleic acid from a number of individuals, isolates, cultivars, strains, varieties, species or genera. Following electrophoresis and transfer of each sample to a solid support a labeled probe or primer of the invention is brought into direct contact with the immobilized DNA for a time and under conditions (e.g., moderate and preferable high stringency conditions) for hybridization of the probe or primer and the DNA to occur. Following washing, the bound probe is detected. A hybridization band or band to which the probe is detected that is present in a sample from an individual, isolate, cultivar, strain, variety, species or genus and not in a sample from another individual, isolate, cultivar, strain, variety, species or genus is considered to be polymorphic.

The band may be present but may be of a different molecular weight and, as a consequence, at a different location on the blot. Accordingly, while the band is present, it is not the same as the band detected in the first sample.

Alternatively, the method comprises performing an amplification reaction with a probe or primer of the invention. For example, a probe or primer amplifies an amplification product in one sample but not in another sample. This does not necessarily mean that the probe or primer only amplifies one product that is in one sample and not in another (however, this is contemplated). Rather, the probe or primer amplifies a number of amplification products one or more of which is polymorphic (i.e. changes between two or more of said individuals, isolates, cultivars, strains, varieties, species or genera).

Preferably, the method is performed using a single probe or primer of the invention.

In one example, the present invention provides a method comprising:
(i) identifying, determining, producing or providing a probe or primer using the method of the present invention; and
(ii) performing an amplification reaction with the probe or primer from (i) with nucleic acid from one or more individuals, isolates, cultivars, strains, varieties or genera, wherein the amplification reaction is performed in the absence of another probe or primer;
(iii) identifying from (ii) amplification of polymorphic nucleic acid between two or more said individuals, isolates, cultivars, strains, varieties, species or genera wherein said polymorphic nucleic acid indicates that the probe or primer is capable of distinguishing between individuals, isolates, cultivars, strains, varieties, species or genera or within an isolate, cultivar, strain, variety, species or genus.

For example, the probe or primer is assessed for its ability to amplify polymorphic nucleic acid between two or more said individuals, isolates, cultivars, strains, varieties, species or genera in an amplification reaction in the absence of another probe or primer using an amplification reaction selected from the group consisting of PCR, RT-PCR, SDA, NASBA, TMA, CPT and QBR. Such methods are described supra and are taken to apply mutatis mutandis to the present method of the invention.

As exemplified herein, the inventors have used PCR to determine a probe or primer capable of amplifying polymorphic nucleic acid between two or more said individuals, isolates, cultivars, strains, varieties, species or genera when used in an amplification reaction in the absence of another probe or primer.

In one example, to assess the ability of a probe or primer to hybridize to polymorphic nucleic acid, one or more hybridizations is/are performed using a single probe or primer, each hybridization comprising nucleic acid from a different individual, isolate, cultivar, strain, variety, species or genus. By comparing hybridizing bands obtained for each sample, informative polymorphisms, hybridizing fragments or amplification products are detected.

By comparing results attained using nucleic acid from a variety of individuals, isolates of an organism, cultivars, strains, varieties, species or genera the present inventors have determined a probe capable of hybridizing to polymorphic nucleic acid between two or more individuals, isolates of an organism, cultivars, strains, varieties, species or genera.

For example, the present inventors have isolated a probe or primer capable of producing an amplification product specific to a strain or a cultivar or an isolate or a variety or a genetically modified form of an organism when used in an amplification reaction in the absence of another probe or primer.

In one example, a probe or primer is capable of hybridizing to polymorphic nucleic acid that is specific to a plurality of individuals, isolates of an organism, cultivars, strains, varieties, species or genera. For example, hybridization to polymorphic nucleic acid that is specific to a species may also be specific to all of the individuals (organisms) and/or cultivars and/or strains and/or varieties of that species. For example, the present inventors have identified a probe or primer that amplifies an amplification product specific for all cultivars of a species of wheat tested to date.

In one example, the method of the invention identifies a probe or primer capable of hybridizing to polymorphic nucleic acid that is specific to a strain, e.g., *Pseudomonas* strain AN5.

As exemplified herein, the present inventors have identified a probe or primer capable of hybridizing to polymorphic nucleic acid that is specific to a variety, e.g., a variety of fungus (e.g., *Gaeumannomyces graminis* var. *graminis* W2P or *G. graminis* var. *tritici* C3).

In another example, the method of the invention identifies a probe or primer capable of hybridizing to polymorphic nucleic acid that is specific to an isolate, e.g., a fungal isolate (e.g., a laboratory isolate of *G. graminis* var. *tritici* and a soil isolate of *G. graminis* var. *tritici*).

In another example, the method of the invention identifies a probe or primer capable of hybridizing to polymorphic nucleic acid that is specific to a cultivar, e.g., a cultivar of wheat (e.g., *Triticum aestivum* cv. condor).

In yet another example, the method of the invention identifies a probe or primer capable of hybridizing to nucleic acid that is specific to a species, e.g., a bacterial species (e.g., *P. fluorescens* or *P. putida* or *T. monococcum* or *T. urartu* or *T. dicoccoides* or *Aegilops squarrosa* or *A. bicornis*).

In a still further example, the method of the invention identifies a probe or primer capable of hybridizing to nucleic acid that is specific to a genus (e.g., *Pseudomonas* or *Escherichia* or *Bacillus* or *Mus* or *Homo* or *Triticum*).

The present invention additionally provides for selecting a probe or primer that is capable of hybridizing to polymorphic nucleic acid between two or more individuals, isolates, cultivars, strains, varieties, species or genera, or within an isolate, strain variety, species or genus. Accordingly, the present invention additionally provides a method comprising:
(i) performing a method supra to thereby identify, determine, produce or provide a probe or primer;
(ii) hybridizing a probe or primer from (i) to nucleic acid from one or more individuals, isolates, cultivars, strains, varieties, species or genera;
(iii) identifying from (ii) hybridization to polymorphic nucleic acid between two or more of said individuals, isolates, cultivars, strains, varieties, species or genera wherein said polymorphic nucleic acid indicates that the probe or primer is capable of distinguishing between individuals, isolates, cultivars, strains, varieties, species or genera or within an isolate, cultivar, strain, variety, species or genus; and
(iv) selecting the probe or primer capable of distinguishing between individuals, isolates, cultivars, strains, varieties, species or genera or within an isolate, cultivar, strain, variety, species or genus.

The present invention additionally accommodates for providing the probe or primer capable of distinguishing between individuals, isolates, cultivars, strains, varieties, species or genera or within an isolate, cultivar, strain, variety, species or genus. Methods for providing the probe or primer are known in the art and/or described herein.

Use of a Probe or Primer of the Invention for Typing or Identification

As will be apparent to the skilled artisan, a probe or primer identified by the method of the present invention is useful for identification of an individual, strain, cultivar, subspecies, species or genus. Accordingly, the present invention additionally provides a method comprising:
(i) performing a method supra to thereby identify, determine, produce or provide a probe or primer;
(ii) hybridizing a probe or primer from (i) to nucleic acid from one or more individuals, isolates, cultivars, strains, varieties, species or genera;
(iii) identifying from (ii) hybridization to polymorphic nucleic acid between two or more of said individuals, isolates, cultivars, strains, varieties, species or genera wherein said polymorphic nucleic acid indicates that the probe or primer is capable of distinguishing between individuals, isolates, cultivars, strains, varieties species or genera;
(iv) selecting a probe or primer from (iii) that hybridizes to polymorphic nucleic acid between two or more of said individuals, isolates, cultivars, strains, varieties, species or genera; and
(v) hybridizing a probe or primer from (iv) to nucleic acid derived from one or more individuals, isolates, cultivars, strains, varieties, species or genera wherein the hybridization obtained characterizes the individual(s), isolate(s), cultivar(s), strain(s), variety or varieties, species, genus or genera.

The present invention additionally provides a method comprising:
(i) hybridizing a probe or primer comprising a sequence set forth in any one of SEQ ID NOs: 1-63, 69, 70, 73, 75 and 77 to 87 or a variant thereof or complementary sequence thereto to nucleic acid from one or more individuals, isolates, cultivars, strains, varieties, species or genera;
(ii) identifying from (ii) hybridization to polymorphic nucleic acid between two or more of said individuals, isolates, cultivars, strains, varieties, species or genera wherein said polymorphic nucleic acid indicates that the probe or primer is capable of distinguishing between individuals, isolates, cultivars, strains, varieties, species or genera;
(iii) selecting a probe or primer from (iii) that hybridizes to polymorphic nucleic acid between two or more of said individuals, isolates, cultivars, strains, varieties, species or genera; and
(iv) hybridizing a probe or primer from (iv) to nucleic acid derived from one or more individuals, isolates, cultivars, strains, varieties, species or genera wherein the hybridization obtained characterizes the individual(s), isolate(s), cultivar(s), strain(s), variety or varieties, species, genus or genera.

In one example, the method comprises comparing the hybridization product obtained at (v) to the hybridization of a reference sample, e.g., a hybridization obtained at (iii). Accordingly, the present invention additionally provides a method comprising:
(i) performing a method supra to thereby identify, determine, produce or provide a probe or primer;
(ii) hybridizing a probe or primer from (i) to nucleic acid from one or more individuals, isolates, cultivars, strains, varieties, species or genera;
(iii) identifying from (ii) hybridization to polymorphic nucleic acid between two or more of said individuals, isolates, cultivars, strains, varieties, species or genera wherein said polymorphic nucleic acid indicates that the probe or primer is capable of distinguishing between individuals, isolates, cultivars, strains, varieties, species or genera;
(iv) selecting a probe or primer from (iii) that hybridizes to polymorphic nucleic acid between two or more of said individuals, isolates, cultivars, strains, varieties, species or genera;
(v) hybridizing a probe or primer from (iv) to nucleic acid derived from one or more individuals, isolates, cultivars, strains, varieties, species or genera;
(vi) hybridizing a probe or primer from (iv) to nucleic acid derived from one or more other individuals, isolates, cultivars, strains, varieties, species or genera
(vii) comparing the hybridization obtained at (v) and (vi) to thereby characterize and/or identify the individual(s), isolate(s), cultivar(s), strain(s), variety or varieties, species, genus or genera.

As will be apparent to the skilled artisan, a similar result attained with the test sample (vi) and the control sample (vi) indicates that the test sample is the same or similar to or related to the control sample.

Naturally, the same read-out for the hybridization should be employed when comparing the hybridization attained with two or more samples, e.g., Southern hybridization or Northern hybridization or a specific amplification format to permit comparisons to be made.

Furthermore, it is preferred that similar hybridization and/or amplification conditions are used. For example, the same hybridization/annealing and/or washing temperatures and/or conditions are used to permit comparisons to be made.

Additionally, in the case of an amplification reaction, it is preferred that the same amplification enzyme, e.g., DNA or RNA polymerase, is used to permit comparisons to be made.

In one example, the control has been identified using the method of the present invention. Alternatively, the control has been identified using another method known in the art.

Any sample comprising nucleic acid from the control sample is useful for the method of the present invention. However, should the identification be based upon, for example, cDNA or mRNA a cell or tissue or component thereof that expresses the nucleic acid required for identification is preferred.

Each of the amplification reactions performed in the present method of the invention may be performed simultaneously or substantially simultaneously. Such a format will facilitate side-by-side comparison of an amplicon produced from a test sample and from a control sample. However, this need not be the case. For example, the amplification reaction using nucleic acid from the control sample is performed in advance of the test sample. Such a control sample may then be used to determine the identity of a number of test samples.

The present invention is also useful as a component of a test or assay for determining the identity of an organism, cultivar, strain, variety, species or genus. For example, a subject is assessed for a phenotypic, biochemical, anatomical or physiological characteristic and the method of the invention is also performed. Accordingly, the method of the invention is additionally useful for confirming the identity of an organism, cultivar, strain, variety, species or genus.

As will be apparent to the skilled artisan, the present invention may equally be performed using a plurality of control samples to facilitate identification of an individual, an isolate of an organism, a cultivar, a strain, a variety, a species or a genus. For example, should an organism, cultivar, strain, variety, species or genus be determined to be similar to a plurality of other organisms, cultivars, strains, varieties, species or genera by methods other than the method of the invention, the method of the invention is useful for determining the comparing the test sample and the plurality of related samples.

In yet another example, the inventive method is performed a plurality of times using different probes/primers, to thereby establish a hybridization profile. In the case of hybridizations which comprise performing an amplification reaction, such a hybridization profile may take the form of a library of amplification products obtained using the different probes or primers in one or more amplification reactions. Such a library is particularly useful for comparing to individual test samples. In this regard, each of the amplification reactions may be analyzed substantially simultaneously (e.g., electrophoresed together) or separately.

In one example, the method of the invention additionally comprises producing or providing the library of hybridization products or amplification products.

Accordingly, the present invention additionally provides a method comprising:

(i) performing a method supra to thereby identify, determine, produce or provide a probe or primer;

(ii) hybridizing a probe or primer from (i) to nucleic acid from one or more individuals, isolates, cultivars, strains, varieties, species or genera;

(iii) identifying from (ii) hybridization to polymorphic nucleic acid between two or more of said individuals, isolates, cultivars, strains, varieties, species or genera wherein said polymorphic nucleic acid indicates that the probe or primer is capable of distinguishing between individuals, isolates, cultivars, strains, varieties, species or genera;

(iv) selecting a probe or primer from (iii) that hybridizes to polymorphic nucleic acid between two or more of said individuals, isolates, cultivars, strains, varieties, species or genera; and (v) producing a library of hybridization profiles for one or more individuals, isolates of an organism, cultivars, strains, varieties, species or genera by a method comprising hybridizing a probe or primer from (iv) to nucleic acid derived from one or more individuals, isolates, cultivars, strains, varieties, species or genera wherein the hybridization obtained characterizes the individual(s), isolate(s), cultivar(s), strain(s), variety or varieties, species, genus or genera;

(vi) hybridizing a probe or primer from (iv) to nucleic acid derived from one or more individuals, isolates, cultivars, strains, varieties, species or genera; and (vii) comparing the hybridization obtained at (vi) to the library of hybridization profiles at (vi) to thereby characterize and/or identify the individual(s), isolate(s), cultivar(s), strain(s), variety or varieties, species, genus or genera.

As will be apparent to the skilled artisan, the method comprises determining a hybridization profile in the library that is similar to that for the test sample to thereby characterize and/or identify the individual(s), isolate(s), cultivar(s), strain(s), variety or varieties, species, genus or genera.

Furthermore, the present invention provides a method of identification that utilizes a library that has been previously prepared.

In an example, the library comprises information concerning hybridization profiles, e.g., amplification products for or specific to one or more individuals, isolates of an organism, cultivars, strains, varieties, species or genera. For example, the library comprises images or data characterizing the hybridization profiles and/or amplification product's in the library.

In one example, the information in the library is stored in a machine-readable form, for example using a computer or a computer program. Such a computer or computer program facilitates the rapid identification of an individual, an isolate of an organism, a cultivar, a strain, a variety, a species or a genus.

The present invention provides a library produced by or for use in the method of the present invention.

In an example, a method of identification according to the present invention comprises performing a plurality of hybridization/amplification reactions each with a single probe or primer capable of hybridizing to polymorphic nucleic acid characteristic of, for example, an individual or a species or a genus, and analyzing the results of each of the amplification reactions. In this regard each of the amplification reactions may be analyzed substantially simultaneously (e.g., electrophoresed together) or separately. Such a method increases the number of amplicons produced and, as a consequence, the number of amplicons specific to an individual, an isolate of an organism, a cultivar, a strain, a variety, a species or a genus. Means for analysis of an amplification product or a hybridization product are known in the art and/or described herein.

Using a number of probes or primers of the invention, the present inventors have been able to putatively identify a specific cultivar of wheat from 13 different cultivars. Furthermore, the inventors have been able to identify related cultivars, showing that the method of the invention is useful for identifying polymorphic nucleic acid that is associated with a trait of interest. Identification of such polymorphic nucleic acid is useful for determining a subject that will or does comprise the trait of interest.

In another example, one or more amplification reactions are produced and digested using, for example, a restriction endonuclease. Methods for digesting nucleic acid with a restriction endonuclease are known in the art and described, for example, in Ausubel et al. (In: Current Protocols in Molecular Biology. Wiley Interscience, ISBN 047 150338, 1987) and Sambrook et al. (In: Molecular Cloning: Molecular Cloning: A Laboratory Manual, Cold Spring Harbor Laboratories, New York, Third Edition 2001). Such a method produces a larger number of fragments for the identification of the source of a sample. As will be apparent to the skilled artisan, a restriction endonuclease that cleaves DNA regularly (e.g., a 4 base cutter) produces a larger number of smaller fragments, while an irregular cutter produces fewer fragments.

The present method potentially has application in, for example, identifying an individual, e.g., for forensics. For example, the method comprises using one or more probes or primers of the invention to amplify one or more amplification products or hybridize to nucleic acid in or from a sample and comparing these results to those attained with the same probe/s or primer/s from a subject. Such an assay facilitates determination of whether or not the sample is from the subject.

The method is additionally useful for, for example, determining whether or not an individual, an isolate of an organism, a cultivar, a strain, a variety, a species or a genus is known or related to another individual, isolate of an organism, cultivar, strain, variety, species or genus. Accordingly, the method is anticipated to be useful for, for example, paternity/maternity testing.

The skilled worker will recognize that a method useful for the identification of an individual, an isolate of an organism, a cultivar, a strain, a variety, a species or a genus is also useful for, for example, determining whether or not a sample comprises an individual, an isolate of an organism, a cultivar, a strain, a variety, a species or a genus of interest. For example, the method of the invention is useful for determining whether or not a sample (e.g., a food sample) comprises an agent associated with a disease or disorder (e.g., a bacterial species that causes disease or disorder in humans).

Accordingly, in one example, performing a hybridization reaction using the probe or primer and nucleic acid from an individual, an isolate of an organism, a cultivar, a strain, a variety, a species or a genus to be identified comprises performing the hybridization reaction with a sample comprising (or thought to comprise) nucleic acid from an individual, an isolate of an organism, a cultivar, a strain, a variety, a species or a genus to be identified.

In an example of the invention, the method additionally comprises providing the sample. For example, the sample is a soil sample, or a food sample, amongst others.

The methods described supra for identifying an individual, isolate of an organism, cultivar, strain, variety, species or genus are to be taken to apply mutatis mutandis to the identification of an individual, isolate of an organism, cultivar, strain, variety, species or genus in a sample.

Furthermore, the present invention is expected to have application in the identification of agents associated with bioterrorism or that require quarantine. For example, a sample derived from a package is analyzed using the method of the present invention to determine the source of any nucleic acid in said sample. For example, an amplification reaction is performed with nucleic acid from a source and another amplification reaction is performed with nucleic acid from *Bacillus anthracis* to determine whether or not the source comprises nucleic acid from *Bacillus anthracis*.

Furthermore, the present invention is useful for identification of, for example, a plant of interest, for example, for identifying a plant that is protected by a plant variety right or a patent.

Alternatively, the method is useful for determining whether or not a plant or variety thereof is in fact new, and suitable for a plant variety right or patent.

Furthermore, as the method of the invention detects genetic diversity, a hereditary disease may be detected using a probe or primer of the invention. For example, a probe or primer of the invention that detects a polymorphism associated with a hereditary disease is useful for diagnosing or determining a subject that suffers from or will develop the disease.

Alternatively, or in addition, the method comprises isolating a hybridizing band or amplification product identified using a method of the invention and characterizing the nucleotide sequence of said hybridizing band or amplification product, for example, sequencing.

As the present invention is useful for detecting low levels of genetic diversity between, for example, individuals, cultivars, varieties, species or genera, it will be apparent to the skilled artisan that the invention is useful for monitoring the level of genetic diversity in a population.

For example, by comparing the hybridization profile (or hybridization product/s or amplification product/s) obtained from one individual in a population to the hybridization profile (or hybridization product/s or amplification product/s) obtained from another one or more individuals from the population.

The performance of a number of hybridization/amplification reactions each with a different probe or primer aids in determining the degree of relatedness of two or more individuals.

Preferably, both of the individuals of the population are related, e.g., of the same species, or subspecies, or variety.

This method is useful for, for example, monitoring the level of genetic diversity and/or inbreeding in stock populations, for example, cattle, sheep or fish. For example, the genetic diversity of a breeding population of animals is monitored using the method of the present invention. Should the population not comprise sufficient genetic diversity, measures may be taken to increase said diversity, for example, a new stud, or a number of new breeding animals, are introduced into the population.

Accordingly, the method is also useful as a component of a process for maintaining genetic diversity within a population. For example, the method is useful for monitoring an inbred (e.g., endangered population) and determining the level of genetic diversity. Such a method is useful in ensuring that the inbred population maintains a level of genetic diversity required for survival.

Furthermore the method is useful for determining whether or not a population is isogenic. For example, in research, for mapping a mutation or polymorphism associated with a disease or disorder. Such studies often involve mating two inbred populations to identify a region of the genome associated with the disease or disorder. The method of the invention provides a rapid means for determining when a population is substantially isogenic (i.e., a subject in the population comprises the region of nucleic acid of interest from one of the inbred lines and the remainder of its genomic DNA is from the second inbred line).

The present invention also encompasses a probe or primer that is specific for an individual, an isolate of an organism, a cultivar, a strain, a variety, a species or a genus identified using the method of the present invention. For example, the probe or primer comprises a nucleotide sequence set forth in any one of SEQ ID NOs: 1-63, 69, 70, 73, 75 and 77 to 87.

Methods of Diagnosis

As will be apparent to the skilled artisan, a method capable of identifying an individual, an isolate of an organism, a cultivar, a strain, a variety, a species or a genus is also anticipated to be useful for, for example, diagnosing a disease or disorder, for example, a disease or disorder caused by an infectious agent. Accordingly, the present invention further provides a method of diagnosing an infection or a disease or disorder in a subject caused by an infectious agent comprising:
(i) performing a method supra to thereby identify, determine, produce or provide a probe or primer;
(ii) hybridizing a probe or primer from (i) to nucleic acid (a) from an individual related to the subject that is known to not carry the infectious agent or from a sample from the subject that is known not to carry the infectious agent or nucleic acid there from, and (b) from the infectious agent or an organism related thereto;
(iii) identifying from (ii) hybridization to polymorphic nucleic acid between nucleic acid (a) and (b) wherein said polymorphic nucleic acid indicates that the probe or primer is capable of distinguishing between (a) and (b);
(iv) selecting a probe or primer from (iii) that hybridizes to polymorphic nucleic acid between (a) and (b); and
(v) hybridizing a probe or primer from (iv) to nucleic acid derived from a subject carrying the infectious agent or suspected of carrying the infectious agent or having the disease or disorder caused by the infectious agent or suspected of having a disease or disorder caused by the infectious agent; and
(vi) detecting the hybridization wherein hybridization to the polymorphic nucleic acid of the infectious agent indicates that the subject carries the infectious agent or has the disease or disorder caused by the infectious agent.

The polymorphic nucleic acid may be determined previously for a predetermined probe or primer, in which case the method may comprise, for example:
(i) hybridizing a probe or primer comprising a sequence set forth in any one of SEQ ID NOs: 1-63, 69, 70, 73, 75 and 77 to 87 or a variant thereof or complementary sequence thereto to nucleic acid derived from a subject carrying the infectious agent or suspected of carrying the infectious agent or having the disease or disorder caused by the infectious agent or suspected of having a disease or disorder caused by the infectious agent; and
(ii) detecting the hybridization wherein hybridization to polymorphic nucleic acid of the infectious agent indicates that the subject carries the infectious agent or has the disease or disorder caused by the infectious agent.

In one example, the method comprises hybridizing one or more probes or primers to nucleic acid from a plurality of infectious organisms to facilitate identification of a probe or primer capable of hybridizing to nucleic acid polymorphic between at least two of said infectious organisms. This facilitates identification of one or more probes or primers capable of differentiating between a plurality of infectious organisms.

As will be apparent to the skilled artisan, the hybridization of the probe or primer to the nucleic acid from the infectious organism/s need not necessarily occur at the same time as the hybridization to the sample from a subject carrying the infectious agent or suspected of carrying the infectious agent or having the disease or disorder caused by the infectious agent or suspected of having a disease or disorder caused by the infectious agent. For example, a library of hybridization profiles is determined for a plurality of infectious organisms, each with an individual probe or primer.

Furthermore, the hybridization of the probe or primer to nucleic acid from the subject or related subject need not necessarily occur at the same time as to the sample suspected of comprising nucleic acid from the infectious organism. For example, a hybridization profile is determined for the subject prior to screening for an infectious organism.

As will be apparent to the skilled artisan, the hybridization of the probe or primer to nucleic acid from the subject suspected of carrying the infectious agent or having the disease or disorder caused by the infectious agent or suspected of having a disease or disorder caused by the infectious agent to determine the hybridization profile need only be obtained from a sample that does not comprise nucleic acid from said suspected infectious organism. For example, should the infectious organism be an infection of the pulmonary system, a skin sample is useful for determining a hybridization profile of the subject.

Alternatively, the probe or primer is hybridized to nucleic acid from a related subject. For example, the probe or primer is hybridized to nucleic acid from a family member. Alternatively, the probe or primer is capable of hybridizing to nucleic acid that is polymorphic between an infectious organism and a subject, but not between individuals. Accordingly, any individual of similar genetic makeup is a suitable control sample, e.g., should the test sample be from a suitable human control sample.

In one example, the method is performed a plurality of times, each with a different probe or primer to determine a hybridization profile for a subject and/or an infectious organism.

The method of the invention encompasses the use of a library, e.g., previously produced library of hybridization profiles of one or more infectious organisms. Suitable methods are described supra and are to be taken to apply mutatis mutandis to the present example of the invention.

In one example, the method for diagnosing a disease or disorder is performed using a sample isolated previously from the subject being tested. Accordingly, the method is performed ex vivo. Accordingly, in one example, the method of diagnosis additionally comprises providing the sample.

For example, the sample is suspected of comprising nucleic acid from the agent that causes the disease or disorder.

Furthermore, the method encompasses the use of a control sample previously isolated from a subject. Other suitable control samples include, for example, a clinical isolate of a pathogenic organism, a laboratory sample of an infectious agent, a biological sample comprising the infectious agent (e.g., a blood sample, a sputum sample, a soil sample, a pollen sample amongst others).

Accordingly, in the case of the diagnosis of a human disorder, the present invention is performed using, for example, a body fluid as a test sample and nucleic acid from one or more clinical isolates as a control sample. Such a method enables the identification of an infectious agent or nucleic acid there from in the biological sample from the subject.

The present invention provides diagnosing an infectious agent other than a human infectious agent. The present invention is applicable to, for example, the diagnosis of a disease in an animal or in a plant. For example, the present inventors have specifically identified an isolate of the oat take-all fungus from a soil sample.

As will be apparent to the skilled artisan, a sample used in the method of diagnosis should be likely to contain nucleic acid from the infectious agent. For example, should the agent be blood borne, a suitable sample is selected from the group consisting of whole blood, serum, plasma, peripheral blood mononuclear cells (PBMC) and a buffy coat fraction.

Preferably, the hybridization of a probe or primer to a nucleic acid is determined using an amplification reaction, for example, an amplification reaction selected from the group consisting of PCR, NASBA, RT mediated amplification, SDA, TMA, CPT and QBR amplification.

Diagnosis of Cancer

The method of diagnoses of the present invention supra are to be taken to apply mutatis mutandis to the diagnosis of cancer. For example, cancer is often associated with amplification or deletion of the region of a genome of a cell. As a probe or primer of the present invention is useful for detecting small levels of genetic diversity (e.g., between different isolates of the same species of fungus), the primers speculated to be are useful for detecting a genetic change associated with a cancer.

Accordingly, the present invention additionally provides a method for diagnosing a cancer in a subject, said method comprising:
(i) performing a method supra to thereby identify, determine, produce or provide a probe or primer;
(ii) hybridizing a probe or primer from (i) to nucleic acid (a) from an individual related to the subject that is known to not have cancer or from a sample from the subject known not to comprise the cancer, and (b) from the cancer or a cancer related thereto;
(iii) identifying from (ii) hybridization to polymorphic nucleic acid between nucleic acid (a) and (b) wherein said polymorphic nucleic acid indicates that the probe or primer is capable of distinguishing between (a) and (b);
(iv) selecting a probe or primer from (iii) that hybridizes to polymorphic nucleic acid between (a) and (b); and
(v) hybridizing a probe or primer from (iv) to nucleic acid derived from a subject having the cancer or suspected of having the cancer; and
(vi) detecting the hybridization wherein hybridization to the polymorphic nucleic acid of the cancer indicates that the subject carries the cancer or suffers from cancer.

The polymorphic nucleic acid may be determined previously for a predetermined probe or primer, in which case the method may comprise, for example:
(i) hybridizing a probe or primer comprising a sequence set forth in any one of SEQ ID NOs: 1-63, 69, 70, 73, 75 and 77 to 87 or a variant thereof or complementary sequence thereto to nucleic acid derived from a subject carrying the cancer or having the cancer or suspected of carrying the cancer or having the cancer; and
(ii) detecting the hybridization wherein hybridization to polymorphic nucleic acid of the cancer indicates that the subject carries the cancer or has the cancer.

For example, the cancer is a cancer known to be associated with a genetic modification, e.g., a cancer selected from the group consisting of a breast cancer, a colorectal cancer, an endometrial cancer, a leukemia cell, a lung cancer, a melanoma, a non-small-cell lung cancer, an ovarian cancer, a prostate cancer, a cervical cancer, a liver cancer and a pancreatic cancer.

The method of the present invention can be performed using a library of hybridization profiles from different cancers and/or cancerous cells, e.g., a cancerous cell line.

As will be apparent to the skilled artisan, the present invention additionally provides a method for diagnosing a specific form of cancer. For example, a hybridization product from a test sample is compared to an amplification product from a variety of cancers to determine the type of cancer a subject suffers from.

In an example of the invention, the method additionally comprises providing the sample comprising the cell suspected of being cancerous. Accordingly, the cell or sample is isolated from a subject, for example, either by surgical biopsy or with a syringe.

As the method of the present invention is useful for determining a genetic alteration in a cancerous cell, the sample used for diagnosis is preferably from a tissue suspected of containing the cancer. Preferably, the sample is derived from a region of tissue suspected of comprising a cancerous cell.

In another example, the method of the invention comprises providing the control sample. In this regard a plurality of control samples may be provided. For example, each of the control samples comprises a cancerous cell. For example, a cancerous cell known to comprise one or more genetic modifications, e.g., an insertion or a deletion.

Alternatively, or in addition, the present method is performed with nucleic acid from a healthy cell to determine the presence of a cancerous cell, i.e., the amplification product produced by a cancerous cell is different to that produced by the healthy cell.

Accordingly, the control sample comprises a cell known not to be cancerous or tumorigenic. Preferably, the cell is of the same type as is contained within the sample being tested to diagnose cancer. For example, should a breast epithelial sample be tested to diagnose cancer, preferably a control sample also comprises one or more breast epithelial cells.

The present invention additionally provides for the use of a probe or primer produced by the method of the present invention in the manufacture of a diagnostic.

The present invention also provides for a method that expedites therapy comprising performing a method of diagnosis described herein and administering a therapeutic amount of a suitable compound for the treatment of the disease or disorder with which the subject is diagnosed.

Isolation and/or Identification of a Nucleic Acid of Interest

Using a probe or primer of the present invention, the inventors have also isolated a nucleic acid adjacent to the site of insertion of a transposon. Such a method is useful in determining a gene or nucleic acid into which the transposon has inserted (e.g., for identification of a gene that produces a phenotype of interest). Accordingly, the present invention additionally provides a method for determining a genetic modification in a cell, tissue or subject comprising:

(i) identifying, determining, providing or producing a probe or primer using a method described supra;
(ii) hybridizing the probe or primer from (i) to nucleic acid from (a) a subject comprising a genetic modification; and (b) a related subject that does not comprise the genetic modification;
(iii) identifying from (ii) hybridization to polymorphic nucleic acid between (a) and (b);
(iv) hybridizing a probe or primer from (iv) to nucleic acid derived from a subject having the genetic modification or suspected of having the genetic modification; and
(v) detecting the hybridization wherein hybridization to the polymorphic nucleic acid of the genetic modification indicates that the subject has the genetic modification.

Optionally, the method comprises isolating the polymorphic nucleic acid. Polymorphic nucleic acid produced using an amplification reaction is amenable to isolation using a method known in the art.

Optionally, the method additionally comprises characterizing the isolated nucleic acid, for example, by sequencing.

In one example of the invention, the genetic modification is an insertion of a heterologous nucleic acid into the nucleic acid, e.g., the genome, of a cell, tissue or organism. Using the sequence of the heterologous sequence, and a probe or primer of the present invention the present inventors have isolated and/or characterized the site of insertion of the heterologous sequence.

Accordingly, the invention provides a method for isolating, identifying and/or characterizing a nucleic acid adjacent to a heterologous nucleic acid, said method comprising:

(i) identifying, determining, providing or producing a probe or primer using a method described supra;
(ii) performing an amplification reaction using the probe or primer (i) with a nucleic acid comprising the heterologous nucleic acid, wherein the amplification reaction is performed using another probe or primer capable of specifically hybridizing to the heterologous nucleic acid, wherein the amplification reaction is performed using (a) nucleic acid derived from a subject with the heterologous nucleic acid and (b) nucleic acid derived from a related subject without the heterologous nucleic acid; and
(iii) identifying an amplification product produced at (ii) from nucleic acid (a) but not nucleic acid (b).

Optionally, the method additionally comprises isolating the amplification product produced using both the probe or primer at (i) and the probe or primer capable of specifically hybridizing to the heterologous nucleic acid. Furthermore, the method optionally comprises characterizing the amplification product, for example, by sequencing.

Such a method is useful for, for example, identifying and/or characterizing nucleic acid adjacent to the site of insertion of, for example, a transgene or a transposon. This method is useful for identifying a gene that is associated with a phenotype of interest. For example, a mutagenesis method is performed, e.g., transposon mediated mutagenesis or gene trapping mutagenesis, an organism with a phenotype of interest determined. By using the method of the present invention, the nucleic acid into which the transgene or transposon has inserted the gene responsible for or associated with the phenotype of interest is identified.

As will be apparent to the skilled artisan the method of the invention is useful for isolating a nucleic acid adjacent to a characterized region of a nucleic acid, for example, for the isolation of a promoter region of a gene when only the cDNA sequence is known, or for isolation/characterization of a 5' non-coding region or a 3' non-coding region or intronic region or a promoter region.

Accordingly, the present invention additionally provides a method for isolating, identifying and/or characterizing a nucleic acid adjacent to a characterized region of a nucleic acid, said method comprising:

(i) identifying, determining, providing or producing a probe or primer using a method described supra;
(ii) performing an amplification reaction using the probe or primer (i) with a nucleic acid comprising the characterized region, wherein the amplification reaction is performed using another probe or primer capable of specifically hybridizing to the characterized region, wherein the amplification reaction is performed using (a) nucleic acid derived from a subject with the characterized region and (b) nucleic acid derived from a related subject without the characterized region; and
(iii) identifying an amplification product produced at (ii) from nucleic acid (a) but not nucleic acid (b).

In another example, the present invention provides a method for isolating, identifying and/or characterizing a nucleic acid adjacent to a characterized region of a nucleic acid, said method comprising:

(i) identifying, determining, providing or producing a probe or primer using a method described supra;
(ii) performing an amplification reaction using the probe or primer (i) with a nucleic acid comprising the characterized region;
(iii) performing an amplification reaction using the probe or primer (i) with a nucleic acid comprising the characterized region, wherein the amplification reaction is performed using another probe or primer capable of specifically hybridizing to the characterized region, wherein the amplification reaction is performed using nucleic acid comprising the characterized region; and
(iv) identifying an amplification product produced at (iii) that is not produced at (ii), wherein the identified amplification product is produced using the probe or primer (i) and the probe or primer capable of specifically hybridizing to the characterized region.

In another example, the method for isolating, identifying and/or characterizing a nucleic acid adjacent to a characterized region of a nucleic acid according to any example hereof comprises performing an initial amplification reaction using a probe or primer capable of hybridizing to the characterized region using nucleic acid comprising the characterized region prior to step (ii).

Optionally, the method additionally comprises isolating the amplicon produced using both the probe or primer at (i) and the probe or primer capable of specifically hybridizing to the characterized region. Furthermore, the method optionally comprises characterizing the amplification product, for example, by sequencing.

Methods for isolating a nucleic acid are known in the art and described, for example in Ausubel et al. (In: Current Protocols in Molecular Biology. Wiley Interscience, ISBN 047 150338, 1987) and Sambrook et al. (In: Molecular Cloning: Molecular Cloning: A Laboratory Manual, Cold Spring Harbor Laboratories, New York, Third Edition 2001). For example, an amplification product is electrophoresed and isolated from a gel using a method known in the art.

Methods for characterizing a sequence are also known in the art. For example an isolated amplification product is sequenced using the dideoxy chain termination method or the Maxam-Gilbert method (see Sambrook et al., Molecular Cloning, A Laboratory Manual (2nd Ed., CSHP, New York 1989); Zyskind et al., *Recombinant DNA Laboratory Manual*, (Acad. Press, 1988)).

Alternatively, an amplification product is isolated and/or characterized using mass-spectrometry. For example, the use of MALDI-TOF-MS is reviewed in Bonk et al. *Neuroscientist* 7: 6-12, 2001.

The invention is further described in the following non-limiting examples.

Example 1

Identification of a Primer Capable of Hybridizing to a Plurality of Sites in a Nucleic Acid The present inventors performed extensive transposon mediated mutagenesis of *Pseudomonas* strain AN5 (a biological control agent against the fungal root pathogen *Gaeumannomyces graminis* var. *tritici*) to characterize this strain. Several mutant varieties were identified. Traditional methods for the isolation and/or characterization of the nucleic acid site into which the transposon had inserted were considered to be both time consuming and expensive. Accordingly, a PCR based method was developed to isolate nucleic acid adjacent to the inserted transposon. In this regard, a primer was designed to hybridize to the transposon, however, as the sequence adjacent to the transposon was unknown a second primer could not be designed for use in an amplification reaction.

Initial attempts using RAPD primers found these primers to be unreliable in that observations could not be consistently reproduced. The inventors also found that primers designed to hybridize to recognition sequences of six base pair restriction endonucleases produced inconsistent results.

Previously, the inventors had produced a number of primers useful for the sequencing of various regions of the *Pseudomonas* strain AN5 genome (e.g., SEQ ID NOs: 1 to 18). All of these primers were 20mers and were capable of hybridizing to their target sequence under relatively stringent conditions.

To test the utility of these primers in a PCR reaction each primer was used individually in a PCR reaction. Each reaction was performed using a QIAGEN kit and comprised the following:

| | |
|---|---|
| Multiplex mix (x2) | 10 µl (including Taq polymerase) |
| supplementary dNTPs (2 mM each) | 0.1 µl |
| primer (10 µM) | 2 µl |
| genomic DNA from *Pseudomonas* AN5 | 1 µl |
| ddH₂O | up to 20 µl |

The PCR reaction was then cycled in a Corbett PCR 960C Thermal cycler using the following annealing conditions:
56° C.—initial 5 cycles
54° C.—final 30 cycles Using these conditions, approximately 70% of primers tested produced multiple amplification products (for example see FIG. 1). These results indicate that certain individual primers designed to anneal to a specific region of the genome of *Pseudomonas* strain AN5 are actually capable of hybridizing to multiple sites in the genome sufficiently close (and in opposite orientations) to produce multiple PCR products. Sequence analysis of known genomic sequences of *Pseudomonas* strain AN5 did not identify areas of conservation corresponding to the primers binding sequence, suggesting that the repetitive areas are small and/or unconserved and that the primers are able to hybridize to variable sequences under relatively high stringency conditions.

Example 2

Primers Hybridize Under Stringent Conditions

The conditions under which a primer of the present invention was determined using a gradient PCR. Using a PCR reaction essentially as described in Example 1 using a primer comprising a nucleotide sequence set forth in SEQ ID NO: 14 the inventors determined the temperatures at which the primer was capable of producing an amplification product.

Figure 2:
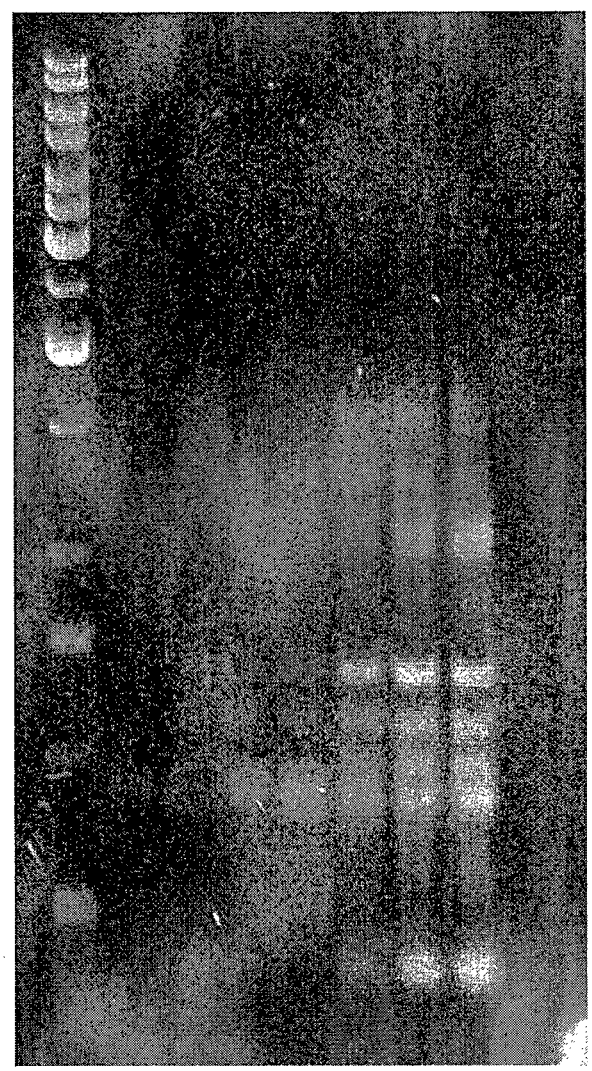
FIG. 2 a photographic representation showing an agarose gel upon which amplification products produced using a primer of the invention have been electrophoresed. Various annealing temperatures were used during the amplification reaction; 1. 60° C., 2. 58.9° C., 3. 57.1° C., 4. 54.4° C., 5. 50.5° C., 6. 47.9° C., 7. 46.1° C., 8. 45.0° C., SS, size standard FIG. 3 a photographic representation showing an agarose gel upon which amplification products using a primer of the invention have been electrophoresed. Each lane represents amplification products produced using a different template DNA but the same primer. 1, *Pseudomonas* strain AN5 genomic DNA, 2, *P. fluorescens* genomic DNA, 3, *P. putida* genomic DNA, 4, *E. coli* genomic DNA, 5, *Bacillus* sp. genomic DNA, SS, size standard.

PCR reactions were cycled in a gradient PCR machine and the following annealing temperatures used:
1. 60° C.
2. 58.9° C.
3. 57.1° C.
4. 54.4° C.
5. 50.5° C.
6. 47.9° C.
7. 46.1° C.
8 45.0° C.
i.e., these numbers correspond to the lane numbers depicted in FIG. 2.

Using these conditions the inventors determined that the primer was capable of hybridizing to a sufficient number of sites in the genome to produce a plurality of amplification products at any temperature tested. The number of products detected was inversely proportional to the magnitude of the annealing temperature used.

Example 3

Hyperprimers Produce Species-Specific Amplification Products

To determine the ability of the primers identified by the present inventors to hybridize to nucleic acid from other bacterial species PCR reactions were performed with nucleic acid from *Pseudomonas* strain AN5 (*P. fluorescens, P. putida, E. coli* or *Bacillus* sp.). Using a single primer that comprised a sequence set forth in SEQ ID NO: 49, SEQ ID NO: 85 and SEQ ID NO: 50 a PCR reaction was produced essentially as described in Example 1.

PCR reactions were then cycled with an annealing temperature of 52° C. for two cycles and 50° C. for 34 cycles.

Figure 3:
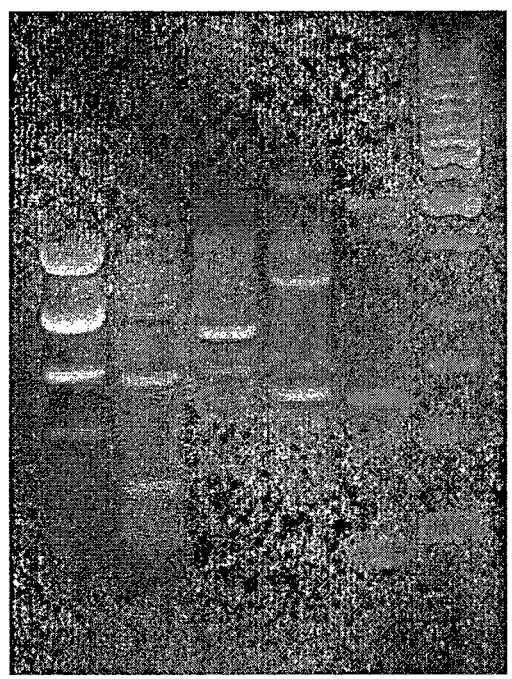
Figure 4:
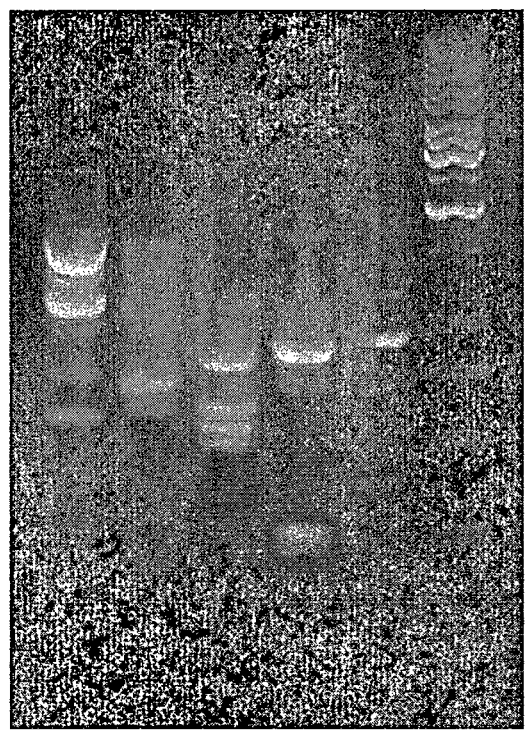
FIG. 4 a photographic representation showing an agarose gel upon which amplification products using a primer of the invention have been electrophoresed. Each lane represents amplification products produced using a different template DNA but the same primer. 1, *Pseudomonas* strain AN5 genomic DNA, 2, *P. fluorescens* genomic DNA, 3, *P. putida* genomic DNA, 4, *E. coli* genomic DNA, 5, *Bacillus* sp. genomic DNA, SS, size standard.
Figure 5:
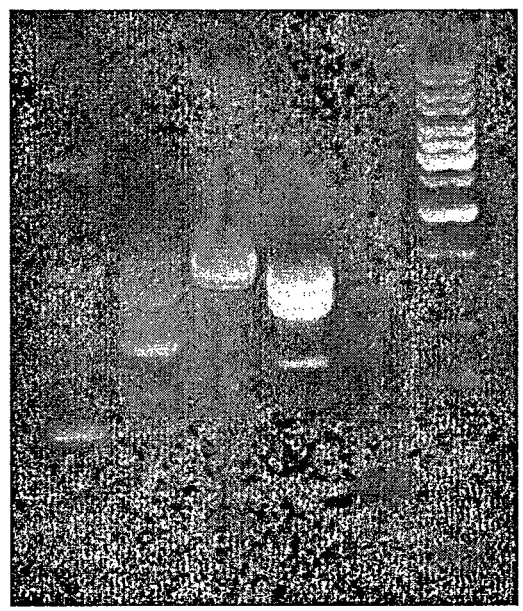
FIG. 5 a photographic representation showing an agarose gel upon which amplification products using a primer of the invention have been electrophoresed. Each lane represents amplification products produced using a different template DNA but the same primer. 1, *Pseudomonas* strain AN5 genomic DNA, 2, *P. fluorescens* genomic DNA, 3, *P. putida* genomic DNA, 4, *E. coli* genomic DNA, 5, *Bacillus* sp. genomic DNA, SS, size standard.

As shown in FIGS. 3, 4 and 5, each of the primers tested was capable of amplifying several amplification products from nucleic acid with each of the bacterial species tested. Furthermore, each of the primers amplified different amplification products for each of the bacteria, permitting identification of the bacteria. These results were consistently attained.

Figure 6:
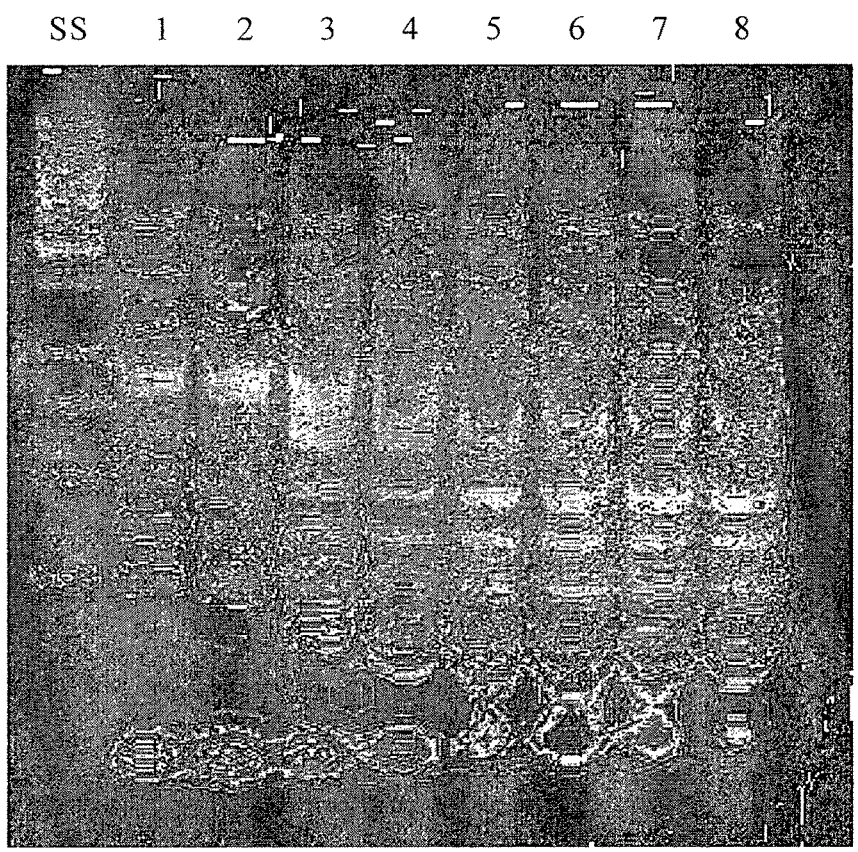
FIG. 6 a photographic representation showing an agarose gel upon which amplification products produced using a primer of the invention have been electrophoresed. The template DNA is from *E. coli*. Various annealing temperatures were used during the amplification reaction; 1. 60° C., 2. 58.9° C., 3. 57.1° C., 4. 54.4° C., 5. 50.5° C., 6. 47.9° C., 7. 46.1° C., 8. 45.0° C., SS, size standard FIG. 7 a photographic representation showing an agarose gel upon which amplification products using a primer of the invention have been electrophoresed. Various sources of template DNA were used. 1. *Pseudomonas* strain AN5 genomic DNA, 2. *Gaeumannomyces graminis* var. *graminis* W2P genomic DNA preparation 1, 3. *Gaeumannomyces graminis* var. *graminis* W2P genomic DNA preparation 2, 4. *Gaeumannomyces graminis* var. *tritici* C3 genomic DNA preparation 1, 5. *Gaeumannomyces graminis* var. *tritici* C3 preparation genomic DNA 2, 6. *Gaeumannomyces graminis* var. *tritici* QW1 (Oat take-all) genomic DNA, SS Size standard.

Furthermore, the inventors used a gradient PCR reaction essentially as described in Example 2 with the exception of the use of *E. coli* genomic DNA rather than *Pseudomonas* strain AN5 genomic DNA. The inventors showed that they were able to consistently amplify a number of amplification products with the primer comprising the sequence set forth in SEQ ID NO: 48 (FIG. 6). Accordingly, this supports the conclusion that the primers of the invention are capable of hybridizing to a sufficient number of sites in the genome of an organism under moderate stringency conditions to facilitate amplification of a number of PCR products.

Example 4

Hyperprimers from Bacteria Amplify Products from Fungal DNA

To determine the ability of the primers identified by the present inventors to hybridize to nucleic acid from a eukaryote (in this case fungus), PCR reactions were performed with nucleic acid from two preparations of gDNA from *Gaeumannomyces graminis* var. *graminis*, two preparations of gDNA from *Gaeumannomyces graminis* var. *tritici* C3 and a preparation of genomic DNA from *Gaeumannomyces graminis* var. *tritici* QW1. Using a single primer that comprised a sequence set forth in SEQ ID NO: 49 a PCR reaction was produced essentially as described in Example 1.

Figure 7:
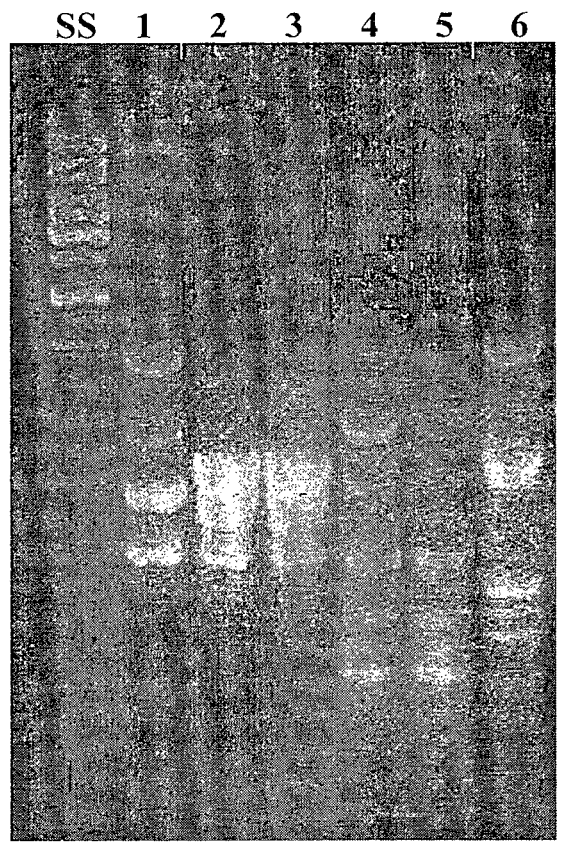

As shown in FIG. 7, the primer was capable of amplifying several amplification products with nucleic acid from each of the yeast species tested. The products produced using the two preparations of gDNA from *Gaeumannomyces graminis* var. *graminis* produced substantially identical amplification products showing the reproducibility of the results, even between samples. Similar results were attained with the two samples from *Gaeumannomyces graminis* var. *tritici* C3. However, the amplification products produced from *Gaeumannomyces graminis* var. *graminis* were different from those produced from *Gaeumannomyces graminis* var. *tritici* C3, demonstrating the utility of the primers in differentiating between varieties (or identifying a variety).

Furthermore, the amplification products generated from *Gaeumannomyces graminis* var. *tritici* C3 were different from those produced using DNA from *Gaeumannomyces graminis* var. *tritici* QW1. *Gaeumannomyces graminis* var. *tritici* QW1 is a soil isolate of the *Gaeumannomyces graminis* var. *tritici* C3 variety. Accordingly, the primer was able to differentiate different isolates of the same variety.

The present inventors also identified four other primers capable of amplifying a number of products from the fungal DNA.

Example 5

Hyperpriming in Eukaryotic Genomes

To determine the ability of the primers identified by the present inventors to hybridize to nucleic acid from additional eukaryotes, PCR reactions were performed with genomic DNA from a human cell line, a mouse cell line and wheat. Using a single primer that comprised a sequence set forth in SEQ ID NO: 51 a PCR reaction was performed essentially as described in Example 1.

Figure 8:
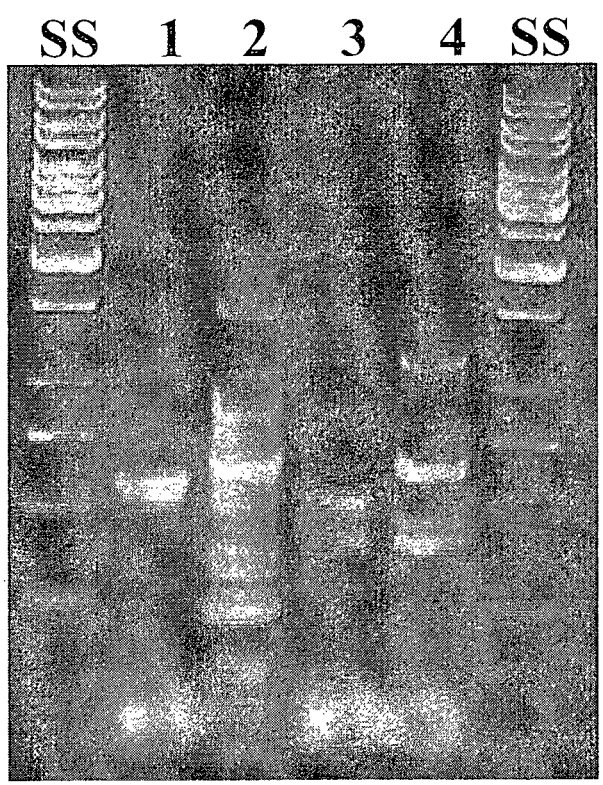
FIG. 8 a photographic representation showing an agarose gel upon which amplification products using a primer of the invention have been electrophoresed. Various sources of template DNA were used. 1. *Pseudomonas* strain AN5 genomic DNA, 2. human cell line genomic DNA, 3. mouse cell line genomic DNA, 4. wheat (Chinese spring), SS, size standard.

As shown in FIG. 8 the primer used was capable of hybridizing to sufficient locations in the nucleic acid in each sample to generate a number of PCR products. The amplicons produced were specific for each of the cells tested, demonstrating that a primer of the invention is capable of hybridizing to nucleic acid from either a related or an unrelated organism. Furthermore, the amplicons was capable of producing primers specific to each genus tested.

Figure 9:
FIG. 9 a photographic representation showing an agarose gel upon which amplification products produced using a primer of the invention have been electrophoresed. The template DNA is from a human cell line, a mouse cell line or wheat (Chinese spring) as indicated. Various annealing temperatures were used during the amplification reaction; 1. 60° C., 2. 58.9° C., 3. 57.1° C., 4. 54.4° C., 5. 50.5° C., 6. 47.9° C., 7. 46.1° C., SS, size standard.

Furthermore, gradient PCR was used to determine the conditions under which PCR products were amplified using a single primer in eukaryotic cells. Using PCR reactions and cycling essentially as described in Example 2 it was found that a primer comprising the sequence set forth in SEQ ID NO: 52 was capable of amplifying a number of PCR products at a variety of temperatures (FIG. 9). Again, the number of PCR products produced was inversely proportional to the magnitude of the annealing temperature.

Figure 10:
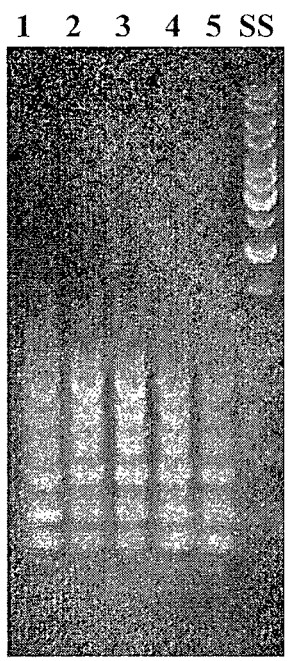
FIG. 10 a photographic representation showing an agarose gel upon which amplification products produced using genomic DNA from a number of inbred mice has been electrophoresed. The amplification products were produced using a single primer of the invention. Lane 1, transgenic mouse, Lanes 2 to 5 wild type littermates, SS size standard.

The ability of a primer to amplify PCR products from gDNA isolated from a mouse was also determined. As shown in FIG. 10, a primer comprising a sequence set forth in SEQ ID NO: 51 is capable of amplifying what appears to be amplification products of identical size from each of the inbred mice. Notwithstanding the presence of a genetic modification (insertion of a GFP encoding construct) into the genome of one of the mice, the hyperprimer is capable of consistently amplifying PCR products characteristic of the strain.

Furthermore, these results demonstrate the ability of a primer of the invention to determine a population of inbred animals.

Example 6

Differentiating Between Varieties of Wheat

Figure 11:
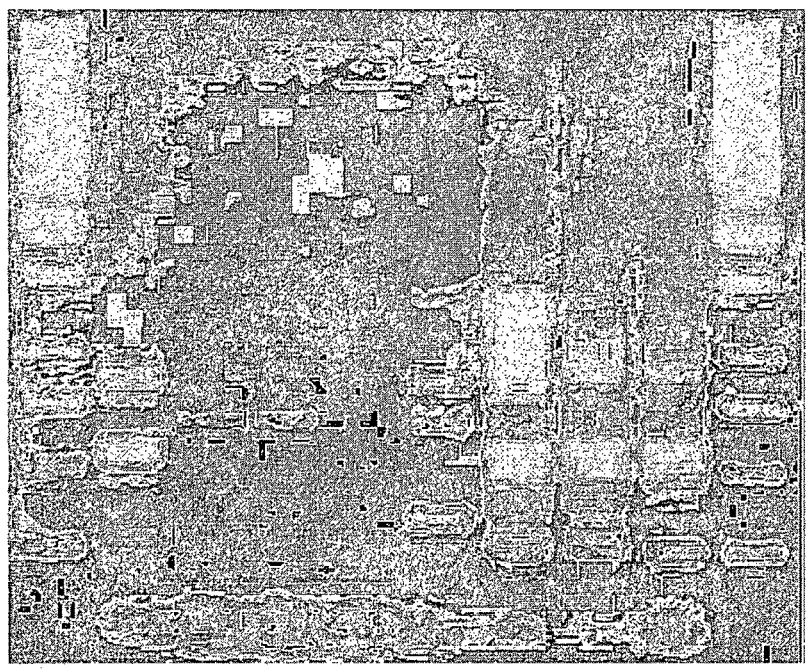
FIG. 11 a photographic representation showing an agarose gel upon which amplification products produced genomic DNA from various cultivars of wheat have been electrophoresed. The amplification products were produced using a single primer of the invention. 1. *Triticum monococcum* (2n=14), 2. *Triticum urartu* (2n=14), 3. *Triticum dicoccoides* (2n=28), 4. *Aegilops squarrosa*, 5. *Aegilops bicornis*, 6. *Triticum aestivum* cv. condor (2n=42), 7. *Triticum aestivum* cv. moncho S, 8. *Triticum aestivum* cv. hartog, SS size standard.

The present inventors also used a number of individual hyperprimers to determine their ability to amplify PCR products from wheat and for their ability to differentiate between genera, species and/or varieties of wheat. Using a primer comprising the sequence set forth in SEQ ID NO: 48 it was found that different amplification products were observed between genera and species of wheat (FIG. 11).

Furthermore, some of the amplification products amplified using gDNA from *Triticum aestivum* cultivar condor were different to those produced using gDNA from *Triticum aestivum* cultivar moncho or hartog. Accordingly, the primer is useful for differentiating between cultivars of wheat.

Of the four other primers screened, all were capable of differentiating between the genera and species of wheat tested.

Example 7

Randomly Produced Primers do not Amplify PCR Products

To determine whether or not a random primer is capable of producing the same results as the primers produced, 5 random 20-mers with similar GC content to the hyperprimers tested were produced.

The primers were used individually in a PCR reaction essentially as described in Example 1. The annealing temperature was 50° C. for 4 cycles and 48° C. for 35 cycles.

No consistent PCR products were observed when the amplification reactions were electrophoresed. DNA tested was *Pseudomonas* strain AN5, *Ps putida*, *Bacillus* sp., *E. coli*, mouse gDNA, human gDNA and wheat gDNA. Accordingly, this result suggests that a random primer is not capable of hybridizing to sufficient sites in the genome of an organism to consistently produce a PCR amplicon. This is in direct contrast to the primers designed by the inventors that were produced using regions of the genome that encode a protein.

Example 8

Longer Hyperprimers Produce More PCR Products

To assess the effect of primer length on the ability of a primer to hybridize to a plurality of sites in the genome of an organism, primers were produced that comprised 25 nucleotides (SEQ ID NOs: 58 to 63). A PCR reaction using each of these primers individually was produced essentially as described in Example 1.

Figure 12:
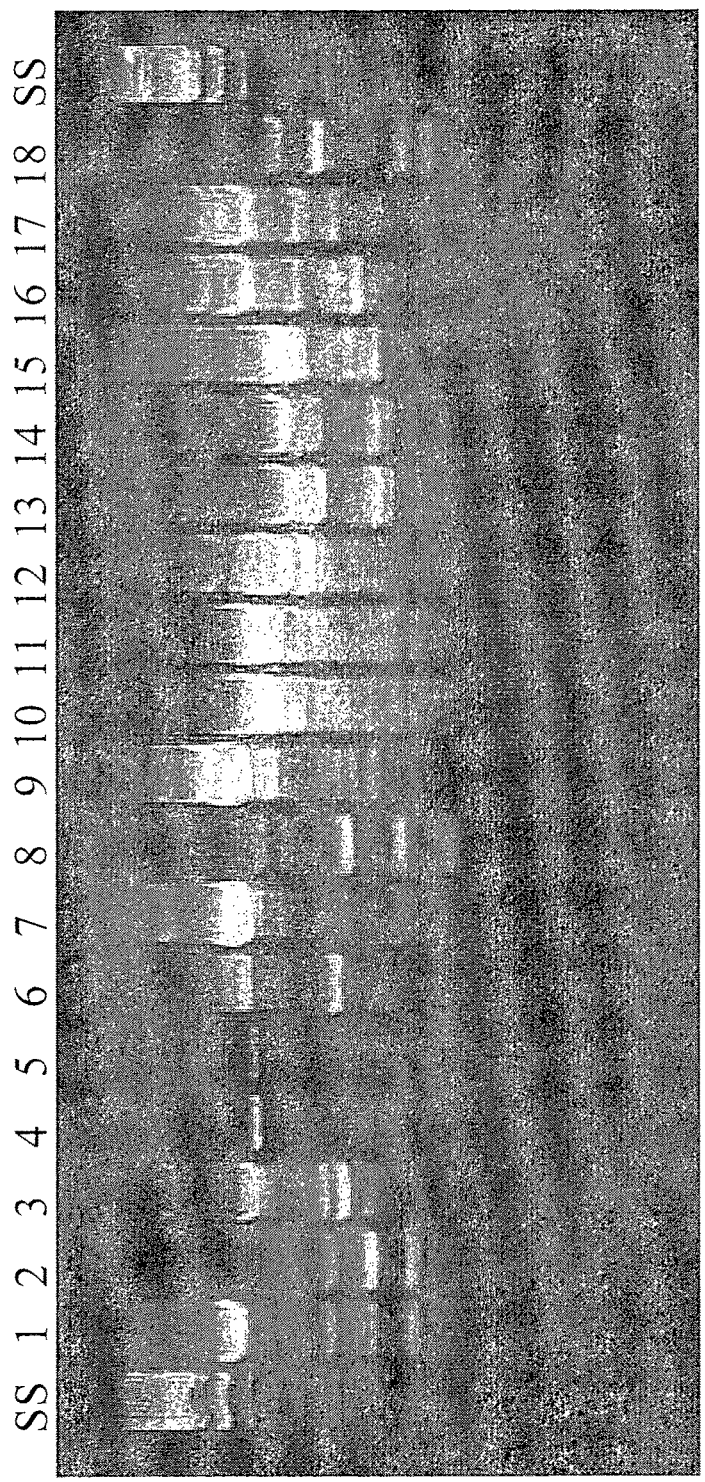
FIG. 12 is a photographic representation showing an agarose gel in which amplification products produced using a 25mer primer of the invention has been used in a PCR reaction with gDNA from *Pseudomonas* strain AN5 (with a transposon insertion) (Lanes 1, 4, 7, 10, 13 and 16), *Pseudomonas* strain AN5 (wild-type) (Lanes 2, 5, 8, 11, 14 and 17) or *E. coli* K12 (Lanes 3, 6, 9, 12, 15 and 18). The same primer was used in lanes 1, 2 and 3; and lanes 4, 5 and 6; and lanes 7, 8 and 9; and lanes 10, 11 and 12; and lanes 13, 14, and 15; and lanes 16, 17 and 18, with different primers being used between each group.

As shown in FIG. 12, the 25-mer primers were capable of amplifying more products than the 20-mer products previously used, in addition to longer products than those previously amplified.

Using the 25-mer primers it is possible to produce an amplification product/s that is specific to *Pseudomonas* strain AN5 or *E. coli*. Furthermore, a number of the primers produced were able to differentiate between *Pseudomonas* strain AN5 with a genetic modification (i.e., a transposon insertion) and *Pseudomonas* strain AN5 without a genetic modification.

Example 9

Isolation of Nucleic Acid Adjacent to the Insertion Site of a Transposon

Various mutants of *Pseudomonas* strain AN5 were produced using transposon mediated mutagenesis and selected for using the tetracycline selectable marker contained from the transposon TN1721 (Schmidt et al., *Molecular and General Genetics*, 172: 53-65, 1979). This transposon also contained a promoter-less lux minigene (lux C, D, A, B, E, I genes) from the transposon Tn4431 (Shaw et al., *Molecular Plant-Microbe Interactions*, 1: 39-45, 1987). The lux gene enables detection of emitted light when activated by an endogenous promoter. Those mutants that produced detectable light were analyzed to determine the sequence of the promoter responsible for activating the lux gene.

10 primers designed to the lux C gene in the transposon were used as a reverse primer to isolate the promoter sequence. Additionally, 30 primers designed against various regions of the AN5 genome were used. PCR reactions were performed using a QIAGEN kit and comprised the following:

| | |
|---|---|
| Multiplex mix (x2) | 10 µl (including Taq polymerase) |
| supplementary dNTPs (2 mM each) | 0.1 µl |
| primer to lux C (10 µM) | 1 µl |
| hyperprimer (10 µM) | 1 µl |
| genomic DNA from *Pseudomonas* AN5 | 1 µl |
| ddH$_2$O | up to 20 µl |

The PCR reaction was then cycled in a Corbett PCR 960C Thermal cycler using the following annealing conditions:
56° C.—initial 5 cycles
54° C.—final 30 cycles PCR reactions were performed using gDNA isolated from *Pseudomonas* strain AN5 either with a transposon insertion or without an insertion (control).

Figure 13:
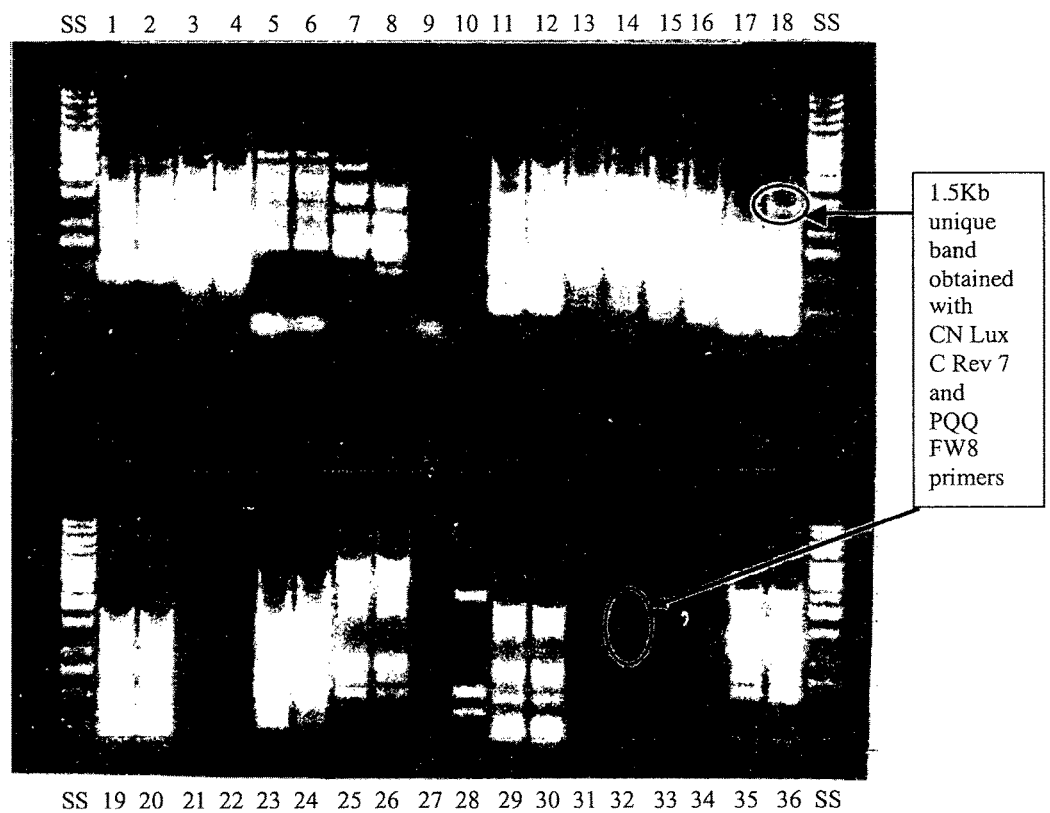
FIG. 13 is a photographic representation showing a 1% agarose gel in which amplification products produced using a primer designed to hybridize to DNA from *Pseudomonas* strain AN5 and a primer designed to hybridize to the luxC gene in the transposon TN4431 have been electrophoresed. Odd numbered lanes contain DNA from *Pseudomonas* strain AN5 (no transposon insert, i.e. controls). Even numbered lanes contain DNA from *Pseudomonas* strain AN5 with a transposon insert. Note the amplification products in lanes 18 and 32 that do not appear in the corresponding control lanes. The size standard is shown at both the left-hand and right-hand sides of the figure. PCR was performed at 50° C./48° C.

As shown in FIG. 13, PCR reactions performed with a primer comprising the sequence set forth in SEQ ID NO: 16 and a variety of additional primers produced similar amplification products in both control and test samples. However, a unique band was observed by the amplification product that used a primer comprising the sequence set forth in SEQ ID NO: 48 as a primer.

The 1.5 kb fragment was isolated and sequenced using each of the primers used to amplify the band individually. Approximately 700 bp of this sequence was obtained, with some of the sequence from the lux C and lux I genes, confirming isolation of the Tn 4431 transposon. Of the remaining sequence obtained, approximately 300 bp showed no homology to any published sequence. 170 bp of sequence showed homology to the tilD or aprD genes of *Pseudomonas brassicacearum* (a gene encoding a protease inhibitor). A promoter site with a transcription factor binding site was also identified. Furthermore, the start site of the *Pseudomonas* strain AN5 tilD gene is in frame with the LUX cassette.

Alternatively, the above method was modified using a nested PCR approach. A standard PCR reaction using a single primer designed in the luciferase gene (or in another part of the transposon) was performed. The primers used for example, were complementary to priming sites at the end of the transposon. The standard PCR amplification was performed prior to the hyperpriming reaction. After this initial standard PCR amplification, the hyperpriming reaction was performed essentially as described above for the 30 primers designed against various regions of the AN5 genome were used.

Products from the parent strain and the strain which has the transposon insert as above were compared to the transposon insert strain, which was analysed using the extra step of using a primer from within the transposon initially in a PCR reaction, i.e. using the nested PCR approach with two step PCR reaction. The nested hyperpriming approach resulted readily detectable unique hyperpriming bands which had the adjacent regions of the transposon insert. The need to screen different hyperprimers decreased with this nested approach and unique hyperpriming bands were generated more frequently in the nested hyperpriming reactions (data not shown). In the nested PCR reaction, the probability of generating hyperpriming bands in the transposon insert region was increased.

Example 10

Strain-Specific Primers

To facilitate detection of *Pseudomonas* strain AN5 in biological samples (e.g., wheat roots) the present inventors developed a PCR reaction that consistently produced an amplification product that is unique to *Pseudomonas* strain AN5 relative to other Pseudomonads tested.

RAPD primers were initially used. A unique 2.4 kb fragment was identified in samples containing *Pseudomonas* strain AN5 but not other Pseudomonads. However, this result was inconsistent as not all samples containing *Pseudomonas* strain AN5 were positively detected. Furthermore, results varied between PCR machines.

Using various combinations of primers described supra the present inventors identified a primer pair GOD51-CTCGGCATTCTGCTTCTGTT (SEQ ID NO: 158) and GOD62-ACACCTTCGGTTTCGCTCTT (SEQ ID NO: 159) that produced a unique 3.2 kb fragment. One of these primers was designed to hybridize to the *Pseudomonas* strain AN5 glucose dehydrogenase gene, while the other hybridized to the *Pseudomonas* strain AN5 purT gene.

In *Pseudomonas* strain AN5 these two genes are adjacent, while in other species of *Pseudomonas* the genes are in excess of 100 kb apart (Nelson et al., *Environ Microbiol.*, 4: 799-808, 2002; Buell et al., *Proc. Natl Acad. Sci. USA*, 100: 10181-10186, 2003; and Stover et al., *Nature*, 406: 959-964, 2000).

Example 11

Isolation of an Uncharacterized Sequence Using Primers

To isolate a region of interest from the *Pseudomonas* strain AN5 genome the present inventors aligned the complete sequences of the PQQ gene region of *Pseudomonas* syringae tomato and *Pseudomonas fluorescens*. These regions were found to be 85% identical. Using the aligned sequences we designed primers for amplification of PCR products from the genome of *Pseudomonas* strain AN5.

We also used a region of 50 to 300 bp preceding and 50 to 300 bp following the PQQ gene for the design of primers.

A number of primers (SEQ ID NOs: 15 and 21 to 47) were designed and used individually in a PCR reaction essentially as described in Example 1. Approximately 50% of primers were found to be able to amplify multiple fragments from the genome of *Pseudomonas* strain AN5.

Combinations of the primers were then used in a PCR reaction. PCR reactions were performed using a QIAGEN kit and comprised the following:

| | |
|---|---|
| Multiplex mix (x2; includes Taq polymerase) | 10 µl |
| supplementary dNTPs (2 mM each) | 0.1 µl |
| primer 1 (10 µM) | 1 µl |
| primer 2 (10 µM) | 1 µl |
| genomic DNA from *Pseudomonas* AN5 | 1 µl |
| ddH₂O | up to 20 µl |

The PCR reaction was then cycled in a Corbett PCR 960C Thermal cycler using the following annealing conditions:
56° C.—5 cycles
54° C.—30 cycles By comparing the amplification products amplified using each primer individually and those produced using the combination of primers, unique amplification products have been identified. The amplification products were then isolated and sequenced. In 90% of cases the amplification product was the gene region of interest.

Figure 14:
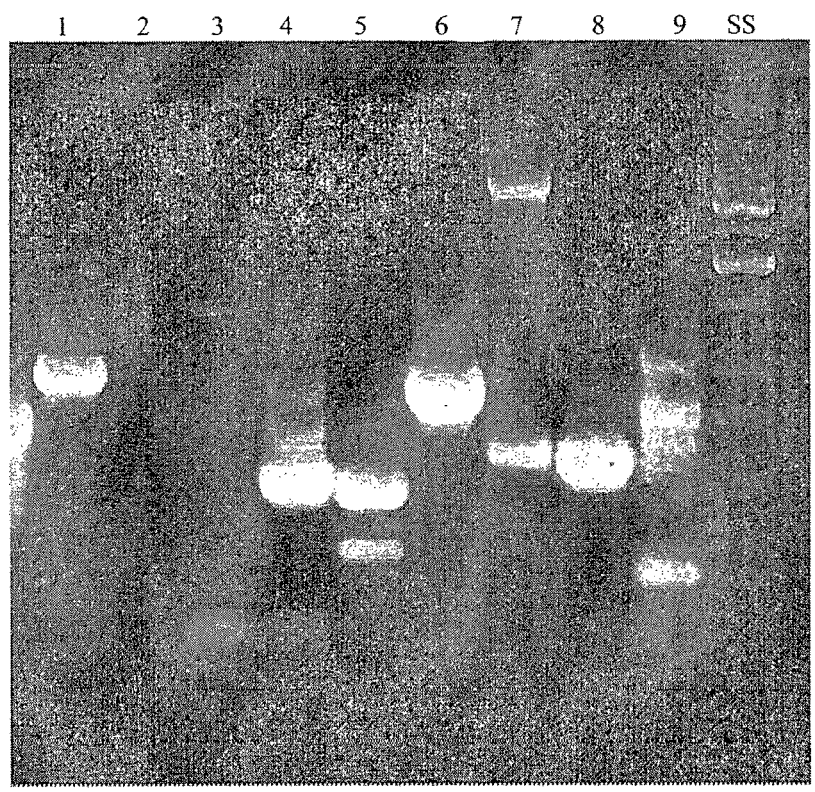
FIG. 14 is a photographic representation showing a 1% agarose gel in which amplification products produced using combinations of primers designed to hybridize to the pqqE region from *Pseudomonas syringae* par. tomato and *Pseudomonas fluorescens* used in amplification reactions with genomic DNA from *Pseudomonas* strain AN5 have been electrophoresed. Lanes 1 to 3 shown amplification products using a primer that hybridizes to *Pseudomonas* strain AN5 genomic DNA despite 11 mismatches (SEQ ID NO: 38) in combination with primers comprising a sequence set forth in SEQ ID NO: 34, SEQ ID NO: 25 or SEQ ID NO: 37, respectively. Lanes 5 to 6 show amplification products using a primer that is complementary to *Pseudomonas* strain AN5 genomic DNA (SEQ ID NO: 44), in that it matches the priming sequence exactly, in combination with primers comprising a sequence set forth in SEQ ID NO: 34, SEQ ID NO: 25 or SEQ ID NO: 37, respectively. Tracks 7, 8 and 9 are not relevant to this study. A size standard is shown at the right-hand side of the figure.

By analyzing the obtained sequence, the sites to which the primers bind have been identified. Surprisingly, primers are capable of hybridizing despite up to 11 nucleotide mismatches (see Table 3) (FIG. 14). From sequence analysis it appears that the sequence of the primer and the hybridization site can be quite divergent (e.g., up to 11 base mismatches). Those primers that did produce a PCR product appeared to either or both the 5' and/or 3' end conserved, with mismatches occurring in the centre of the primer and/or one end of the primer. Furthermore, as shown in FIG. 15 (showing the sequence of a number of primers analyzed and the sites of any mismatches) regions that did not match the sequence to which the primer hybridized were interspersed and/or flanked by regions of the primer that would hybridize.

TABLE 3

Primers used to amplify the PQQ gene region from *Pseudomonas* strain AN5, and the number of mismatches between the primer and the site to which it hybridize

| Primer sequence | Number of mismatches | SEQ ID NO: |
|---|---|---|
| CGCGCGGGCCAGGAGCACAT | 3 | 15 |
| TGAACGACGTGTGGCCCAGC | 0 | 21 |
| GGCGGCTTCAGGAAAA | 0 | 22 |
| GGCTTGCTCAGCATGCTA | 0 | 23 |
| ATGGTCTACAGGACGTACGA | 0 | 24 |
| AGCGCGTGTAACCCTTT | 0 | 25 |
| CTATCCGTCCCACCACGCA | 0 | 26 |

TABLE 3-continued

Primers used to amplify the PQQ gene region from *Pseudomonas* strain AN5, and the number of mismatches between the primer and the site to which it hybridize

| Primer sequence | Number of mismatches | SEQ ID NO: |
|---|---|---|
| ACGGGGTCGGCAAGTACGT | 0 | 27 |
| CCTGAAGGATGATCAAGCT | 11 | 28 |
| TGATCGGCGGCGCTGATCGA | 1 | 29 |
| CCGAACTCGGTCACGACAT | 0 | 30 |
| TGGCGGAGCTGACCTAT | 0 | 31 |
| CTGCAATGCCCCTACTGTTC | 0 | 32 |
| CAGCGACGAACAGGTGAACA | 0 | 33 |
| GCCCAGGGCTACCCGATGT | 0 | 34 |
| TGAAGCAATGGGTAGCCGTG | 0 | 35 |
| GATGGGCTACCACGAGTTGA | 0 | 36 |
| TCAACCGCTTCCGCGGCTAT | 0 | 37 |
| CCGTGCCGCTCCTGGGATGA | 0 | 38 |
| CTCCACGGGCGACGCCAGCAA | 0 | 39 |
| CGACCCGGTGTGCAGCAAATC | 2 | 40 |
| CACCACGGGGTGATCCTCAA | 0 | 41 |
| TTTGAGTGCGGTCATCGGGTT | 2 | 42 |
| CTCTGCGGAGTAGCGTTTTAG | 5 | 43 |
| TGAAGCGGCTCGAGCTGCAG | 4 | 44 |
| TTATGGCGGGGCTTCTGCCG | 4 | 45 |
| TTATGGCGGGGCTTCTGCCG | 4 | 46 |
| TGCGGCGTCAGGCAGTGCTT | 7 | 47 |

Example 12

Analysis of the Occurrence of a Hyperprimer Sequence in Genomes

To determine the number of times that the sequence of a hyperprimer occurred in the genome of a number of organisms a BLAST search was performed. The sequence analyzed is set forth in SEQ ID NO: 54. Using this form of analysis it was found that up to 13 bases of the primer showed homology to approximately 280 sites in the genome of *Ps. putida* and 160 sites in the genome of *Ps. aeruginosa*. Organisms evolutionarily diverse from *Pseudomonas* strain AN5 (used to design the primer) showed fewer sites of homology, yet the primer was still capable of producing a plurality of amplification products using nucleic acid from their genomes. Results of the BLAST analysis are set forth in Table 4.

TABLE 4

Approximate number of sites in the genome that show homology to a hyperprimer

| Species | Nucleotides homologous to 20 residues of primer Number of bases | Primer - Number of homologous regions in genome (approximately) obtained by blastn search |
|---|---|---|
| *Pseudomonas putida* KT2440 | 10-13 | 280 |
| *Pseudomonas aeruginosa* PAO1 | 10-13 | 160 |
| *Escherichia coli* K12 | 12-14 | 25 |
| *Bacillus subtilis* subsp. *subtilis* str. 168 | 10-13 | 24 |
| *Arabidopsis thaliana* | 13-14 | 9 |
| *Oryza sativa* | 13-15 | 9 |
| *Drosphila melanoagaster* | 13-14 | 35 |
| *Mus musculus* | 14-15 | 75 |
| *Homo sapiens* | 15-16 | 20 |

Example 13

Identification of Codons Useful for the Production of Hyperprimers in a Variety of Organisms The following example is described with reference to determining useful codons from Pseudomonads. The same methodology was used to determine the preferred codons set forth in Tables 1 and 2.

Figure 16:
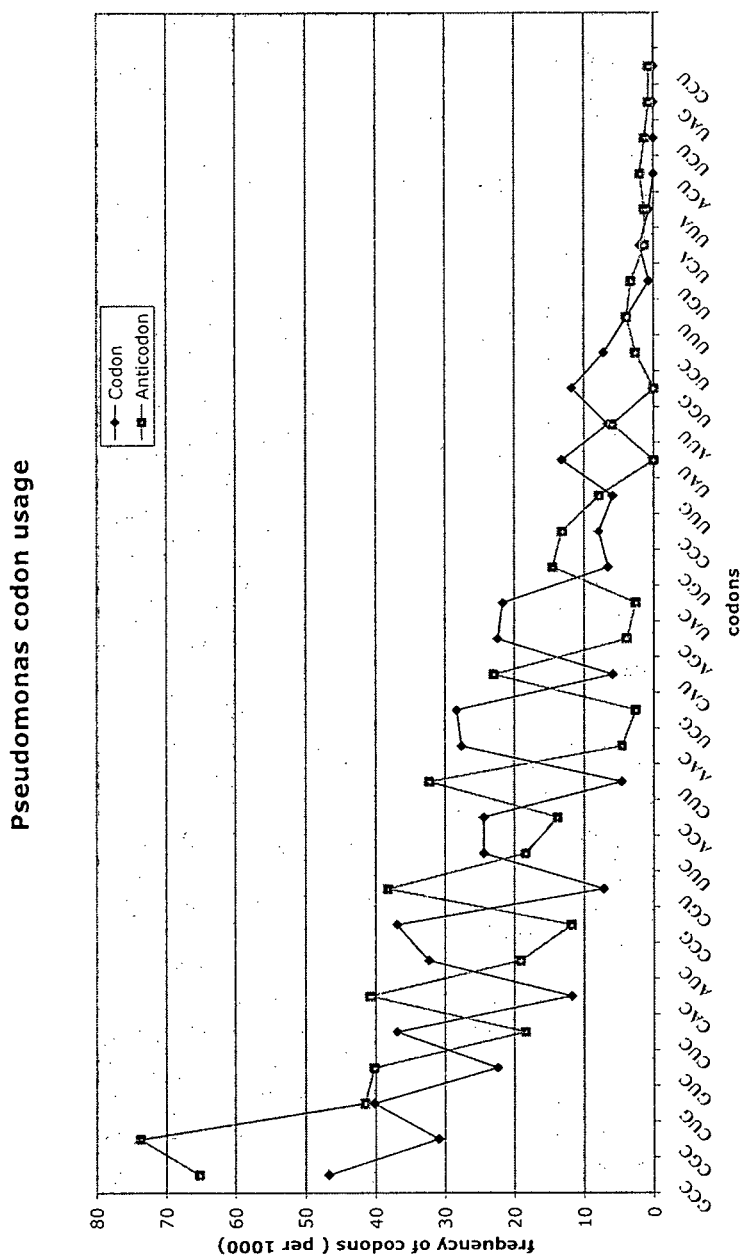
FIG. 16 is a graphical representation showing the frequency of occurrence of codons and the complements thereof in *Pseudomonas*. Frequency is shown as number of occurrences in 1000 codons.

Codon usage information was obtained for *Pseudomonas* sp. from Department of Plant Gene Research, Kazusa DNA Research Institute, Japan. The frequencies of each codon and the complement thereof was determined and the average of the frequencies ascertained. Codons were then sorted with regard to the average of the frequencies. Using this information the graph depicted in FIG. 16 was produced. This graph shows that there is a trend for codons with a high frequency of usage to also have a complementary anticodon that also generally has a high frequency of usage.

Example 14

Production of Hyperprimers Using Codon Usage Information

Figure 17:
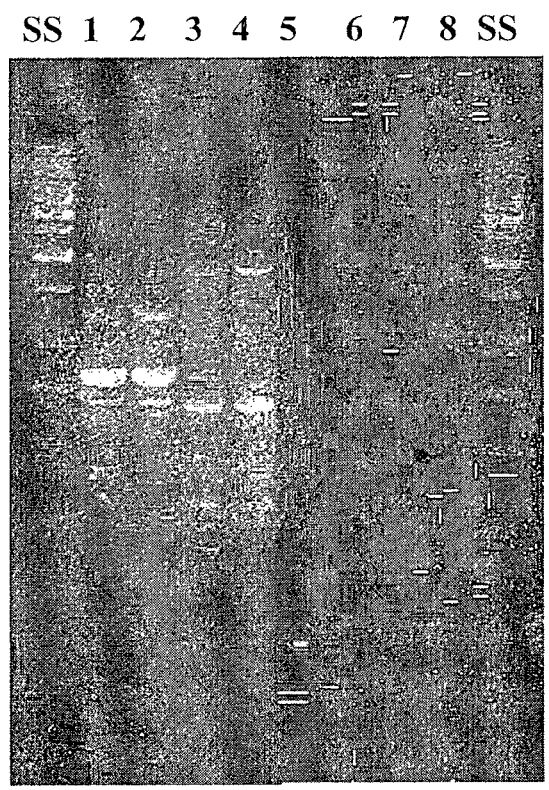
FIG. 17 is a photographic representation showing a gel on which amplification products produced using a primer comprising codons with a high usage or a low usage in humans were used in an amplification reaction with genomic DNA from a human cell line. Lane 1, Human T cell line DNA with a primer (SEQ ID NO: 69) comprising codons with a high usage in humans; Lane 2 Human BM cell line DNA with a primer (SEQ ID NO: 69) comprising codons with a high usage in humans; Lane 3 Human T cell line DNA with a primer (SEQ ID NO: 70) comprising codons with a high usage in humans; Lane 4 Human BM cell line DNA with a primer (SEQ ID NO: 70) comprising codons with a high usage in humans; Lane 5 Human T cell line DNA with a primer (SEQ ID NO: 71) comprising codons with a low usage in humans; Lane 6 Human BM cell line DNA with a primer (SEQ ID NO: 71) comprising codons with a low usage in humans; Lane 7 Human T cell line DNA with a primer (SEQ ID NO: 72) comprising codons with a low usage in humans; Lane 8 Human BM cell line DNA with a primer (SEQ ID NO: 72) comprising codons with a low usage in humans; and SS—Size standards.

Using the codon usage information for humans set forth in Tables 1 and 2 primers were synthesized using codons with a high usage (SEQ ID NOs: 69 and 70). Furthermore, primers were synthesized using codons with a low usage (SEQ ID NOs: 71 and 72). In PCR reactions performed essentially as described in Example 1 using a single primer with two different human cell lines it was found that the high codon usage primers produced a number of amplification products. In contrast, the low codon usage primers produced no detectable amplification products (FIG. 17).

Figure 18:
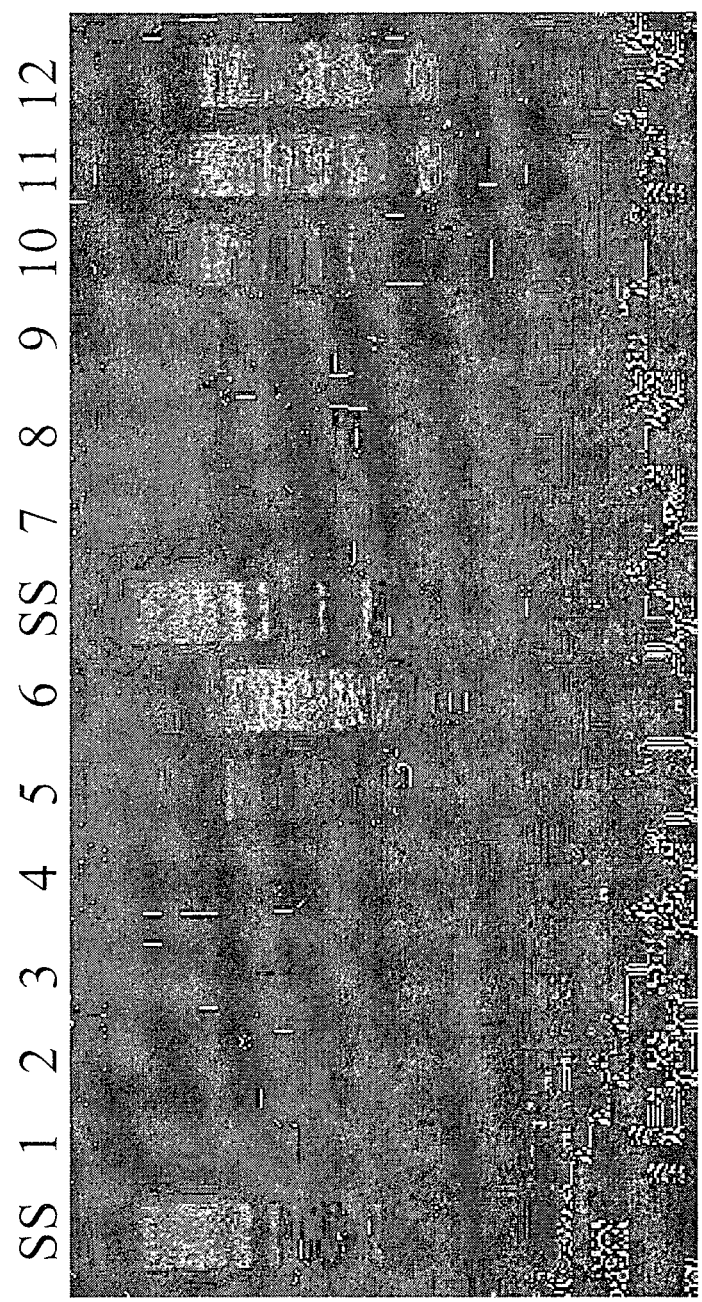
FIG. 18 is a photographic representation showing a gel on which amplification products generated using primers (SEQ ID NOs: 86 and 87) that incorporate codons of moderate use in humans were electrophoresed. Amplification reactions were performed using genomic DNA from a human T cell Lines. Lanes 1 to 6 amplification performed with a primer with sequence SEQ ID NO: 86, Lane 1—60° C., Lane 2—58.9° C., Lane 3—57.1° C., Lane 4—54.4° C., Lane 5—50.5° C., Lane 6—47.9° C.; Lanes 7 to 12 amplification performed with a primer with sequence SEQ ID NO: 87, Lane 1—60° C., Lane 2—58.9° C., Lane 3—57.1° C., Lane 4—54.4° C., Lane 5—50.5° C., Lane 6—47.9° C.

Furthermore, when primers comprised codons with moderate use (Table 2) (SEQ ID NOs: 86 and 87) a plurality of amplification products were obtained at moderate annealing temperatures. These amplification products were not observed under high stringency conditions (FIG. 18).

Figure 19:
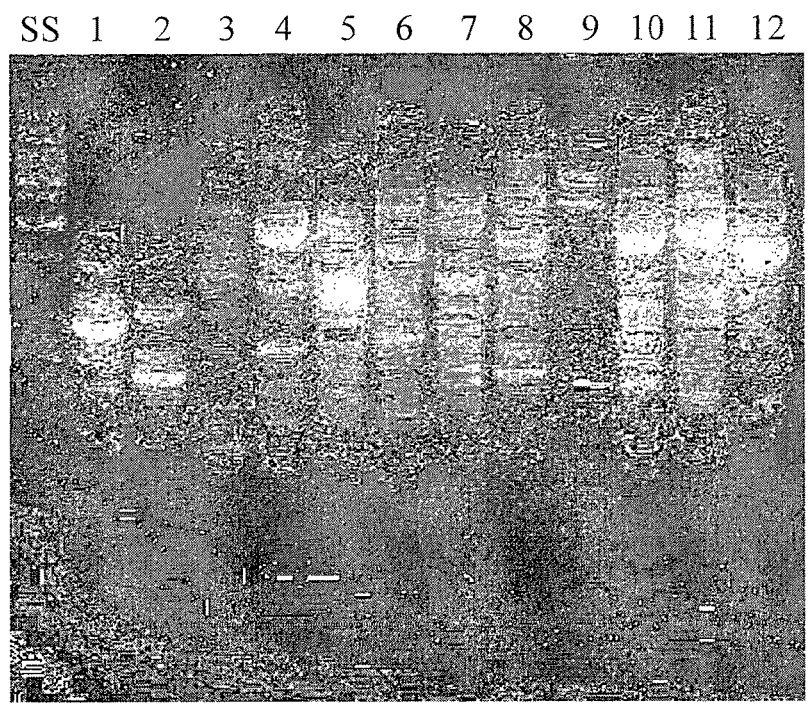
FIG. 19 is a photographic representation showing a gel on which amplification products generated using primers (SEQ ID NOs: 82 to 85) that incorporate codons of high use in Pseudomonas syringae par. tomato were electrophoresed. Tracks 1-3 PCR was performed with a primer of sequence SEQ ID NO: 82; Tracks 4-6 PCR was performed with a primer of sequence SEQ ID NO: 83; Tracks 7-9 PCR was performed with a primer of sequence SEQ ID NO: 84; Tracks 10-12 PCR was performed with a primer of sequence SEQ ID NO: 85. Tracks 1, 4, 7, 10—amplification reaction performed with genomic DNA from Pseudomonas strain AN5 DNA Tracks 2, 5, 8, 11—amplification reaction performed with genomic DNA from Pseudomonas syringae par. tomato DNA. Tracks 3, 6, 9, 12—amplification reaction performed with genomic DNA from Bacillus species DNA. SS Size standards

Furthermore a number of hyperprimers were synthesized that comprised high codon usage for *Pseudomonas syringae* par. tomato (SEQ ID NOs: 82 to 85). All of these primers produced a plurality of amplification products when used alone in a PCR reaction using genomic DNA from *P. syringae* par. tomato (FIG. 19).

These primers also produced a number of amplification products using genomic DNA from *Pseudomonas* strain AN5 or *Bacillus*. These results demonstrate the ability of the inventors to reproducibly design a probe or primer capable of hybridizing to a plurality of sites in a nucleic acid under moderate to high stringency conditions based only on the codon usage bias of that organism.

Example 15

Design of Hyperprimers Capable of Producing Increased Numbers of Amplification Products Two primers designed based on codon usage bias for humans comprised the sequence set forth in SEQ ID NOs: 73 and 75. One primer (SEQ ID NO: 73) was reverse of the other (3' to 5'), i.e., the codons were arranged in the reverse order.

The primers contained repeats of several codons, albeit not consecutive repeats. Interestingly the amino acid sequence encoded by each primer comprised a significant repeat of leucine (SEQ ID NOs: 74 and 76), as shown below:

```
                                            (SEQ ID NO: 73)
    5' CTG CTC GCC CTC CTG TTC CTG CTC 3'

(SEQ ID NO: 74)
       Leu Leu Ala Leu Leu Phe Leu Leu (SEQ ID NO: 75)
    3' CTC CTG TTC CTG CTC GCC CTC CTG 5'

(SEQ ID NO: 76)
       Leu Leu Phe Leu Leu Ala Leu Leu
```

Figure 20:
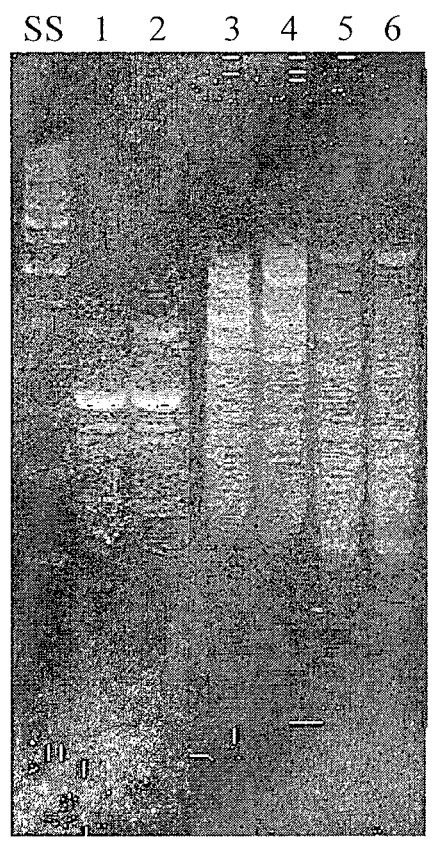
FIG. 20 is a photographic representation showing a gel on which amplification products using a primer that produces an increased number of amplification products have been electrophoresed. Lane 1 Human T cell line DNA amplified with primer with sequence SEQ ID NO: 69; Lane 2 Human BM cell line DNA amplified with primer with sequence SEQ ID NO: 69; Human T cell line DNA amplified with primer with sequence SEQ ID NO: 73; Human BM cell line DNA amplified with primer with sequence SEQ ID NO: 73; Human T cell line DNA amplified with primer with sequence SEQ ID NO: 75; Human BM cell line DNA amplified with primer with sequence SEQ ID NO: 75; and SS—Size standards.

When used alone in a PCR reaction performed essentially as described in Example 1 each primer produced a significant number of amplification products with two human cell lines (FIG. 20).

Figure 21:
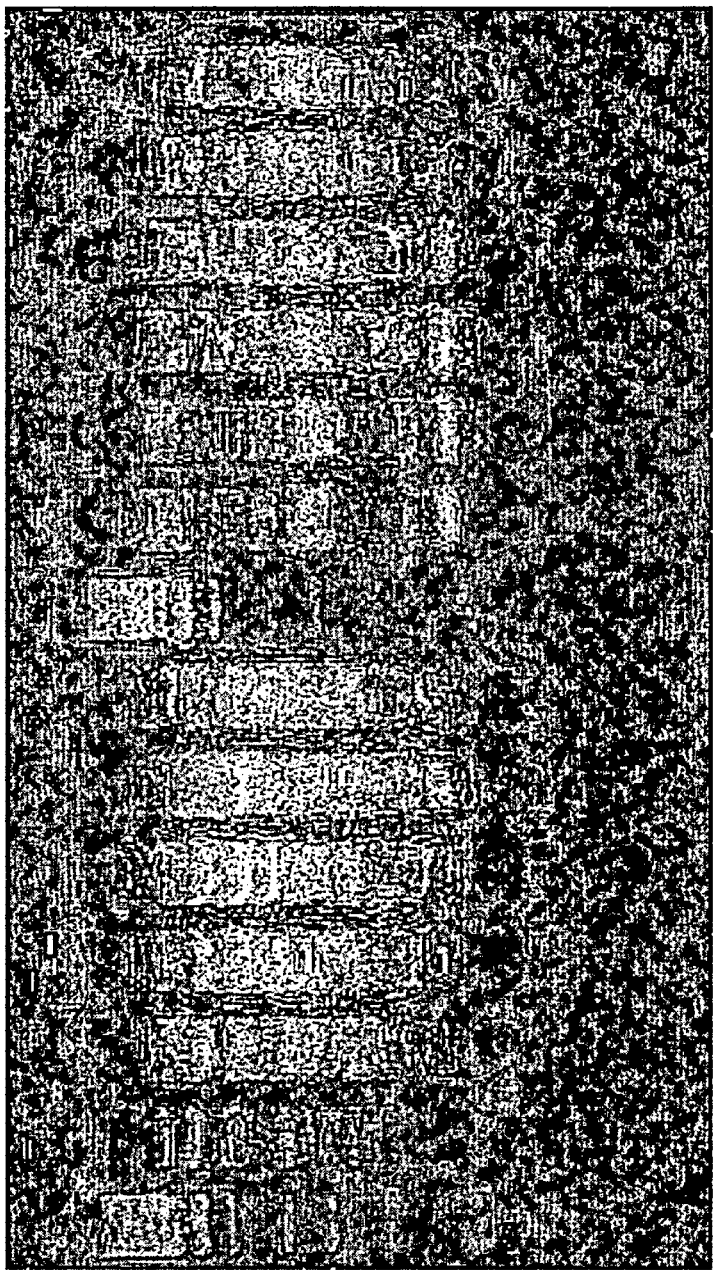
FIG. 21 is a photographic representation showing a gel on which amplification products generated using primers (SEQ ID NOs: 73 and 75) that produce increased numbers of amplification products when used alone in a PCR reaction were electrophoresed. Amplification reactions were performed using genomic DNA from a human T cell Lines. Lanes 1 to 6 amplification performed with a primer with sequence SEQ ID NO: 73, Lane 1—60° C., Lane 2—58.9° C. Lane 3—57.1° C., Lane 4—54.4° C., Lane 5—50.5° C., Lane 6—47.9° C.; Lanes 7 to 12 amplification performed with a primer with sequence SEQ ID NO: 75, Lane 1—60° C., Lane 2—58.9° C., Lane 3—57.1° C., Lane 4—54.4° C., Lane 5—50.5° C., Lane 6—47.9° C.

Using various hybridization temperatures ranging from 60° C. to 47.9° C. it was found that these amplification products were produced under high stringency conditions in the PCR reaction (FIG. 21).

Figure 22:
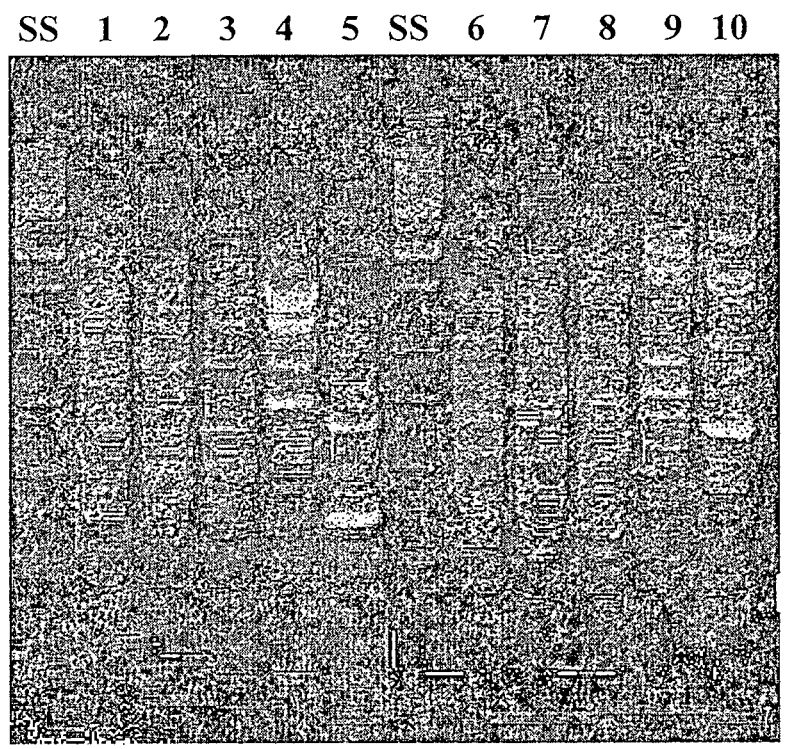
FIG. 22 is a photographic representation showing a gel on which amplification products generated using primers SEQ ID NOs: 73 and 75) that produce increased numbers of amplification products when used alone in a PCR reaction were electrophoresed. Amplification reactions were performed with a variety of template nucleic acids. Lanes 1 to 5, amplifications were performed with primer of sequence SEQ ID NO: 73. Lane 1 Human T cell line A DNA; Lane 2 Mouse cell line DNA; Lane 3 Mouse tail DNA; Lane 4 Bacillus bacterial DNA; Lane 5 Pseudomonas strain AN5 bacterial DNA. Lanes 6 to 10 amplifications were performed with primer of sequence SEQ ID NO: 75. Lane 6 Human T cell line A DNA; Lane 7 Mouse cell line DNA; Lane 8 Mouse tail DNA; Lane 9 Bacillus bacterial DNA; Lane 9 Pseudomonas strain AN5 bacterial DNA; and SS size standard.

Furthermore, these same primers generated a significant number of amplification products using DNA from other organisms (FIG. 22).

Example 16

The effect of nucleotide analogues on the hybridization of a hyperprimer Three primers that were routinely used were re-synthesized, such that uridine replaced thiamine, to determine if their ability to hybridize to a plurality of sites in a nucleic acid had changed. The primers comprised the following nucleotide sequences:

```
        Uridine analogue primer
                                            (SEQ ID NO: 77)
        AUUUGUGUCGAGUCGGUGAAG Standard primer
                                            (SEQ ID NO: 78)
        ATTTGTGTCGAGTCGGTGAAG Uridine analogue primer
                                            (SEQ ID NO: 79)
        GCCCACGGCUACCCGAUGGU
```

-continued

```
Standard primer
                                   (SEQ ID NO: 80)
GCCCACGGCTACCCGATGGT Uridine analogue primer
                                   (SEQ ID NO: 81)
AGCUUGUCGAGCGCGUUCAG Standard primer
                                   (SEQ ID NO: 48)
AGCTTGTCGAGCGCGTTCAG
```

Figure 23:
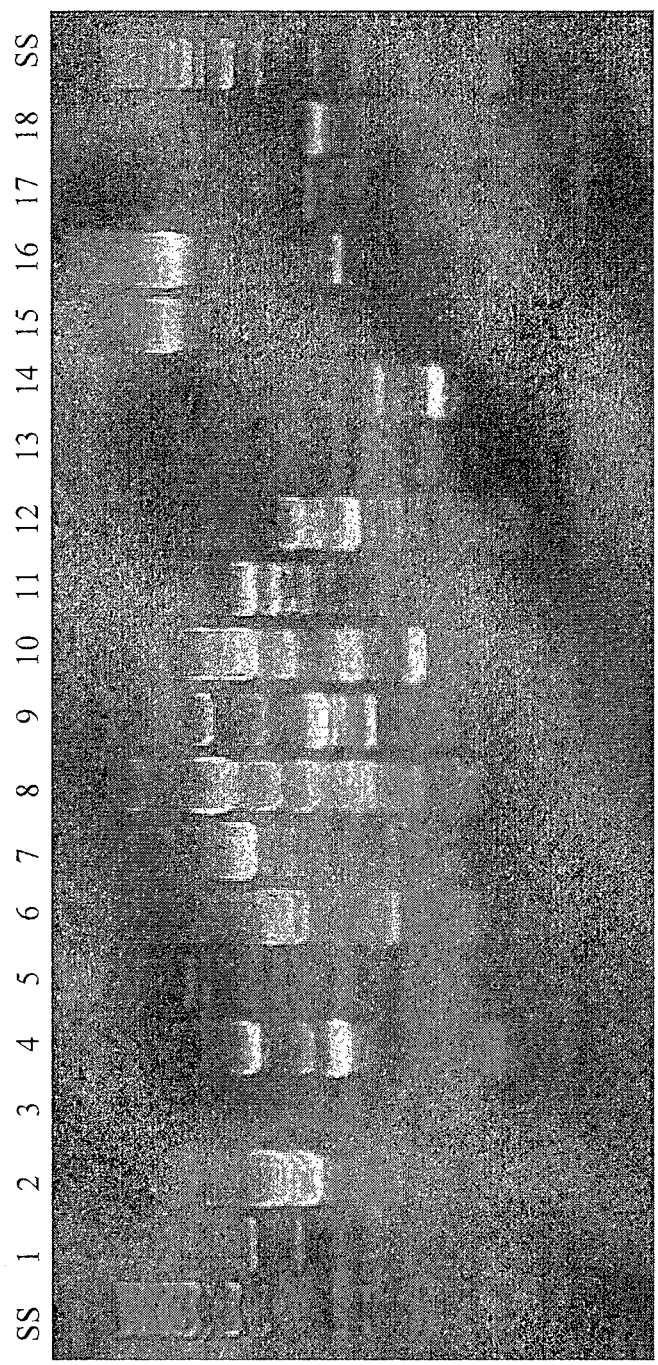
FIG. 23 is a graphical representation showing the effect of substitution of uracil for thymine in a probe or primer of the invention. Amplification reactions were performed with a primer containing either uracil or thymine. Lane 1 Pseudomonas strain AN5 DNA amplification performed with a primer comprising the sequence set forth in SEQ ID NO: 77; Lane 2. Pseudomonas strain AN5 DNA amplification performed with a primer comprising the sequence set forth in SEQ ID NO: 78; Lane 3. E. coli K-12 DNA amplification performed with a primer comprising the sequence set forth in SEQ ID NO: 77; Lane 4. E. coli K-12 DNA amplification performed with a primer comprising the sequence set forth in SEQ ID NO: 78; Lane 5. Wheat DNA amplification performed with a primer comprising the sequence set forth in SEQ ID NO: 77; Lane 6. Wheat DNA amplification performed with a primer comprising the sequence set forth in SEQ ID NO: 75; Lane 7. Pseudomonas strain AN5 DNA amplification performed with a primer comprising the sequence set forth in SEQ ID NO: 79; Lane 8, Pseudomonas strain AN5 DNA amplification performed with a primer comprising the sequence set forth in SEQ ID NO: 80; Lane 9, E. coli K-12 DNA amplification performed with a primer comprising the sequence set forth in SEQ ID NO: 79; Lane 10. E. coli K-12 DNA amplification performed with a primer comprising the sequence set forth in SEQ ID NO: 80; Lane 11, Wheat DNA amplification performed with a primer comprising the sequence set forth in SEQ ID NO: 79; Lane 12. Wheat DNA amplification performed with a primer comprising the sequence set forth in SEQ ID NO: 80; Lane 13. Pseudomonas strain AN5 DNA amplification performed with a primer comprising the sequence set forth in SEQ ID NO: 81; Lane 14, Pseudomonas strain AN5 DNA amplification performed with a primer comprising the sequence set forth in SEQ ID NO: 82; Lane 15. E. coli K-12 DNA amplification performed with a primer comprising the sequence set forth in SEQ ID NO: 81; Lane 16, E. coli K-12 DNA amplification performed with a primer comprising the sequence set forth in SEQ ID NO: 82; Lane 17, Wheat DNA amplification performed with a primer comprising the sequence set forth in SEQ ID NO: 81; Lane 18. Wheat DNA amplification performed with a primer comprising the sequence set forth in SEQ ID NO: 82.

All primers were used individually in a PCR reaction performed essentially as described in Example 1. The amplification products generated using primers comprising uridine were compared with those produced using the parent primer (FIG. 23). Amplification products were produced using nucleic acid from a number of different organisms.

The amplification products produced were different between the standard primer and the uracil substituted primers in most cases.

Example 17

Effect of Polymerase on Amplification

To determine whether or not the polymerase used for amplification with a primer of the invention affected the amplification products generated, different types of polymerase were used.

For this assay, PfuUltra™ DNA polymerase (Stratagene) isolated from *Pyrococcus furiosus* was initially tested.

PfuUltra™ DNA polymerase has one of the lowest error rates of any thermostable DNA polymerase studied to date.

Figure 24:
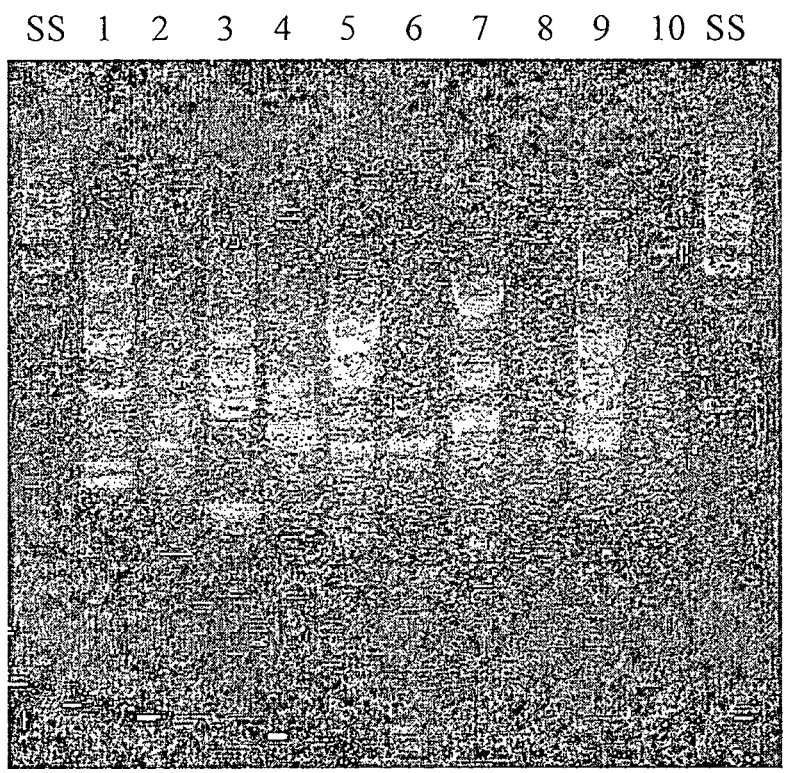
FIG. 24 is a photographic representation showing the effect of the type of polymerase on the amplification products produced using a primer comprising the sequence set forth in SEQ ID NO 55. PCR reactions were performed using this primer alone with one of Qiagen multiplex master mix (Taq polymerase)—Lanes 1, 3, 5 or 7, or Stratagene pfu ultra polymerase—Lane 2, or Qiagen pfu polymerase—Lanes 4, 6, and 8. Template DNA used was: genomic DNA from Pseudomonas strain AN5—Lanes 1 and 2; genomic DNA from E. coli K-12—Lanes 3 and 4, genomic DNA from wheat—Lanes 5 and 6, and genomic DNA from a human T cell line—Lanes 7 and 8. SS—size standard.

A direct comparison of amplification products amplified using Pfu or Taq with the same primer is shown in FIG. 24. This figure shows that the amplification products obtained are different when using different polymerases. Tracks 1 and 2 used *Pseudomonas* strain AN5 genomic DNA for amplification. Tracks 3 and 4 used *E. coli* K-12 genomic DNA for PCR amplification. Tracks 5 and 6 used wheat genomic DNA for PCR amplification. Tracks 7 and 8 used mouse genomic DNA for PCR amplification. Tracks 9 and 10 used human genomic DNA for PCR amplification. The odd tracks used Taq DNA polymerase, while the even tracks used PfuUltra™ DNA polymerase. The primer MUCFW4 (SEQ ID NO: 55) was used for priming in all cases. SS is DNA size standards. There are generally less amplicons produced with Pfu than Taq.

Figure 25:
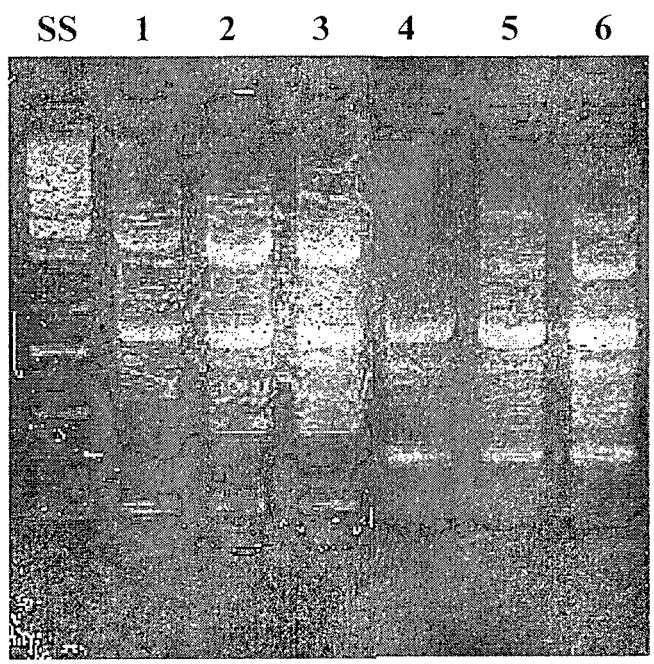
FIG. 25 is a photographic representation showing the effect of Taq polymerase from different sources on the amplification products produced using a primer comprising the sequence set forth in SEQ ID NO 55. PCR reactions were performed using this primer alone and a polymerase from Qiagen multiplex master mix—Lanes 1 and 4; Qiagen hot start Taq—Lanes 2 and 5; and Qiagen Taq—Lanes 3 and 6. Template DNA used was: genomic DNA from Pseudomonas strain AN5—Lanes 1 to 3 and genomic DNA from E. coli K-12—Lanes 4 to 6. SS—size standard.

Following this study it was determined whether or not different types of Taq produced different amplicons. To address this question the following products were tested:
Qiagen multiplex master mix
Qiagen hot start Taq
Qiagen Taq PCR reactions were performed essentially as described in Example 1. Tracks 1 to 3 used wheat genomic DNA for amplification. Tracks 4 to 6 used human genomic DNA for amplification. primer MUCFW4 (SEQ ID NO: 55) was used for priming in all cases. SS is DNA size standards As shown in FIG. 25 each of the Taq preparations produced substantially the same result.

Example 18

Identification of Wheat Varieties and Cultivars Using Hyperprimers

To determine the ability of the probes or primers of the invention to differentiate between genetically related organisms, DNA was isolated from thirteen cultivars of wheat (*Triticum aestivum*). DNA was independently isolated twice from two cultivars to confirm the repeatability of any results attained. PCR reactions were performed using eight different primers (each used individually) including primers comprising the nucleotide sequence set forth in SEQ ID NO: 48, SEQ ID NO: 52, SEQ ID NO: 53, SEC ID NO: 55 and SEQ ID NO: 57.

Figure 26:
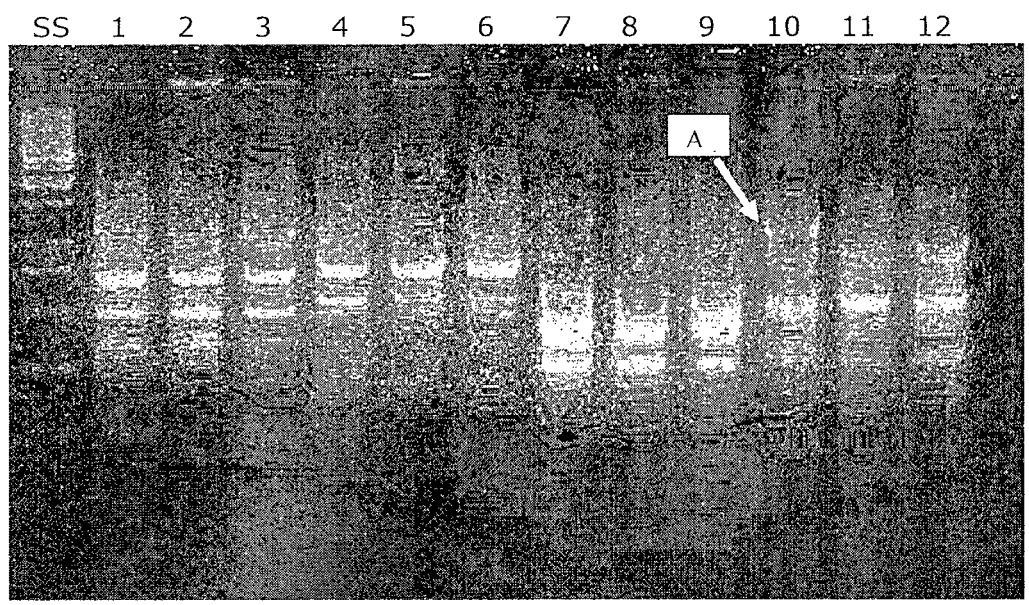
FIG. 26 is a photographic representation showing amplification products produced from genomic DNA of various cultivars of wheat using a primer of the invention. Wheat genomic DNA used was: Triticum aestivum cv. condor—Lanes 1, 4, 7, 10; Triticum aestivum cv. monchos S—Lanes 2, 5, 8, 11; and Triticum aestivum cv. hartog—Lanes 3, 6, 9, 12. Primers used comprised the sequence set forth in SEQ ID NO: 53—Lanes 1 to 3; SEQ ID NO: 48—Lanes 4 to 6; SEQ ID NO: 52—Lanes 7 to 9; and SEQ ID NO: 55—Lanes 10 to 12. Symbol "A" indicates amplification products specific to one or more cultivars of wheat.

Crude touchdown PCR reactions were performed with an annealing temperature of 50° C. for the initial 5 cycles and 48° C. for the subsequent 35 cycles. FIG. 26 shows the amplicons produced using one of three primers each used in a reaction with genomic DNA from *Tr. aestivum* (CONDOR), *Tr. aestivum* (MONCHO S) or *Tr. aestivum* (HARTOG). As can be seen, the primer comprising the sequence set forth in SEQ ID NO: 55 amplified a product that was unique to *Tr. aestivum* (CONDOR).

Figure 27:
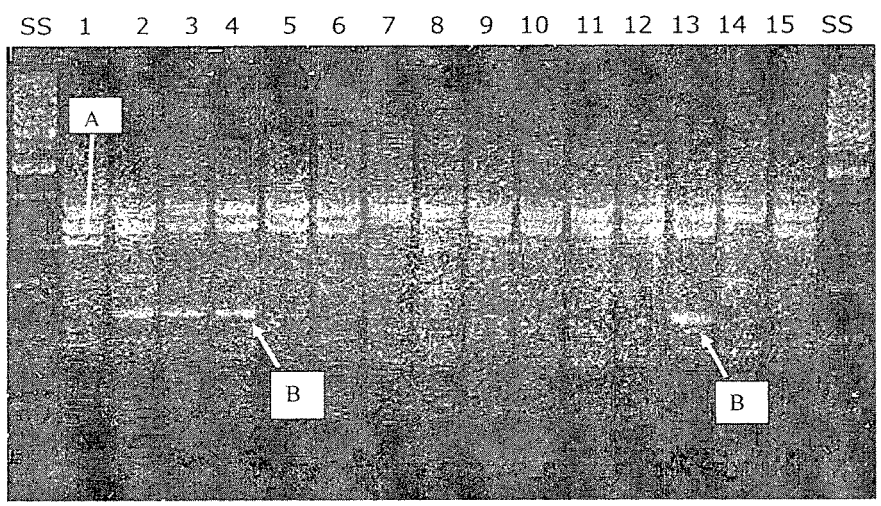
FIG. 27 is a photographic representation showing amplification products produced from genomic DNA of various cultivars of wheat using a primer of the invention. Wheat cultivars used were: Lane 1, thirteen cultivars of wheat cv. sunmist; Lane 2, *Triticum aestivum* cv. condor—DNA prep 1; Lane 3, *Triticum aestivum* cv. skua; Lane 4, *Triticum aestivum* cv. torres; Lane 5, *Triticum aestivum* cv. canna; Lane 6, *Triticum aestivum* cv. bodallin; Lane 7, *Triticum aestivum* cv. timson; Lane 8, *Triticum aestivum* cv. songlen; Lane 9, *Triticum aestivum* cv. blade; Lane 10, *Triticum aestivum* cv. machete; Lane 12, *Triticum aestivum* cv. hartog—DNA prep 1; Lane 13, *Triticum aestivum* cv. mulgara; Lane 14, *Triticum aestivum* cv. condor—DNA prep 2; Lane 15, *Triticum aestivum* cv. monchos S; Lane 16, *Triticum aestivum* cv. hartog—DNA prep 2. The primer used comprised the sequence set forth in SEQ ID NO: 78. Symbols "A" and "B" indicate amplification products specific to one or more cultivars of wheat.

PCR reactions were then performed essentially as described above using nucleic acid from each of thirteen cultivars of wheat. As shown in FIG. 27, a primer comprising the sequence set forth in SEQ ID NO: 85 amplified a product specific to wheat cultivar sunmist in addition to an amplification product only detected in *Tr. aestivum* (CONDOR), *Tr. aestivum* (SKUA) and *Tr. aestivum* (TORRES).

Additionally, this specific amplification product was detected in two preparations of DNA from *Tr. aestivum* (CONDOR), demonstrating the reproducibility of this method.

Figure 28:
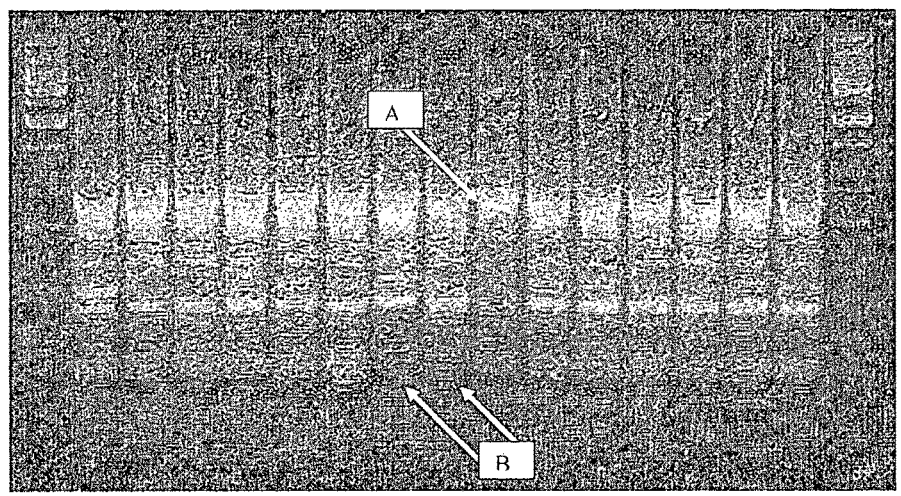
FIG. 28 is a photographic representation showing amplification products produced from genomic DNA of various cultivars of wheat using a primer of the invention. Wheat cultivars used were: Lane 1, *Triticum aestivum* cv. sunmist; Lane 2, *Triticum aestivum* cv. condor—DNA prep 1; Lane 3, *Triticum aestivum* cv. skua; Lane 4, *Triticum aestivum* cv. torres; Lane 5, *Triticum aestivum* cv. canna; Lane 6, *Triticum aestivum* cv. bodallin; Lane 7, *Triticum aestivum* cv. timson; Lane 8, *Triticum aestivum* cv. songlen; Lane 9, *Triticum aestivum* cv. blade; Lane 10, *Triticum aestivum* cv. machete; Lane 12, *Triticum aestivum* cv. hartog—DNA prep 1; Lane 13, *Triticum aestivum* cv. mulgara; Lane 14, *Triticum aestivum* cv. condor—DNA prep 2; Lane 15, *Triticum aestivum* cv. monchos S; Lane 16, *Triticum aestivum* cv. hartog—DNA prep 2. The primer used comprised the sequence set forth in SEQ ID NO: 56. Symbols "A" and "B" indicate amplification products specific to one or more cultivars of wheat.

Using a primer comprising the nucleotide sequence set forth in SEQ ID NO: 56 a unique amplification product was detected for *Tr. aestivum* (BLADE: FIG. 28), using conditions essentially as described above. Furthermore, an amplification product was detected that was only detected in *Tr. aestivum* (TIMSON) and *Triticum aestivum* (SONGLEN).

Figure 29:
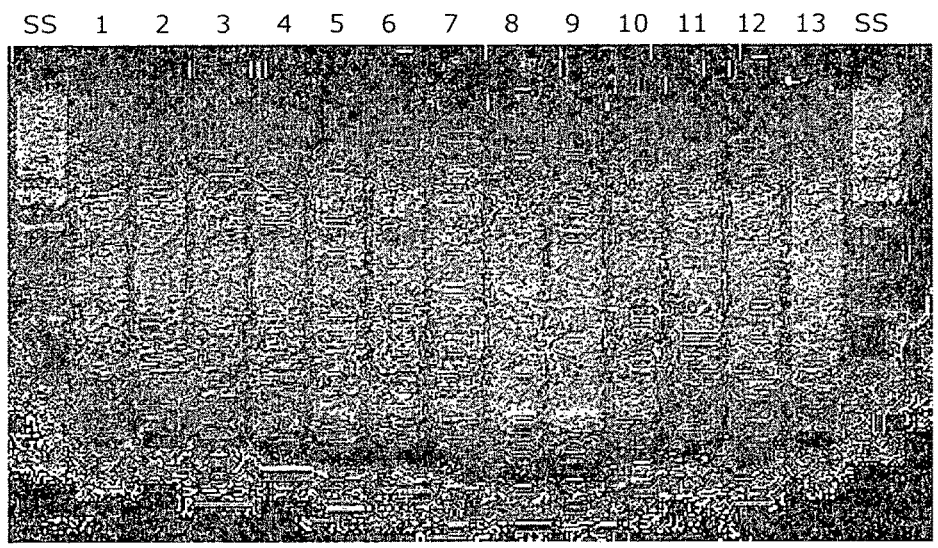
FIG. 29 is a photographic representation showing amplification products produced from genomic DNA of various cultivars of wheat using a primer of the invention. Wheat cultivars used were: Lane 1, *Triticum aestivum* cv. sunmist; Lane 2, *Triticum aestivum* cv. condor Lane 3, *Triticum aestivum* cv. skua; Lane 4, *Triticum aestivum* cv. torres; Lane 5, *Triticum aestivum* cv. canna; Lane 6, *Triticum aestivum* cv. bodallin; Lane 7, *Triticum aestivum* cv. timson; Lane 8, *Triticum aestivum* cv. songlen; Lane 9, *Triticum aestivum* cv. blade; Lane 10, *Triticum aestivum* cv. machete; Lane 11, *Triticum aestivum* cv. hartog; Lane 12, *Triticum aestivum* cv. mulgara; and Lane 13, *Triticum aestivum* cv. monchos S. The primer used comprised the sequence set forth in SEQ ID NO: 57.

A number, of primers including a primer comprising the nucleotide sequence SEQ ID NO: 57, produced a large number of amplification products under conditions essentially as described above. As can be seen in FIG. 29, a number of the amplification products are specific to individual cultivars of wheat.

Furthermore, as observed in each of FIGS. 25 to 29, each primer amplified a number of products that were consistently observed in all cultivars tested. Accordingly, any of these amplification products may be useful for identifying a wheat strain of the genus and species Tr. aestivum.

Example 19

Determining the Site of Hybridization of a Hyperprimer in a Eukaryote

The amplification products amplified using the method described in Example 5 and Example 8 are separated via electrophoresis and specific major products are excised and isolated using the QIAGEN gel extraction kit essentially as described by the manufacturer.

Purified amplification products are then individually cloned into the pGEM-T Easy vector (Promega) essentially as described by the manufacturer. This vector enables cloning of amplicons produced using Taq polymerase.

Using a primer capable of hybridizing to the T7 promoter in the pGEM vector (TAATACGACTCACTATAGGG; SEQ ID NO: 67) or the SP6 promoter (ATTTAGGTGACAC-TATAG; SEQ ID NO: 68) the sequence of the insert is determined. This sequence allows the amplification product to be determined.

By analyzing this sequence in silico (using BLAST) the sequence of the entire region is determined. Using the determined sequence, the sequence of the site to which the hyperprimer hybridizes is determined.

Example 20

NASBA Analysis of mRNA Expression Using a Hyperprimer

To determine the ability of a hyperprimer to amplify products from mRNA a nucleic acid sequence based amplification (NASBA) method is used.

RNA is extracted from *Pseudomonas* strain AN5 culture, an *E. coli* culture, a human cell line and a mouse cell line using the Qiagen RNeasy miniprep kit.

For amplification, the primer comprising the sequence set forth in SEQ ID NO: 62 is produced, fused to a nucleic acid comprising the sequence-AATTCTAATACGACTCAC-TATAGGGAGA (i.e., comprising the T7 RNA polymerase-binding and preferred transcriptional initiation sites, SEQ ID NO: 64) to produce the amplification primer comprising the sequence set forth in SEQ ID NO: 65.

The NASBA reaction is performed by adding 5 µl 2.5 mM KCl, 15 mM MgCl2, 1.25 mM each deoxynucleoside triphosphate, 2.5 mM each ribonucleoside-59-triphosphate, 0.25 mM biotin-11-UTP [Sigma Chemical Co.], 14 mM dithiothreitol, and 1 pmol each of the amplification primer), heating the resultant mixture at 65° C. for 5 min, then equilibrating it to 41° C., and adding 2 µl of a mixture containing 8 U of avian myeloblastosis virus reverse transcriptase, 40 U of T7 RNA polymerase (Pharmacia), 0.1 U of RNase H (Pharmacia), 12.5 U of RNasin (Promega), and 2.6 mg of bovine serum albumin (Boehringer Mannheim). This mixture is incubated at 41° C. for 90 min. Amplified samples (NASBA product) are then kept on ice until the assay of amplimers.

Amplification products are then analyzed using gel electrophoresis.

Example 21

Determining the Site of Insertion of a Heterologous Nucleic Acid in a Mouse

Using gDNA from the mouse described in Example 5 comprising the GFP insertion, the site of the insertion is determined using a hyperprimer and a primer designed to hybridize specifically to GFP.

Several primers (comprising the sequence set forth in SEQ ID NOs: 58 to 63) were used in a PCR reaction in combination with the GFP specific primer comprising the sequence set forth in SEQ ID NO: 66. PCR reactions were performed essentially as described in Example 12.

Each of the primers (SEQ ID NO: 58 to 63) were simultaneously used individually in a PCR reaction, essentially as described in Example 9.

Furthermore, each of the previously described PCR reactions were performed with a control mouse, i.e., non-transgenic littermates which do not incorporate the GFP encoding region.

By analyzing a gel on which each amplification product has been electrophoresed, major products that occur using the GFP primer with a primer in the transgenic mouse but not the wild-type mouse are identified and isolated. Furthermore, bands that occur using a single primer in the transgenic mouse but not the wild-type control are identified and isolated.

Example 22

Detecting Prostate Cancer Using a Hyperprimer

To determine the ability of a hyperprimer to detect a genetic change associated with prostate cancer laser micro dissection of prostate cancer tissue is used to isolate cancerous cells and normal cells.

Matched prostate and adjacent normal prostate tissues are obtained from patients who had undergone radical prostatectomy. The tissues are immediately embedded in Tissue-Tek OCT (Miles) and frozen at −70° C. A laser-gene capture micro dissection (LCM) instrument is used to micro dissect tumors from 1-µm frozen sections. Initial sections are stained by hematoxylin and eosin, and these stained sections are used as optical templates for identification and isolation of tumor and normal cells from serial unstained sections from the same block. Normal cells and tumor cells dissected by LCM are digested with proteinase K and extracted with phenol/chloroform, followed by ethanol precipitation. Furthermore, to ensure the DNA integrity, all DNA samples are analyzed by PCR for β-actin gene amplification.

PCR reactions are performed using each 25-mer oligonucleotide (SEQ ID NOs: 58 to 63) individually. PCR reactions contain 5 ng of DNA template, 50 ng of each primer, 0.5 unit of AmpliTaq Gold (Perkin-Elmer), PCR buffer at 1× concentration, 200 mM dNTP mix in a 50 µl final volume. PCR reactions are performed with either gDNA from cancerous tissue or gDNA from normal tissue. Reactions are cycled essentially as described in Example 5.

Amplification products are then electrophoresed. Products that consistently occur in a number of samples from cancerous tissue and not the normal tissue are considered to be markers of prostate cancer.

Example 23

Detection of a Point Mutation Using a Hyperprimer

*Pseudomonas aeruginosa* strain PAO 503 is mutated using ethyl methane sulfonate (EMS) mutagenesis essentially as described in Bryan and Kwan *Antimicrob. Agent. Chemo.* 19: 358-364, 1998. EMS induces small mutations and point mutations into the genome. Cells are allowed to recover from mutagenesis and individual colonies isolated.

Putative mutant colonies are then grown in culture and genomic DNA is isolated.

PCR reactions are performed using each of the 25mer oligonucleotides (SEQ ID NOs: 58 to 63) individually. Each reaction is performed using a QIAGEN kit and comprised the following:

| | |
|---|---|
| Multiplex mix (2x, includes Taq polymerase) | 10 µl |
| supplementary dNTPs (2 mM each) | 0.1 µl |
| primer (10 µM) | 2 µl |
| genomic DNA | 1 µl |
| ddH$_2$O | up to 20 µl |

The PCR reaction was then cycled in a Corbett PCR 960C Thermal cycler using the following annealing conditions:
56° C.—5 cycles
54° C.—30 cycles Each PCR reaction is also performed with gDNA isolated form the unmutated parental strain, *Pseudomonas aeruginosa* strain PAO 503.

Following electrophoresis of the amplification products amplified, the amplification product's specific for each mutated clone is compared to the control reaction and each of the other reactions in order to identify differentials between amplicon profiles.

Example 24

Differentiating Between Monozygotic Twins Using a Primer of the Invention

To determine the level of genetic differences detected using a probe or primer of the invention, PCR is performed using genomic DNA from monozygotic twins using a single primer of the invention.

Genomic DNA is isolated from monozygotic twins and used in the following PCR reaction:

| | |
|---|---|
| QIAGEN mutiplex master mix | 10 μl |
| 2 mM dNTP | 0.1 μl |
| 10 μM primer | 1 μl |
| DNA | 2 μl |
| H$_2$O | 6.9 μl |
| Total Vol. | 20 μl |

Reactions are then cycled under the following conditions:
Cycle 1 (1×)
1. 95° C. 15 min.
2. 56° C. 1 min.
3. 72° C. 4 min
Cycle 2 (4×)
1. 94° C. 1 min.
2. 56° C. 1 min.
3. 72° C. 4 min
Cycle 3 (35×)
1. 94° C. 1 min.
2. 54° C. 1 min.
3. 72° C. 4 min
Cycle 4
4° ∝

The primer used for this assay comprises the nucleotide sequence set forth in SEQ ID NO: 55.

Figure 30:
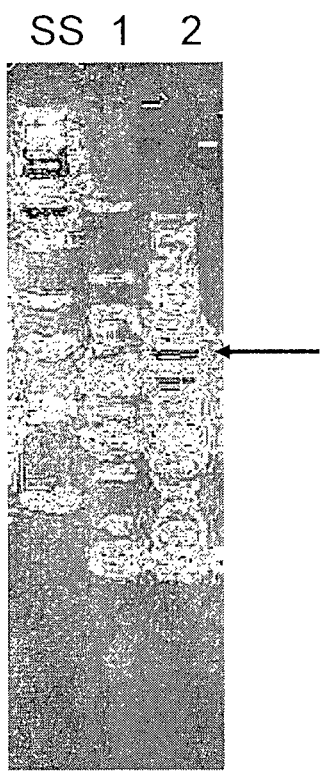
FIG. 30 is a photographic representation showing amplification products produced using a primer of the invention to amplify nucleic acid from genomic DNA from monozygotic twins. PCR reactions were performed with a primer comprising the sequence set forth in SEQ ID NO: 55. Lane 1 shows amplification products produced using genomic DNA from monozygotic twin 1 and Lane 2 shows amplification products produced using genomic DNA from monozygotic twin 2. The arrow indicates an amplification product specific to one of the monozygotic twins. SS, size standard.

PCR reactions are then electrophoresed. Using relatively high stringency conditions the inventors detected at least one amplification product that was specific to one of the twins (FIG. 30). As the twins were both derived from the same zygote, they would be likely to contain almost identical genotypes. Theoretically, detection of genetic differences would reflect the detection of changes that have arisen during the embryonic development of each twin. Such changes would most likely only occur in a fraction of the cells of the twin in question. Accordingly, the data attained suggests the ability of a probe or primer to detect even minor genetic differences between almost genetically identical individuals.

Example 25

Genotyping Fungi with a Primer of the Invention

Using the primers described in Example 15 that produce an increased number of amplification products when used alone in a PCR reaction, the inventors detected differences between different species and varieties of fungus. Genomic DNA was isolated from *Ascophera apis* (chalkbrood)—bee fungus, *Ascophera apis* (chalkbrood), *Gaeumannomyces graminis* var *tritici* C3 (pathogenic), *Gaeumannomyces graminis* var *graminis* W2P (non-pathogenic) and *Gaeumannomyces graminis* var *tritici* QW1 (pathogenic with lower virulence than C3). PCR was performed using a primer comprising the nucleotide sequence set forth in SEQ ID NO: 73 or SEQ ID NO: 75. Reactions were performed essentially as described in Example 1.

Figure 31:
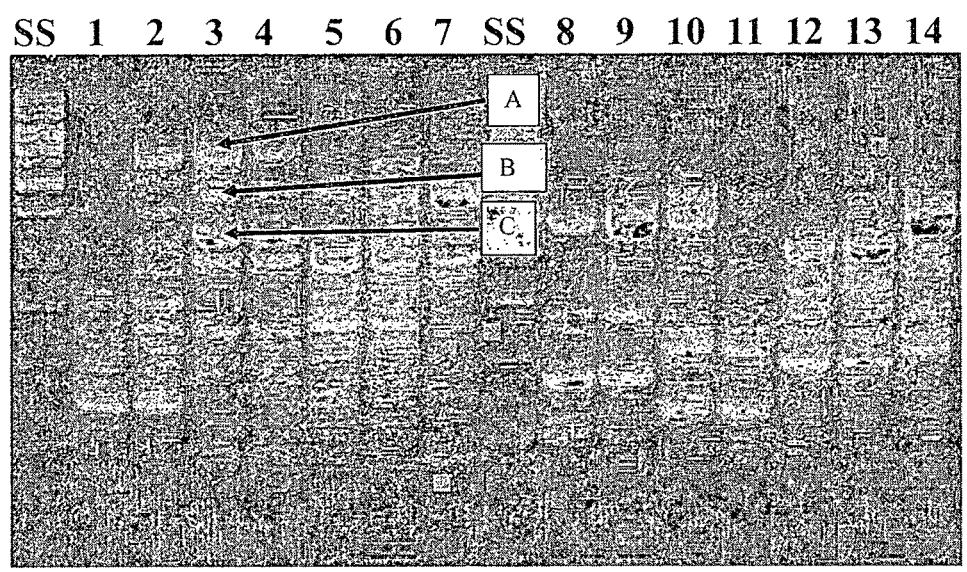
FIG. 31 is a photographic representation showing amplification products produced using a primer of the invention to amplify nucleic acid from genomic DNA from one of a variety of fungi. PCR reactions were performed with a primer comprising the sequence set forth in SEQ ID NO: 73 or SEQ ID NO: 75. Genomic DNA was used from the following organisms: Lanes 1 and 8, *Ascophera apis* (chalkbrood)—bee fungus; Lanes 2 and 9, *Ascophera apis* (chalkbrood); Lanes 3 and 10, *Gaeumannomyces graminis* var *tritici* C3 preparation 1 (pathogenic)—take-all fungus; Lanes 4 and 11, *Gaeumannomyces graminis* var *tritici* C3 preparation 2 (pathogenic); Lanes 5 and 12, *Gaeumannomyces graminis* var *graminis* W2P preparation 1 (non-pathogenic); Lanes 6 and 13, *Gaeumannomyces graminis* var *graminis* W2P preparation 2 (non-pathogenic); and Lanes 7 and 14, *Gaeumannomyces graminis* var *tritici* QW1 preparation 1 (pathogenic, lower virulence than C3). "A" indicates an amplification product specific to *Gaeumannomyces graminis* var *tritici* C3. "B" indicates an amplification product specific to *Gaeumannomyces* sp. "C" indicates an amplification reaction specific to *Gaeumannomyces graminis* var *tritici*. SS, size standard.

Following thermal cycling, PCR reactions were electrophoresed. As shown in FIG. 31, a number of amplification products were detected that were specific for either a specific genera of fungus or a particular species of fungus or a specific strain of fungus.

Furthermore, results attained with these primers demonstrate that they amplify an increased number of amplification products when used in a PCR reaction alone. This occurs even using genomic DNA from an organism genetically diverse to that to which the primers were designed to hybridize (i.e., a human). Similar results were attained in humans, mice and bacteria. Accordingly, these primers are most likely useful for determining nucleic acid from a specific genera, species or variety.

Example 26

Sequence Confirmation of Organism-Specific Amplification Products Produced Using Hyperprimers Hyperpriming bands have been observed in a range of organisms. To show these hyperpriming bands are not artifacts and have been generated from the genome of the organism used in the PCR reaction the identity of a number hyperpriming bands generated in different organisms was determined.

A hyperpriming reaction using a single primer that comprised a sequence as set forth in SEQ ID NO: 57 (GOD1) or SEQ ID NO: 78 (GOD18) was performed essentially as described in Example 1 and using genomic DNA from a variety of organisms as DNA template. Several hyperpriming bands were generated from each hyperpriming reaction. A number of hyperpriming bands from each reaction were isolated from agarose gels and each cloned into the pGEM T easy vector (Promega Pty Ltd.) at a site flanked by the Sp6 and T7 priming sites for sequencing. The DNA sequence of each of the hyperpriming DNA fragments was determined using Sp6 and T7 primers. Two additional primers were designed to anneal upstream of the Sp6 and T7 priming sites on vector sequence and were also used for sequencing. Table 5 summarizes the number of hyperpriming DNA fragments analysed from the different organisms.

TABLE 5

Summary of hyperpriming DNA fragments analyzed by sequencing

| | Number of hyperprimer fragments analyzed | |
|---|---|---|
| Organism | Hyperprimer GOD 1 (SEQ ID NO: 57) | Hyperprimer GOD 18 (SEQ ID NO: 78) |
| *Pseudomonas aeruginosa* PAO | 7 | 4 |
| *Escherichia coli* K-12 | 5 | 4 |
| *Bacillus subtilis* | 5 | 5 |

TABLE 5-continued

Summary of hyperpriming DNA fragments analyzed by sequencing

| Organism | Number of hyperprimer fragments analyzed | |
|---|---|---|
| | Hyperprimer GOD 1 (SEQ ID NO: 57) | Hyperprimer GOD 18 (SEQ ID NO: 78) |
| Triticum aestivum (wheat) | 1 | 1 |
| Arabidopsis thaliana | 1 | 1 |
| Mus musculus (mouse) | 1 | 1 |
| Homo sapien (human) | 1 | 1 |

A full double strand DNA sequence was obtained for the hyperpriming fragment analysed. The identity of the hyperpriming DNA fragment was determined in a NCBI blastn search. Table 6 and 7 summarizes the sequence homology observed of candidate hyperpriming fragments from these different organisms in a NCBI blastn search.

In all cases it was found that the hyperpriming DNA fragments showed very strong sequence homology to the genomic DNA of the organism (i.e., DNA template) used in the PCR reaction to generate it. Although all the organisms selected for this study had significant genomic DNA sequence available in the NCBI database, the sequence available in NCBI data base may be limited for some hosts. Accordingly, the sequence homology obtained from the NCBI blastn search is limited to the sequence deposited in the database, thus the strongest homology obtained by this method may be a closely related sequence if the actual sequence for the species analysed is not available in the database. Despite this limitation, the data shows that only in one example, a Triticum aestivum (wheat) 1.1 Kb GOD1 (SEQ ID NO: 57) hyperpriming DNA fragment analysed showed significant sequence homology to sub clone of Triticum monococcum, genome, as corresponding sequence for this region is not yet available for Triticum aestivum. In any event, the hyperpriming band analysed shows strong sequence homology to a very close relative of Triticum species, which is the available sequence in the database.

These data establishes the identity, and the origin of the hyperpriming band observed in hyperpriming reactions. Accordingly, the hyperpriming bands observed are not artifacts but are PCR generated DNA fragments specific to the DNA template added to the hyperpriming PCR reaction.

TABLE 6

Sequence homology of candidate bacterial Hyperpriming DNA fragments analyzed

| Organism | Hyper-primer | Fragment Size (approximate) | DNA sequence homology observed |
|---|---|---|---|
| Pseudomonas aeruginosa PAO | GOD1 SEQ ID NO: 57 | 0.85 Kb | Approximately 856 bp of the hyperpriming fragment DNA sequence shows strong homology (99%, E value 0.0) to a conserved hypothetical protein in the Pseudomonas aeruginosa PAO1, complete genome - Refer to FIG. 32 |
| Pseudomonas aeruginosa PAO | GOD18 SEQ ID NO: 78 | 0.85 Kb | Approximately 601 bp of the hyperpriming fragment DNA sequence shows strong homology (100%, E value 0.0) to a probable outer membrane receptor for iron transport in the Pseudomonas aeruginosa PAO1, complete genome - Refer to FIG. 33 |
| Escherichia coli K-12 | GOD1 SEQ ID NO: 57 | 1.1 Kb | Approximately 949 bp of the hyperpriming fragment DNA sequence shows strong homology (99%, E value 0.0) to a glycoside hydrolase family 3 domain protein in the Escherichia coli K-12, strain DH1 complete genome - Refer to FIG. 34 |
| Escherichia coli K-12 | GOD18 SEQ ID NO: 78 | 0.85 Kb | Approximately 851 bp of the hyperpriming fragment DNA sequence shows strong homology (99%, E value 0.0) to a protein of unknown function (CsiD) in the Escherichia coli K-12, strain DH1 complete genome - Refer to FIG. 35 |
| Bacillus subtilis | GOD1 SEQ ID NO: 57 | 2.5 Kb | Approximately 2404 bp of the hyperpriming fragment DNA sequence shows strong homology (95%, E value 0.0) to 4 ribonuclease J2, protein enhancing factor in the Bacillus subtilis complete genome. In this example, a small segment of the query hyperpriming fragment sequence was only single stranded (<250 bp)-Refer to FIG. 36 |
| Bacillus subtilis | GOD18 SEQ ID NO: 78 | 1.2 Kb | Approximately 851 bp of the hyperpriming fragment DNA sequence shows strong homology (91%, E value 0.0) to a putative aldo/keto reductase dephosphoco-enzyme A kinase in the Bacillus subtilis complete genome - Refer to FIG. 37 |

TABLE 7

Sequence homology of candidate eukaryotic Hyperpriming DNA fragments analyzed

| Organism | Hyper-primer | Fragment Size (approximate) | DNA sequence homology observed |
|---|---|---|---|
| Triticum aestivum (wheat) | GOD1 SEQ ID NO: 57 | 1.1 Kb | Approximately 838 bp of the Triticum aestivum hyperpriming fragment DNA sequence shows strong homology (94%, E value 0.0) to subclone of Triticum monococcum, genome - Refer to FIG. 38 |
| Triticum aestivum (wheat) | GOD1 SEQ ID NO: 57 | 0.6 Kb | Approximately 411 bp of the Triticum aestivum hyperpriming fragment DNA sequence shows strong homology (96%, E value 0.0) to Triticum aestivum cultivar Renan clone BAC 930H14, complete sequence. - Refer to FIG. 39 |
| Arabidopsis thaliana | GOD18 SEQ ID NO: 78 | 0.5 Kb | Approximately 410 bp of the Arabidopsis thaliana hyperpriming fragment DNA sequence shows strong homology (99%, E value 0.0) to |

TABLE 7-continued

Sequence homology of candidate eukaryotic Hyperpriming DNA fragments analyzed

| Organism | Hyper-primer | Fragment Size (approximate) | DNA sequence homology observed |
|---|---|---|---|
| Mus musculus (mouse) | GOD1 SEQ ID NO: 57 | 0.95 Kb | Arabidopsis thaliana, DNA chromosome 4 - Refer to FIG. 40 Approximately 769 bp of the Mus musculus hyperpriming fragment DNA sequence with Mus musculus BAC clone RP24-473A18 from chromosome 9, complete sequence - Refer to FIG. 41 |
| Mus musculus (mouse) | GOD1 SEQ ID NO: 57 | 0.8 Kb | Approximately 769 bp of the Mus musculus hyperpriming fragment DNA sequence with mouse DNA sequence from clone RP23-206E3 on chromosome 11 which contains a novel gene, complete sequence - Refer to FIG. 42 |
| Homo sapien (human) | GOD1 SEQ ID NO: 57 | 0.65 Kb | Approximately 620 bp of the Homo sapien hyperpriming fragment DNA sequence shows homology with Homo sapiens CTD (carboxy-terminal domain, RNA polymerase II, polypeptide A) phosphatase, subunit 1 (CTDP1) on chromosome18. - Refer to FIG. 43 |

Example 27

Differentiating Between Bacterial Isolates from Bee Guts

The method and primers of the invention were shown by the inventors to be useful in demonstrating the microbial gut community diversity in the Australian honey bee comprises gram-positive, gram-negative and gram-variable bacteria with distinct colony morphology. The relatedness of the bacterial isolates is useful in determining an association of bacterial isolates with inhibition of Chalkbrood fungus.

Example 27: Methods

27. Methods: Isolation of Bee Gut Bacteria on Specific Enrichment Media

Two bee colonies were sampled from the ACT for an initial indication of the microbial environment within the colony. Samples were taken from comb honey, beebread, larvae, nurse bees and worker bees. An Australian wide survey of nurse bees was then carried out as outlined. In all cases, the bacterial count (cfu/ml) data was log 10-transformed. Data obtained was evaluated statistically using Genstat version 9.0. Mann-Whitney U (Wilcoxon rank-sum) test for non-parametric analysis was used to compare cfu/ml of bee gut between different samples. Observed differences were considered significant at p≤0.05. Bacteria were isolated from the honey bee gut on specific enrichment media. Bacteria were selected on Tryptic Soy Agar (TSA), Eosin Methylene Blue Agar (EMB), modified Gould Media (mS1) and Glucose Calcium Carbonate Media (G-CaCO3). For each isolation, the colonies with visually different colony morphology from the different enrichment media, were transferred on TSA, purified a number of times and stored. All isolates were categorised using gram staining.

27. Methods: Bioassays of Bee Gut Bacterial Isolates

Bacteria isolated and purified from the enrichment media on TSA were tested for Chalkbrood inhibition using bioassays. Bacterial isolates were ranked according to their ability to inhibit the growth of the fungal pathogen. This is expressed by a zone of inhibition (Dhingra and Sinclair, 2000).

The percentage of inhibition was calculated using the following formula (Montealegre, 2003):

$$\% \text{ Inhibition} = [1-(\text{fungal growth/control growth})] \times 100$$

In all cases, the comparisons were done based on a minimum average of six replications. Bacterial isolates that resulted in 30% inhibition or more were stored in sucrose-glycerol solution for further analysis. All isolates that showed no biocontrol or those that had inhibition of <30% in Chalkbrood bioassays were discarded.

27. Methods: Differentiation of Bee Gut Bacterial Isolates that Inhibit Chalkbrood Using Hyperpriming Bee gut bacteria isolated from four bees of a single colony were separated on the basis of gram staining. Gram positive and gram negative isolates were analysed as separate groups by hyperpriming PCR. In each case hyperpriming PCR reactions were run independently on every isolate with three different primers separately and run with two different DNA isolations for each of the bacterial isolates. As well all hyperpriming reactions were repeated. If the banding pattern observed for all three Hyperpriming primers showed >90% similarity then the bacterial isolates were considered to be closely related. Only one candidate bacterial strain from this batch of isolates was used for further characterisation. Chalkbrood inhibiting bacterial isolates from around Australia that have been characterised.

In all instances, the banding patterns observed were highly consistent and repeatable with different DNA isolations, PCR machines and Qiagen Multiplex kits. Analysis of the hyperpriming banding patterns was done by visual inspection for the measurement of fragment sizes for all comparisons in this study.

27. Methods: Hyperpriming Method

An inoculum comprising five to ten single colonies (from TSA plates) was suspended in 1 ml of dH$_2$O. A 10$^{-2}$ dilution of this culture was heat shocked at 95° C. for 10 min. An aliquot of the 10$^{-2}$ dilution of lyzed cells was then added to the PCR Reaction mix. The primers used for Gram-positive cells were different to the primers used for Gram-negative cells (see Table 8 for primer sequences for Hyperpriming PCR). A Qiagen multiplex PCR kit was used to carry out the hyperpriming reactions (Cat no: 206143, Qiagen Pty. Ltd.).

The PCR reaction was set up as follows:

| Component Reaction mix: | Volume/reaction |
|---|---|
| QIAGEN Multiplex PCR Master Mix | 7.5 µl |
| dNTPs | 0.1 µl |
| Primer: [10 µM] | 1.0 µl |
| Lyzed cells (−2 dilution) | 6.4 µl |
| Total volume | 15 µl |

The PCR reaction was then run in a BioRAD iCycler (Thermalcycler, BioRAD Pty. Ltd.) using the following cycle runs:

|    | Time | Cycles (Gram positive) | Cycles (Gram negative) |
|----|------|------------------------|------------------------|
| 1. | 95° C. 15:00 | x1 | x1 |
|    | 50° C. 0:30 | | |
|    | 72° C. 4:00 | | |
| 2. | 95° C. 0:30 | x4 | x4 |
|    | 50° C. 0:30 | | |
|    | 72° C. 4:00 | | |
| 3. | 95° C. 0:30 | x45 | x35 |
|    | 48° C. 0:30 | | |
|    | 72° C. 4:00 | | |
| 4. | 4° C. ∞ | hold | hold |

TABLE 8

Primer sequences used for Hyperpriming PCR

| Bacterial Strains | Primer | Primer Sequence (5' → 3') | SEQ ID NO: |
|-------------------|--------|---------------------------|------------|
| Gram positive | G2 | -GTTTGGCGACCCTGCT- | 88 |
|  | P-Fw8 | -GCCCACGGCTACCCGATGGT- | 89 |
|  | M-Fw3 | -TATGCAAGCCCAGCAGCCGTT- | 90 |
| Gram negative | G1 | -GACATGACGCACGGTCAG- | 91 |
|  | P-Fw11 | -CGACCCGGTGTGCAGCAAGT- | 92 |
|  | M-Fw4 | -GCAGCCGTTGTTGCAGGAAA- | 93 |

27. Methods: PCR Conditions Used for Isolation of 16S rDNA Fragments

Multiplex PCR was performed on select candidate strains using 16S rDNA primers to amplify 16S rDNA fragments from bacterial genomes for DNA sequencing. 5 mls of nutrient broth was inoculated with a single colony. Bacterial culture was grown aerobically with vigorous shaking at 25° C. for 18-20 hours until about exponential phase and DNA was then isolated from 1 ml of the sample culture. Samples were centrifuged at 13.2×1000 rpm for 1 min, supernatant was discarded and the pellet was resuspended in 200 µl of DPEC-treated water. Pelleted cells were then denatured at 95° C. for 10-15 mins. An aliquot of the lyzed cells was analysed using QIAGEN Multiplex PCR kit (Cat no: 206143) in a standard reaction on candidate bacterial strains. 16S rRNA gene was amplified using the universal 16S rDNA forward and reverse primers BSF 8/20 (5'-AGAGTTTGATCCTGGCTCAG-3'; SEQ ID NO: 94) and BSR 534/18 (5'-ATTACCGCGGCTGCTGGC-3'; SEQ ID NO: 95). Primers for 16S rRNA amplification were designed according to the European Ribosomal RNA website (rrna.ui-a.ac.be/ssu/index.html; Department Biochemie, Universiteit Antwerpen, Belgium; (Wuyts, van de and Winkelmans, 2002). The 500 bp DNA product was isolated on 1% agarose by gel electrophoresis, excised then purified using the Qiagen Gel Extraction kit. Samples of pure DNA were sent to the AGRF Sequencing Facilities, The University of Queensland, Brisbane for sequencing.

16 rDNA PCR Conditions:

| Component Reaction mix: | Volume/reaction |
|-------------------------|-----------------|
| QIAGEN Multiplex PCR Master Mix | 7.6 µl |
| Forward Primer: 16s rDNA BSF 8/20 [10 µM] | 0.5 µl |
| Reverse Primer: 16s rDNA BSR 534/18 [10 µM] | 0.5 µl |
| Rnase-free water | 5.4 µl |
| Template DNA: | 1.0 µl |
| Total volume | 15 µl |

The reaction was then run in a BioRAD iCycler using the following cycle runs:

|    | Time | Cycles |
|----|------|--------|
| 1. | 94° C. 2:00 | x1 |
| 2. | 94° C. 0:30 | x4 |
|    | 56° C. 0:45 | |
|    | 72° C. 1:00 | |
| 3. | 94° C. 0:30 | x25 |
|    | 54° C. 0:45 | |
|    | 72° C. 1:00 | |
| 4. | 72° C. 10:00 | x1 |
|    | 4° C. ∞ | hold |

TABLE 9

Primer sequences used for 16S rRNA sequencing

|  | Primer | Primer Sequence (5' → 3') | SEQ ID NO: |
|---|--------|---------------------------|------------|
| Forward Primer | BSF 8/20 | -AGAGTTTGATCCTGGCTCAG- | 94 |
| Reverse Primer | BSR 534/18 | -ATTACCGCGGCTGCTGGC- | 95 |

27. Methods: Agarose Gel Electrophoresis

PCR products obtained through Hyperpriming or multiplex reactions were separated using agarose gel electrophoresis. DNA was visualised in the gel by addition of ethidium bromide (EtBr) at a concentration of 20 µl (10 mg/ml solution) to 100 ml of agarose solution. The gel was photographed under UV (260 nm) in a gel doc system. Gels were made using 1×TAE buffer. They were run between 1.5 to 3 hours at a 50-100 milliamps depending on the PCR protocol. 0.7-2% agarose gels were used to separate PCR fragments using a standard BioRad gel system (biorad.com). A 0.7% gel showed a good separation (resolution) of large DNA fragments (5-10 kb) and a 2% gel showed a good resolution of small fragments (0.2-1 kb).

27. Methods: Extraction of DNA from Gels

DNA fragments were extracted from 1% Agarose gels and purified on a QIAquick column using the QIAquick Gel Extraction Kit (Qiagen Corp, Cat No 28704). The basic principle for isolation involves the preferential binding of DNA to acidified silica matrix when the chaotropic salt (Sodium iodide) concentration is high enough (>3M) and the pH is close to 8. Absorption is around 95% if the pH is 7.5, and is reduced drastically at higher pH. Impurities are efficiently washed away and pure DNA is eluted with a small volume (30 µl) with mQ water, ready to use in all subsequent reactions. This kit has a wide range for DNA isolation (between 100 bp to 10 kb). (Reproduced from the web site: qiagen.com/default.aspx?).

27. Methods: DNA Sequencing

DNA sequencing was performed by ACRF Biomolecular Research Facility at the John Curtin School of Medical Research, ANU (brfjcs.anu.edu.au), and the AGRF Sequencing Facility at the University of Queensland (agrf.org.au/index.php?id=23). Sequencing primers used are as set forth in Table 9.

27. Methods: Isolation and DNA Screening of 16S rDNA Gene Fragment by PCR

Confirmation of Hyperpriming analysis identifying bacterial isolates as close relatives was done in parallel with two different bacterial isolates that inhibited the Chalkbrood fungus. Numerous candidates in the same isolation (from the same batch/region) were identified as very close relatives by Hyperpriming analysis banding pattern. In each case four isolates that had similar Hyperpriming banding pattern (>90% identity with banding pattern) with three independent Hyperpriming primers were used with 16S rDNA primers to generate the 500 bp fragment. The 16S rDNA fragments were purified and sequenced. In a similar fashion another three isolates that showed similarity to another bacterial isolate was analysed in the same manner. The relatedness of each group of these bacterial isolates was determined by phylogenetic analysis of the double stranded 500 bp 16S rDNA sequence obtained.

27. Methods: Phylogenetic Analysis

The double stranded 16S rDNA sequence obtained for the bacterial isolates from the honey bee gut was corrected and trimmed using Sequencher 6.0. Each of the sequences obtained was used in a BLAST search of the GenBank non-redundant database to identify 16S (ribosomal RNA) sequences with greater than 96% identity and the highest levels of similarity as estimated using expect values (ref BLAST). Only 16S rDNA sequence was considered from bacterial strains that had been accurately and independently identified. Where possible sequences from strains from the American Type Culture Collection (ATCC) were used, and those from bacterial species that were poorly characterised and non-culturable bacteria were excluded from the analysis.

Sequences from the bacterial isolates and GenBank were grouped using the similarity scores and knowledge of their taxonomy, and separate datasets were compiled for each major grouping. Out-group sequences from other bacterial groups, including a representative from each of the groups identified in this work, were included in each sequence dataset.

Sequence datasets were aligned using MAFFT (ebi.ac.uk/Tools/mafft/). MAFFT (Multiple Alignment using Fast Fourier Transform) is a high speed multiple sequence alignment program which is frequently used to align large numbers of sequences for phylogenetic analysis (Katoh et al., 2002; Nagarajan and Keich, 2008). Maximum likelihood phylogenetic trees were found by using PhyML 3.0 to search by subtree pruning and regrafting from 10 random starting trees (Guindon et al., 2005). Each of the substitution models available in PhyML were used, including the most complex model, which was a general time-reversible model with a proportion of invariant sites and a gamma distribution of site-rate variants across four categories (GTR+I+G; Lanave et al., 1984). Bootstrap values >50% were shown at the nodal branches. Corresponding phylogenetic trees were derived from the partial 16S rRNA sequences are shown.

Example 27: Results

27. Results: Hyperpriming Analysis of Chalkbrood Inhibiting Bacterial Isolates

The relatedness of the bacterial isolates that could inhibit Chalkbrood was determined using hyperprimers according to the invention. Bacterial isolates from within each state were compared together on the same gel. Gram positive bacteria were analysed with hyperpriming reactions using three independent hyperpriming primers essentially as described above for Hyperpriming method. A representative example of the hyperpriming DNA profile of gram negative bacterial strains is shown in FIG. 44 (*a*). The lanes marked with an arrow all had a banding pattern which had >90% similarity. The banding pattern was also >90% similar when two other primers were used in independent reactions (data not shown). These data demonstrate that the bacterial isolates were very closely related and probably the same genera and species. One isolate was chosen for further characterisation.

Similarly, gram negative isolates from one state were analysed separately in hyperpriming reactions with three different primers. A representative example of the hyperpriming DNA profile of gram positive bacterial strains is shown in FIG. 44 (*b*). When three independent hyperpriming reactions with different primers gave banding patterns with >90% similarity, the bacterial isolates were considered to belong to the same genera and species.

Overall, 158 potentially unique bacterial strains were identified from the 170 Australian isolates using this method.

27. Results: Hyperpriming Analysis for Determining Relatedness of Bacterial Strains Subsequent to the analysis of bee bacterial isolates which could inhibit Chalkbrood, hyperpriming analysis was used to identify closely related strains. To identify closely related bacterial species using banding patterns, four different bacterial bee gut isolates from a region that showed a similar banding pattern with the hyperpriming primer P-Fw11 (FIG. 45, Group A) were chosen (isolates A1, A2, A3 and A4). They also gave a similar banding with two other hyperpriming primers in independent reactions (data not shown). Four isolates (B1, B2, B3 and B4) which gave a similar hyperpriming banding profile to each other (FIG. 45, Group B) but completely different to the A1-A4 isolates were also characterised. They also gave a similar banding pattern when two other hyperpriming primers were used in independent reactions (data not shown).

Figure 45:
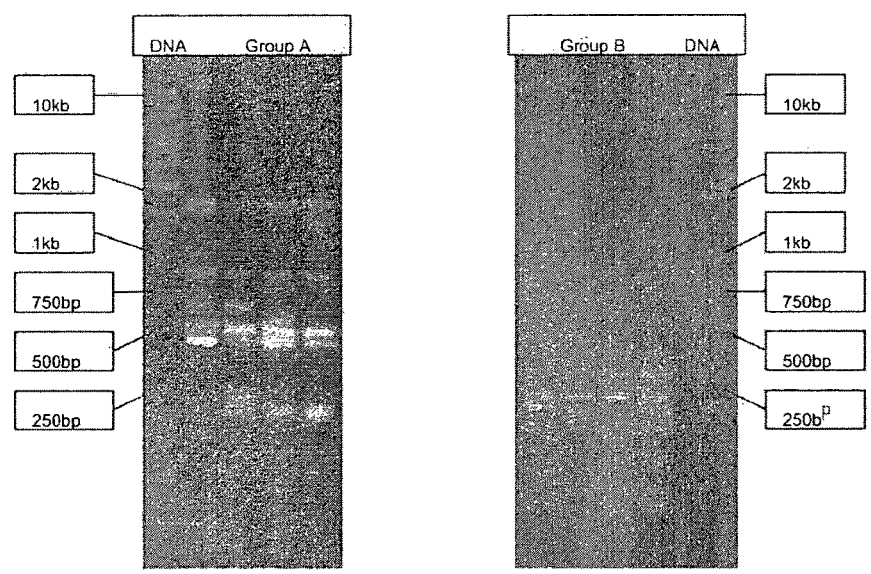
FIG. 45 is a photographic representation of a 1% agarose electrophoresis gel showing a Hyperpriming PCR DNA profile obtained using the primer P-Fw11 (10 μM). A and B represent one example of two bacterial isolate groups from the bee gut. Members from group A have a different colony morphology to those from group B. Banding patterns show that the members in group A are similar to each other. Likewise, the DNA banding profiles from group B show that these isolates are similar to each other. Isolates A and B were cultured on TSA media for determining colony morphology. DNA represents DNA fragments used as size standards.

FIG. 45 demonstrates the banding patterns of isolates A and B are totally different. The 500 bp 16S rDNA gene sequence was isolated and analysed as described above under methods in all eight cases. Isolate A1 showed a strong homology (100%, E value 0.0) to *Bacillus pumilus* in a NCBI Blast search (FIG. 46, Table 3). On the other hand, isolate B1 showed strong homology to *Bacillus sphaericus* (FIG. 47, Table 3; 100% identity, E value 0.0). In the case of group A there was >90% bootstrap value between the four isolates.

Figure 48:
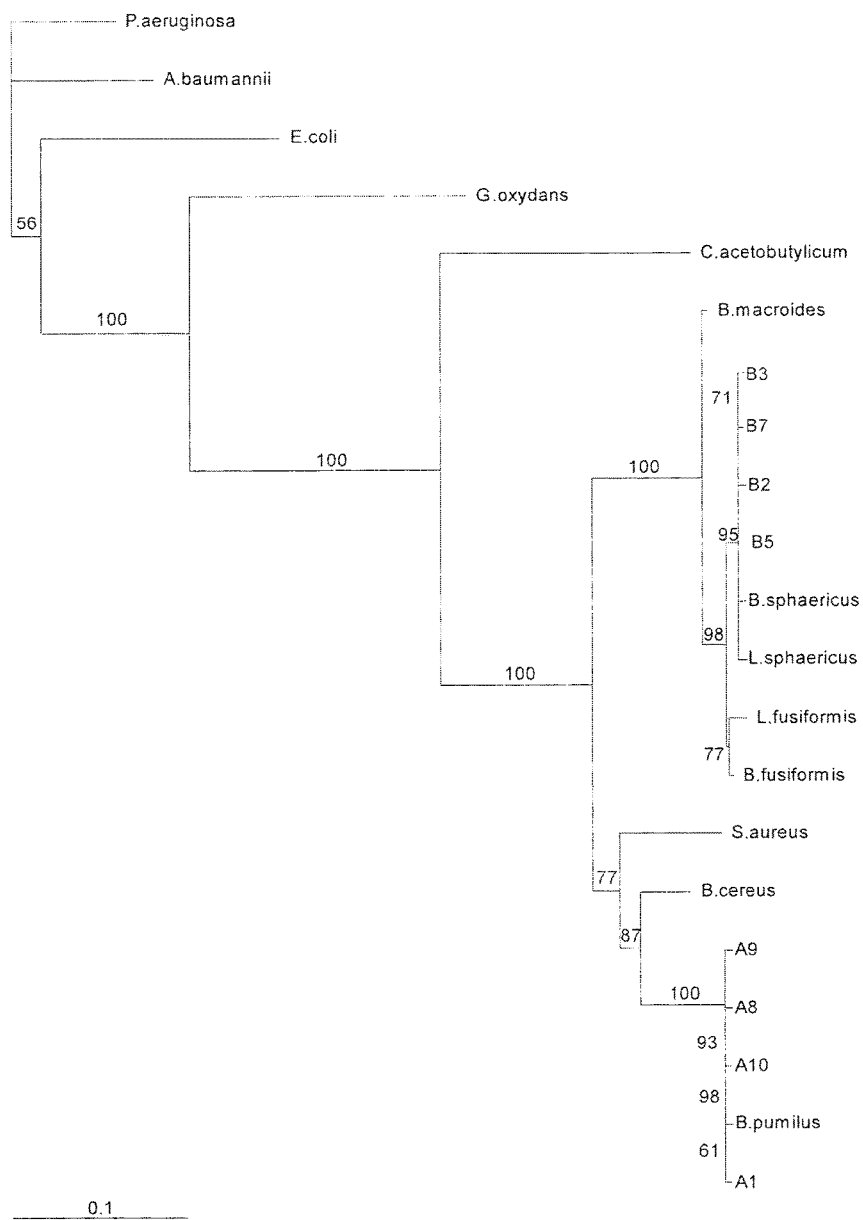
FIG. 48 is a schematic representation of a Maximum-Likelihood phylogenetic tree based on partial 16S rRNA bacterial sequences (~500 bp). Bootstrap values detected for 100 replicates are shown before the nodes. The bacterial 16S rRNA sequences from four isolates of each colony morphology (A and B) are shown.

As described above, the phylogenetic analysis of the NCBI blast data (for all eight isolates) led to the construction of the phylogenetic tree (FIG. 48). As shown, all the bee bacterial gut isolates in the A group (A1, A2, A3, A4) which showed similar Hyperpriming banding pattern, fall into a closely related group, whose closest known relative is *Bacillus pumilus*. While the B group (B1, B2, B3, B4) bee gut isolates fall into a group where all four isolates show close relatedness in terms of phylogeny. The closest known relative is *B. sphaericus/L. sphaericus*. In the case of group B they fell into one branch of the group (>95% bootstrap value).

The 16S rDNA sequence phylogeny confirmed there was a very strong relatedness between the bacterial isolates that had been suggested by hyperpriming analysis. Both group A and group B belonged to the *Bacillus* genera by 16S rDNA phylogenetic analysis. However, they were shown to be related to two different species (group A—*B. pumilus* and group B—*B. sphaericus*).

TABLE 10

Validation of Bacterial strain A and B using 16S rRNA partial sequence homology to other diverse bacterial strains compared to GenBank database

| Bacterial Isolate | Accession Number (GenBank) | Bacterial Strain Identification | Max ID (%) |
|---|---|---|---|
| A1 | EU624442.1 | *Bacillus pumilus* strain SS-02 16S ribosomal RNA gene, partial sequence | 100% |
| | EF040562.1 | Marine bacterium CS-54 16S ribosomal RNA gene, partial sequence | 100% |
| | AY039415.1 | Soil bacterium S76M1 16S ribosomal RNA gene, partial sequence | 100% |
| | AY039400.1 | Earthworm burrow bacterium B6D1 16S ribosomal RNA gene, partial sequence | 100% |
| | AY911074.1 | Marine sediment bacterium ISA-7332 16S ribosomal RNA gene, partial sequence | 100% |
| A8 | EU624442.1 | *Bacillus pumilus* strain SS-02 16S ribosomal RNA gene, partial sequence | 100% |
| | EF040562.1 | Marine bacterium CS-54 16S ribosomal RNA gene, partial sequence | 100% |
| | AY039415.1 | Soil bacterium S76M1 16S ribosomal RNA gene, partial sequence | 100% |
| | AY039400.1 | Earthworm burrow bacterium B6D1 16S ribosomal RNA gene, partial sequence | 100% |
| | AY911144.1 | Marine sediment bacterium ISA-7278 16S ribosomal RNA gene, partial sequence | 99% |
| A9 | EU624442.1 | *Bacillus pumilus* strain SS-02 16S ribosomal RNA gene, partial sequence | 100% |
| | EF040562.1 | Marine bacterium CS-54 16S ribosomal RNA gene, partial sequence | 100% |
| | AY911074.1 | Marine sediment bacterium ISA-7332 16S ribosomal RNA gene, partial sequence | 100% |
| | AY039415.1 | Soil bacterium S76M1 16S ribosomal RNA gene, partial sequence | 100% |
| | AY039400.1 | Earthworm burrow bacterium B6D1 16S ribosomal RNA gene, partial sequence | 100% |
| | EU384279.1 | *Streptomyces* sp. A515 Ydz-FQ 16S ribosomal RNA gene, partial sequence | 99% |
| A10 | EU624442.1 | *Bacillus pumilus* strain SS-02 16S ribosomal RNA gene, partial sequence | 100% |
| | AY911074.1 | Marine sediment bacterium ISA-7332 16S ribosomal RNA gene, partial sequence | 100% |
| | AY039415.1 | Soil bacterium S76M1 16S ribosomal RNA gene, partial sequence | 100% |
| | AY039400.1 | Earthworm burrow bacterium B6D1 16S ribosomal RNA gene, partial sequence | 100% |
| | EU384279.1 | *Streptomyces* sp. A515 Ydz-FQ 16S ribosomal RNA gene, partial sequence | 99% |
| B2 | AB271742.1 | *Bacillus sphaericus* gene for 16S rRNA, partial sequence | 100% |
| | AB363739.1 | *Lysinibacillus sphaericus* gene for 16S rRNA, partial sequence, strain: NBRC 3525 | 99% |
| | EU187498.1 | *Lysinibacillus fusiformis* strain X-25 16S ribosomal RNA gene, partial sequence | 98% |
| | AY039399.1 | Earthworm burrow bacterium B3D5 16S ribosomal RNA gene, partial sequence | 97% |
| | DQ826583.1 | *Bacillus fusiformis* strain LL 60 16S ribosomal RNA gene, partial sequence | 97% |
| B3 | AB271742.1 | *Bacillus sphaericus* gene for 16S rRNA, partial sequence | 100% |
| | AB363739.1 | *Lysinibacillus sphaericus* gene for 16S rRNA, partial sequence, strain: NBRC 3525 | 99% |
| | EU187498.1 | *Lysinibacillus fusiformis* strain X-25 16S ribosomal RNA gene, partial sequence | 98% |
| | AY039399.1 | Earthworm burrow bacterium B3D5 16S ribosomal RNA gene, partial sequence | 97% |
| | DQ826583.1 | *Bacillus fusiformis* strain LL 60 16S ribosomal RNA gene, partial sequence | 97% |
| B5 | AM903104.1 | *Bacillus sphaericus* 16S rRNA gene, isolate JG-7B | 100% |
| | AB363739.1 | *Lysinibacillus sphaericus* gene for 16S rRNA, partial sequence, strain: NBRC 3525 | 99% |
| | EU187498.1 | *Lysinibacillus fusiformis* strain X-25 16S ribosomal RNA gene, partial sequence | 98% |
| | AM062692.1 | *Bacillus fusiformis* strain 16S rRNA gene, isolate p227 | 98% |
| | AB362285.1 | *Bacillus macroides* gene for 16S rRNA, partial sequence | 97% |
| B7 | AB271742.1 | *Bacillus sphaericus* gene for 16S rRNA, partial sequence | 100% |
| | AB244482.1 | *Lysinibacillus sphaericus* gene for 16S rRNA, partial sequence, strain: limp 5-1 | 99% |
| | EU187493.1 | *Lysinibacillus fusiformis* strain X-9 16S ribosomal RNA gene, partial sequence | 98% |
| | AY039399.1 | Earthworm burrow bacterium B3D5 16S ribosomal RNA gene, partial sequence | 97% |
| | DQ826583.1 | *Bacillus fusiformis* strain LL 60 16S ribosomal RNA gene, partial sequence | 97% |

Notes:
NCBI Nucleotide BLAST search done on Mar. 06, 2008 (http://blast.ncbi.nlm.nih.gov/Blast.cgi);
Sequence homology < 97% excluded from the table;
Confirmed bacteria with both Genera and species included in the table;
All unidentified searches (e.g. Uncultured bacteria sp.) excluded from the table;
FIGS. 46 and 47 is a representative example for the best alignment of sequence data (homology 100%).

Example 27: Discussion

A total of 92 hives were sampled across all Australian States (which had apiaries) from 33 different locations. Hyperpriming according to the invention was used as the initial screen to determine the relatedness of bacterial isolates. A >90% level of similarity between the banding patterns of two different bacterial isolates based on three independent hyperpriming reactions (with three different primers) demonstrated a close relatedness, indicating the isolates belong to the same bacterial species.

Use of 500 bp partial DNA sequence of the 16S rDNA gene in typing bee gut bacterial isolates was very effective in determining phylogenetic relatedness of bacterial isolates and that hyperpriming is a useful method to differentiate closely related organisms (i.e. bacterial species) based on low levels of genetic variation present.

Accordingly, in this example, the present inventors have shown that the hyperpriming method and primers of the invention were useful for differentiating between species of the same genera. This has further application for quickly discriminating between different bacterial species that inhibit Chalkbrood for further analysis. Using the hyperpriming method for determining relatedness of bee gut bacterial species provides a wide range of bee bacterial species that can inhibit Chalkbrood.

Example 27: References

Dhingra, O. D. and J. B. Sinclair (2000). Basic Plant Pathology Methods. Florida (US), CRC Press, Inc.

Gilliam, M., J. O. Moffet and N. M. Kauffeld (1983). "Examination of Floral Nectar of Citrus, Cotton and Arizona Desert Plants for Microbes." Apidologie 14(4): 299-302.

Guindon, S., F. Lethiec, P. Duroux and O. Gascuel (2005). "PHYML Online—a web server for fast maximum likelihood-based phylogenetic inference." Nucleic Acids Research 33: W557-9.

Hugenholtz, P., B. M. Goebel and N. R. Pace (1998). "Impact of Culture-Independent Studies on the Emerging Phylogenetic View of Bacterial Diversity." Journal of Bacteriology. 180(18): 4765-4774.

Katoh, K., K. Misawa, K. Kuma and T. Miyata (2002). "MAFFT: a novel method for rapid multiple sequence alignment based on fast Fourier transform." Nucleic Acid Research 30(14): 3059-3066.

Lanave, C., G. Preparata, C. Sacone and G. Serio (1984). "A New Method for Calculating Evolutionary Substitution Rates." Journal of Molecular Evolution 20(1): 86-93.

Manning, R. and M. Harvey (2002). "Fatty Acids in Honeybee-Collected Pollens from Six Endemic Western Australian Eucalypts and the Possible Significance to the Western Australian Beekeeping Industry." Australian Journal of Experimental Agriculture 42(2): 217-223.

Montealegre, J. R. (2003). "Selection of Bioantagonistic Bacteria to be used in Biological Control of *Rhizoctoma solani* in Tomato." Electronic Journal of Biotechnology 6(2): 115-127.

Muyzer, G. and K. Small (1998). "Application of Denaturing Gradient Gel Electrophoresis (DGGE) and Temperature Gradient Gel Electrophoresis (TGGE) in Microbial Ecology." Antonie van Leeuwenhoek 73: 127-141.

Nagarajan, N. and U. Keich (2008). "FAST: Fourier transform based algorithms for significance testing of ungapped multiple alignments 10.1093/bioinformatics/btm594." Bioinformatics 24(4): 577-578.

Pace, N. R. (1997). "A Molecular View of Microbial Diversity of the Biosphere." Science 276(5313): 734-740.

Staley, J. T. and J. J. Gosink (1999). "POLES APART: Biodiversity and Biogeography of Sea Ice Bacteria." Annual Review of Microbiology 53: 189-215.

Wang, R. F., W. W. Cao and C. E. Cerniglia (1996). "PCR Detection and Quantitation of Predominant Anaerobic Bacteria in Human and Animal Fecal Samples." Applied and Environmental Microbiology 62(4): 1242-1247.

Wuyts, J., Y. van de Peer and T. Winkelmans (2002). "The European Database on Small Subunit Ribosomal RNA." Nucleic Acids Research 30(1): 183-185.

Example 28

Design of Hyperprimers which have Repeated Codons and/or Anti-Codons

Primers comprising repeated codons and/or anti-codons were designed based on codon usage bias. Such primers were designed by choosing the most frequent codons and/or anti-codons and consecutively repeating such high frequency codons and/or anti-codons to design the primers.

Using the codon usage information as set forth in Tables 1 and 2, the most frequent codons and anti-codons as determined for different organisms was as follows:

Most Frequent Codons and Anti-Codons
*Pseudomonas*/Bacteria—G/C Rich Organisms
codons—GCC CGC CTG GTC CTC
anti-codons—GGC GCG CAG GAC GAG
Humans/Mouse
codons—CTG CTC GCC TTC
anti-codons—CAG GAG GGC GAA
Wheat/Rice
codons—CTC GCC GTC CTG CTT
anti-codons—GAG GGC GAC CAG AAG
*E. coli*/bacteria—A/T rich organism
codons—CTG ATC TTC TTT CGC GCC ACC
anti-codons—CAG GAT GAA AAA GCG GGC GGT From the above information, primers were synthesized comprising two or more codons and/or two or more anti-codons which were repeated to generate the sequence of the hyperprimers as shown in Tables 11 and 12.

TABLE 11

Primers designed based, on most frequent codons and/or anticodons usage in Humans.

| Primer | Oligonucleotide Sequence 3' → 5' | SEQ ID NO: |
|---|---|---|
| HS-15 | CTGCTCGCCCTGCTCGCCCTGCTC | 96 |
| HS-16 | CTGCTCGCCCTGCTCGCCCTCCTG | 97 |
| HS-17 | CTCCTGGCCCTCCTGTTCCTGCTC | 98 |
| HS-18 | CTCCTGTTCCTCCTGGCCCTCCTG | 99 |
| HS-19 | CTCCTGTTCCTCCTGTTCCTGCTC | 100 |
| HS-20 | CTCCTGTTCCTCCTGTTCCTCCTG | 101 |
| HS-21 | CTGCTCGCCTTCCTGCTCGCCCTGCTC | 102 |
| HS-22 | CTGCTCGCCTTCCTGCTCGCCCTCCTG | 103 |
| HS-23 | CTGCTCGCCCTGCTCTTCGCCCTCCTG | 104 |
| HS-24 | CTGCTCGCCCTCCTGTTCGCCCTGCTC | 105 |
| HS-25 | CTCCTGGCCCTCCTGTTCGCCCTCCTG | 106 |
| HS-26 | CTCCTGGCCCTCCTGTTCGCCCTGCTC | 107 |
| HS-27 | CTCCTGGCCCTCCTGTTCGCCCTCCTG | 108 |
| HS-28 | CTGCTCGCCCTGCTCGCCCTGCTCCTCCTG | 109 |
| HS-29 | CTGCTCGCCCTGCTCTTCCTGCTCCTCCTG | 110 |

TABLE 11-continued

Primers designed based, on most frequent codons and/or anticodons usage in Humans.

| Primer | Oligonucleotide Sequence 3' → 5' | SEQ ID NO: |
|---|---|---|
| HS-30 | CTCCTGGCCCTGCTCCTCCTGTTCCTGCTC | 111 |
| HS-31 | CTCCTGCTGCTCTTCCTGCTCGCCCTGCTC | 112 |
| HS-32 | CTCCTGCTGCTCTTCCTGCTCTTCCTGCTC | 113 |
| HS-33 | CTCCTGCTGCTCTTCCTCCTGGCCCTCCTG | 114 |
| HS-34 | CTCCTGCTGCTCTTCCTCCTGTTCCTGCTC | 115 |
| HS-35 | CTGCTCGCCCTGCTCCTCCTGGCCCTGCTCCTCCTG | 116 |
| HS-36 | CTGCTCGCCCTGCTCCTCCTGTTCCTGCTCCTCCTG | 117 |
| HS-37 | CTGCTCCTCCTGTTCCTCCTGTTCCTCCTGCTGCTC | 118 |
| HS-38 | CTCCTGCTGCTCGCCCTGCTCGCCCTGCTCCTCCTG | 119 |
| HS-39 | CTGCTCCTCCTGGCCCTCCTGCTGCTCGCCCTCCTG | 120 |
| HS-40 | CTGCTCCTCCTGGCCCTCCTGCTGCTCTTCCTCCTG | 121 |
| HS-41 | CTCCTGCTGCTCTTCCTCCTGCTGCTCTTCCTCCTG | 122 |
| HS-42 | CTCCTGCTGCTCTTCCTGCTCCTCCTGTTCCTGCTCCTCCTG | 123 |
| HS-43 | CTCCTGCTGCTCTTCCTGCTCCTCCTGGCCCTCCTGCTGCTC | 124 |
| HS-44 | CTCCTGCTGCTCTTCCTCCTGCTGCTCTTCCTCCTGCTGCTC | 125 |

TABLE 12

Primers designed based on most frequent codons and/or anticodons usage in Pseudomonas.

| Primer | 3' Codon 1 | Codon 2 | Codon 3 | Codon 4 | Codon 5 | Codon 6 | 5' Codon 7 | SEQ ID NO: |
|---|---|---|---|---|---|---|---|---|
| PS-6 | GCC | GGC | CTG | CAG | CGC | GAC | CTC | 126 |
| PS-7 | GCC | GGC | CTG | CAG | CGC | GAG | CTC | 127 |
| PS-8 | GCC | GGC | CTG | CGC | CAG | CTC | GAC | 128 |
| PS-9 | GCC | GGC | CTG | CGC | CTC | GAC | CAG | 129 |
| PS-10 | GGC | CAG | CTG | CGC | CTC | GAC | GCC | 130 |
| PS-11 | GCC | GGC | CAG | CGC | CTG | CTC | GAC | 131 |
| PS-12 | GCC | GGC | CTG | CGC | GAC | GTC | CAG | 132 |
| PS-13 | GCC | GGC | CTG | CGC | GAC | CAG | CTC | 133 |
| PS-14 | GCC | CTG | CAG | CGC | GAC | GGC | CTC | 134 |
| PS-15 | GCC | CTG | CAG | CGC | GAC | GGC | CTC | 135 |
| PS-16 | GCC | GGC | CAG | CGC | GAC | CTC | GIG | 136 |
| PS-17 | GGC | CAG | CTG | CGC | GAG | GAC | GCC | 137 |
| PS-18 | GCC | CTG | CAG | CGC | GAG | GAC | GGC | 138 |
| PS-19 | GGC | CTG | CAG | CGC | GCC | GAG | GTC | 139 |
| PS-20 | GGC | CAG | CTG | CGC | GCC | GAG | GTC | 140 |
| PS-21 | GCC | GGC | CAG | CTC | CTG | CGC | GAG | 141 |

TABLE 12-continued

Primers designed based on most frequent codons and/or anticodons usage in Pseudomonas.

| Primer | 3' Codon 1 | Codon 2 | Codon 3 | Codon 4 | Codon 5 | Codon 6 | 5' Codon 7 | SEQ ID NO: |
|---|---|---|---|---|---|---|---|---|
| PS-22 | GGC | CTG | CAG | CTC | GAC | GCC | GCG | 142 |
| PS-23 | GGC | GCC | CTG | CTC | GAG | GAC | CAG | 143 |
| PS-24 | GGC | CAG | CTG | CTC | GCC | CGC | GCG | 144 |
| PS-25 | GGC | CTG | CAG | CTC | GCC | GAC | GCG | 145 |
| PS-26 | GCC | GGC | CAG | CTC | GCG | GTC | CTG | 146 |
| PS-27 | GGC | GCC | CAG | CTC | GCG | GTC | CTG | 147 |
| PS-28 | GCC | CTG | CAG | CTC | GGC | GCG | GAG | 148 |
| PS-29 | GCC | CAG | CTG | CTC | GGC | GCG | GAG | 149 |
| PS-30 | GGC | GCC | CAG | CTG | CTC | CGC | GAC | 150 |
| PS-31 | GCC | GGC | CAG | CTG | CTC | GAG | GAC | 151 |
| PS-32 | GGC | GCC | CAG | CTG | CTC | GAG | GAC | 152 |
| PS-33 | GGC | GCC | CTG | GAC | CGC | GAG | CAG | 153 |
| PS-34 | GCC | GGC | CTG | GAC | CGC | GCG | CAG | 154 |
| PS-35 | GCC | GGC | CAG | GTC | GCG | GAG | CTG | 155 |
| PS-36 | GGC | GCC | CAG | GAC | GTC | GAG | CTG | 156 |
| PS-37 | GCC | GGC | CAG | GAC | GTC | GCG | CTG | 157 |

All these primers were tested in a PCR reaction using DNA from the organism from which the primer design was based essentially as described in Example 1. Hyperpriming bands produced using such primers produced more hyperpriming bands than compared to hyperprimers designed without repeating the most frequent codons and/or anticodons.

Figure 49:
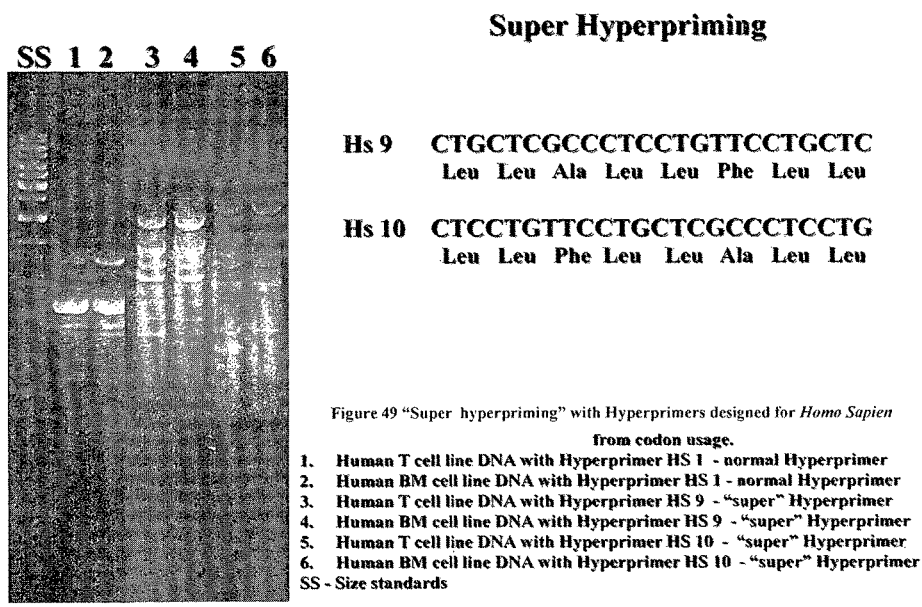
FIG. 49 is a photographic representation of hyperpriming bands obtained with HS1 compared to HS9 and HS10 which were designed to have repeated codons in them along with codons that code for amino acids which are more prevalent at active sites of proteins. (CTGCTCGCCCTCCTGTTCCT-GCTC (SEQ ID NO: 166); CTCCTGTTCC TGCTCGC-CCTCCTG (SEQ ID NO: 167).

FIG. 49 shows a representative example using hyperprimers which have repeated codons (coding for amino acids such as leucine considered to be more prevalent at active sites in proteins) e.g., HS9 and HS10 (SEQ ID NOs: 73 and 74), which give more hyperpriming bands for human DNA, compared to hyperprimers designed without repeats, e.g., HS1 (SEQ ID NO: 69).

What is claimed is:

1. A method for amplifying a reproducible product profile from a double stranded target nucleic acid using a single primer capable of hybridizing to both a sense and an antisense strand of the double stranded target nucleic acid, wherein the single primer was produced using a method comprising:
   (a) determining codon usage frequency of codons occurring in the sense strand of the double stranded target nucleic acid;
   (b) determining codon usage frequency of anti-codons occurring in the anti-sense strand of the double stranded target nucleic acid;
   (c) identifying at least one preferred codon of the double stranded target nucleic acid, wherein the at least one preferred codon corresponds to a codon having a usage frequency of codons as determined in step (a) of at least 10 per 1000 and having a sequence that is the reverse complement of an anti-codon having a usage frequency of anti-codons as determined in step (b) of at least 10 per 1000 of the double stranded target nucleic acid; and
   (d) identifying at least one preferred anti-codon of the double stranded target nucleic, wherein the at least one preferred anti-codon corresponds to an anti-codon having a usage frequency of anti-codons as determined in step (b) of at least 10 per 1000 and having a sequence that is the reverse complement of a codon having a usage frequency of codons as determined in step (a) of at least 10 per 1000 of the double stranded target nucleic acid;
   (e) selecting a primer nucleic acid sequence consisting of codon sequences selected from the group consisting of preferred codon sequences, preferred anti-codon sequences, and combinations thereof, wherein the primer nucleic acid comprises at least 15 nucleotides, and wherein the primer nucleic acid sequence is mismatched to the target nucleic acid by at least one nucleotide; and
   (f) synthesizing a primer having said primer nucleic acid sequence selected in step (e) or the complement thereof to produce the single primer capable of hybridizing to both the sense and the antisense strand of the double stranded target nucleic acid, wherein the single primer is capable of amplifying at least one nucleic acid fragment comprising a coding region of the double stranded target nucleic acid in a reproducible manner under conditions of medium or high stringency, the method comprising
   (i) contacting the single primer with the double stranded target nucleic acid; and
   (ii) amplifying, by repeatedly extending the single primer using a polymerase, a reproducible product profile from the double stranded target nucleic acid that is specific to the double stranded target nucleic acid and capable of differentiating the double stranded target nucleic acid from other nucleic acids.

2. The method of claim 1, wherein a combined usage frequency of both the preferred codon and the anti-codon that is complementary to the preferred codon in the double stranded target nucleic acid equals at least 40 per 1000 of the double stranded target nucleic acid.

3. The method of claim 1, wherein the frequency of the preferred codon in the target nucleic acid compared to the frequency of the anti-codon that is complementary to the preferred codon in the target nucleic acid occurs at a ratio not greater than 4:1, or wherein the frequency of the preferred anti-codon in the target nucleic acid compared to the frequency of the codon that is complementary to the preferred anti-codon in the target nucleic acid occurs at a ratio not greater than 4:1.

4. The method of claim 1, wherein the primer nucleic acid sequence selected in step (e) comprises the preferred codon that is the most frequent codon in the sense strand of the double stranded target nucleic acid.

5. The method of claim 4, wherein the primer nucleic acid sequence selected in step (e) comprises multiple copies of the preferred codon that is the most frequent codon in the sense strand of the double stranded target nucleic acid.

6. The method of claim 1, wherein the primer nucleic acid sequence selected in step (e) comprises the preferred anti-codon that is the most frequent anti-codon in the anti-sense strand of the double stranded target nucleic acid.

7. The method of claim 6, wherein the primer nucleic acid sequence in the primer comprises multiple copies of the preferred anti-codon that is the most frequent anti-codon in the anti-sense strand of the double stranded target nucleic acid.

8. The method of claim 1, wherein the primer nucleic acid sequence selected in step (e) is capable of binding to codons in the sense strand of the double stranded target nucleic acid encoding one or more amino acids selected from the group consisting of leucine, lysine, phenylalanine and alanine.

9. The method of claim 1, wherein the primer nucleic acid sequence selected in step (e) comprises one or more DNA base analogues.

10. The method of claim 1, wherein the target nucleic acid originates from a virus, a bacteria, a fungi, a yeast, a protozoa, a plant or a mammal.

11. The method of claim 10, wherein the bacteria is an *E. coli*, or belonging to the genus *Pseudomonas* or *Salmonella*.

12. The method of claim 1, wherein the primer nucleic acid sequence selected in step (e) is capable of hybridizing to at least one preferred codon encoded on the sense strand of the double stranded target nucleic acid; and is capable of hybridizing to at least one preferred anti-codon encoded on the antisense strand of the double stranded target nucleic acid.

13. The method of claim 1, wherein a combined frequency of both the preferred anti-codon and the codon that is complementary to the preferred anti-codon in the target nucleic acid equals a codon usage bias of least 40 per 1000 of the double stranded target nucleic acid.

14. A method for amplifying a reproducible product profile that identifies a specific organism in a sample using a single primer, wherein the single primer is capable of hybridizing to both a sense and an antisense strand of a double stranded target nucleic acid of the specific organism, wherein the method comprises:
(i) providing the single primer, wherein the single primer was produced by a method comprising:
(a) determining codon usage frequency of codons occurring in the sense strand of the double stranded target nucleic acid;
(b) determining codon usage frequency of anti-codons occurring in the anti-sense strand of the double stranded target nucleic acid;
(c) identifying at least one preferred codon of the double stranded target nucleic acid, wherein the at least one preferred codon corresponds to a codon having a usage frequency of codons as determined in step (a) of at least 10 per 1000 and having a sequence that is the reverse complement of an anti-codon having a usage frequency of anti-codons as determined in step (b) of at least 10 per 1000 of the double stranded target nucleic acid; and
(d) identifying at least one preferred anti-codon of the double stranded target nucleic, wherein the at least one preferred anti-codon corresponds to an anti-codon having a usage frequency of anti-codons as determined in step (b) of at least 10 per 1000 and having a sequence that is the reverse complement of a codon having a usage frequency of codons as determined in step (a) of at least 10 per 1000 of the double stranded target nucleic acid;
(e) selecting a primer nucleic acid sequence consisting of codon sequences selected from the group consisting of preferred codon sequences, preferred anti-codon sequences, and combinations thereof, wherein the primer nucleic acid comprises at least 15 nucleotides, and wherein the primer nucleic acid sequence is mismatched to the target nucleic acid by at least one nucleotide; and
(f) synthesizing a single primer having said primer nucleic acid sequence selected in step (e) or the complement thereof to produce the single primer capable of hybridizing to both the sense and the antisense strand of the double stranded target nucleic acid, wherein the single primer is capable of amplifying at least one nucleic acid fragment comprising a coding region of the double stranded target nucleic acid in a reproducible manner under conditions of medium or high stringency;
(ii) contacting the sample with the single primer; and
(iii) amplifying, by repeatedly extending the single primer using a polymerase, a reproducible product profile that comprises at least one nucleic acid fragment comprising a coding region of the double stranded target nucleic acid in a reproducible manner under conditions of medium or high stringency, wherein the product profile is unique to the specific organism.

15. The method of claim 14, wherein a combined usage frequency of both the preferred codon and the anti-codon that is complementary to the preferred codon in the double stranded target nucleic acid equals at least 40 per 1000 of the double stranded target nucleic acid.

16. The method of claim 14, wherein the frequency of the preferred codon in the target nucleic acid compared to the frequency of the anti-codon that is complementary to the preferred codon in the target nucleic acid occurs at a ratio not greater than 4:1, or wherein the frequency of the preferred anti-codon in the target nucleic acid compared to the frequency of the codon that is complementary to the preferred anti-codon in the target nucleic acid occurs at a ratio not greater than 4:1.

17. The method of claim 14, wherein the primer nucleic acid sequence selected in step (e) comprises the preferred codon that is the most frequent codon in the sense strand of the double stranded target nucleic acid.

18. The method of claim 17, wherein the primer nucleic acid sequence selected in step (e) comprises multiple copies of the preferred codon that is the most frequent codon in the sense strand of the double stranded target nucleic acid.

19. The method of claim 14, wherein the primer nucleic acid sequence selected in step (e) comprises the preferred anti-codon that is the most frequent anti-codon in the anti-sense strand of the double stranded target nucleic acid.

20. The method of claim 19, wherein the primer nucleic acid sequence in the primer comprises multiple copies of the preferred anti-codon that is the most frequent anti-codon in the anti-sense strand of the double stranded target nucleic acid.

21. The method of claim 14, wherein the primer nucleic acid sequence selected in step (e) is capable of binding to codons in the sense strand of the double stranded target nucleic acid encoding one or more amino acids selected from the group consisting of leucine, lysine, phenylalanine and alanine.

22. The method of claim 14, wherein the primer nucleic acid sequence selected in step (e) comprises one or more DNA base analogues.

23. The method of claim 14, wherein the target nucleic acid originates from a virus, a bacteria, a fungi, a yeast, a protozoa, a plant or a mammal.

24. The method of claim 23, wherein the bacteria is an *E. coli*, or belonging to the genus *Pseudomonas* or *Salmonella*.

25. The method of claim 14, wherein the primer nucleic acid sequence selected in step (e) is capable of hybridizing to at least one preferred codon encoded on the sense strand of the double stranded target nucleic acid; and is capable of hybridizing to at least one preferred anti-codon encoded on the antisense strand of the double stranded target nucleic acid.

26. The method of claim 14, wherein a combined frequency of both the preferred anti-codon and the codon that is complementary to the preferred anti-codon in the target nucleic acid equals a codon usage bias of least 40 per 1000 of the double stranded target nucleic acid.

27. A method for amplifying a product from a double stranded target nucleic acid from an organism in a sample, the method comprising:
  (i) providing a single primer that was produced using a method comprising:
    (a) determining codon usage frequency of codons occurring in the sense strand of the double stranded target nucleic acid;
    (b) determining codon usage frequency of anti-codons occurring in the anti-sense strand of the double stranded target nucleic acid;
    (c) identifying at least one preferred codon of the double stranded target nucleic acid, wherein the at least one preferred codon corresponds to a codon having a usage frequency of codons as determined in step (a) of at least 10 per 1000 and having a sequence that is the reverse complement of an anti-codon having a usage frequency of anti-codons as determined in step (b) of at least 10 per 1000 of the double stranded target nucleic acid; and
    (d) identifying at least one preferred anti-codon of the double stranded target nucleic, wherein the at least one preferred anti-codon corresponds to an anti-codon having a usage frequency of anti-codons as determined in step (b) of at least 10 per 1000 and having a sequence that is the reverse complement of a codon having a usage frequency of codons as determined in step (a) of at least 10 per 1000 of the double stranded target nucleic acid;
    (e) selecting a primer nucleic acid sequence consisting of codon sequences selected from the group consisting of preferred codon sequences, preferred anti-codon sequences, and combinations thereof, wherein the primer nucleic acid comprises at least nucleotides, and wherein the primer nucleic acid sequence is mismatched to the target nucleic acid by at least one nucleotide; and
    (f) synthesizing a primer having said primer nucleic acid sequence selected in step (e) or the complement thereof to produce the single primer capable of hybridizing to both the sense and the antisense strand of the double stranded target nucleic acid;
  (ii) contacting the sample comprising the double stranded target nucleic acid with the single primer, wherein the primer hybridizes to both the sense and antisense strands of the target nucleic acid; and
  (ii) amplifying, by repeatedly extending the single primer using a polymerase, at least one nucleic acid fragment comprising a coding region of the double stranded target nucleic acid in a reproducible manner under conditions of medium or high stringency, wherein the amplified fragment is unique to the organism.

* * * * *

UNITED STATES PATENT AND TRADEMARK OFFICE
CERTIFICATE OF CORRECTION

PATENT NO.        : 10,081,832 B2
APPLICATION NO.   : 13/514524
DATED             : September 25, 2018
INVENTOR(S)       : Murali Nayudu et al.

It is certified that error appears in the above-identified patent and that said Letters Patent is hereby corrected as shown below:

In the Claims

In Column 154, Lines 24-25, Claim 27, delete "nucleotides," and insert -- 15 nucleotides, --;

In Column 154, Line 37, Claim 27, delete "(ii)" and insert -- (iii) --.

Signed and Sealed this
Twenty-second Day of January, 2019

Andrei Iancu
*Director of the United States Patent and Trademark Office*

SEQUENCE LISTING

<160> NUMBER OF SEQ ID NOS: 167

<210> SEQ ID NO 1
<211> LENGTH: 20
<212> TYPE: DNA
<213> ORGANISM: Artificial
<220> FEATURE:
<223> OTHER INFORMATION: synthetic oligonucleotide - CM-PUP-FW1

<400> SEQUENCE: 1
actcgcctcc cagtttcaca          20

<210> SEQ ID NO 2
<211> LENGTH: 20
<212> TYPE: DNA
<213> ORGANISM: Artificial
<220> FEATURE:
<223> OTHER INFORMATION: synthetic oligonucleotide - CM-PUP-FW2

<400> SEQUENCE: 2
acaccctgcc ctgcgcccaa          20

```
<210> SEQ ID NO 3
<211> LENGTH: 20
<212> TYPE: DNA
<213> ORGANISM: Artificial
<220> FEATURE:
<223> OTHER INFORMATION: synthetic oligonucleotide - CM-PUP-FW3

<400> SEQUENCE: 3
gaactgcttt ggcagggtaa                                               20

<210> SEQ ID NO 4
<211> LENGTH: 20
<212> TYPE: DNA
<213> ORGANISM: Artificial
<220> FEATURE:
<223> OTHER INFORMATION: synthetic oligonucleotide - CM-PUP-REV1

<400> SEQUENCE: 4
cgcaggctgc cgttgcgaaa                                               20

<210> SEQ ID NO 5
<211> LENGTH: 20
<212> TYPE: DNA
<213> ORGANISM: Artificial
<220> FEATURE:
<223> OTHER INFORMATION: synthetic oligonucleotide - CM-PUP-REV2

<400> SEQUENCE: 5
ttgcaatgga cgactgtgta                                               20

<210> SEQ ID NO 6
<211> LENGTH: 20
<212> TYPE: DNA
<213> ORGANISM: Artificial
<220> FEATURE:
<223> OTHER INFORMATION: synthetic oligonucleotide - CM-PUP-REV3

<400> SEQUENCE: 6
cggagaggcc ttgcacaaca                                               20

<210> SEQ ID NO 7
<211> LENGTH: 20
<212> TYPE: DNA
<213> ORGANISM: Artificial
<220> FEATURE:
<223> OTHER INFORMATION: synthetic oligonucleotide - CM-PUP-FW4

<400> SEQUENCE: 7
atgggccacc tggcgcagaa                                               20

<210> SEQ ID NO 8
<211> LENGTH: 20
<212> TYPE: DNA
<213> ORGANISM: Artificial
<220> FEATURE:
<223> OTHER INFORMATION: synthetic oligonucleotide - CM-PUP-FW5

<400> SEQUENCE: 8
ccgggtatgc tggaagtgtt                                               20

<210> SEQ ID NO 9
<211> LENGTH: 20
<212> TYPE: DNA
<213> ORGANISM: Artificial
<220> FEATURE:
<223> OTHER INFORMATION: synthetic oligonucleotide - CM-PUP-FW6
```

```
<400> SEQUENCE: 9
ctgcccgagc cacgcaagct                                               20

<210> SEQ ID NO 10
<211> LENGTH: 20
<212> TYPE: DNA
<213> ORGANISM: Artificial
<220> FEATURE:
<223> OTHER INFORMATION: synthetic oligonucleotide - CM-PUP-REV4

<400> SEQUENCE: 10
tcgcagggcc gcttcgaact                                               20

<210> SEQ ID NO 11
<211> LENGTH: 20
<212> TYPE: DNA
<213> ORGANISM: Artificial
<220> FEATURE:
<223> OTHER INFORMATION: synthetic oligonucleotide - CM-PUP-REV5

<400> SEQUENCE: 11
acggatgatg gatgtggtaa                                               20

<210> SEQ ID NO 12
<211> LENGTH: 20
<212> TYPE: DNA
<213> ORGANISM: Artificial
<220> FEATURE:
<223> OTHER INFORMATION: synthetic oligonucleotide - CM-PUP-REV6

<400> SEQUENCE: 12
cgagtggcac ggccttcata                                               20

<210> SEQ ID NO 13
<211> LENGTH: 20
<212> TYPE: DNA
<213> ORGANISM: Artificial
<220> FEATURE:
<223> OTHER INFORMATION: synthetic oligonucleotide - CM-PUP-FW7

<400> SEQUENCE: 13
cccgccgtga cgtggagcat                                               20

<210> SEQ ID NO 14
<211> LENGTH: 20
<212> TYPE: DNA
<213> ORGANISM: Artificial
<220> FEATURE:
<223> OTHER INFORMATION: synthetic oligonucleotide - CM-PUP-FW8

<400> SEQUENCE: 14
attaccttgc agcattacac                                               20

<210> SEQ ID NO 15
<211> LENGTH: 20
<212> TYPE: DNA
<213> ORGANISM: Artificial
<220> FEATURE:
<223> OTHER INFORMATION: synthetic oligonucleotide - CM-PUP-FW9

<400> SEQUENCE: 15
cgcgcgggcc aggagcacat                                               20

<210> SEQ ID NO 16
<211> LENGTH: 20
```

```
<212> TYPE: DNA
<213> ORGANISM: Artificial
<220> FEATURE:
<223> OTHER INFORMATION: synthetic oligonucleotide - CM-PUP-REV7

<400> SEQUENCE: 16
cagctccgcc agcaaccaca                                              20

<210> SEQ ID NO 17
<211> LENGTH: 20
<212> TYPE: DNA
<213> ORGANISM: Artificial
<220> FEATURE:
<223> OTHER INFORMATION: synthetic oligonucleotide - CM-PUP-REV8

<400> SEQUENCE: 17
attgcagcgg gcaacgatag                                              20

<210> SEQ ID NO 18
<211> LENGTH: 20
<212> TYPE: DNA
<213> ORGANISM: Artificial
<220> FEATURE:
<223> OTHER INFORMATION: synthetic oligonucleotide - CM-PUP-REV9

<400> SEQUENCE: 18
tccagcgggt tggaacagta                                              20

<210> SEQ ID NO 19
<211> LENGTH: 17
<212> TYPE: DNA
<213> ORGANISM: Artificial
<220> FEATURE:
<223> OTHER INFORMATION: synthetic oligonucleotide - CM-TN5-1CRA

<400> SEQUENCE: 19
cgttcaggac gctactt                                                 17

<210> SEQ ID NO 20
<211> LENGTH: 17
<212> TYPE: DNA
<213> ORGANISM: Artificial
<220> FEATURE:
<223> OTHER INFORMATION: synthetic oligonucleotide - CM-TN5-2MUR

<400> SEQUENCE: 20
gcaagtcctg cgatgaa                                                 17

<210> SEQ ID NO 21
<211> LENGTH: 20
<212> TYPE: DNA
<213> ORGANISM: Artificial
<220> FEATURE:
<223> OTHER INFORMATION: synthetic oligonucleotide - FWII

<400> SEQUENCE: 21
tgaacgacgt gtggcccagc                                              20

<210> SEQ ID NO 22
<211> LENGTH: 16
<212> TYPE: DNA
<213> ORGANISM: Artificial
<220> FEATURE:
<223> OTHER INFORMATION: synthetic oligonucleotide - FW10

<400> SEQUENCE: 22
```

-continued ggcggcttca ggaaaa                                                       16

<210> SEQ ID NO 23
<211> LENGTH: 18
<212> TYPE: DNA
<213> ORGANISM: Artificial
<220> FEATURE:
<223> OTHER INFORMATION: synthetic oligonucleotide - REVI

<400> SEQUENCE: 23
ggcttgctca gcatgcta                                                     18

<210> SEQ ID NO 24
<211> LENGTH: 20
<212> TYPE: DNA
<213> ORGANISM: Artificial
<220> FEATURE:
<223> OTHER INFORMATION: synthetic oligonucleotide - FW10

<400> SEQUENCE: 24
atggtctaca ggacgtacga                                                   20

<210> SEQ ID NO 25
<211> LENGTH: 17
<212> TYPE: DNA
<213> ORGANISM: Artificial
<220> FEATURE:
<223> OTHER INFORMATION: synthetic oligonucleotide - REVJ

<400> SEQUENCE: 25
agcgcgtgta acccttt                                                      17

<210> SEQ ID NO 26
<211> LENGTH: 19
<212> TYPE: DNA
<213> ORGANISM: Artificial
<220> FEATURE:
<223> OTHER INFORMATION: synthetic oligonucleotide - FW9

<400> SEQUENCE: 26
ctatccgtcc caccacgca                                                    19

<210> SEQ ID NO 27
<211> LENGTH: 19
<212> TYPE: DNA
<213> ORGANISM: Artificial
<220> FEATURE:
<223> OTHER INFORMATION: synthetic oligonucleotide - REVK

<400> SEQUENCE: 27
acggggtcgg caagtacgt                                                    19

<210> SEQ ID NO 28
<211> LENGTH: 19
<212> TYPE: DNA
<213> ORGANISM: Artificial
<220> FEATURE:
<223> OTHER INFORMATION: synthetic oligonucleotide - FW2

<400> SEQUENCE: 28
cctgaaggat gatcaagct                                                    19

<210> SEQ ID NO 29
<211> LENGTH: 20
<212> TYPE: DNA
<213> ORGANISM: Artificial

```
<220> FEATURE:
<223> OTHER INFORMATION: synthetic oligonucleotide - FW3

<400> SEQUENCE: 29
tgatcggcgg cgctgatcga                                               20

<210> SEQ ID NO 30
<211> LENGTH: 19
<212> TYPE: DNA
<213> ORGANISM: Artificial
<220> FEATURE:
<223> OTHER INFORMATION: synthetic oligonucleotide - FW4

<400> SEQUENCE: 30
ccgaactcgg tcacgacat                                                19

<210> SEQ ID NO 31
<211> LENGTH: 17
<212> TYPE: DNA
<213> ORGANISM: Artificial
<220> FEATURE:
<223> OTHER INFORMATION: synthetic oligonucleotide - FW5

<400> SEQUENCE: 31
tggcggagct gacctat                                                  17

<210> SEQ ID NO 32
<211> LENGTH: 20
<212> TYPE: DNA
<213> ORGANISM: Artificial
<220> FEATURE:
<223> OTHER INFORMATION: synthetic oligonucleotide - FW6

<400> SEQUENCE: 32
ctgcaatgcc cctactgttc                                               20

<210> SEQ ID NO 33
<211> LENGTH: 20
<212> TYPE: DNA
<213> ORGANISM: Artificial
<220> FEATURE:
<223> OTHER INFORMATION: synthetic oligonucleotide - FW7

<400> SEQUENCE: 33
cagcgacgaa caggtgaaca                                               20

<210> SEQ ID NO 34
<211> LENGTH: 19
<212> TYPE: DNA
<213> ORGANISM: Artificial
<220> FEATURE:
<223> OTHER INFORMATION: synthetic oligonucleotide - FW8

<400> SEQUENCE: 34
gcccagggct acccgatgt                                                19

<210> SEQ ID NO 35
<211> LENGTH: 20
<212> TYPE: DNA
<213> ORGANISM: Artificial
<220> FEATURE:
<223> OTHER INFORMATION: synthetic oligonucleotide - REVA

<400> SEQUENCE: 35
tgaagcaatg ggtagccgtg                                               20
```

<210> SEQ ID NO 36
<211> LENGTH: 20
<212> TYPE: DNA
<213> ORGANISM: Artificial
<220> FEATURE:
<223> OTHER INFORMATION: synthetic oligonucleotide - REVB

<400> SEQUENCE: 36
gatgggctac cacgagttga                                              20

<210> SEQ ID NO 37
<211> LENGTH: 20
<212> TYPE: DNA
<213> ORGANISM: Artificial
<220> FEATURE:
<223> OTHER INFORMATION: synthetic oligonucleotide - FW12

<400> SEQUENCE: 37
tcaaccgctt ccgcggctat                                              20

<210> SEQ ID NO 38
<211> LENGTH: 20
<212> TYPE: DNA
<213> ORGANISM: Artificial
<220> FEATURE:
<223> OTHER INFORMATION: synthetic oligonucleotide - FW13

<400> SEQUENCE: 38
ccgtgccgct cctgggatga                                              20

<210> SEQ ID NO 39
<211> LENGTH: 21
<212> TYPE: DNA
<213> ORGANISM: Artificial
<220> FEATURE:
<223> OTHER INFORMATION: synthetic oligonucleotide - FW14

<400> SEQUENCE: 39
ctccacgggc gacgccagca a                                            21

<210> SEQ ID NO 40
<211> LENGTH: 21
<212> TYPE: DNA
<213> ORGANISM: Artificial
<220> FEATURE:
<223> OTHER INFORMATION: synthetic oligonucleotide - FW11

<400> SEQUENCE: 40
cgacccggtg tgcagcaaat c                                            21

<210> SEQ ID NO 41
<211> LENGTH: 20
<212> TYPE: DNA
<213> ORGANISM: Artificial
<220> FEATURE:
<223> OTHER INFORMATION: synthetic oligonucleotide - FW15

<400> SEQUENCE: 41
caccacgggg tgatcctcaa                                              20

<210> SEQ ID NO 42
<211> LENGTH: 21
<212> TYPE: DNA
<213> ORGANISM: Artificial
<220> FEATURE:
<223> OTHER INFORMATION: synthetic oligonucleotide - REVC2

-continued

<400> SEQUENCE: 42
tttgagtgcg gtcatcgggt t                                               21

<210> SEQ ID NO 43
<211> LENGTH: 21
<212> TYPE: DNA
<213> ORGANISM: Artificial
<220> FEATURE:
<223> OTHER INFORMATION: synthetic oligonucleotide - REVD2

<400> SEQUENCE: 43
ctctgcggag tagcgtttta g                                               21

<210> SEQ ID NO 44
<211> LENGTH: 20
<212> TYPE: DNA
<213> ORGANISM: Artificial
<220> FEATURE:
<223> OTHER INFORMATION: synthetic oligonucleotide - REVF2

<400> SEQUENCE: 44
tgaagcggct cgagctgcag                                                 20

<210> SEQ ID NO 45
<211> LENGTH: 20
<212> TYPE: DNA
<213> ORGANISM: Artificial
<220> FEATURE:
<223> OTHER INFORMATION: synthetic oligonucleotide - REVG2

<400> SEQUENCE: 45
ttatggcggg gcttctgccg                                                 20

<210> SEQ ID NO 46
<211> LENGTH: 20
<212> TYPE: DNA
<213> ORGANISM: Artificial
<220> FEATURE:
<223> OTHER INFORMATION: synthetic oligonucleotide - REVG2

<400> SEQUENCE: 46
ttatggcggg gcttctgccg                                                 20

<210> SEQ ID NO 47
<211> LENGTH: 20
<212> TYPE: DNA
<213> ORGANISM: Artificial
<220> FEATURE:
<223> OTHER INFORMATION: synthetic oligonucleotide - REVH2

<400> SEQUENCE: 47
tgcggcgtca ggcagtgctt                                                 20

<210> SEQ ID NO 48
<211> LENGTH: 20
<212> TYPE: DNA
<213> ORGANISM: Artificial
<220> FEATURE:
<223> OTHER INFORMATION: synthetic oligonucleotide - MUCFW2

<400> SEQUENCE: 48
agcttgtcga gcgcgttcag                                                 20

<210> SEQ ID NO 49

-continued

<211> LENGTH: 16
<212> TYPE: DNA
<213> ORGANISM: Artificial
<220> FEATURE:
<223> OTHER INFORMATION: synthetic oligonucleotide - GOD2

<400> SEQUENCE: 49
gtttggcgac cctgct                                                    16

<210> SEQ ID NO 50
<211> LENGTH: 20
<212> TYPE: DNA
<213> ORGANISM: Artificial
<220> FEATURE:
<223> OTHER INFORMATION: synthetic oligonucleotide - NgcFW3

<400> SEQUENCE: 50
aaacacctgc tgtcgatgaa                                                20

<210> SEQ ID NO 51
<211> LENGTH: 17
<212> TYPE: DNA
<213> ORGANISM: Artificial
<220> FEATURE:
<223> OTHER INFORMATION: synthetic oligonucleotide - GOD4

<400> SEQUENCE: 51
atcgtgaaca gccagtc                                                   17

<210> SEQ ID NO 52
<211> LENGTH: 21
<212> TYPE: DNA
<213> ORGANISM: Artificial
<220> FEATURE:
<223> OTHER INFORMATION: synthetic oligonucleotide - MUCFW3

<400> SEQUENCE: 52
taaagccctg cagcagccgt t                                              21

<210> SEQ ID NO 53
<211> LENGTH: 21
<212> TYPE: DNA
<213> ORGANISM: Artificial
<220> FEATURE:
<223> OTHER INFORMATION: synthetic oligonucleotide - MUCFW1

<400> SEQUENCE: 53
atgctaaccc aggaagagga t                                              21

<210> SEQ ID NO 54
<211> LENGTH: 20
<212> TYPE: DNA
<213> ORGANISM: Artificial
<220> FEATURE:
<223> OTHER INFORMATION: synthetic oligonucleotide - MUCFW

<400> SEQUENCE: 54
taaagccctg caggccttgt                                                20

<210> SEQ ID NO 55
<211> LENGTH: 20
<212> TYPE: DNA
<213> ORGANISM: Artificial
<220> FEATURE:
<223> OTHER INFORMATION: synthetic oligonucleotide - MUCFW4

<400> SEQUENCE: 55

```
gcagccgttg ttgcaggaaa                                              20

<210> SEQ ID NO 56
<211> LENGTH: 18
<212> TYPE: DNA
<213> ORGANISM: Artificial
<220> FEATURE:
<223> OTHER INFORMATION: synthetic oligonucleotide - MUCREV3

<400> SEQUENCE: 56
actaggctgc tgaccgaa                                                18

<210> SEQ ID NO 57
<211> LENGTH: 18
<212> TYPE: DNA
<213> ORGANISM: Artificial
<220> FEATURE:
<223> OTHER INFORMATION: synthetic oligonucleotide - GOD1

<400> SEQUENCE: 57
gacatgacgc acggtcag                                                18

<210> SEQ ID NO 58
<211> LENGTH: 25
<212> TYPE: DNA
<213> ORGANISM: Artificial
<220> FEATURE:
<223> OTHER INFORMATION: synthetic oligonucleotide

<400> SEQUENCE: 58
cttgtaacgc gctttcccac caacg                                        25

<210> SEQ ID NO 59
<211> LENGTH: 25
<212> TYPE: DNA
<213> ORGANISM: Artificial
<220> FEATURE:
<223> OTHER INFORMATION: synthetic oligonucleotide

<400> SEQUENCE: 59
taaagacttc gcgctgatac cagac                                        25

<210> SEQ ID NO 60
<211> LENGTH: 25
<212> TYPE: DNA
<213> ORGANISM: Artificial
<220> FEATURE:
<223> OTHER INFORMATION: synthetic oligonucleotide

<400> SEQUENCE: 60
agccgccctg atgctccatc acttc                                        25

<210> SEQ ID NO 61
<211> LENGTH: 25
<212> TYPE: DNA
<213> ORGANISM: Artificial
<220> FEATURE:
<223> OTHER INFORMATION: synthetic oligonucleotide

<400> SEQUENCE: 61
acagatttag cccagtcggc cgcac                                        25

<210> SEQ ID NO 62
<211> LENGTH: 25
<212> TYPE: DNA
```

```
<213> ORGANISM: Artificial
<220> FEATURE:
<223> OTHER INFORMATION: synthetic oligonucleotide

<400> SEQUENCE: 62
atattttgcc aattgggcgg cgacg                                              25

<210> SEQ ID NO 63
<211> LENGTH: 25
<212> TYPE: DNA
<213> ORGANISM: Artificial
<220> FEATURE:
<223> OTHER INFORMATION: synthetic oligonucleotide

<400> SEQUENCE: 63
ggataaatcg gtaagcgcct tcctg                                              25

<210> SEQ ID NO 64
<211> LENGTH: 28
<212> TYPE: DNA
<213> ORGANISM: Artificial
<220> FEATURE:
<223> OTHER INFORMATION: T7 RNA polymerase-binding and preferred
      transcriptional initiation sites - T7RNApol binding site

<400> SEQUENCE: 64
aattctaata cgactcacta tagggaga                                           28

<210> SEQ ID NO 65
<211> LENGTH: 53
<212> TYPE: DNA
<213> ORGANISM: Artificial
<220> FEATURE:
<223> OTHER INFORMATION: synthetic oligonucleotide - containing a T7
      RNA polymerase binding site

<400> SEQUENCE: 65
aattctaata cgactcacta tagggagaag ccgccctgat gctccatcac ttc               53

<210> SEQ ID NO 66
<211> LENGTH: 19
<212> TYPE: DNA
<213> ORGANISM: Artificial
<220> FEATURE:
<223> OTHER INFORMATION: synthetic oligonucleotide - GFP primer

<400> SEQUENCE: 66
acagggccat cgccaattg                                                     19

<210> SEQ ID NO 67
<211> LENGTH: 20
<212> TYPE: DNA
<213> ORGANISM: Artificial
<220> FEATURE:
<223> OTHER INFORMATION: synthetic oligonucleotide - T7 primer

<400> SEQUENCE: 67
taatacgact cactataggg                                                    20

<210> SEQ ID NO 68
<211> LENGTH: 18
<212> TYPE: DNA
<213> ORGANISM: Artificial
<220> FEATURE:
<223> OTHER INFORMATION: synthetic oligonucleotide - SP6 primer

<400> SEQUENCE: 68
```
atttaggtga cactatag                                                      18

<210> SEQ ID NO 69
<211> LENGTH: 24
<212> TYPE: DNA
<213> ORGANISM: Artificial
<220> FEATURE:
<223> OTHER INFORMATION: synthetic oligonucleotide - HS1

<400> SEQUENCE: 69
ctgctcgcct tcatcagctc catt                                               24

<210> SEQ ID NO 70
<211> LENGTH: 24
<212> TYPE: DNA
<213> ORGANISM: Artificial
<220> FEATURE:
<223> OTHER INFORMATION: synthetic oligonucleotide - HS2

<400> SEQUENCE: 70
atttccagca tcttcgccct cctg                                               24

<210> SEQ ID NO 71
<211> LENGTH: 24
<212> TYPE: DNA
<213> ORGANISM: Artificial
<220> FEATURE:
<223> OTHER INFORMATION: synthetic oligonucleotide - HS13

<400> SEQUENCE: 71
tagttatcgc gttcacgccc gata                                               24

<210> SEQ ID NO 72
<211> LENGTH: 24
<212> TYPE: DNA
<213> ORGANISM: Artificial
<220> FEATURE:
<223> OTHER INFORMATION: synthetic oligonucleotide - HS14

<400> SEQUENCE: 72
ataccgcgct cacgttcgtt atag                                               24

<210> SEQ ID NO 73
<211> LENGTH: 24
<212> TYPE: DNA
<213> ORGANISM: Artificial
<220> FEATURE:
<223> OTHER INFORMATION: synthetic oligonucleotide - HS9
<220> FEATURE:
<221> NAME/KEY: CDS
<222> LOCATION: (1)..(24)

<400> SEQUENCE: 73 ctg ctc gcc ctc ctg ttc ctg ctc                                          24
Leu Leu Ala Leu Leu Phe Leu Leu
1               5

<210> SEQ ID NO 74
<211> LENGTH: 8
<212> TYPE: PRT
<213> ORGANISM: Artificial
<220> FEATURE:
<223> OTHER INFORMATION: Synthetic Construct

<400> SEQUENCE: 74

Leu Leu Ala Leu Leu Phe Leu Leu

```
<210> SEQ ID NO 75
<211> LENGTH: 24
<212> TYPE: DNA
<213> ORGANISM: Artificial
<220> FEATURE:
<223> OTHER INFORMATION: synthetic oligonucleotide - HS10
<220> FEATURE:
<221> NAME/KEY: CDS
<222> LOCATION: (1)..(24)

<400> SEQUENCE: 75 ctc ctg ttc ctg ctc gcc ctc ctg                                  24
Leu Leu Phe Leu Leu Ala Leu Leu
1               5

<210> SEQ ID NO 76
<211> LENGTH: 8
<212> TYPE: PRT
<213> ORGANISM: Artificial
<220> FEATURE:
<223> OTHER INFORMATION: Synthetic Construct

<400> SEQUENCE: 76

Leu Leu Phe Leu Leu Ala Leu Leu
1               5

<210> SEQ ID NO 77
<211> LENGTH: 21
<212> TYPE: RNA
<213> ORGANISM: Artificial
<220> FEATURE:
<223> OTHER INFORMATION: synthetic oligonucleotide - GOD18 uracil

<400> SEQUENCE: 77
auuugugucg agucggugaa g                                          21

<210> SEQ ID NO 78
<211> LENGTH: 21
<212> TYPE: DNA
<213> ORGANISM: Artificial
<220> FEATURE:
<223> OTHER INFORMATION: synthetic oligonucleotide - GOD18

<400> SEQUENCE: 78
atttgtgtcg agtcggtgaa g                                          21

<210> SEQ ID NO 79
<211> LENGTH: 20
<212> TYPE: RNA
<213> ORGANISM: Artificial
<220> FEATURE:
<223> OTHER INFORMATION: synthetic oligonucleotide - pqq E-FW8 uracil

<400> SEQUENCE: 79
gcccacggcu acccgauggu                                            20

<210> SEQ ID NO 80
<211> LENGTH: 20
<212> TYPE: DNA
<213> ORGANISM: Artificial
<220> FEATURE:
<223> OTHER INFORMATION: synthetic oligonucleotide - pqq E-FW8

<400> SEQUENCE: 80
gcccacggct acccgatggt                                            20
```

<210> SEQ ID NO 81
<211> LENGTH: 20
<212> TYPE: RNA
<213> ORGANISM: Artificial
<220> FEATURE:
<223> OTHER INFORMATION: synthetic oligonucleotide - Muc-FW2 uracil

<400> SEQUENCE: 81
agcuugucga gcgcguucag                                              20

<210> SEQ ID NO 82
<211> LENGTH: 24
<212> TYPE: DNA
<213> ORGANISM: Artificial
<220> FEATURE:
<223> OTHER INFORMATION: synthetic oligonucleotide - PS1

<400> SEQUENCE: 82
ctggcccgcg tcttcatcct ggcc                                         24

<210> SEQ ID NO 83
<211> LENGTH: 24
<212> TYPE: DNA
<213> ORGANISM: Artificial
<220> FEATURE:
<223> OTHER INFORMATION: synthetic oligonucleotide - PS2

<400> SEQUENCE: 83
gccctgatct tcgtccgcgc cctg                                         24

<210> SEQ ID NO 84
<211> LENGTH: 24
<212> TYPE: DNA
<213> ORGANISM: Artificial
<220> FEATURE:
<223> OTHER INFORMATION: synthetic oligonucleotide - PS3

<400> SEQUENCE: 84
ctggcccgcg ccctggtcct ggcc                                         24

<210> SEQ ID NO 85
<211> LENGTH: 24
<212> TYPE: DNA
<213> ORGANISM: Artificial
<220> FEATURE:
<223> OTHER INFORMATION: synthetic oligonucleotide - PS4

<400> SEQUENCE: 85
ggccctggtc ctggcccgcg cctg                                         24

<210> SEQ ID NO 86
<211> LENGTH: 24
<212> TYPE: DNA
<213> ORGANISM: Artificial
<220> FEATURE:
<223> OTHER INFORMATION: synthetic oligonucleotide - HS11

<400> SEQUENCE: 86
acctggccct gctcttgtac tttg                                         24

<210> SEQ ID NO 87
<211> LENGTH: 24
<212> TYPE: DNA
<213> ORGANISM: Artificial
<220> FEATURE:

<223> OTHER INFORMATION: synthetic oligonucleotide - HS12

<400> SEQUENCE: 87
ttgacttgtt cttgcccttg gacc                                         24

<210> SEQ ID NO 88
<211> LENGTH: 16
<212> TYPE: DNA
<213> ORGANISM: Artificial
<220> FEATURE:
<223> OTHER INFORMATION: synthetic oligonucleotide - G2 primer

<400> SEQUENCE: 88
gtttggcgac cctgct                                                  16

<210> SEQ ID NO 89
<211> LENGTH: 19
<212> TYPE: DNA
<213> ORGANISM: Artificial
<220> FEATURE:
<223> OTHER INFORMATION: synthetic oligonucleotide - P-Fw8 primer

<400> SEQUENCE: 89
gccacggcta cccgatggt                                               19

<210> SEQ ID NO 90
<211> LENGTH: 21
<212> TYPE: DNA
<213> ORGANISM: Artificial
<220> FEATURE:
<223> OTHER INFORMATION: synthetic oligonucleotide - M-Fw3 primer

<400> SEQUENCE: 90
tatgcaagcc cagcagccgt t                                            21

<210> SEQ ID NO 91
<211> LENGTH: 18
<212> TYPE: DNA
<213> ORGANISM: Artificial
<220> FEATURE:
<223> OTHER INFORMATION: synthetic oligonucleotide - G1 primer

<400> SEQUENCE: 91
gacatgacgc acggtcag                                                18

<210> SEQ ID NO 92
<211> LENGTH: 20
<212> TYPE: DNA
<213> ORGANISM: Artificial
<220> FEATURE:
<223> OTHER INFORMATION: synthetic oligonucleotide - P-Fw11 primer

<400> SEQUENCE: 92
cgacccggtg tgcagcaagt                                              20

<210> SEQ ID NO 93
<211> LENGTH: 20
<212> TYPE: DNA
<213> ORGANISM: Artificial
<220> FEATURE:
<223> OTHER INFORMATION: synthetic oligonucleotide - M-Fw4 primer

<400> SEQUENCE: 93
gcagccgttg ttgcaggaaa                                              20

```
<210> SEQ ID NO 94
<211> LENGTH: 20
<212> TYPE: DNA
<213> ORGANISM: Artificial
<220> FEATURE:
<223> OTHER INFORMATION: synthetic oligonucleotide - BSF 8/20 primer

<400> SEQUENCE: 94
agagtttgat cctggctcag                                              20

<210> SEQ ID NO 95
<211> LENGTH: 18
<212> TYPE: DNA
<213> ORGANISM: Artificial
<220> FEATURE:
<223> OTHER INFORMATION: synthetic oligonucleotide - BSR 534/18 primer

<400> SEQUENCE: 95
attaccgcgg ctgctggc                                                18

<210> SEQ ID NO 96
<211> LENGTH: 24
<212> TYPE: DNA
<213> ORGANISM: Artificial
<220> FEATURE:
<223> OTHER INFORMATION: synthetic oligonucleotide - HS-15

<400> SEQUENCE: 96
ctgctcgccc tgctcgccct gctc                                         24

<210> SEQ ID NO 97
<211> LENGTH: 24
<212> TYPE: DNA
<213> ORGANISM: Artificial
<220> FEATURE:
<223> OTHER INFORMATION: synthetic oligonucleotide - HS-16

<400> SEQUENCE: 97
ctgctcgccc tgctcgccct cctg                                         24

<210> SEQ ID NO 98
<211> LENGTH: 24
<212> TYPE: DNA
<213> ORGANISM: Artificial
<220> FEATURE:
<223> OTHER INFORMATION: synthetic oligonucleotide - HS-17

<400> SEQUENCE: 98
ctcctggccc tcctgttcct gctc                                         24

<210> SEQ ID NO 99
<211> LENGTH: 24
<212> TYPE: DNA
<213> ORGANISM: Artificial
<220> FEATURE:
<223> OTHER INFORMATION: synthetic oligonucleotide - HS-18

<400> SEQUENCE: 99
ctcctgttcc tcctggccct cctg                                         24

<210> SEQ ID NO 100
<211> LENGTH: 24
<212> TYPE: DNA
<213> ORGANISM: Artificial
<220> FEATURE:
<223> OTHER INFORMATION: synthetic oligonucleotide - HS-19
```

<400> SEQUENCE: 100
ctcctgttcc tcctgttcct gctc                                          24

<210> SEQ ID NO 101
<211> LENGTH: 24
<212> TYPE: DNA
<213> ORGANISM: Artificial
<220> FEATURE:
<223> OTHER INFORMATION: synthetic oligonucleotide - HS-20

<400> SEQUENCE: 101
ctcctgttcc tcctgttcct cctg                                          24

<210> SEQ ID NO 102
<211> LENGTH: 27
<212> TYPE: DNA
<213> ORGANISM: Artificial
<220> FEATURE:
<223> OTHER INFORMATION: synthetic oligonucleotide - HS-21

<400> SEQUENCE: 102
ctgctcgcct tcctgctcgc cctgctc                                       27

<210> SEQ ID NO 103
<211> LENGTH: 27
<212> TYPE: DNA
<213> ORGANISM: Artificial
<220> FEATURE:
<223> OTHER INFORMATION: synthetic oligonucleotide - HS-22

<400> SEQUENCE: 103
ctgctcgcct tcctgctcgc cctcctg                                       27

<210> SEQ ID NO 104
<211> LENGTH: 27
<212> TYPE: DNA
<213> ORGANISM: Artificial
<220> FEATURE:
<223> OTHER INFORMATION: synthetic oligonucleotide - HS-23

<400> SEQUENCE: 104
ctgctcgccc tgctcttcgc cctcctg                                       27

<210> SEQ ID NO 105
<211> LENGTH: 27
<212> TYPE: DNA
<213> ORGANISM: Artificial
<220> FEATURE:
<223> OTHER INFORMATION: synthetic oligonucleotide - HS-24

<400> SEQUENCE: 105
ctgctcgccc tcctgttcgc cctgctc                                       27

<210> SEQ ID NO 106
<211> LENGTH: 27
<212> TYPE: DNA
<213> ORGANISM: Artificial
<220> FEATURE:
<223> OTHER INFORMATION: synthetic oligonucleotide - HS-25

<400> SEQUENCE: 106
ctcctggccc tcctgttcgc cctcctg                                       27

<210> SEQ ID NO 107
<211> LENGTH: 27

```
<212> TYPE: DNA
<213> ORGANISM: Artificial
<220> FEATURE:
<223> OTHER INFORMATION: synthetic oligonucleotide - HS-26

<400> SEQUENCE: 107
ctcctggccc tcctgttcgc cctgctc                                            27

<210> SEQ ID NO 108
<211> LENGTH: 27
<212> TYPE: DNA
<213> ORGANISM: Artificial
<220> FEATURE:
<223> OTHER INFORMATION: synthetic oligonucleotide - HS-27

<400> SEQUENCE: 108
ctcctggccc tcctgttcgc cctcctg                                            27

<210> SEQ ID NO 109
<211> LENGTH: 30
<212> TYPE: DNA
<213> ORGANISM: Artificial
<220> FEATURE:
<223> OTHER INFORMATION: synthetic oligonucleotide - HS-28

<400> SEQUENCE: 109
ctgctcgccc tgctcgccct gctcctcctg                                         30

<210> SEQ ID NO 110
<211> LENGTH: 30
<212> TYPE: DNA
<213> ORGANISM: Artificial
<220> FEATURE:
<223> OTHER INFORMATION: synthetic oligonucleotide - HS-29

<400> SEQUENCE: 110
ctgctcgccc tgctcttcct gctcctcctg                                         30

<210> SEQ ID NO 111
<211> LENGTH: 30
<212> TYPE: DNA
<213> ORGANISM: Artificial
<220> FEATURE:
<223> OTHER INFORMATION: synthetic oligonucleotide - HS-30

<400> SEQUENCE: 111
ctcctggccc tgctcctcct gttcctgctc                                         30

<210> SEQ ID NO 112
<211> LENGTH: 30
<212> TYPE: DNA
<213> ORGANISM: Artificial
<220> FEATURE:
<223> OTHER INFORMATION: synthetic oligonucleotide - HS-31

<400> SEQUENCE: 112
ctcctgctgc tcttcctgct cgccctgctc                                         30

<210> SEQ ID NO 113
<211> LENGTH: 30
<212> TYPE: DNA
<213> ORGANISM: Artificial
<220> FEATURE:
<223> OTHER INFORMATION: synthetic oligonucleotide - HS-32

<400> SEQUENCE: 113
```
ctcctgctgc tcttcctgct cttcctgctc                                              30

<210> SEQ ID NO 114
<211> LENGTH: 30
<212> TYPE: DNA
<213> ORGANISM: Artificial
<220> FEATURE:
<223> OTHER INFORMATION: synthetic oligonucleotide - HS-33

<400> SEQUENCE: 114
ctcctgctgc tcttcctcct ggccctcctg                                              30

<210> SEQ ID NO 115
<211> LENGTH: 30
<212> TYPE: DNA
<213> ORGANISM: Artificial
<220> FEATURE:
<223> OTHER INFORMATION: synthetic oligonucleotide - HS-34

<400> SEQUENCE: 115
ctcctgctgc tcttcctcct gttcctgctc                                              30

<210> SEQ ID NO 116
<211> LENGTH: 36
<212> TYPE: DNA
<213> ORGANISM: Artificial
<220> FEATURE:
<223> OTHER INFORMATION: synthetic oligonucleotide - HS-35

<400> SEQUENCE: 116
ctgctcgccc tgctcctcct ggccctgctc ctcctg                                       36

<210> SEQ ID NO 117
<211> LENGTH: 36
<212> TYPE: DNA
<213> ORGANISM: Artificial
<220> FEATURE:
<223> OTHER INFORMATION: synthetic oligonucleotide - HS-36

<400> SEQUENCE: 117
ctgctcgccc tgctcctcct gttcctgctc ctcctg                                       36

<210> SEQ ID NO 118
<211> LENGTH: 36
<212> TYPE: DNA
<213> ORGANISM: Artificial
<220> FEATURE:
<223> OTHER INFORMATION: synthetic oligonucleotide - HS-37

<400> SEQUENCE: 118
ctgctcctcc tgttcctcct gttcctcctg ctgctc                                       36

<210> SEQ ID NO 119
<211> LENGTH: 36
<212> TYPE: DNA
<213> ORGANISM: Artificial
<220> FEATURE:
<223> OTHER INFORMATION: synthetic oligonucleotide - HS-38

<400> SEQUENCE: 119
ctcctgctgc tcgccctgct cgccctgctc ctcctg                                       36

<210> SEQ ID NO 120
<211> LENGTH: 36
<212> TYPE: DNA
<213> ORGANISM: Artificial

<220> FEATURE:
<223> OTHER INFORMATION: synthetic oligonucleotide - HS-39

<400> SEQUENCE: 120
ctgctcctcc tggccctcct gctgctcgcc ctcctg    36

<210> SEQ ID NO 121
<211> LENGTH: 36
<212> TYPE: DNA
<213> ORGANISM: Artificial
<220> FEATURE:
<223> OTHER INFORMATION: synthetic oligonucleotide - HS-40

<400> SEQUENCE: 121
ctgctcctcc tggccctcct gctgctcttc ctcctg    36

<210> SEQ ID NO 122
<211> LENGTH: 36
<212> TYPE: DNA
<213> ORGANISM: Artificial
<220> FEATURE:
<223> OTHER INFORMATION: synthetic oligonucleotide - HS-41

<400> SEQUENCE: 122
ctcctgctgc tcttcctcct gctgctcttc ctcctg    36

<210> SEQ ID NO 123
<211> LENGTH: 42
<212> TYPE: DNA
<213> ORGANISM: Artificial
<220> FEATURE:
<223> OTHER INFORMATION: synthetic oligonucleotide - HS-42

<400> SEQUENCE: 123
ctcctgctgc tcttcctgct cctcctgttc ctgctcctcc tg    42

<210> SEQ ID NO 124
<211> LENGTH: 42
<212> TYPE: DNA
<213> ORGANISM: Artificial
<220> FEATURE:
<223> OTHER INFORMATION: synthetic oligonucleotide - HS-43

<400> SEQUENCE: 124
ctcctgctgc tcttcctgct cctcctggcc ctcctgctgc tc    42

<210> SEQ ID NO 125
<211> LENGTH: 42
<212> TYPE: DNA
<213> ORGANISM: Artificial
<220> FEATURE:
<223> OTHER INFORMATION: synthetic oligonucleotide - HS-44

<400> SEQUENCE: 125
ctcctgctgc tcttcctcct gctgctcttc ctcctgctgc tc    42

<210> SEQ ID NO 126
<211> LENGTH: 21
<212> TYPE: DNA
<213> ORGANISM: Artificial
<220> FEATURE:
<223> OTHER INFORMATION: synthetic oligonucleotide - PS-6

<400> SEQUENCE: 126
gccggcctgc agcgcgacct c    21

<210> SEQ ID NO 127
<211> LENGTH: 21
<212> TYPE: DNA
<213> ORGANISM: Artificial
<220> FEATURE:
<223> OTHER INFORMATION: synthetic oligonucleotide - PS-7

<400> SEQUENCE: 127
gccggcctgc agcgcgagct c            21

<210> SEQ ID NO 128
<211> LENGTH: 21
<212> TYPE: DNA
<213> ORGANISM: Artificial
<220> FEATURE:
<223> OTHER INFORMATION: synthetic oligonucleotide - PS-8

<400> SEQUENCE: 128
gccggcctgc gccagctcga c            21

<210> SEQ ID NO 129
<211> LENGTH: 21
<212> TYPE: DNA
<213> ORGANISM: Artificial
<220> FEATURE:
<223> OTHER INFORMATION: synthetic oligonucleotide - PS-9

<400> SEQUENCE: 129
gccggcctgc gcctcgacca g            21

<210> SEQ ID NO 130
<211> LENGTH: 21
<212> TYPE: DNA
<213> ORGANISM: Artificial
<220> FEATURE:
<223> OTHER INFORMATION: synthetic oligonucleotide - PS-10

<400> SEQUENCE: 130
ggccagctgc gcctcgacgc c            21

<210> SEQ ID NO 131
<211> LENGTH: 21
<212> TYPE: DNA
<213> ORGANISM: Artificial
<220> FEATURE:
<223> OTHER INFORMATION: synthetic oligonucleotide - PS-11

<400> SEQUENCE: 131
gccggccagc gcctgctcga c            21

<210> SEQ ID NO 132
<211> LENGTH: 21
<212> TYPE: DNA
<213> ORGANISM: Artificial
<220> FEATURE:
<223> OTHER INFORMATION: synthetic oligonucleotide - PS-12

<400> SEQUENCE: 132
gccggcctgc gcgacgtcca g            21

<210> SEQ ID NO 133
<211> LENGTH: 21
<212> TYPE: DNA
<213> ORGANISM: Artificial
<220> FEATURE:
<223> OTHER INFORMATION: synthetic oligonucleotide - PS-13

```
<400> SEQUENCE: 133
gccggcctgc gcgaccagct c                                              21

<210> SEQ ID NO 134
<211> LENGTH: 21
<212> TYPE: DNA
<213> ORGANISM: Artificial
<220> FEATURE:
<223> OTHER INFORMATION: synthetic oligonucleotide - PS-14

<400> SEQUENCE: 134
gccctgcagc gcgacggcct c                                              21

<210> SEQ ID NO 135
<211> LENGTH: 21
<212> TYPE: DNA
<213> ORGANISM: Artificial
<220> FEATURE:
<223> OTHER INFORMATION: synthetic oligonucleotide - PS-15

<400> SEQUENCE: 135
gccctgcagc gcgacggcct c                                              21

<210> SEQ ID NO 136
<211> LENGTH: 21
<212> TYPE: DNA
<213> ORGANISM: Artificial
<220> FEATURE:
<223> OTHER INFORMATION: synthetic oligonucleotide - PS-16

<400> SEQUENCE: 136
gccggccagc gcgacctcct g                                              21

<210> SEQ ID NO 137
<211> LENGTH: 21
<212> TYPE: DNA
<213> ORGANISM: Artificial
<220> FEATURE:
<223> OTHER INFORMATION: synthetic oligonucleotide - PS-17

<400> SEQUENCE: 137
ggccagctgc gcgaggacgc c                                              21

<210> SEQ ID NO 138
<211> LENGTH: 21
<212> TYPE: DNA
<213> ORGANISM: Artificial
<220> FEATURE:
<223> OTHER INFORMATION: synthetic oligonucleotide - PS-18

<400> SEQUENCE: 138
gccctgcagc gcgaggacgg c                                              21

<210> SEQ ID NO 139
<211> LENGTH: 21
<212> TYPE: DNA
<213> ORGANISM: Artificial
<220> FEATURE:
<223> OTHER INFORMATION: synthetic oligonucleotide - PS-19

<400> SEQUENCE: 139
ggcctgcagc gcgccgaggt c                                              21

<210> SEQ ID NO 140
```

```
<211> LENGTH: 21
<212> TYPE: DNA
<213> ORGANISM: Artificial
<220> FEATURE:
<223> OTHER INFORMATION: synthetic oligonucleotide - PS-20

<400> SEQUENCE: 140
ggccagctgc gcgccgaggt c                                              21

<210> SEQ ID NO 141
<211> LENGTH: 21
<212> TYPE: DNA
<213> ORGANISM: Artificial
<220> FEATURE:
<223> OTHER INFORMATION: synthetic oligonucleotide - PS-21

<400> SEQUENCE: 141
gccggccagc tcctgcgcga g                                              21

<210> SEQ ID NO 142
<211> LENGTH: 21
<212> TYPE: DNA
<213> ORGANISM: Artificial
<220> FEATURE:
<223> OTHER INFORMATION: synthetic oligonucleotide - PS-22

<400> SEQUENCE: 142
ggcctgcagc tcgacgccgc g                                              21

<210> SEQ ID NO 143
<211> LENGTH: 21
<212> TYPE: DNA
<213> ORGANISM: Artificial
<220> FEATURE:
<223> OTHER INFORMATION: synthetic oligonucleotide - PS-23

<400> SEQUENCE: 143
ggcgccctgc tcgaggacca g                                              21

<210> SEQ ID NO 144
<211> LENGTH: 21
<212> TYPE: DNA
<213> ORGANISM: Artificial
<220> FEATURE:
<223> OTHER INFORMATION: synthetic oligonucleotide - PS-24

<400> SEQUENCE: 144
ggccagctgc tcgcccgcgc g                                              21

<210> SEQ ID NO 145
<211> LENGTH: 21
<212> TYPE: DNA
<213> ORGANISM: Artificial
<220> FEATURE:
<223> OTHER INFORMATION: synthetic oligonucleotide - PS-25

<400> SEQUENCE: 145
ggcctgcagc tcgccgacgc g                                              21

<210> SEQ ID NO 146
<211> LENGTH: 21
<212> TYPE: DNA
<213> ORGANISM: Artificial
<220> FEATURE:
<223> OTHER INFORMATION: synthetic oligonucleotide - PS-26

<400> SEQUENCE: 146
```

-continued gccggccagc tcgcggtcct g                                            21

<210> SEQ ID NO 147
<211> LENGTH: 21
<212> TYPE: DNA
<213> ORGANISM: Artificial
<220> FEATURE:
<223> OTHER INFORMATION: synthetic oligonucleotide - PS-27

<400> SEQUENCE: 147
ggcgcccagc tcgcggtcct g                                            21

<210> SEQ ID NO 148
<211> LENGTH: 21
<212> TYPE: DNA
<213> ORGANISM: Artificial
<220> FEATURE:
<223> OTHER INFORMATION: synthetic oligonucleotide - PS-28

<400> SEQUENCE: 148
gccctgcagc tcggcgcgga g                                            21

<210> SEQ ID NO 149
<211> LENGTH: 21
<212> TYPE: DNA
<213> ORGANISM: Artificial
<220> FEATURE:
<223> OTHER INFORMATION: synthetic oligonucleotide - PS-29

<400> SEQUENCE: 149
gcccagctgc tcggcgcgga g                                            21

<210> SEQ ID NO 150
<211> LENGTH: 21
<212> TYPE: DNA
<213> ORGANISM: Artificial
<220> FEATURE:
<223> OTHER INFORMATION: synthetic oligonucleotide - PS-30

<400> SEQUENCE: 150
ggcgcccagc tgctccgcga c                                            21

<210> SEQ ID NO 151
<211> LENGTH: 21
<212> TYPE: DNA
<213> ORGANISM: Artificial
<220> FEATURE:
<223> OTHER INFORMATION: synthetic oligonucleotide - PS-31

<400> SEQUENCE: 151
gccggccagc tgctcgagga c                                            21

<210> SEQ ID NO 152
<211> LENGTH: 21
<212> TYPE: DNA
<213> ORGANISM: Artificial
<220> FEATURE:
<223> OTHER INFORMATION: synthetic oligonucleotide - PS-32

<400> SEQUENCE: 152
ggcgcccagc tgctcgagga c                                            21

<210> SEQ ID NO 153
<211> LENGTH: 21
<212> TYPE: DNA

```
<213> ORGANISM: Artificial
<220> FEATURE:
<223> OTHER INFORMATION: synthetic oligonucleotide - PS-33

<400> SEQUENCE: 153
ggcgccctgg accgcgagca g                                              21

<210> SEQ ID NO 154
<211> LENGTH: 21
<212> TYPE: DNA
<213> ORGANISM: Artificial
<220> FEATURE:
<223> OTHER INFORMATION: synthetic oligonucleotide - PS-34

<400> SEQUENCE: 154
gccggcctgg accgcgcgca g                                              21

<210> SEQ ID NO 155
<211> LENGTH: 21
<212> TYPE: DNA
<213> ORGANISM: Artificial
<220> FEATURE:
<223> OTHER INFORMATION: synthetic oligonucleotide - PS-35

<400> SEQUENCE: 155
gccggccagg tcgcggagct g                                              21

<210> SEQ ID NO 156
<211> LENGTH: 21
<212> TYPE: DNA
<213> ORGANISM: Artificial
<220> FEATURE:
<223> OTHER INFORMATION: synthetic oligonucleotide - PS-36

<400> SEQUENCE: 156
ggcgcccagg acgtcgagct g                                              21

<210> SEQ ID NO 157
<211> LENGTH: 21
<212> TYPE: DNA
<213> ORGANISM: Artificial
<220> FEATURE:
<223> OTHER INFORMATION: synthetic oligonucleotide - PS-37

<400> SEQUENCE: 157
gccggccagg acgtcgcgct g                                              21

<210> SEQ ID NO 158
<211> LENGTH: 20
<212> TYPE: DNA
<213> ORGANISM: Artificial
<220> FEATURE:
<223> OTHER INFORMATION: synthetic oligonucleotide - GOD51

<400> SEQUENCE: 158
ctcggcattc tgcttctgtt                                                20

<210> SEQ ID NO 159
<211> LENGTH: 20
<212> TYPE: DNA
<213> ORGANISM: Artificial
<220> FEATURE:
<223> OTHER INFORMATION: synthetic oligonucleotide - GOD62

<400> SEQUENCE: 159
acaccttcgg tttcgctctt                                                20
```

<210> SEQ ID NO 160
<211> LENGTH: 19
<212> TYPE: DNA
<213> ORGANISM: Artificial
<220> FEATURE:
<223> OTHER INFORMATION: synthetic oligonucleotide

<400> SEQUENCE: 160
cctgaaggca tgatcaagt                                                    19

<210> SEQ ID NO 161
<211> LENGTH: 20
<212> TYPE: DNA
<213> ORGANISM: Artificial
<220> FEATURE:
<223> OTHER INFORMATION: synthetic oligonucleotide

<400> SEQUENCE: 161
cagaacaggc cccgcgaagt                                                   20

<210> SEQ ID NO 162
<211> LENGTH: 21
<212> TYPE: DNA
<213> ORGANISM: Artificial
<220> FEATURE:
<223> OTHER INFORMATION: synthetic oligonucleotide

<400> SEQUENCE: 162
gattttgcga tgaggcgtag g                                                 21

<210> SEQ ID NO 163
<211> LENGTH: 20
<212> TYPE: DNA
<213> ORGANISM: Artificial
<220> FEATURE:
<223> OTHER INFORMATION: synthetic oligonucleotide

<400> SEQUENCE: 163
gacgtcgagc tcggcgaagt                                                   20

<210> SEQ ID NO 164
<211> LENGTH: 429
<212> TYPE: DNA
<213> ORGANISM: Bacillus pumilus

<400> SEQUENCE: 164
cgtcaaggtg cgagcagtta ctctcgcact tgttcttccc taacaacaga gctttacgat        60
ccgaaaacct tcatcactca cgcggcgttg ctccgtcaga ctttcgtcca ttgcggaaga       120
ttccctactg ctgcctcccg taggagtctg ggccgtgtct cagtcccagt gtggccgatc       180
accctctcag gtcggctacg catcgtcgcc ttggtgagcc attaccccac caactagcta       240
atgcgccgcg gtccatctg taagtgacag ccgaaaccgt cttcatcct tgaaccatgc         300 ggttcaagga actatccggt attagctccg gtttcccgga gttatcccag tcttacaggc       360
aggttaccca cgtgttactc acccgtccgc cgctaacatc cgggagcaag ctcccttctg       420
tccgctcga                                                              429

<210> SEQ ID NO 165
<211> LENGTH: 438
<212> TYPE: DNA
<213> ORGANISM: Bacillus sphaericus

```
<400> SEQUENCE: 165
atgcaagtcc agcgaacaga gaaggagctt gctcctttga cgttagcggc ggacgggtga      60
gtaacacgtg ggcaacctac cctatagttt gggataactc cgggaaaccg gggctaatac     120
cgaataatct tttgtccctc atgggacaat actgaaagac ggtttcggct gtcgctatag     180
gatgggcccg cggcgcatta gctagttggt gaggtaacgg ctcaccaagg caacgatgcg     240
tagccgacct gagagggtga tcggccacac tgggactgag acacggccca gactcctacg     300
ggaggcagca gtagggaatc ttccacaatg ggcgaaagcc tgatggagca acgccgcgtg     360
agtgaagaag gatttcggtt cgtaaaactc tgttgtaagg gaagaacaag tacagtagta     420
actggctgta ccttgacg                                                   438

<210> SEQ ID NO 166
<211> LENGTH: 24
<212> TYPE: DNA
<213> ORGANISM: Artificial
<220> FEATURE:
<223> OTHER INFORMATION: synthetic oligonucleotide

<400> SEQUENCE: 166
ctgctcgccc tcctgttcct gctc                                             24

<210> SEQ ID NO 167
<211> LENGTH: 24
<212> TYPE: DNA
<213> ORGANISM: Artificial
<220> FEATURE:
<223> OTHER INFORMATION: synthetic oligonucleotide

<400> SEQUENCE: 167
ctcctgttcc tgctcgccct cctg                                             24
```